United States Patent
Halem et al.

(10) Patent No.: US 9,439,943 B2
(45) Date of Patent: Sep. 13, 2016

(54) USE OF MELANOCORTINS TO TREAT INSULIN SENSITIVITY

(71) Applicant: Ipsen Pharma S.A.S., Boulogne Billancourt (FR)

(72) Inventors: Heather A. Halem, Westborough, MA (US); Michael DeWitt Culler, Hopkinton, MA (US); Andrew A. Butler, Kirkwood, MO (US)

(73) Assignee: Ipsen Pharma S.A.S., Boulogne-Billancourt (FR)

( * ) Notice: Subject to any disclaimer, the term of this patent is extended or adjusted under 35 U.S.C. 154(b) by 0 days.

(21) Appl. No.: 14/844,128

(22) Filed: Sep. 3, 2015

(65) Prior Publication Data

US 2015/0366934 A1  Dec. 24, 2015

Related U.S. Application Data

(63) Continuation of application No. 12/740,917, filed as application No. PCT/US2008/012490 on Nov. 5, 2008, now Pat. No. 9,155,777.

(60) Provisional application No. 61/001,933, filed on Nov. 5, 2007.

(51) Int. Cl.
  *A61K 38/12* (2006.01)
  *A61K 38/33* (2006.01)
  *A61K 38/04* (2006.01)

(52) U.S. Cl.
  CPC .............. *A61K 38/12* (2013.01); *A61K 38/04* (2013.01); *A61K 38/33* (2013.01)

(58) Field of Classification Search
  None
  See application file for complete search history.

(56) References Cited

U.S. PATENT DOCUMENTS

| 6,689,938 | B2 | 2/2004 | Brennan et al. | |
| 8,563,000 | B2 * | 10/2013 | Dong | C07K 14/68 424/185.1 |
| 2006/0276485 | A1 | 12/2006 | Soeberdt et al. | |
| 2007/0123453 | A1 | 5/2007 | Heiman et al. | |
| 2007/0244054 | A1 | 10/2007 | Sensfuss et al. | |
| 2012/0135923 | A1 | 5/2012 | Halem et al. | |

FOREIGN PATENT DOCUMENTS

| WO | 2004087159 A1 | 10/2004 |
| WO | WO 2004099246 A2 | 11/2004 |
| WO | 2005000339 A2 | 1/2005 |
| WO | 2006049933 A2 | 5/2006 |
| WO | 2007008684 A2 | 1/2007 |
| WO | 2007008704 A2 | 1/2007 |
| WO | WO 2007067341 A2 | 6/2007 |
| WO | 2008147556 A2 | 12/2008 |
| WO | 2008156677 A2 | 12/2008 |

OTHER PUBLICATIONS

Howard, Barbara V., "Insulin Resistance and Lipid Metabolism," Am J Cardiol, 1999, vol. 84: pp. 28J-32J.
http://www.cdc.gov/healthyweightlassessing/bmi/adult_bmi/index.html#Oefinition; pp. 1-4; obtained Dec. 23, 2012.
Fan, W. et al., "The Central Melanocortin System of Directly Regulating Serum Insulin Levels," Endo., 2000, vol. 141: 3072-3079.
Heijboer, A.C. et al., "Intracerebroventricular Administration of Melanotan II Increases Insulin Sensitivity of Glucose Disposal in Mice," Diabetologia, 2005, vol. 48: 1621-1626.
Banno, R. et al., "The Melanocortin Agonist Melanotan II Increases Insulin Sensitivity in OLETF Rats," Peptides, 2004, vol. 25: 1279-1286.
Obici et al., "Central Melanocortin Receptors Regulate Insulin Action," J. Clin. Inv., 2001, 108:1079-1085.
Pierroz et al., "Effects of Acute and Chronic Administration of the Melanocortin Agonist MTII in Mice with Diet-Induced Obesity," Diabetes, 2002, 51:1337-1345.
Hochgeschwender et al., "Altered Glucose Homeostasis in Proopiomelanocortin-Null Mouse Mutants Lacking Central and Peripheral Melanocortin," Endocrinology, 2003, 144(12):5194-5202.
Kishi, Toshiro et al., "Expression of Melanocortin 4 Receptor mRNA in the Central Nervous System of the Rat," J of Comparative Neurology, 2003, vol. 457, pp. 213-235.
Oshiro, Y. et al., "Molecular scanning for mutations in the melanocortin-4 receptor gene in obese/diabetic Japanese," Ann. Hum. Genet., 1999, vol. 63, pp. 483-487.

* cited by examiner

*Primary Examiner* — Lianko Garyu
(74) *Attorney, Agent, or Firm* — Eileen J. Ennis; Ipsen Bioscience, Inc.

(57) ABSTRACT

The present invention relates to peptide ligands of the melanocortin receptors, in particular the melanocortin-4 receptor, and as such, are useful in the treatment of disorders responsive to the activation of this receptor, such as insulin resistance.

17 Claims, 11 Drawing Sheets

Figure 2B
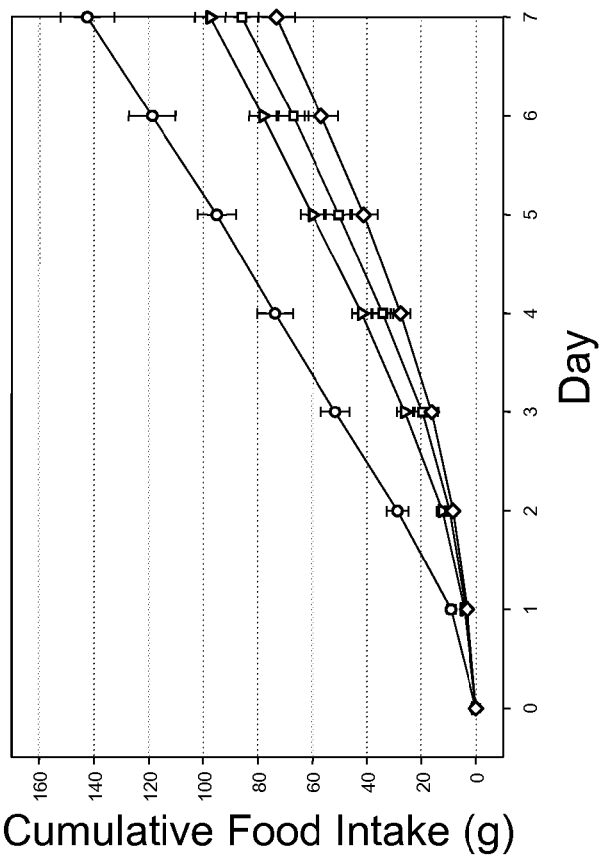
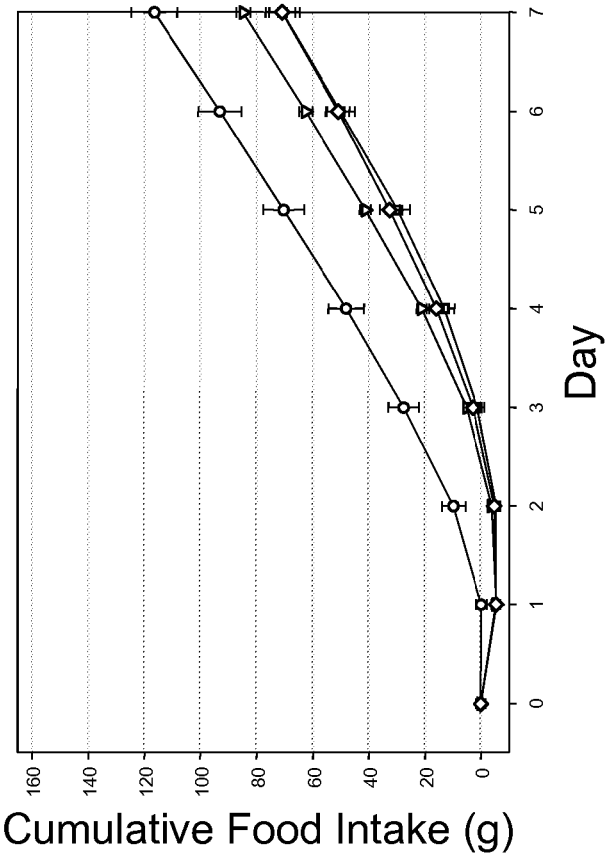

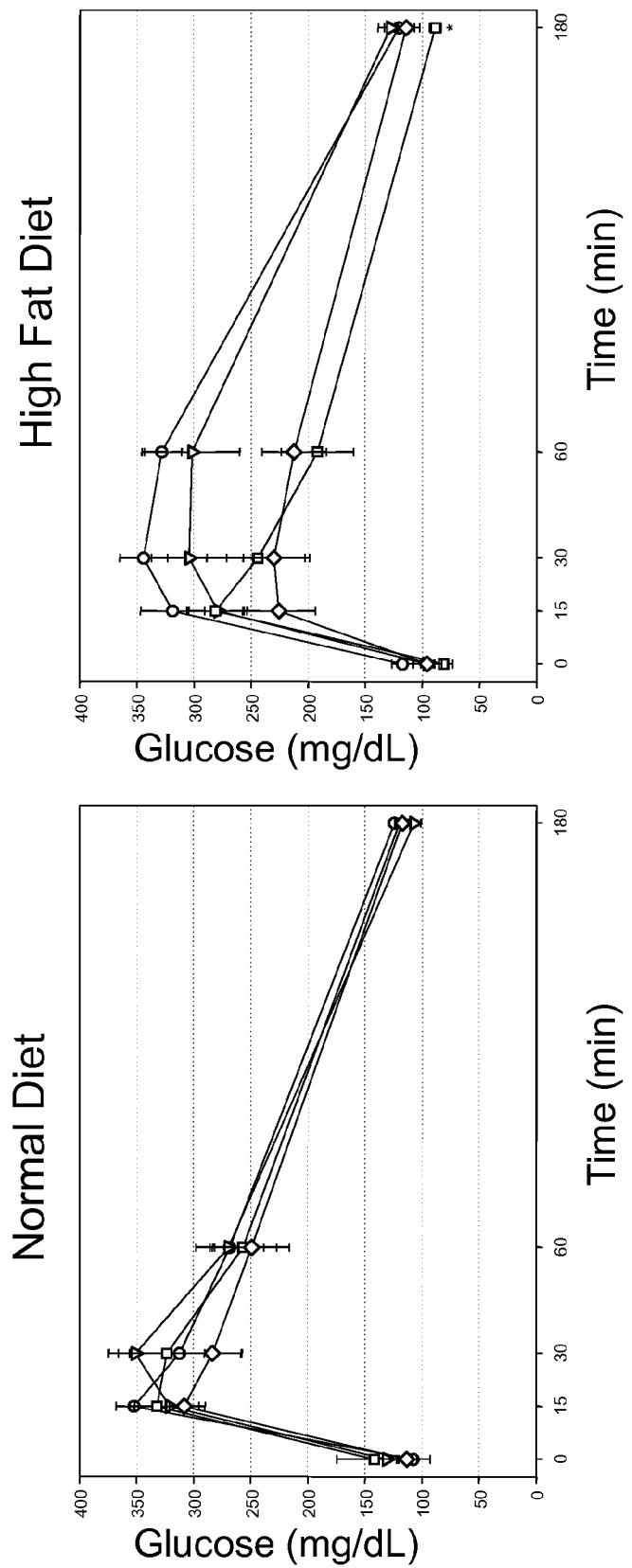

under 35 U.S.C. §371 of
USE OF MELANOCORTINS TO TREAT INSULIN SENSITIVITY

This application is a continuation application of pending U.S. Ser. No. 12/740,917, filed May 17, 2010, which is a United States national filing under 35 U.S.C. §371 of international (PCT) application No. PCT/US2008/012490, filed Nov. 5, 2008 and designating the US, which claims priority to U.S. provisional application No. 61/001,933, filed Nov. 5, 2007, each of which is hereby incorporated by reference in its entirety.

SEQUENCE LISTING

The instant application contains a Sequence Listing which has been submitted in ASCII format via EFS-Web, and is hereby incorporated by reference in its entirety. The ASCII copy, is named "183P_PCT2_US-A_SeqListing_01_05 May_2015 ST25.txt", created on May 1, 2015, and has the file size of 234,000 bytes.

BACKGROUND OF THE INVENTION

Melanocortins are a family of regulatory peptides which are formed by post-translational processing of pro-hormone pro-opiomelanocortin (POMC; 131 amino acids in length). POMC is processed into three classes of hormones; the melanocortins, adrenocorticotropin hormone, and various endorphins (e.g. lipotropin) (Cone et al., Recent Prog. Horm. Res., 51:287-317, (1996); Cone et al., Ann. N.Y. Acad. Sci., 31:342-363, (1993)).

Five melanocortin receptors (MC-R) have been characterized to date. These include melanocyte-specific receptor (MC1-R), corticoadrenal-specific ACTH receptor (MC2-R), melacortin-3 (MC3-R), melanocortin-4 (MC4-R) and melanocortin-5 receptor (MC5-R). All of the melanocortin receptors respond to the peptide hormone class of melanocyte stimulating hormones (MSH) (Cone et al., Ann. N.Y. Acad. Sci., 680:342-363 (1993); Cone et al., Recent Prog. Horm. Res., 51:287-318 (1996)).

There has been great interest in melanocortin (MC-R) receptors as targets for the design of novel therapeutics to treat disorders of body weight such as obesity and cachexia. One of the receptors, MC4-R, is a 332 amino acid transmembrane protein expressed in brain as well as placental and gut tissues (Cone et al., Ann. N.Y. Acad. Sci., 680:342-363 (1993); Cone et al., Recent Prog. Horm. Res., 51:287-318 (1996)). Recent pharmacological confirmation has established that central MC4-R receptors are the prime mediators of the anorexic and orexigenic effects reported for melanocortin agonists and antagonists, respectively (Giraudo et al., Brain Res., 809:302-306 (1998); Farooqi et al., NE J Med., 348:1085-1095 (2003); MacNeil et al., Eu. J. Pharm., 44:141-157 (2002); MacNeil et al., Eu. J. Pharm., 450:93-109 (2002); Kask et al., NeuroReport, 10:707-711 (1999); Chen et al., Transgenic Res., 9:145-54, (2000); Marsh et al., Nat Genet., 21:119-22, (1999); Balthasar et al., Cell, 123:493-505 (2005)).

Complications of body weight disorders commonly include an inability to produce and utilize insulin, often resulting in faulty glucose regulation. The consequence of failure to properly control glucose metabolism affects many aspects of overall health including energy metabolism, neuropathy and heart disease. Current progress with receptor-selective melanocortin receptor ligands evidences the therapeutic potential of melanocortin receptor activation, particularly MC4-R, in the treatment of glucose regulation, including insulin metabolism.

SUMMARY OF THE INVENTION

The present invention is directed to the use of peptides which are ligands of one or more of the melanocortin receptors (MC-R), or the pharmaceutically-acceptable salts thereof, to treat mammals suffering from insulin resistance. In one embodiment, the ligands are agonists to the melanocortin 4 receptor. In a preferred embodiment, the melanocortin receptor ligands are according to the formulae described herein or are selected from particular peptides described herein.

The insulin resistant subject mammals may be obese or overweight and may lose weight as a result of the administration of the peptides of the invention. The insulin resistant subject mammals may also be normal weight or lean. The insulin resistant condition of the subject mammals may be treated independent of weight loss. In addition, the subject mammals may be human subjects of any age, such as an infant, a child, an adult or an elderly adult.

In the first embodiment, the invention provides a method to treat insulin resistance in a mammalian subject, with or without weight loss, by the administration of a therapeutically effective amount of a melanocortin receptor 4 ligand according to Formula (I) and pharmaceutically acceptable salts, hydrates, solvates or prodrugs thereof (see International Patent Application Publication Number WO 2007/008704, incorporated herein by reference in its entirety):

$$(R^2R^3)\text{-}A^1\text{-}c(A^2\text{-}A^3\text{-}A^4\text{-}A^5\text{-}A^6\text{-}A^7\text{-}A^8\text{-}A^9)\text{-}A^{10}\text{-}R^1 \quad (I)$$

wherein:

$A^1$ is Acc, HN—$(CH_2)_m$—C(O), L- or D-amino acid, or deleted;

$A^2$ is Cys, D-Cys, hCys, D-hCys, Pen, D-Pen, Asp, or Glu;

$A^3$ is Gly, Ala, β-Ala, Gaba, Aib, D-amino acid, or deleted;

$A^4$ is His, 2-Pal, 3-Pal, 4-Pal, Taz, 2-Thi, 3-Thi, or $(X^1,X^2,X^3,X^4,X^5)$Phe;

$A^5$ is D-Phe, D-1-Nal, D-2-Nal, D-Trp, D-Bal, D-$(X^1,X^2, X^3,X^4,X^5)$Phe, L-Phe or D-(Et)Tyr;

$A^6$ is Arg, hArg, Dab, Dap, Lys, Orn, or HN—CH $((CH_2)_n$—$N(R^4R^5))$—C(O);

$A^7$ is Trp, 1-Nal, 2-Nal, Bal, Bip, D-Trp, D-1-Nal, D-2-Nal, D-Bal or D-Bip;

$A^8$ is Gly, D-Ala, Acc, Ala, β-Ala, Gaba, Apn, Ahx, Aha, HN—$(CH_2)_s$—C(O), or deleted;

$A^9$ is Cys, D-Cys, hCys, D-hCys, Pen, D-Pen, Dab, Dap, Orn, or Lys;

$A^{10}$ is Acc, HN—$(CH_2)_t$—C(O), L- or D-amino acid, or deleted;

$R^1$ is OH or $NH_2$;

each of $R^2$ and $R^3$ is, independently for each occurrence, selected from the group consisting of H, $(C_1\text{-}C_{30})$alkyl, $(C_1\text{-}C_{30})$heteroalkyl, $(C_1\text{-}C_{30})$acyl, $(C_2\text{-}C_{30})$alkenyl, $(C_2\text{-}C_{30})$ alkynyl, aryl$(C_1\text{-}C_{30})$alkyl, aryl$(C_1\text{-}C_{30})$acyl, substituted $(C_1\text{-}C_{30})$alkyl, substituted $(C_1\text{-}C_{30})$ heteroalkyl, substituted $(C_1\text{-}C_{30})$acyl, substituted $(C_2\text{-}C_{30})$alkenyl, substituted $(C_2\text{-}C_{30})$ alkynyl, substituted aryl$(C_1\text{-}C_{30})$alkyl, and substituted aryl$(C_1\text{-}C_{30})$acyl;

each of $R^4$ and $R^5$ is, independently for each occurrence, H, $(C_1\text{-}C_{40})$alkyl, $(C_1\text{-}C_{40})$ heteroalkyl, $(C_1\text{-}C_{40})$acyl, $(C_2\text{-}C_{40})$alkenyl, $(C_2\text{-}C_{40})$alkynyl, aryl$(C_1\text{-}C_{40})$alkyl, aryl$(C_1\text{-}C_{40})$ acyl, substituted $(C_1\text{-}C_{40})$alkyl, substituted $(C_1\text{-}C_{40})$ heteroalkyl, substituted $(C_1\text{-}C_{40})$ acyl, substituted $(C_2\text{-}C_{40})$ alkenyl, substituted ($C_2$-$C_{40}$)alkynyl, substituted aryl($C_1$-$C_{40}$) alkyl, substituted aryl($C_1$-$C_{40}$)acyl, ($C_1$-$C_{40}$) alkylsulfonyl, or —C(NH)—NH$_2$;

m is, independently for each occurrence, 1, 2, 3, 4, 5, 6 or 7;

n is, independently for each occurrence, 1, 2, 3, 4 or 5;

s is, independently for each occurrence, 1, 2, 3, 4, 5, 6, or 7;

t is, independently for each occurrence, 1, 2, 3, 4, 5, 6, or 7;

$X^1$, $X^2$, $X^3$, $X^4$, and $X^5$ each is, independently for each occurrence, H, F, Cl, Br, I, ($C_{1-10}$)alkyl, substituted ($C_{1-10}$) alkyl, ($C_{2-10}$)alkenyl, substituted ($C_{2-10}$)alkenyl, ($C_{2-10}$) alkynyl, substituted ($C_{2-10}$)alkynyl, aryl, substituted aryl, OH, NH$_2$, NO$_2$, or CN; provided that (I). when $R^4$ is ($C_1$-$C_{40}$)acyl, aryl($C_1$-$C_{40}$)acyl, substituted ($C_1$-$C_{40}$)acyl, substituted aryl($C_1$-$C_{40}$)acyl, ($C_1$-$C_{40}$) alkylsulfonyl, or —C(NH)—NH$_2$, then $R^5$ is H or ($C_1$-$C_{40}$) alkyl, ($C_1$-$C_{40}$)heteroalkyl, ($C_2$-$C_{40}$)alkenyl, ($C_2$-$C_{40}$) alkynyl, aryl($C_1$-$C_{40}$) alkyl, substituted ($C_1$-$C_{40}$)alkyl, substituted ($C_1$-$C_{40}$)heteroalkyl, substituted ($C_2$-$C_{40}$)alkenyl, substituted ($C_2$-$C_{40}$)alkynyl, or substituted aryl($C_1$-$C_{40}$) alkyl;

(II). when $R^2$ is ($C_1$-$C_{30}$)acyl, aryl($C_1$-$C_{30}$)acyl, substituted ($C_1$-$C_{30}$)acyl, or substituted aryl($C_1$-$C_{30}$)acyl, then $R^3$ is H, ($C_1$-$C_{30}$)alkyl, ($C_1$-$C_{30}$)heteroalkyl, ($C_2$-$C_{30}$)alkenyl, ($C_2$-$C_{30}$)alkynyl, aryl($C_1$-$C_{30}$)alkyl, substituted ($C_1$-$C_{30}$) alkyl, substituted ($C_1$-$C_{30}$)heteroalkyl, substituted ($C_2$-$C_{30}$) alkenyl, substituted ($C_2$-$C_{30}$) alkynyl, or substituted aryl($C_1$-$C_{30}$)alkyl;

(III). either $A^3$ or $A^8$ or both must be present in said compound;

(IV). when $A^2$ is Cys, D-Cys, hCys, D-hCys, Pen, or D-Pen, then $A^9$ is Cys, D-Cys, hCys, D-hCys, Pen, or D-Pen;

(V). when $A^2$ is Asp or Glu, then $A^9$ is Dab, Dap, Orn, or Lys;

(VI). when $A^8$ is Ala or Gly, then $A^1$ is not Nle; and (VII). when $A^1$ is deleted, then $R^2$ and $R^3$ cannot both be H; or pharmaceutically acceptable salts thereof.

In one aspect of the first embodiment, the invention provides a method to treat insulin resistance in a mammalian subject, with or without weight loss, by the administration of a therapeutically effective amount of a subgroup of melanocortin receptor ligands of the immediate foregoing Formula I, wherein:

$A^1$ is A6c, Arg, D-Arg, Cha, D-Cha, hCha, Chg, D-Chg, Gaba, Ile, Leu, hLeu, Met, β-hMet, 2-Nal, D-2-Nal, Nip, Nle, Oic, Phe, D-Phe, hPhe, hPro, Val, or deleted;

$A^2$ is Asp, Cys, D-Cys, hCys, D-hCys, Glu, Pen, or D-Pen;

$A^3$ is D-Abu, Aib, Ala, β-Ala, D-Ala, D-Cha, Gaba, D-Glu, Gly, D-Ile, D-Leu, D-Tle, D-Val, or deleted;

$A^4$ is His or 3-Pal;

$A^5$ is D-Bal, D-1-Nal, D-2-Nal, D-Phe, D-Trp, or D-(Et) Tyr;

$A^6$ is Arg, or hArg;

$A^7$ is Bal, Bip, 1-Nal, 2-Nal, Trp, D-Trp;

$A^8$ is A6c, D-Ala, Aha, Ahx, Ala, β-Ala, Apn, Gaba, Gly or deleted;

$A^9$ is Cys, D-Cys, hCys, D-hCys, Lys, Pen, or D-Pen;

$A^{10}$ is Thr, or deleted;

wherein at least one of $A^3$ or $A^8$ is deleted, but not both, or pharmaceutically acceptable salts thereof.

More preferred compounds of the immediately foregoing group of ligands according to Formula (I) useful to treat insulin resistance in a mammalian subject, with or without weight loss, are compounds of the formula:

SEQ ID NO: 1
Ac-Nle-c(Asp-His-D-Phe-Arg-Trp-β-Ala-Lys)-NH$_2$;

SEQ ID NO: 1
Ac-Nle-c(Asp-His-D-Phe-Arg-Trp-A6c-Lys)-NH$_2$;

SEQ ID NO: 2
Ac-Nle-c(Cys-His-D-Phe-Arg-Trp-Ahx-Cys)-NH$_2$;

SEQ ID NO: 3
D-Phe-c(Cys-His-D-Phe-Arg-Trp-Ala-D-Cys)-Thr-NH$_2$;

SEQ ID NO: 3
D-Phe-c(Cys-His-D-Phe-Arg-Trp-β-Ala-D-Cys)-Thr-NH$_2$;

SEQ ID NO: 3
D-Phe-c(Cys-His-D-Phe-Arg-Trp-Gaba-D-Cys)-Thr-NH$_2$;

SEQ ID NO: 2
Ac-Nle-c(Cys-His-D-Phe-Arg-Trp-Apn-Cys)-NH$_2$;

SEQ ID NO: 4
Ac-Nle-c(Asp-His-D-Phe-Arg-Trp-Apn-Lys)-NH$_2$;

SEQ ID NO: 5
Ac-A6c-c(Asp-His-D-Phe-Arg-Trp-Gaba-Lys)-NH$_2$;

SEQ ID NO: 6
Ac-D-2-Nal-c(Asp-His-D-Phe-Arg-Trp-Gaba-Lys)-NH$_2$;

SEQ ID NO: 6
Ac-Cha-c(Asp-His-D-Phe-Arg-Trp-Gaba-Lys)-NH$_2$;

SEQ ID NO: 6
Ac-Nle-c(Asp-His-D-Phe-Arg-Trp-Gaba-Lys)-NH$_2$;

SEQ ID NO: 7
Ac-Nle-c(Cys-D-Ala-His-D-Phe-Arg-Trp-Cys)-NH$_2$;

SEQ ID NO: 7
Ac-Nle-c(Cys-β-Ala-His-D-Phe-Arg-Trp-Cys)-NH$_2$;

SEQ ID NO: 7
Ac-Nle-c(Cys-Gaba-His-D-Phe-Arg-Trp-Cys)-NH$_2$;

SEQ ID NO: 7
Ac-Nle-c(Cys-Aib-His-D-Phe-Arg-Trp-Cys)-NH$_2$;

SEQ ID NO: 7
Ac-Nle-c(Cys-Gly-His-D-Phe-Arg-Trp-Cys)-NH$_2$;

SEQ ID NO: 8
Ac-Nle-c(D-Cys-Ala-His-D-Phe-Arg-Trp-Cys)-NH$_2$;

SEQ ID NO: 8
Ac-Nle-c(D-Cys-D-Ala-His-D-Phe-Arg-Trp-Cys)-NH$_2$;

SEQ ID NO: 8
Ac-Nle-c(D-Cys-β-Ala-His-D-Phe-Arg-Trp-Cys)-NH$_2$;

SEQ ID NO: 8
Ac-Nle-c(D-Cys-Gaba-His-D-Phe-Arg-Trp-Cys)-NH$_2$;

SEQ ID NO: 8
Ac-Nle-c(D-Cys-Aib-His-D-Phe-Arg-Trp-Cys)-NH$_2$;

SEQ ID NO: 8
Ac-Nle-c(D-Cys-Gly-His-D-Phe-Arg-Trp-Cys)-NH$_2$;

SEQ ID NO: 9
Ac-Nle-c(Cys-D-Ala-His-D-Phe-Arg-Trp-D-Cys)-NH$_2$;

SEQ ID NO: 9
Ac-Nle-c(Cys-β-Ala-His-D-Phe-Arg-Trp-D-Cys)-NH$_2$;

SEQ ID NO: 9
Ac-Nle-c(Cys-Gaba-His-D-Phe-Arg-Trp-D-Cys)-NH$_2$;

SEQ ID NO: 9
Ac-Nle-c(Cys-Aib-His-D-Phe-Arg-Trp-D-Cys)-NH$_2$;

SEQ ID NO: 9
Ac-Nle-c(Cys-Gly-His-D-Phe-Arg-Trp-D-Cys)-NH$_2$;

SEQ ID NO: 10
Ac-Nle-c(D-Cys-Ala-His-D-Phe-Arg-Trp-D-Cys)-NH$_2$;

SEQ ID NO: 10
Ac-Nle-c(D-Cys-D-Ala-His-D-Phe-Arg-Trp-D-Cys)-NH$_2$;

SEQ ID NO: 10
Ac-Nle-c(D-Cys-β-Ala-His-D-Phe-Arg-Trp-D-Cys)-NH$_2$;

SEQ ID NO: 10
Ac-Nle-c(D-Cys-Gaba-His-D-Phe-Arg-Trp-D-Cys)-NH$_2$;

SEQ ID NO: 10
Ac-Nle-c(D-Cys-Aib-His-D-Phe-Arg-Trp-D-Cys)-NH$_2$;

SEQ ID NO: 11
Ac-Oic-c(Asp-His-D-Phe-Arg-Trp-Gaba-Lys)-NH$_2$;

SEQ ID NO: 11
Ac-Chg-c(Asp-His-D-Phe-Arg-Trp-Gaba-Lys)-NH$_2$;

SEQ ID NO: 11
Ac-hCha-c(Asp-His-D-Phe-Arg-Trp-Gaba-Lys)-NH$_2$;

SEQ ID NO: 11
Ac-D-Cha-c(Asp-His-D-Phe-Arg-Trp-Gaba-Lys)-NH$_2$;

SEQ ID NO: 11
Ac-Nip-c(Asp-His-D-Phe-Arg-Trp-Gaba-Lys)-NH$_2$;

SEQ ID NO: 11
Ac-hPro-c(Asp-His-D-Phe-Arg-Trp-Gaba-Lys)-NH$_2$;

SEQ ID NO: 11
Ac-hLeu-c(Asp-His-D-Phe-Arg-Trp-Gaba-Lys)-NH$_2$;

SEQ ID NO: 11
Ac-hCha-c(Asp-His-D-Phe-Arg-Trp-Gaba-Lys)-NH$_2$;

SEQ ID NO: 11
Ac-Phe-c(Asp-His-D-Phe-Arg-Trp-Gaba-Lys)-NH$_2$;

SEQ ID NO: 11
Ac-D-Phe-c(Asp-His-D-Phe-Arg-Trp-Gaba-Lys)-NH$_2$;

SEQ ID NO: 11
Ac-D-Chg-c(Asp-His-D-Phe-Arg-Trp-Gaba-Lys)-NH$_2$;

SEQ ID NO: 12
n-butanoyl-Cha-c(Asp-His-D-Phe-Arg-Trp-Gaba-Lys)-NH$_2$;

SEQ ID NO: 11
Ac-hPhe-c(Asp-His-D-Phe-Arg-Trp-Gaba-Lys)-NH$_2$;

SEQ ID NO: 11
Ac-β-hMet-c(Asp-His-D-Phe-Arg-Trp-Gaba-Lys)-NH$_2$;

SEQ ID NO: 11
Ac-Gaba-c(Asp-His-D-Phe-Arg-Trp-Gaba-Lys)-NH$_2$;

SEQ ID NO: 13
Ac-Cha-c(Asp-His-D-Phe-Arg-D-Trp-Ala-Lys)-NH$_2$;

SEQ ID NO: 13
Ac-hCha-c(Asp-His-D-Phe-Arg-D-Trp-Ala-Lys)-NH$_2$;

SEQ ID NO: 13
Ac-Leu-c(Asp-His-D-Phe-Arg-D-Trp-Ala-Lys)-NH$_2$;

SEQ ID NO: 13
Ac-hLeu-c(Asp-His-D-Phe-Arg-D-Trp-Ala-Lys)-NH$_2$;

SEQ ID NO: 13
Ac-Phe-c(Asp-His-D-Phe-Arg-D-Trp-Ala-Lys)-NH$_2$;

SEQ ID NO: 14
Ac-Nle-c(Asp-His-D-Phe-Arg-D-Trp-D-Ala-Lys)-NH$_2$;

SEQ ID NO: 14
Ac-Nle-c(Asp-His-D-Phe-Arg-D-Trp-β-Ala-Lys)-NH$_2$;

SEQ ID NO: 14
Ac-Nle-c(Asp-His-D-Phe-Arg-D-Trp-Gaba-Lys)-NH$_2$;

SEQ ID NO: 14
Ac-Nle-c(Asp-His-D-Phe-Arg-D-Trp-Aha-Lys)-NH$_2$;

SEQ ID NO: 14
Ac-Nle-c(Asp-His-D-Phe-Arg-D-Trp-Apn-Lys)-NH$_2$;

SEQ ID NO: 15
Ac-Nle-c(Cys-His-D-Phe-Arg-D-Trp-Apn-Cys)-NH$_2$;

SEQ ID NO: 15
Ac-Nle-c(Cys-His-D-Phe-Arg-D-Trp-Gaba-Cys)-NH$_2$;

SEQ ID NO: 15
Ac-Nle-c(Cys-His-D-Phe-Arg-D-Trp-Ahx-Cys)-NH$_2$;

SEQ ID NO: 15
Ac-Nle-c(Cys-His-D-Phe-Arg-D-Trp-β-Ala-Cys)-NH$_2$;

SEQ ID NO: 15
Ac-Nle-c(Cys-His-D-Phe-Arg-D-Trp-D-Ala-Cys)-NH$_2$;

SEQ ID NO: 16
Ac-Nle-c(Cys-D-Ala-His-D-2-Nal-Arg-Trp-Cys)-NH$_2$;

SEQ ID NO: 16
Ac-Nle-c(Cys-D-Ala-His-D-2-Nal-Arg-2-Nal-Cys)-NH$_2$;

SEQ ID NO: 16
Ac-Nle-c(Cys-D-Ala-His-D-2-Nal-Arg-1-Nal-Cys)-NH$_2$;

SEQ ID NO: 17
n-butanoyl-Nle-c(Cys-D-Ala-His-D-Phe-Arg-2-Nal-Cys)-NH$_2$;

SEQ ID NO: 17
n-butanoyl-Nle-c(Cys-D-Ala-His-D-Phe-Arg-Trp-Cys)-NH$_2$;

SEQ ID NO: 18
Ac-Nle-c(Cys-D-Ala-His-D-Phe-Arg-2-Nal-Cys)-NH$_2$;

SEQ ID NO: 18
Ac-Nle-c(Cys-D-Ala-His-D-Phe-Arg-1-Nal-Cys)-NH$_2$;

SEQ ID NO: 18
Ac-Nle-c(Cys-D-Ala-His-D-Phe-Arg-Bal-Cys)-NH$_2$;

SEQ ID NO: 61
Ac-Nle-c(Cys-D-Glu-His-D-Phe-Arg-Trp-Cys)-NH$_2$;

SEQ ID NO: 19
Ac-Nle-c(Asp-His-D-Phe-Arg-Trp-D-Ala-Lys)-NH$_2$;

SEQ ID NO: 20
Ac-Nle-c(Cys-D-Ala-His-D-2-Nal-Arg-Bal-Cys)-NH$_2$;

SEQ ID NO: 21
Ac-Nle-c(Pen-D-Ala-His-D-Phe-Arg-Trp-Cys)-NH$_2$;

SEQ ID NO: 22
Ac-Nle-c(Cys-D-Ala-His-D-Phe-Arg-Trp-Pen)-NH$_2$;

SEQ ID NO: 22
Ac-Nle-c(Pen-D-Ala-His-D-Phe-Arg-Trp-Pen)-NH$_2$;

SEQ ID NO: 23
D-Phe-c(Cys-His-D-Phe-hArg-Trp-β-Ala-D-Cys)-Thr-NH₂;

SEQ ID NO: 24
D-Phe-c(Cys-His-D-(Et)Tyr-Arg-Trp-β-Ala-D-Cys)-Thr-NH₂;

SEQ ID NO: 25
D-Phe-c(Cys-His-D-Phe-Arg-Bip-β-Ala-D-Cys)-Thr-NH₂;

SEQ ID NO: 24
D-Phe-c(Cys-His-D-(Et)Tyr-hArg-Trp-β-Ala-D-Cys)-Thr-NH₂;

SEQ ID NO: 26
D-Phe-c(Cys-His-D-Phe-hArg-Bip-β-Ala-D-Cys)-Thr-NH₂;

SEQ ID NO: 26
D-Phe-c(Cys-His-D-(Et)Tyr-hArg-Bip-β-Ala-D-Cys)-Thr-NH₂;

SEQ ID NO: 27
Nle-c(Cys-His-D-Phe-Arg-Trp-Apn-Cys)-NH₂;

SEQ ID NO: 28
Ac-Nle-c(Asp-D-Ala-His-D-Phe-Arg-Trp-Lys)-NH₂;

SEQ ID NO: 28
Ac-Nle-c(Asp-D-Ala-His-D-Phe-Arg-Bal-Lys)-NH₂;

SEQ ID NO: 29
Ac-Nle-c(Cys-D-Ala-His-D-Phe-Arg-Trp-Pen)-OH;

SEQ ID NO: 30
Ac-Nle-c(Cys-D-Abu-His-D-Phe-Arg-Trp-Cys)-NH₂;

SEQ ID NO: 30
Ac-Nle-c(Cys-D-Val-His-D-Phe-Arg-Trp-Cys)-NH₂;

SEQ ID NO: 30
Ac-Nle-c(Cys-D-Ile-His-D-Phe-Arg-Trp-Cys)-NH₂;

SEQ ID NO: 30
Ac-Nle-c(Cys-D-Leu-His-D-Phe-Arg-Trp-Cys)-NH₂;

SEQ ID NO: 30
Ac-Nle-c(Cys-D-Tle-His-D-Phe-Arg-Trp-Cys)-NH₂;

SEQ ID NO: 30
Ac-Nle-c(Cys-D-Cha-His-D-Phe-Arg-Trp-Cys)-NH₂;

SEQ ID NO: 31
Ac-Nle-c(Pen-His-D-Phe-Arg-Trp-Gaba-Cys)-NH₂;

SEQ ID NO: 32
Ac-Nle-c(Cys-His-D-Phe-Arg-Trp-Gaba-Pen)-NH₂;

SEQ ID NO: 32
Ac-Nle-c(Pen-His-D-Phe-Arg-Trp-Gaba-Pen)-NH₂;

SEQ ID NO: 33
Ac-Leu-c(Cys-His-D-Phe-Arg-Trp-Gaba-Cys)-NH₂;

SEQ ID NO: 33
Ac-Cha-c(Cys-His-D-Phe-Arg-Trp-Gaba-Cys)-NH₂;

SEQ ID NO: 33
Ac-Ile-c(Cys-His-D-Phe-Arg-Trp-Gaba-Cys)-NH₂;

SEQ ID NO: 33
Ac-Phe-c(Cys-His-D-Phe-Arg-Trp-Gaba-Cys)-NH₂;

SEQ ID NO: 33
Ac-Val-c(Cys-His-D-Phe-Arg-Trp-Gaba-Cys)-NH₂;

SEQ ID NO: 33
Ac-2-Nal-c(Cys-His-D-Phe-Arg-Trp-Gaba-Cys)-NH₂;

SEQ ID NO: 34
Nle-c(Cys-His-D-Phe-Arg-Trp-Gaba-Cys)-NH₂;

SEQ ID NO: 34
Phe-c(Cys-His-D-Phe-Arg-Trp-Gaba-Cys)-NH₂;

SEQ ID NO: 35
Ac-Nle-c(Cys-3-Pal-D-Phe-Arg-Trp-Gaba-Cys)-NH₂;

SEQ ID NO: 36
Ac-Nle-c(Cys-D-Ala-His-D-Phe-Arg-Trp-Cys)-OH;

SEQ ID NO: 37
Ac-Nle-c(Cys-His-Phe-Arg-D-Trp-Gaba-Cys)-NH₂;

SEQ ID NO: 38
Ac-Nle-c(Asp-His-D-2-Nal-Arg-Trp-Ala-Lys)-NH₂;

SEQ ID NO: 38
Ac-Nle-c(Asp-His-D-2-Nal-Arg-Trp-β-Ala-Lys)-NH₂;

SEQ ID NO: 39
Ac-Nle-c(Cys-His-D-2-Nal-Arg-Trp-Gaba-Cys)-NH₂;

SEQ ID NO: 39
Ac-Nle-c(Cys-His-D-2-Nal-Arg-Trp-Ahx-Cys)-NH₂;

SEQ ID NO: 40
Ac-hPhe-c(Asp-His-D-2-Nal-Arg-Trp-Gaba-Lys)-NH₂;

SEQ ID NO: 40
Ac-Cha-c(Asp-His-D-2-Nal-Arg-Trp-Gaba-Lys)-NH₂;

SEQ ID NO: 41
Ac-Nle-c(Asp-His-D-Phe-Arg-Trp-β-Ala-Lys)-OH;

SEQ ID NO: 42
Ac-Nle-c(Cys-His-D-Phe-Arg-Trp-Ahx-Cys)-OH;

SEQ ID NO: 43
D-Phe-c(Cys-His-D-Phe-Arg-Trp-Ala-D-Cys)-Thr-OH;

SEQ ID NO: 43
D-Phe-c(Cys-His-D-Phe-Arg-Trp-β-Ala-D-Cys)-Thr-OH;

SEQ ID NO: 43
D-Phe-c(Cys-His-D-Phe-Arg-Trp-Gaba-D-Cys)-Thr-OH;

SEQ ID NO: 42
Ac-Nle-c(Cys-His-D-Phe-Arg-Trp-Apn-Cys)-OH;

SEQ ID NO: 41
Ac-Nle-c(Asp-His-D-Phe-Arg-Trp-Apn-Lys)-OH;

SEQ ID NO: 44
Ac-Cha-c(Asp-His-D-Phe-Arg-Trp-Gaba-Lys)-OH;

SEQ ID NO: 44
Ac-Nle-c(Asp-His-D-Phe-Arg-Trp-Gaba-Lys)-OH;

SEQ ID NO: 29
Ac-Nle-c(Cys-D-Ala-His-D-Phe-Arg-Trp-Cys)-OH;

SEQ ID NO: 44
Ac-Chg-c(Asp-His-D-Phe-Arg-Trp-Gaba-Lys)-OH;

SEQ ID NO: 44
Ac-D-Cha-c(Asp-His-D-Phe-Arg-Trp-Gaba-Lys)-OH;

SEQ ID NO: 44
Ac-hCha-c(Asp-His-D-Phe-Arg-Trp-Gaba-Lys)-OH;

SEQ ID NO: 44
Ac-D-Chg-c(Asp-His-D-Phe-Arg-Trp-Gaba-Lys)-OH;

-continued

```
                                                SEQ ID NO: 44
Ac-hPhe-c(Asp-His-D-Phe-Arg-Trp-Gaba-Lys)-OH;

SEQ ID NO: 45
Ac-Nle-c(Cys-His-D-Phe-Arg-D-Trp-Gaba-Cys)-OH;

SEQ ID NO: 45
Ac-Nle-c(Cys-His-D-Phe-Arg-D-Trp-Ahx-Cys)-OH;

SEQ ID NO: 45
Ac-Nle-c(Cys-His-D-Phe-Arg-D-Trp-β-Ala-Cys)-OH;

SEQ ID NO: 45
Ac-Nle-c(Cys-His-D-Phe-Arg-D-Trp-D-Ala-Cys)-OH;

SEQ ID NO: 46
Ac-Nle-c(Cys-D-Ala-His-D-2-Nal-Arg-Trp-Cys)-OH;

SEQ ID NO: 46
Ac-Nle-c(Cys-D-Ala-His-D-2-Nal-Arg-2-Nal-Cys)-OH;

SEQ ID NO: 46
Ac-Nle-c(Cys-D-Ala-His-D-2-Nal-Arg-1-Nal-Cys)-OH;

SEQ ID NO: 46
Ac-Nle-c(Cys-D-Ala-His-D-2-Nal-Arg-Bal-Cys)-OH;

SEQ ID NO: 47
Ac-Nle-c(Pen-D-Ala-His-D-Phe-Arg-Trp-Cys)-OH;

SEQ ID NO: 29
Ac-Nle-c(Cys-D-Ala-His-D-Phe-Arg-Trp-Pen)-OH;

SEQ ID NO: 48
Ac-Nle-c(Cys-His-D-Phe-Arg-Trp-Gaba-Pen)-OH;

SEQ ID NO: 49
Ac-Arg-c(Cys-D-Ala-His-D-2-Nal-Arg-Trp-Cys)-NH2;

SEQ ID NO: 50
Ac-Arg-c(Cys-D-Ala-His-D-Phe-Arg-Trp-Cys)-NH2;

SEQ ID NO: 50
Ac-D-Arg-c(Cys-D-Ala-His-D-Phe-Arg-Trp-Cys)-NH2;

SEQ ID NO: 51
Ac-D-Arg-c(Cys-D-Ala-His-D-Phe-Arg-Trp-Pen)-NH2;

SEQ ID NO: 52
Ac-D-Arg-c(Cys-His-D-Phe-Arg-Trp-Gaba-Pen)-NH2;

SEQ ID NO: 52
Ac-Arg-c(Cys-His-D-Phe-Arg-Trp-Gaba-Pen)-NH2;

SEQ ID NO: 51
Ac-Arg-c(Cys-D-Ala-His-D-Phe-Arg-Trp-Pen)-NH2;

SEQ ID NO: 53
Ac-D-Arg-c(Asp-His-D-Phe-Arg-Trp-Ala-Lys)-NH2;

SEQ ID NO: 53
Ac-Arg-c(Asp-His-D-Phe-Arg-Trp-Ala-Lys)-NH2;

SEQ ID NO: 7
Ac-Nle-c(Cys-D-Ala-His-D-Phe-Arg-Trp-Cys)-NH2;

SEQ ID NO: 24
D-Phe-c(Cys-His-D-(Et)Tyr-Arg-Trp-β-Ala-D-Cys)-

Thr-NH2;

SEQ ID NO: 27
Nle-c(Cys-His-D-Phe-Arg-Trp-Apn-Cys)-NH2;

SEQ ID NO: 32
Ac-Nle-c(Cys-His-D-Phe-Arg-Trp-Gaba-Pen)-NH2;

SEQ ID NO: 34
Nle-c(Cys-His-D-Phe-Arg-Trp-Gaba-Cys)-NH2;

SEQ ID NO: 1
Ac-Nle-c(Asp-His-D-Phe-Arg-Trp-β-Ala-Lys)-NH2;

SEQ ID NO: 2
Ac-Nle-c(Cys-His-D-Phe-Arg-Trp-Ahx-Cys)-NH2;

SEQ ID NO: 3
D-Phe-c(Cys-His-D-Phe-Arg-Trp-β-Ala-D-Cys)-Thr-

NH2;

SEQ ID NO: 3
D-Phe-c(Cys-His-D-Phe-Arg-Trp-Gaba-D-Cys)-Thr-NH2;

SEQ ID NO: 2
Ac-Nle-c(Cys-His-D-Phe-Arg-Trp-Apn-Cys)-NH2;

SEQ ID NO: 4
Ac-Nle-c(Asp-His-D-Phe-Arg-Trp-Apn-Lys)-NH2;

SEQ ID NO: 6
Ac-Cha-c(Asp-His-D-Phe-Arg-Trp-Gaba-Lys)-NH2;

SEQ ID NO: 6
Ac-Nle-c(Asp-His-D-Phe-Arg-Trp-Gaba-Lys)-NH2;

SEQ ID NO: 11
Ac-Chg-c(Asp-His-D-Phe-Arg-Trp-Gaba-Lys)-NH2;

SEQ ID NO: 11
Ac-hCha-c(Asp-His-D-Phe-Arg-Trp-Gaba-Lys)-NH2;

SEQ ID NO: 11
Ac-D-Chg-c(Asp-His-D-Phe-Arg-Trp-Gaba-Lys)-NH2;

SEQ ID NO: 11
Ac-hPhe-c(Asp-His-D-Phe-Arg-Trp-Gaba-Lys)-NH2;

SEQ ID NO: 15
Ac-Nle-c(Cys-His-D-Phe-Arg-D-Trp-β-Ala-Cys)-NH2;

SEQ ID NO: 21
Ac-Nle-c(Pen-D-Ala-His-D-Phe-Arg-Trp-Cys)-NH2;

SEQ ID NO: 22
Ac-Nle-c(Cys-D-Ala-His-D-Phe-Arg-Trp-Pen)-NH2;

SEQ ID NO: 23
D-Phe-c(Cys-His-D-Phe-hArg-Trp-β-Ala-D-Cys)-

Thr-NH2;

SEQ ID NO: 25
D-Phe-c(Cys-His-D-Phe-Arg-Bip-β-Ala-D-Cys)-

Thr-NH2;

SEQ ID NO: 24
D-Phe-c(Cys-His-D-(Et)Tyr-hArg-Trp-β-Ala-D-Cys)-

Thr-NH2;

SEQ ID NO: 26
D-Phe-c(Cys-His-D-Phe-hArg-Bip-β-Ala-D-Cys)-Thr-

NH2;

SEQ ID NO: 26
D-Phe-c(Cys-His-D-(Et)Tyr-hArg-Bip-β-Ala-D-Cys)-

Thr-NH2;

SEQ ID NO: 28
Ac-Nle-c(Asp-D-Ala-His-D-Phe-Arg-Trp-Lys)-NH2;

SEQ ID NO: 28
Ac-Nle-c(Asp-D-Ala-His-D-Phe-Arg-Bal-Lys)-NH2;

SEQ ID NO: 29
Ac-Nle-c(Cys-D-Ala-His-D-Phe-Arg-Trp-Pen)-OH;
```

-continued

Ac-Nle-c(Cys-D-Abu-His-D-Phe-Arg-Trp-Cys)-NH$_2$;  SEQ ID NO: 30

Ac-Nle-c(Cys-D-Val-His-D-Phe-Arg-Trp-Cys)-NH$_2$;  SEQ ID NO: 30

Ac-Nle-c(Cys-D-Ile-His-D-Phe-Arg-Trp-Cys)-NH$_2$;  SEQ ID NO: 30

Ac-Nle-c(Cys-D-Leu-His-D-Phe-Arg-Trp-Cys)-NH$_2$;  SEQ ID NO: 30

Ac-Nle-c(Cys-D-Tle-His-D-Phe-Arg-Trp-Cys)-NH$_2$;  SEQ ID NO: 30

Ac-Nle-c(Cys-D-Cha-His-D-Phe-Arg-Trp-Cys)-NH$_2$;  SEQ ID NO: 30

Ac-Nle-c(Pen-His-D-Phe-Arg-Trp-Gaba-Cys)-NH$_2$;  SEQ ID NO: 31

Ac-Nle-c(Pen-His-D-Phe-Arg-Trp-Gaba-Pen)-NH$_2$;  SEQ ID NO: 32

Ac-Leu-c(Cys-His-D-Phe-Arg-Trp-Gaba-Cys)-NH$_2$;  SEQ ID NO: 33

Ac-Cha-c(Cys-His-D-Phe-Arg-Trp-Gaba-Cys)-NH$_2$;  SEQ ID NO: 33

Ac-Ile-c(Cys-His-D-Phe-Arg-Trp-Gaba-Cys)-NH$_2$;  SEQ ID NO: 33

Ac-Phe-c(Cys-His-D-Phe-Arg-Trp-Gaba-Cys)-NH$_2$;  SEQ ID NO: 33

Ac-Val-c(Cys-His-D-Phe-Arg-Trp-Gaba-Cys)-NH$_2$;  SEQ ID NO: 33

Ac-2-Nal-c(Cys-His-D-Phe-Arg-Trp-Gaba-Cys)-NH$_2$;  SEQ ID NO: 33

Phe-c(Cys-His-D-Phe-Arg-Trp-Gaba-Cys)-NH$_2$;  SEQ ID NO: 34

Ac-Nle-c(Cys-3-Pal-D-Phe-Arg-Trp-Gaba-Cys)-NH$_2$;  SEQ ID NO: 35

Ac-Nle-c(Cys-D-Ala-His-D-Phe-Arg-Trp-Cys)-OH;  SEQ ID NO: 36

Ac-Nle-c(Cys-His-Phe-Arg-D-Trp-Gaba-Cys)-NH$_2$;  SEQ ID NO: 37

Ac-Nle-c(Cys-D-Ala-His-D-2-Nal-Arg-Trp-Cys)-NH$_2$;  SEQ ID NO: 16

Ac-Nle-c(Cys-D-Ala-His-D-2-Nal-Arg-2-Nal-Cys)-NH$_2$;  SEQ ID NO: 16

Ac-Nle-c(Cys-D-Ala-His-D-2-Nal-Arg-Bal-Cys)-NH$_2$;  SEQ ID NO: 20

Ac-Nle-c(Asp-His-D-2-Nal-Arg-Trp-Ala-Lys)-NH$_2$;  SEQ ID NO: 38

Ac-Nle-c(Asp-His-D-2-Nal-Arg-Trp-β-Ala-Lys)-NH$_2$;  SEQ ID NO: 38

Ac-Nle-c(Cys-His-D-2-Nal-Arg-Trp-Gaba-Cys)-NH$_2$;  SEQ ID NO: 39

Ac-Nle-c(Cys-His-D-2-Nal-Arg-Trp-Ahx-Cys)-NH$_2$;  SEQ ID NO: 39

Ac-hPhe-c(Asp-His-D-2-Nal-Arg-Trp-Gaba-Lys)-NH$_2$;  SEQ ID NO: 40

Ac-Cha-c(Asp-His-D-2-Nal-Arg-Trp-Gaba-Lys)-NH$_2$;  SEQ ID NO: 40 or

Ac-Arg-c(Cys-D-Ala-His-D-2-Nal-Arg-Trp-Cys)-NH$_2$;  SEQ ID NO: 49 or pharmaceutically acceptable salts thereof.

In the second embodiment, the invention provides a method to treat insulin resistance in a mammalian subject, with or without weight loss, by the administration of a therapeutically effective amount of a melanocortin receptor ligand according to Formula (II) and pharmaceutically acceptable salts, hydrates, solvates or prodrugs thereof (see International Patent Application Publication Number WO 2007/008704 incorporated herein by reference in its entirety):

$$(R^2R^3)\text{-}A^1\text{-}c(A^2\text{-}A^3\text{-}A^4\text{-}A^5\text{-}A^6\text{-}A^7\text{-}A^8\text{-}A^9)\text{-}NH_2 \quad (II)$$

wherein:

$A^1$ is Nle or deleted;
$A^2$ is Cys or Asp;
$A^3$ is Glu or D-Ala;
$A^4$ is His;
$A^5$ is D-Phe;
$A^6$ is Arg;
$A^7$ is Trp, 2-Nal or Bal;
$A^8$ is Gly, Ala, D-Ala, β-Ala, Gaba or Apn;
$A^9$ is Cys or Lys;
each of $R^2$ and $R^3$ is independently selected from the group consisting of H or $(C_1\text{-}C_6)$acyl;
provided that
(I). when $R^2$ is $(C_1\text{-}C_6)$acyl, then $R^3$ is H; and
(II). when $A^2$ is Cys, then $A^9$ is Cys, or a pharmaceutically acceptable salt thereof.

More preferred of the immediately foregoing group of compounds which are useful to treat insulin resistance in a mammalian subject, with or without weight loss, are compounds of the formula:

Ac-Nle-c(Cys-D-Ala-His-D-Phe-Arg-Trp-Gly-Cys)-NH$_2$;  SEQ ID NO: 54

Ac-Nle-c(Cys-D-Ala-His-D-Phe-Arg-Trp-D-Ala-Cys)-NH$_2$;  SEQ ID NO: 54

Ac-Nle-c(Cys-D-Ala-His-D-Phe-Arg-Trp-β-Ala-Cys)-NH$_2$;  SEQ ID NO: 54

Ac-Nle-c(Cys-D-Ala-His-D-Phe-Arg-Trp-Gaba-Cys)-NH$_2$;  SEQ ID NO: 54

Ac-Nle-c(Cys-D-Ala-His-D-Phe-Arg-Trp-Apn-Cys)-NH$_2$;  SEQ ID NO: 54

Ac-c(Cys-Glu-His-D-Phe-Arg-Trp-Ala-Cys)-NH$_2$;  SEQ ID NO: 55

Ac-c(Cys-Glu-His-D-Phe-Arg-2-Nal-Ala-Cys)-NH$_2$;  SEQ ID NO: 55

Ac-c(Cys-D-Ala-His-D-Phe-Arg-Trp-Ala-Cys)-NH$_2$;  SEQ ID NO: 56

-continued

Ac-c(Cys-D-Ala-His-D-Phe-Arg-2-Nal-Ala-Cys)-NH₂;  (SEQ ID NO: 56)

Ac-Nle-c(Cys-D-Ala-His-D-Phe-Arg-Trp-Ala-Cys)-NH₂;  (SEQ ID NO: 57)

Ac-Nle-c(Cys-D-Ala-His-D-Phe-Arg-Trp-β-Ala-Cys)-NH₂;  (SEQ ID NO: 57)

Ac-Nle-c(Cys-D-Ala-His-D-Phe-Arg-Trp-Gaba-Cys)-NH₂;  (SEQ ID NO: 57)

or

Ac-Nle-c(Asp-D-Ala-His-D-Phe-Arg-Bal-Ala-Lys)-NH₂;  (SEQ ID NO: 58)

or a pharmaceutically acceptable salt thereof.

In the third embodiment, the invention provides a method to treat insulin resistance in a mammalian subject, with or without weight loss, by the administration of a therapeutically effective amount of a melanocortin receptor compound according to Formula (III), and pharmaceutically acceptable salts, hydrates, solvates or prodrugs thereof (see International Application Publication Number WO 2007/008684, incorporated herein by reference in its entirety):

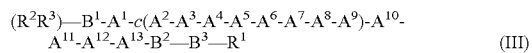

$$(R^2R^3)\text{—}B^1\text{-}A^1\text{-}c(A^2\text{-}A^3\text{-}A^4\text{-}A^5\text{-}A^6\text{-}A^7\text{-}A^8\text{-}A^9)\text{-}A^{10}\text{-}A^{11}\text{-}A^{12}\text{-}A^{13}\text{-}B^2\text{—}B^3\text{—}R^1 \quad (III)$$

wherein:

$B^1$ is a peptide moiety which contains 5, 6, 7, 8, 9, 10, 11, 12, 13, 14, or 15 amino acids, wherein at least 5 amino acids are independently selected from the group consisting of L-Arg, D-Arg, L-hArg and D-hArg, or $B^1$ is optionally deleted;

$A^1$ is Acc, HN—(CH₂)$_m$—C(O), L- or D-amino acid or deleted;

$A^2$ is Cys, D-Cys, hCys, D-hCys, Pen, D-Pen, Asp or Glu;

$A^3$ is Gly, Glu, Ala, β-Ala, Gaba, Aib, D-amino acid or deleted;

$A^4$ is His, 2-Pal, 3-Pal, Taz, 2-Thi, 3-Thi or (X¹,X²,X³,X⁴,X⁵)Phe;

$A^5$ is D-Phe, D-1-Nal, D-2-Nal, D-Trp, D-Bal, D-(X¹,X²,X³,X⁴,X⁵)Phe, D-(Et)Tyr, D-Dip, D-Bip or D-Bpa;

$A^6$ is Arg, hArg, Dab, Dap, Lys, Orn or HN—CH((CH₂)$_n$—N(R⁴R⁵))—C(O);

$A^7$ is Trp, 1-Nal, 2-Nal, Bal, Bip, Dip, Bpa, D-Trp, D-1-Nal, D-2-Nal, D-Bal, D-Bip, D-Dip or D-Bpa;

$A^8$ is Gly, D-Ala, Acc, Ala, β-Ala, Gaba, Apn, Ahx, Aha, HN—(CH₂)$_s$—C(O) or deleted;

$A^9$ is Cys, D-Cys, hCys, D-hCys, Pen, D-Pen, Dab, Dap, Orn or Lys;

$A^{10}$ is Acc, HN—(CH₂)$_t$—C(O), Pro, hPro, 3-Hyp, 4-Hyp, Thr, an L- or D-amino acid or deleted;

$A^{11}$ is Pro, hPro, 3-Hyp, 4-Hyp or deleted;

$A^{12}$ is Lys, Dab, Dap, Arg, hArg or deleted;

$A^{13}$ is Asp, Glu or deleted;

$B^2$ is a peptide moiety containing 1, 2, 3, 4, or 5 amino acids or deleted, $B^3$ is a peptide moiety which contains 5, 6, 7, 8, 9, 10, 11, 12, 13, 14 or 15 amino acids wherein at least 5 amino acids are independently selected from the group consisting of L-Arg, D-Arg, L-hArg and D-hArg, or is deleted;

$R^1$ is OH or NH₂;

$R^2$ and $R^3$ each is, independently for each occurrence, selected from the group consisting of H, (C₁-C₃₀)alkyl, (C₁-C₃₀)heteroalkyl, (C₁-C₃₀)acyl, (C₂-C₃₀)alkenyl, (C₂-C₃₀)alkynyl, aryl(C₁-C₃₀)alkyl, aryl(C₁-C₃₀)acyl, substituted (C₁-C₃₀)alkyl, substituted (C₁-C₃₀)heteroalkyl, substituted (C₁-C₃₀)acyl, substituted (C₂-C₃₀)alkenyl, substituted (C₂-C₃₀)alkynyl, substituted aryl(C₁-C₃₀)alkyl and substituted aryl(C₁-C₃₀)acyl;

$R^4$ and $R^5$ each is, independently for each occurrence, H, (C₁-C₄₀)alkyl, (C₁-C₄₀)heteroalkyl, (C₁-C₄₀)acyl, (C₂-C₄₀)alkenyl, (C₂-C₄₀)alkynyl, aryl(C₁-C₄₀)alkyl, aryl(C₁-C₄₀)acyl, substituted (C₁-C₄₀)alkyl, substituted (C₁-C₄₀)heteroalkyl, substituted (C₁-C₄₀)acyl, substituted (C₂-C₄₀)alkenyl, substituted (C₂-C₄₀)alkynyl, substituted aryl(C₁-C₄₀)alkyl, substituted aryl(C₁-C₄₀)acyl, (C₁-C₄₀)alkylsulfonyl or C(NH)—NH₂;

n is, independently for each occurrence, 1, 2, 3, 4 or 5;

m is, independently for each occurrence, 1, 2, 3, 4, 5, 6 or 7;

s is, independently for each occurrence, 1, 2, 3, 4, 5, 6 or 7;

t is, independently for each occurrence, 1, 2, 3, 4, 5, 6 or 7;

X¹, X², X³, X⁴ and X⁵ each is, independently for each occurrence, H, F, Cl, Br, I, (C₁₋₁₀)alkyl, substituted (C₁₋₁₀)alkyl, (C₂₋₁₀)alkenyl, substituted (C₂₋₁₀)alkenyl, (C₂₋₁₀)alkynyl, substituted (C₂₋₁₀)alkynyl, aryl, substituted aryl, OH, NH₂, NO₂ or CN; provided that:

(I) when R⁴ is (C₁-C₄₀)acyl, aryl(C₁-C₄₀)acyl, substituted (C₁-C₄₀)acyl, substituted aryl(C₁-C₄₀)acyl, (C₁-C₄₀)alkylsulfonyl or C(NH)—NH₂, then R⁵ is H, (C₁-C₄₀)alkyl, (C₁-C₄₀)heteroalkyl, (C₂-C₄₀)alkenyl, (C₂-C₄₀)alkynyl, aryl(C₁-C₄₀)alkyl, substituted (C₁-C₄₀)alkyl, substituted (C₁-C₄₀)heteroalkyl, substituted (C₂-C₄₀)alkenyl, substituted (C₂-C₄₀)alkynyl or substituted aryl(C₁-C₄₀)alkyl;

(II) when R² is (C₁-C₃₀)acyl, aryl(C₁-C₃₀)acyl, substituted (C₁-C₃₀)acyl or substituted aryl(C₁-C₃₀)acyl, then R³ is H, (C₁-C₃₀)alkyl, (C₁-C₃₀)heteroalkyl, (C₂-C₃₀)alkenyl, (C₂-C₃₀)alkynyl, aryl(C₁-C₃₀)alkyl, substituted (C₁-C₃₀)alkyl, substituted (C₁-C₃₀)heteroalkyl, substituted (C₂-C₃₀)alkenyl, substituted (C₂-C₃₀)alkynyl or substituted aryl(C₁-C₃₀)alkyl;

(III) neither $B^1$ nor $B^2$ contains one or more of the following amino acid sequences: Arg-(Lys)₂-(Arg)₂-Gln-(Arg)₃ (SEQ ID NO:294), Tyr-Ala-Arg-Lys-Ala-(Arg)₂-Gln-Ala-(Arg)₂ (SEQ ID NO:295), Tyr-Ala-Arg-(Ala)₂-(Arg)₂-(Ala)₂-(Arg)₂ (SEQ ID NO:296), Tyr-Ala-(Arg)₉ (SEQ ID NO:297), Tyr-(Ala)₃-(Arg)₇ (SEQ ID NO:298), Tyr-Ala-Arg-Ala-Pro-(Arg)₂-Ala-(Arg)₃ (SEQ ID NO:299) or Tyr-Ala-Arg-Ala-Pro-(Arg)₂-Pro-(Arg)₂ (SEQ ID NO:300);

(IV) either $B^1$ or $B^2$ or both must be present in said compound;

(V) when $A^2$ is Cys, D-Cys, hCys, D-hCys, Pen or D-Pen, then $A^9$ is Cys, D-Cys, hCys, D-hCys, Pen or D-Pen; and (VI) when $A^2$ is Asp or Glu, then $A^9$ is Dab, Dap, Orn or Lys; or pharmaceutically acceptable salts thereof.

In one aspect of the third embodiment, the invention is directed to the use of compounds of Formula (III) to treat insulin resistance in a mammalian subject, with or without weight loss, wherein $B^1$ is Arg-Lys-Gln-Lys-(Arg)₅ (SEQ ID NO:301), Arg-(Lys)₂-Arg-Gln-(Arg)₄ (SEQ ID NO:302), Arg-(Lys)₂-(Arg)₃-Gln-(Arg)₂ (SEQ ID NO:303), Arg-(Lys)₂-(Arg)₄-Gln-Arg (SEQ ID NO:304), Arg-(Lys)₂-(Arg)₅-Gln (SEQ ID NO:305), Arg-(Lys)₂-Gln-(Arg)₅ (SEQ ID NO:306), Arg-Gln-(Lys)₂-(Arg)₅ (SEQ ID NO:307), Arg-Gln-(Arg)₇ (SEQ ID NO:308), Arg-Gln-(Arg)₅ (SEQ ID NO:309), (Arg)₂-Gln-(Arg)₆ (SEQ ID NO:310), (Arg)₂-Gln-(Arg)₇ (SEQ ID NO:311), (Arg)₃-Gln-(Arg)₅ (SEQ ID NO:312), (Arg)₃-Gln-(Arg)₆ (SEQ ID NO:313), (Arg)₄-Gln-(Arg)₄ (SEQ ID NO:314), (Arg)₄-Gln-(Arg)₅ (SEQ ID NO:315), (Arg)₅ (SEQ ID NO:316), (Arg)₅-Gln-(Arg)₃ (SEQ ID NO:317), (Arg)₅-Gln-(Arg)₄ (SEQ ID NO:318), (Arg)₆ (SEQ ID NO:319), (Arg)₆-Gln-(Arg)₃ (SEQ ID NO:320), (Arg)₇ (SEQ ID NO:321), (Arg)₇-Gln-(Arg)₂ (SEQ ID NO:322), (Arg)₈ (SEQ ID NO:323), (Arg)₈-Gln-Arg (SEQ ID NO:324), (Arg)₉ (SEQ ID NO:325), (Arg)₉-Gln (SEQ ID NO:326), (D-Arg)₅, (D-Arg)₆, (D-Arg)₇, (D-Arg)₈, (D-Arg)₉, Gln-Arg-(Lys)₂-(Arg)₅ (SEQ ID NO:327), Gln-(Arg)₈ (SEQ ID NO:328), Gln-(Arg)₉ (SEQ ID NO:329), Tyr-Gly-Arg-(Lys)₂-(Arg)₂-Gln-(Arg)₃ (SEQ ID NO:330); Tyr-Gly-Arg-(Lys)₂-(Arg)₂-Gln-(Arg)₃-Doc (SEQ ID NO:331); or deleted;

B² is β-Ala, β-Ala-Gly, β-Ala-Tyr, β-Ala-Tyr-Gly, (β-Ala)₂, (β-Ala)₂-Gly, (β-Ala)₂-Tyr, (β-Ala)₂-Tyr-Gly (SEQ ID NO:332), Doc, Doc-Gly, Doc-Tyr, Doc-Tyr-Gly, (Doc)₂, (Doc)₂-Gly, (Doc)₂-Tyr, (Doc)₂-Tyr-Gly (SEQ ID NO:333), or deleted;

B³ is Arg-Lys-Gln-Lys-(Arg)₅ (SEQ ID NO:301), Arg-Lys-(Arg)₃-Gln-(Arg)₃ (SEQ ID NO:334), Arg-(Lys)₂-Arg-Gln-(Arg)₄ (SEQ ID NO:302), Arg-(Lys)₂-Gln-(Arg)₅ (SEQ ID NO:306), Arg-(Lys)₂-(Arg)₂-Gln-(Arg)₃ (SEQ ID NO:294), Arg-(Lys)₂-(Arg)₃-Gln-(Arg)₂ (SEQ ID NO:303), Arg-(Lys)₂-(Arg)₄-Gln-Arg (SEQ ID NO:304), Arg-(Lys)₂-(Arg)₅-Gln (SEQ ID NO:305), Arg-Gln-(Lys)₂-(Arg)₅ (SEQ ID NO:307), Arg-Gln-(Arg)₇ (SEQ ID NO:308), Arg-Gln-(Arg)₈ (SEQ ID NO:309), (Arg)₂-Lys-(Arg)₂-Gln-(Arg)₃ (SEQ ID NO:335), (Arg)₂-Gln-(Arg)₆ (SEQ ID NO:310), (Arg)₂-Gln-(Arg)₇ (SEQ ID NO:311), (Arg)₃-Gln-(Arg)₅ (SEQ ID NO:312), (Arg)₃-Gln-(Arg)₆ (SEQ ID NO:313), (Arg)₄-Gln-(Arg)₄ (SEQ ID NO:314), (Arg)₄-Gln-(Arg)₅ (SEQ ID NO:315), (Arg)₅ (SEQ ID NO:316), (Arg)₅-Gln-(Arg)₃ (SEQ ID NO:317), (Arg)₅-Gln-(Arg)₄ (SEQ ID NO:318), (Arg)₆ (SEQ ID NO:319), (Arg)₆-Gln-(Arg)₃ (SEQ ID NO:320), (Arg)₇ (SEQ ID NO:321), (Arg)₇-Gln-(Arg)₂ (SEQ ID NO:322), (Arg)₈ (SEQ ID NO:323), (Arg)s-Gln-Arg (SEQ ID NO:324), (Arg)₉ (SEQ ID NO:325), (Arg)₉-Gln (SEQ ID NO:326), (D-Arg)₅, (D-Arg)₆, (D-Arg)₇, (D-Arg)s, (D-Arg)₉, Gln-Arg-(Lys)₂-(Arg)₅ (SEQ ID NO:327), Gln-(Arg)₈ (SEQ ID NO:328), Gln-(Arg)₉ (SEQ ID NO:329), or deleted;

A¹ is A6c, Cha, hCha, Chg, D-Chg, hChg, Gaba, hLeu, Met, β-hMet, D-2-Nal, Nip, Nle, Oic, Phe, D-Phe, hPhe, hPro, or deleted;

A² is Cys

A³ is D-Abu, Aib, Ala, β-Ala, D-Ala, D-Cha, Gaba, Glu, Gly, D-Ile, D-Leu, D-Met, D-Nle, D-Phe, D-Tle, D-Trp, D-Tyr, D-Val, or deleted;

A⁴ is His;

A⁵ is D-Bal, D-1-Nal, D-2-Nal, D-Phe, D-(X¹,X²,X³,X⁴,X⁵)Phe, D-Trp, or D-(Et)Tyr;

A⁶ is Arg or hArg;

A⁷ is Bal, Bip, 1-Nal, 2-Nal, Trp, or D-Trp;

A⁸ is A5c, A6c, Aha, Ahx, Ala, β-Ala, Apn, Gaba, Gly, or deleted;

A⁹ is Cys, D-Cys, hCys, D-hCys, Lys, Pen, or D-Pen;

A¹⁰ is Pro, Thr or deleted;

A¹¹ is Pro or deleted;

A¹² is arg, Lys, or deleted;

A¹³ is Asp or deleted;

each of R² and R³ is, independently, H or acyl;

or pharmaceutically acceptable salts thereof.

Preferred ligands of the immediately foregoing group of compounds according to Formula (III), useful to treat insulin resistance in a mammalian subject, with or without weight loss, are compounds of the formula:

```
                                                          (SEQ ID NO: 60)
Tyr-Gly-Arg-(Lys)₂-(Arg)₂-Gln-(Arg)₃-Nle-c(Asp-His-D-2-Nal-Arg-Trp-Lys)-NH₂;

(SEQ ID NO: 61)
Tyr-Gly-Arg-(Lys)₂-(Arg)₂-Gln-(Arg)₃-Doc-Nle-c(Asp-His-D-2-Nal-Arg-Trp-Lys)-NH₂;

(SEQ ID NO: 62)
Nle-c(Asp-His-D-2-Nal-Arg-Trp-Lys)-β-Ala-Tyr-Gly-Arg-(Lys)₂-(Arg)₂-Gln-(Arg)₃-NH₂;

(SEQ ID NO: 62)
Ac-Nle-c(Asp-His-D-2-Nal-Arg-Trp-Lys)-β-Ala-Tyr-Gly-Arg-(Lys)₂-(Arg)₂-Gln-(Arg)₃-
NH₂;

(SEQ ID NO: 63)
Nle-c(Asp-His-D-2-Nal-Arg-Trp-Lys)-(Doc)₂-Tyr-Gly-Arg-(Lys)₂-(Arg)₂-Gln-(Arg)₃-NH₂;

(SEQ ID NO: 64)
Ac-Nle-c(Asp-His-D-2-Nal-Arg-Trp-Lys)-(Pro)₂-Lys-Asp-Tyr-Gly-Arg-(Lys)₂-(Arg)₂-Gln-
(Arg)₃-NH₂;

(SEQ ID NO: 65)
Ac-c(Cys-Glu-His-D-2-Nal-Arg-Trp-Gly-Cys)-(Pro)₂-Lys-Asp-Tyr-Gly-Arg-(Lys)₂-(Arg)₂-
Gln-(Arg)₃-NH₂;

(SEQ ID NO: 66)
Ac-Nle-c(Asp-His-D-2-Nal-Arg-Trp-Lys)-(β-Ala)₂-Tyr-Gly-Arg-(Lys)₂-(Arg)₂-Gln-(Arg)₃-
NH₂;

(SEQ ID NO: 67)
Ac-Nle-c(Asp-His-D-2-Nal-Arg-Trp-Lys)-(Pro)₂-Lys-Asp-Doc-Tyr-Gly-Arg-(Lys)₂-(Arg)₂-
Gln-(Arg)₃-NH₂;
```

-continued (SEQ ID NO: 68)
Ac-c(Cys-Glu-His-D-2-Nal-Arg-Trp-Gly-Cys)-(Pro)$_2$-Lys-Asp-Doc-Tyr-Gly-Arg-(Lys)$_2$-(Arg)$_2$-Gln-(Arg)$_3$-NH$_2$;

(SEQ ID NO: 69)
Ac-c(Cys-Glu-His-D-2-Nal-Arg-Trp-Ala-Cys)-(Pro)$_2$-Lys-Asp-β-Ala-Tyr-Gly-Arg-(Lys)$_2$-(Arg)$_2$-Gln-(Arg)$_3$-NH$_2$;

(SEQ ID NO: 69)
Ac-c(Cys-Glu-His-D-2-Nal-Arg-Trp-Ala-Cys)-(Pro)$_2$-Lys-Asp-Doc-Tyr-Gly-Arg-(Lys)$_2$-(Arg)$_2$-Gln-(Arg)$_3$-NH$_2$;

(SEQ ID NO: 70)
Ac-Nle-c(Asp-His-D-2-Nal-Arg-Trp-Lys)-(Doc)$_2$-Tyr-Gly-Arg-(Lys)$_2$-(Arg)$_2$-Gln-(Arg)$_3$-NH$_2$;

(SEQ ID NO: 71)
Ac-c(Cys-Glu-His-D-2-Nal-Arg-2-Nal-Ala-Cys)-(Pro)$_2$-Lys-Asp-β-Ala-Tyr-Gly-Arg-(Lys)$_2$-(Arg)$_2$-Gln-(Arg)$_3$-NH$_2$;

(SEQ ID NO: 72)
Ac-c(Cys-Glu-His-D-2-Nal-Arg-Bal-Ala-Cys)-(Pro)$_2$-Lys-Asp-β-Ala-(Arg)$_5$-Gln-(Arg)$_3$-NH$_2$;

(SEQ ID NO: 73)
Ac-c(Cys-Glu-His-D-2-Nal-Arg-Bal-Ala-Cys)-(Pro)$_2$-Lys-Asp-β-Ala-Gly-(Arg)$_5$-Gln-(Arg)$_3$-NH$_2$;

(SEQ ID NO: 74)
Ac-c(Cys-Glu-His-D-2-Nal-Arg-Bal-Ala-Cys)-(Pro)$_2$-Lys-Asp-β-Ala-Tyr-Gly-(Arg)$_5$-Gln-(Arg)$_3$-NH$_2$;

(SEQ ID NO: 75)
Ac-c(Cys-Glu-His-D-2-Nal-Arg-Trp-Ala-Cys)-(Pro)$_2$-Lys-Asp-β-Ala-Tyr-Gly-Arg-(Lys)$_2$-Arg-Gln-(Arg)$_4$-NH$_2$;

(SEQ ID NO: 76)
Ac-c(Cys-Glu-His-D-2-Nal-Arg-Trp-Ala-Cys)-(Pro)$_2$-Lys-Asp-β-Ala-Tyr-Gly-Arg-(Lys)$_2$-Gln-(Arg)$_5$-NH$_2$;

(SEQ ID NO: 77)
Ac-c(Cys-Glu-His-D-2-Nal-Arg-Trp-Ala-Cys)-(Pro)$_2$-Lys-Asp-β-Ala-Tyr-Gly-Arg-Lys-Gln-Lys-(Arg)$_5$-NH$_2$;

(SEQ ID NO: 78)
Ac-c(Cys-Glu-His-D-2-Nal-Arg-Trp-Ala-Cys)-(Pro)$_2$-Lys-Asp-β-Ala-Tyr-Gly-Arg-(Lys)$_2$-(Arg)$_4$-Gln-Arg-NH$_2$;

(SEQ ID NO: 79)
Ac-c(Cys-Glu-His-D-2-Nal-Arg-Bal-Ala-Cys)-(Pro)$_2$-Lys-Asp-β-Ala-Tyr-Aib-Arg-(Lys)$_2$-(Arg)$_2$-Gln-(Arg)$_3$-NH$_2$;

(SEQ ID NO: 80)
Ac-c(Cys-Glu-His-D-2-Nal-Arg-1-Nal-Ala-Cys)-(Pro)$_2$-Arg-Asp-β-Ala-(Arg)$_5$-Gln-(Arg)$_3$-NH$_2$;

(SEQ ID NO: 80)
Ac-c(Cys-Glu-His-D-2-Nal-Arg-1-Nal-Ala-Cys)-(Pro)$_2$-Lys-Asp-β-Ala-(Arg)$_5$-Gln-(Arg)$_3$-NH$_2$;

(SEQ ID NO: 81)
Ac-c(Cys-Glu-His-D-2-Nal-Arg-1-Nal-Ala-Cys)-(Pro)$_2$-Lys-Asp-β-Ala-(Arg)$_6$-Gln-(Arg)$_3$-NH$_2$;

(SEQ ID NO: 82)
Ac-c(Cys-Glu-His-D-2-Nal-Arg-2-Nal-Ala-Cys)-(Pro)$_2$-Arg-Asp-β-Ala-(Arg)$_5$-Gln-(Arg)$_3$-
NH$_2$;

(SEQ ID NO: 82)
Ac-c(Cys-Glu-His-D-2-Nal-Arg-2-Nal-Ala-Cys)-(Pro)$_2$-Lys-Asp-β-Ala-(Arg)$_5$-Gln-(Arg)$_3$-
NH$_2$;

(SEQ ID NO: 81)
Ac-c(Cys-Glu-His-D-2-Nal-Arg-2-Nal-Ala-Cys)-(Pro)$_2$-Lys-Asp-β-Ala-(Arg)$_6$-Gln-(Arg)$_3$-
NH$_2$;

(SEQ ID NO: 83)
Ac-c(Cys-Glu-His-D-2-Nal-Arg-Bal-Ala-Cys)-(Pro)$_2$-Arg-Asp-β-Ala-(Arg)$_6$-Gln-(Arg)$_3$-
NH$_2$;

(SEQ ID NO: 84)
Ac-c(Cys-Glu-His-D-2-Nal-Arg-Bal-Ala-Cys)-(Pro)$_2$-Arg-Asp-β-Ala-(Arg)$_5$-Gln-(Arg)$_3$-
NH$_2$;

(SEQ ID NO: 83)
Ac-c(Cys-Glu-His-D-2-Nal-Arg-Bal-Ala-Cys)-(Pro)$_2$-Lys-Asp-β-Ala-(Arg)$_6$-Gln-(Arg)$_3$-
NH$_2$;

(SEQ ID NO: 85)
Ac-c(Cys-Glu-His-D-2-Nal-Arg-Trp-Ala-Cys)-(Pro)$_2$-Lys-Asp-β-Ala-Tyr-Gly-Arg-(Lys)$_2$-
(Arg)$_3$-Gln-(Arg)$_2$-NH$_2$;

(SEQ ID NO: 86)
Ac-c(Cys-Glu-His-D-2-Nal-Arg-Trp-Ala-Cys)-(Pro)$_2$-Lys-Asp-β-Ala-Tyr-Gly-Arg-Gln-
(Lys)$_2$-(Arg)$_5$-NH$_2$;

(SEQ ID NO: 87)
Ac-c(Cys-Glu-His-D-2-Nal-Arg-Trp-Ala-Cys)-(Pro)$_2$-Lys-Asp-β-Ala-Tyr-Gly-Arg-(Lys)$_2$-
(Arg)$_5$-Gln-NH$_2$;

(SEQ ID NO: 71)
Ac-c(Cys-Glu-His-D-2-Nal-Arg-1-Nal-Ala-Cys)-(Pro)$_2$-Lys-Asp-β-Ala-Tyr-Gly-Arg-
(Lys)$_2$-(Arg)$_2$-Gln-(Arg)$_3$-NH$_2$;

(SEQ ID NO: 71)
Ac-c(Cys-Glu-His-D-2-Nal-Arg-Bal-Ala-Cys)-(Pro)$_2$-Lys-Asp-β-Ala-Tyr-Gly-Arg-(Lys)$_2$-
(Arg)$_2$-Gln-(Arg)$_3$-NH$_2$;

(SEQ ID NO: 88)
Ac-c(Cys-Glu-His-D-2-Nal-Arg-1-Nal-Ala-Cys)-(Pro)$_2$-Lys-Asp-β-Ala-(Arg)$_2$-Lys-(Arg)$_2$-
Gln-(Arg)$_3$-NH$_2$;

(SEQ ID NO: 89)
Ac-c(Cys-Glu-His-D-2-Nal-Arg-1-Nal-Ala-Cys)-(Pro)$_2$-Lys-Asp-β-Ala-Arg-Lys-(Arg)$_3$-
Gln-(Arg)$_3$-NH$_2$;

(SEQ ID NO: 88)
Ac-c(Cys-Glu-His-D-2-Nal-Arg-2-Nal-Ala-Cys)-(Pro)$_2$-Lys-Asp-β-Ala-(Arg)$_2$-Lys-(Arg)$_2$-
Gln-(Arg)$_3$-NH$_2$;

(SEQ ID NO: 90)
Ac-c(Cys-Glu-His-D-2-Nal-Arg-2-Nal-Ala-Cys)-(Pro)$_2$-Lys-Asp-β-Ala-Tyr-Gly-(Arg)$_2$-
Lys-(Arg)$_2$-Gln-(Arg)$_3$-NH$_2$;

(SEQ ID NO: 91)
Ac-c(Cys-Glu-His-D-2-Nal-Arg-2-Nal-Ala-Cys)-(Pro)$_2$-Lys-Asp-β-Ala-Gly-(Arg)$_2$-Lys-
(Arg)$_2$-Gln-(Arg)$_3$-NH$_2$;

(SEQ ID NO: 92)
Ac-c(Cys-Glu-His-D-2-Nal-Arg-2-Nal-Ala-Cys)-(Pro)$_2$-Lys-Asp-β-Ala-Gly-Arg-Lys-(Arg)$_3$-Gln-(Arg)$_3$-NH$_2$;

(SEQ ID NO: 93)
Ac-c(Cys-Glu-His-D-2-Nal-Arg-1-Nal-Ala-Cys)-(Pro)$_2$-Lys-Asp-β-Ala-(Arg)$_2$-Lys-(Arg)$_2$-Gln-(Arg)$_3$-NH$_2$;

(SEQ ID NO: 94)
Ac-c(Cys-Glu-His-D-2-Nal-Arg-1-Nal-Ala-Cys)-(Pro)$_2$-Lys-Asp-β-Ala-Arg-Lys-(Arg)$_3$-Gln-(Arg)$_3$-NH$_2$;

(SEQ ID NO: 95)
Ac-c(Cys-Glu-His-D-2-Nal-Arg-1-Nal-Ala-Cys)-(Pro)$_2$-Lys-Asp-β-Ala-Tyr-Gly-(Arg)$_2$-Lys-(Arg)$_2$-Gln-(Arg)$_3$-NH$_2$;

(SEQ ID NO: 96)
Ac-c(Cys-Glu-His-D-2-Nal-Arg-1-Nal-Ala-Cys)-(Pro)$_2$-Lys-Asp-β-Ala-Tyr-Gly-Arg-Lys-(Arg)$_3$-Gln-(Arg)$_3$-NH$_2$;

(SEQ ID NO: 97)
Ac-c(Cys-Glu-His-D-2-Nal-Arg-1-Nal-Ala-Cys)-(Pro)$_2$-Lys-Asp-β-Ala-Gly-(Arg)$_2$-Lys-(Arg)$_2$-Gln-(Arg)$_3$-NH$_2$;

(SEQ ID NO: 92)
Ac-c(Cys-Glu-His-D-2-Nal-Arg-1-Nal-Ala-Cys)-(Pro)$_2$-Lys-Asp-β-Ala-Gly-Arg-Lys-(Arg)$_3$-Gln-(Arg)$_3$-NH$_2$;

(SEQ ID NO: 98)
Ac-c(Cys-Glu-His-D-2-Nal-Arg-2-Nal-Ala-Cys)-(Pro)$_2$-Lys-Asp-β-Ala-(Arg)$_2$-Lys-(Arg)$_2$-Gln-(Arg)$_3$-NH$_2$;

(SEQ ID NO: 99)
Ac-c(Cys-Glu-His-D-2-Nal-Arg-2-Nal-Ala-Cys)-(Pro)$_2$-Lys-Asp-β-Ala-Arg-Lys-(Arg)$_3$-Gln-(Arg)$_3$-NH$_2$;

(SEQ ID NO: 100)
Ac-c(Cys-Glu-His-D-2-Nal-Arg-2-Nal-Ala-Cys)-(Pro)$_2$-Lys-Asp-β-Ala-Tyr-Gly-(Arg)$_2$-Lys-(Arg)$_2$-Gln-(Arg)$_3$-NH$_2$;

(SEQ ID NO: 101)
Ac-c(Cys-Glu-His-D-2-Nal-Arg-2-Nal-Ala-Cys)-(Pro)$_2$-Lys-Asp-β-Ala-Tyr-Gly-Arg-Lys-(Arg)$_3$-Gln-(Arg)$_3$-NH$_2$;

(SEQ ID NO: 102)
Ac-c(Cys-Glu-His-D-2-Nal-Arg-2-Nal-Ala-Cys)-(Pro)$_2$-Lys-Asp-β-Ala-Gly-(Arg)$_2$-Lys-(Arg)$_2$-Gln-(Arg)$_3$-NH$_2$;

(SEQ ID NO: 103)
Ac-c(Cys-Glu-His-D-2-Nal-Arg-2-Nal-Ala-Cys)-(Pro)$_2$-Lys-Asp-β-Ala-Gly-Arg-Lys-(Arg)$_3$-Gln-(Arg)$_3$-NH$_2$;

(SEQ ID NO: 104)
Ac-c(Cys-Glu-His-D-2-Nal-Arg-Bal-Ala-Cys)-(Pro)$_2$-Lys-Asp-β-Ala-(Arg)$_2$-Lys-(Arg)$_2$-Gln-(Arg)$_3$-NH$_2$;

(SEQ ID NO: 105)
Ac-c(Cys-Glu-His-D-2-Nal-Arg-Bal-Ala-Cys)-(Pro)$_2$-Lys-Asp-β-Ala-Arg-Lys-(Arg)$_3$-Gln-(Arg)$_3$-NH$_2$;

(SEQ ID NO: 100)
Ac-c(Cys-Glu-His-D-2-Nal-Arg-Bal-Ala-Cys)-(Pro)$_2$-Lys-Asp-β-Ala-Tyr-Gly-(Arg)$_2$-Lys-(Arg)$_2$-Gln-(Arg)$_3$-NH$_2$;

-continued (SEQ ID NO: 101)
Ac-c(Cys-Glu-His-D-2-Nal-Arg-Bal-Ala-Cys)-(Pro)$_2$-Lys-Asp-β-Ala-Tyr-Gly-Arg-Lys-(Arg)$_3$-Gln-(Arg)$_3$-NH$_2$;

(SEQ ID NO: 102)
Ac-c(Cys-Glu-His-D-2-Nal-Arg-Bal-Ala-Cys)-(Pro)$_2$-Lys-Asp-β-Ala-Gly-(Arg)$_2$-Lys-(Arg)$_2$-Gln-(Arg)$_3$-NH$_2$;

(SEQ ID NO: 103)
Ac-c(Cys-Glu-His-D-2-Nal-Arg-Bal-Ala-Cys)-(Pro)$_2$-Lys-Asp-β-Ala-Gly-Arg-Lys-(Arg)$_3$-Gln-(Arg)$_3$-NH$_2$;

(SEQ ID NO: 106)
Ac-c(Cys-Glu-His-D-2-Nal-Arg-Trp-Ala-Cys)-(Pro)$_2$-Lys-Asp-β-Ala-Tyr-Gly-Arg-(Lys)$_2$-Arg-Gln-(Arg)$_4$-NH$_2$;

(SEQ ID NO: 107)
Ac-c(Cys-Glu-His-D-2-Nal-Arg-Trp-Ala-Cys)-(Pro)$_2$-Lys-Asp-β-Ala-Tyr-Gly-Arg-(Lys)$_2$-Gln-(Arg)$_5$-NH$_2$;

(SEQ ID NO: 108)
Ac-c(Cys-Glu-His-D-2-Nal-Arg-Trp-Ala-Cys)-(Pro)$_2$-Lys-Asp-β-Ala-Tyr-Gly-Arg-Lys-Gln-Lys-(Arg)$_5$-NH$_2$;

(SEQ ID NO: 109)
Ac-c(Cys-Glu-His-D-2-Nal-Arg-Trp-Ala-Cys)-(Pro)$_2$-Lys-Asp-β-Ala-Tyr-Gly-Arg-Gln-(Lys)$_2$-(Arg)$_5$-NH$_2$;

(SEQ ID NO: 110)
Ac-c(Cys-Glu-His-D-2-Nal-Arg-Trp-Ala-Cys)-(Pro)$_2$-Lys-Asp-β-Ala-Tyr-Gly-Arg-(Lys)$_2$-(Arg)$_3$-Gln-(Arg)$_2$-NH$_2$;

(SEQ ID NO: 111)
Ac-c(Cys-Glu-His-D-2-Nal-Arg-Trp-Ala-Cys)-(Pro)$_2$-Lys-Asp-β-Ala-Tyr-Gly-Arg-(Lys)$_2$-(Arg)$_4$-Gln-Arg-NH$_2$;

(SEQ ID NO: 112)
Ac-c(Cys-Glu-His-D-2-Nal-Arg-Trp-Ala-Cys)-(Pro)$_2$-Lys-Asp-β-Ala-Tyr-Gly-Arg-(Lys)$_2$-(Arg)$_5$-Gln-NH$_2$;

(SEQ ID NO: 113)
Ac-c(Cys-Glu-His-D-2-Nal-Arg-Trp-Ala-Cys)-(Pro)$_2$-Lys-Asp-β-Ala-(Arg)$_5$-Gln-(Arg)$_3$-NH$_2$;

(SEQ ID NO: 113)
Ac-c(Cys-Glu-His-D-2-Nal-Arg-Trp-Ala-Cys)-(Pro)$_2$-Arg-Asp-β-Ala-(Arg)$_5$-Gln-(Arg)$_3$-NH$_2$;

(SEQ ID NO: 114)
Ac-c(Cys-Glu-His-D-2-Nal-Arg-Trp-Ala-Cys)-(Pro)$_2$-Lys-Asp-β-Ala-Tyr-Gly-(Arg)$_5$-Gln-(Arg)$_3$-NH$_2$;

(SEQ ID NO: 114)
Ac-c(Cys-Glu-His-D-2-Nal-Arg-Trp-Ala-Cys)-(Pro)$_2$-Arg-Asp-β-Ala-Tyr-Gly-(Arg)$_5$-Gln-(Arg)$_3$-NH$_2$;

(SEQ ID NO: 115)
Ac-c(Cys-Glu-His-D-2-Nal-Arg-Trp-Ala-Cys)-(Pro)$_2$-Lys-Asp-β-Ala-(Arg)$_5$-Gln-(Arg)$_4$-NH$_2$;

(SEQ ID NO: 115)
Ac-c(Cys-Glu-His-D-2-Nal-Arg-Trp-Ala-Cys)-(Pro)$_2$-Arg-Asp-β-Ala-(Arg)$_5$-Gln-(Arg)$_4$-NH$_2$;

-continued (SEQ ID NO: 116)
Ac-c(Cys-Glu-His-D-2-Nal-Arg-Trp-Ala-Cys)-(Pro)$_2$-Lys-Asp-β-Ala-Tyr-Gly-(Arg)$_5$-Gln-(Arg)$_4$-NH$_2$;

(SEQ ID NO: 116)
Ac-c(Cys-Glu-His-D-2-Nal-Arg-Trp-Ala-Cys)-(Pro)$_2$-Arg-Asp-β-Ala-Tyr-Gly-(Arg)$_5$-Gln-(Arg)$_4$-NH$_2$;

(SEQ ID NO: 117)
Ac-c(Cys-Glu-His-D-2-Nal-Arg-1-Nal-Ala-Cys)-(Pro)$_2$-Lys-Asp-β-Ala-(Arg)$_5$-Gln-(Arg)$_3$-NH$_2$;

(SEQ ID NO: 117)
Ac-c(Cys-Glu-His-D-2-Nal-Arg-1-Nal-Ala-Cys)-(Pro)$_2$-Arg-Asp-β-Ala-(Arg)$_5$-Gln-(Arg)$_3$-NH$_2$;

(SEQ ID NO: 118)
Ac-c(Cys-Glu-His-D-2-Nal-Arg-1-Nal-Ala-Cys)-(Pro)$_2$-Lys-Asp-β-Ala-(Arg)$_5$-Gln-(Arg)$_4$-NH$_2$;

(SEQ ID NO: 118)
Ac-c(Cys-Glu-His-D-2-Nal-Arg-1-Nal-Ala-Cys)-(Pro)$_2$-Arg-Asp-β-Ala-(Arg)$_5$-Gln-(Arg)$_4$-NH$_2$;

(SEQ ID NO: 119)
Ac-c(Cys-Glu-His-D-2-Nal-Arg-1-Nal-Ala-Cys)-(Pro)$_2$-Lys-Asp-β-Ala-(Arg)$_6$-Gln-(Arg)$_3$-NH$_2$;

(SEQ ID NO: 119)
Ac-c(Cys-Glu-His-D-2-Nal-Arg-1-Nal-Ala-Cys)-(Pro)$_2$-Arg-Asp-β-Ala-(Arg)$_6$-Gln-(Arg)$_3$-NH$_2$;

(SEQ ID NO: 120)
Ac-c(Cys-Glu-His-D-2-Nal-Arg-1-Nal-Ala-Cys)-(Pro)$_2$-Lys-Asp-β-Ala-Tyr-Gly-(Arg)$_5$-Gln-(Arg)$_3$-NH$_2$;

(SEQ ID NO: 120)
Ac-c(Cys-Glu-His-D-2-Nal-Arg-1-Nal-Ala-Cys)-(Pro)$_2$-Arg-Asp-β-Ala-Tyr-Gly-(Arg)$_5$-Gln-(Arg)$_3$-NH$_2$;

(SEQ ID NO: 121)
Ac-c(Cys-Glu-His-D-2-Nal-Arg-1-Nal-Ala-Cys)-(Pro)$_2$-Lys-Asp-β-Ala-Tyr-Gly-(Arg)$_5$-Gln-(Arg)$_4$-NH$_2$;

(SEQ ID NO: 121)
Ac-c(Cys-Glu-His-D-2-Nal-Arg-1-Nal-Ala-Cys)-(Pro)$_2$-Arg-Asp-β-Ala-Tyr-Gly-(Arg)$_5$-Gln-(Arg)$_4$-NH$_2$;

(SEQ ID NO: 122)
Ac-c(Cys-Glu-His-D-2-Nal-Arg-1-Nal-Ala-Cys)-(Pro)$_2$-Lys-Asp-β-Ala-Tyr-Gly-(Arg)$_6$-Gln-(Arg)$_3$-NH$_2$;

(SEQ ID NO: 122)
Ac-c(Cys-Glu-His-D-2-Nal-Arg-1-Nal-Ala-Cys)-(Pro)$_2$-Arg-Asp-β-Ala-Tyr-Gly-(Arg)$_6$-Gln-(Arg)$_3$-NH$_2$;

(SEQ ID NO: 123)
Ac-c(Cys-Glu-His-D-2-Nal-Arg-2-Nal-Ala-Cys)-(Pro)$_2$-Lys-Asp-β-Ala-(Arg)$_5$-Gln-(Arg)$_3$-NH$_2$;

(SEQ ID NO: 123)
Ac-c(Cys-Glu-His-D-2-Nal-Arg-2-Nal-Ala-Cys)-(Pro)$_2$-Arg-Asp-β-Ala-(Arg)$_5$-Gln-(Arg)$_3$-NH$_2$;

-continued

Ac-c(Cys-Glu-His-D-2-Nal-Arg-2-Nal-Ala-Cys)-(Pro)$_2$-Lys-Asp-β-Ala-(Arg)$_6$-Gln-(Arg)$_3$-NH$_2$; (SEQ ID NO: 124)

Ac-c(Cys-Glu-His-D-2-Nal-Arg-2-Nal-Ala-Cys)-(Pro)$_2$-Arg-Asp-β-Ala-(Arg)$_6$-Gln-(Arg)$_3$-NH$_2$; (SEQ ID NO: 124)

Ac-c(Cys-Glu-His-D-2-Nal-Arg-2-Nal-Ala-Cys)-(Pro)$_2$-Lys-Asp-β-Ala-(Arg)$_5$-Gln-(Arg)$_4$-NH$_2$; (SEQ ID NO: 125)

Ac-c(Cys-Glu-His-D-2-Nal-Arg-2-Nal-Ala-Cys)-(Pro)$_2$-Arg-Asp-β-Ala-(Arg)$_5$-Gln-(Arg)$_4$-NH$_2$; (SEQ ID NO: 125)

Ac-c(Cys-Glu-His-D-2-Nal-Arg-2-Nal-Ala-Cys)-(Pro)$_2$-Lys-Asp-β-Ala-Tyr-Gly-(Arg)$_5$-Gln-(Arg)$_3$-NH$_2$; (SEQ ID NO: 126)

Ac-c(Cys-Glu-His-D-2-Nal-Arg-2-Nal-Ala-Cys)-(Pro)$_2$-Arg-Asp-β-Ala-Tyr-Gly-(Arg)$_5$-Gln-(Arg)$_3$-NH$_2$; (SEQ ID NO: 126)

Ac-c(Cys-Glu-His-D-2-Nal-Arg-2-Nal-Ala-Cys)-(Pro)$_2$-Lys-Asp-β-Ala-Tyr-Gly-(Arg)$_6$-Gln-(Arg)$_3$-NH$_2$; (SEQ ID NO: 127)

Ac-c(Cys-Glu-His-D-2-Nal-Arg-2-Nal-Ala-Cys)-(Pro)$_2$-Arg-Asp-β-Ala-Tyr-Gly-(Arg)$_6$-Gln-(Arg)$_3$-NH$_2$; (SEQ ID NO: 127)

Ac-c(Cys-Glu-His-D-2-Nal-Arg-2-Nal-Ala-Cys)-(Pro)$_2$-Lys-Asp-β-Ala-Tyr-Gly-(Arg)$_5$-Gln-(Arg)$_4$-NH$_2$; (SEQ ID NO: 128)

Ac-c(Cys-Glu-His-D-2-Nal-Arg-2-Nal-Ala-Cys)-(Pro)$_2$-Arg-Asp-β-Ala-Tyr-Gly-(Arg)$_5$-Gln-(Arg)$_4$-NH$_2$; (SEQ ID NO: 128)

Ac-c(Cys-Glu-His-D-2-Nal-Arg-Bal-Ala-Cys)-(Pro)$_2$-Lys-Asp-β-Ala-(Arg)$_5$-Gln-(Arg)$_3$-NH$_2$; (SEQ ID NO: 129)

Ac-c(Cys-Glu-His-D-2-Nal-Arg-Bal-Ala-Cys)-(Pro)$_2$-Arg-Asp-β-Ala-(Arg)$_5$-Gln-(Arg)$_3$-NH$_2$; (SEQ ID NO: 129)

Ac-c(Cys-Glu-His-D-2-Nal-Arg-Bal-Ala-Cys)-(Pro)$_2$-Lys-Asp-β-Ala-(Arg)$_5$-Gln-(Arg)$_4$-NH$_2$; (SEQ ID NO: 130)

Ac-c(Cys-Glu-His-D-2-Nal-Arg-Bal-Ala-Cys)-(Pro)$_2$-Arg-Asp-β-Ala-(Arg)$_5$-Gln-(Arg)$_4$-NH$_2$; (SEQ ID NO: 130)

Ac-c(Cys-Glu-His-D-2-Nal-Arg-Bal-Ala-Cys)-(Pro)$_2$-Lys-Asp-β-Ala-(Arg)$_6$-Gln-(Arg)$_3$-NH$_2$; (SEQ ID NO: 131)

Ac-c(Cys-Glu-His-D-2-Nal-Arg-Bal-Ala-Cys)-(Pro)$_2$-Arg-Asp-β-Ala-(Arg)$_6$-Gln-(Arg)$_3$-NH$_2$; (SEQ ID NO: 131)

(SEQ ID NO: 132)
Ac-c(Cys-Glu-His-D-2-Nal-Arg-Bal-Ala-Cys)-(Pro)$_2$-Lys-Asp-β-Ala-Gly-(Arg)$_5$-Gln-(Arg)$_3$-NH$_2$;

(SEQ ID NO: 133)
Ac-c(Cys-Glu-His-D-2-Nal-Arg-Bal-Ala-Cys)-(Pro)$_2$-Lys-Asp-β-Ala-Tyr-Gly-(Arg)$_5$-Gln-(Arg)$_3$-NH$_2$;

(SEQ ID NO: 133)
Ac-c(Cys-Glu-His-D-2-Nal-Arg-Bal-Ala-Cys)-(Pro)$_2$-Arg-Asp-β-Ala-Tyr-Gly-(Arg)$_5$-Gln-(Arg)$_3$-NH$_2$;

(SEQ ID NO: 134)
Ac-c(Cys-Glu-His-D-2-Nal-Arg-Bal-Ala-Cys)-(Pro)$_2$-Lys-Asp-β-Ala-Tyr-Gly-(Arg)$_5$-Gln-(Arg)$_4$-NH$_2$;

(SEQ ID NO: 134)
Ac-c(Cys-Glu-His-D-2-Nal-Arg-Bal-Ala-Cys)-(Pro)$_2$-Arg-Asp-β-Ala-Tyr-Gly-(Arg)$_5$-Gln-(Arg)$_4$-NH$_2$;

(SEQ ID NO: 135)
Ac-c(Cys-Glu-His-D-2-Nal-Arg-Bal-Ala-Cys)-(Pro)$_2$-Lys-Asp-β-Ala-Tyr-Gly-(Arg)$_6$-Gln-(Arg)$_3$-NH$_2$;

(SEQ ID NO: 135)
Ac-c(Cys-Glu-His-D-2-Nal-Arg-Bal-Ala-Cys)-(Pro)$_2$-Arg-Asp-β-Ala-Tyr-Gly-(Arg)$_6$-Gln-(Arg)$_3$-NH$_2$;

(SEQ ID NO: 136)
Ac-Nle-c(Cys-D-Ala-His-D-Phe-Arg-Trp-Cys)-(Doc)$_2$-Tyr-Gly-Arg-(Lys)$_2$-(Arg)$_2$-Gln-(Arg)$_3$-NH$_2$;

(SEQ ID NO: 137)
Ac-Nle-c(Cys-D-Ala-His-D-Phe-Arg-Trp-Cys)-β-Ala-Tyr-Gly-Arg-(Lys)$_2$-Arg-Gln-(Arg)$_4$-NH$_2$;

(SEQ ID NO: 136)
Ac-Nle-c(Cys-D-Ala-His-D-Phe-Arg-Trp-Cys)-Doc-Tyr-Gly-Arg-(Lys)$_2$-(Arg)$_2$-Gln-(Arg)$_3$-NH$_2$;

(SEQ ID NO: 138)
Ac-Nle-c(Cys-D-Ala-His-D-Phe-Arg-Trp-Cys)-β-Ala-(Arg)$_5$-Gln-(Arg)$_3$-NH$_2$;

(SEQ ID NO: 138)
Ac-Nle-c(Cys-D-Ala-His-D-Phe-Arg-Trp-Cys)-β-Ala-Gly-(Arg)$_5$-Gln-(Arg)$_3$-NH$_2$;

(SEQ ID NO: 138)
Ac-Nle-c(Cys-D-Ala-His-D-Phe-Arg-Trp-Cys)-β-Ala-Gly-(Arg)$_5$-Gln-(Arg)$_3$-NH$_2$;

(SEQ ID NO: 139)
Ac-Nle-c(Cys-D-Ala-His-D-Phe-Arg-Trp-Cys)-β-Ala-Tyr-Gly-(Arg)$_5$-Gln-(Arg)$_3$-NH$_2$;

(SEQ ID NO: 140)
Ac-Nle-c(Cys-D-Ala-His-D-Phe-Arg-Trp-Cys)-β-Ala-Gly-(Arg)$_5$-Gln-(Arg)$_4$-NH$_2$;

(SEQ ID NO: 141)
Ac-Nle-c(Cys-D-Ala-His-D-Phe-Arg-Trp-Cys)-β-Ala-Tyr-Gly-(Arg)$_2$-Lys-(Arg)$_2$-Gln-(Arg)$_3$-NH$_2$;

(SEQ ID NO: 142)
Ac-Nle-c(Cys-D-Ala-His-D-Phe-Arg-Trp-Cys)-β-Ala-Tyr-Gly-Arg-Lys-(Arg)$_3$-Gln-(Arg)$_3$-NH$_2$;

(SEQ ID NO: 141)
Ac-Nle-c(Cys-D-Ala-His-D-Phe-Arg-Trp-Cys)-β-Ala-Gly-(Arg)$_2$-Lys-(Arg)$_2$-Gln-(Arg)$_3$-NH$_2$;

-continued

```
                                                   (SEQ ID NO: 142)
Ac-Nle-c(Cys-D-Ala-His-D-Phe-Arg-Trp-Cys)-β-Ala-Gly-Arg-Lys-(Arg)₃-Gln-(Arg)₃-
NH₂;

(SEQ ID NO: 143)
Ac-Nle-c(Cys-D-Ala-His-D-Phe-Arg-Trp-Cys)-β-Ala-(Arg)₂-Lys-(Arg)₂-Gln-(Arg)₃-NH₂;

(SEQ ID NO: 144)
Ac-Nle-c(Cys-D-Ala-His-D-Phe-Arg-Trp-Cys)-β-Ala-Arg-Lys-(Arg)₃-Gln-(Arg)₃-NH₂;

(SEQ ID NO: 145)
Ac-Nle-c(Cys-D-Ala-His-D-Phe-Arg-Trp-Cys)-β-Ala-Tyr-Gly-Arg-(Lys)₂-Arg-Gln-(Arg)₄-
NH₂;

(SEQ ID NO: 146)
Ac-Nle-c(Cys-D-Ala-His-D-Phe-Arg-Trp-Cys)-Doc-Tyr-Gly-Arg-(Lys)₂-(Arg)₂-Gln-
(Arg)₃-NH₂;

(SEQ ID NO: 148)
Ac-Nle-c(Cys-D-Ala-His-D-Phe-Arg-Trp-Cys)-β-Ala-(Arg)₅-Gln-(Arg)₃-NH₂;

(SEQ ID NO: 147)
Ac-Nle-c(Cys-D-Ala-His-D-Phe-Arg-Trp-Cys)-β-Ala-Gly-(Arg)₅-Gln-(Arg)₃-NH₂;

(SEQ ID NO: 147)
Ac-Nle-c(Cys-D-Ala-His-D-Phe-Arg-Trp-Cys)-β-Ala-Tyr-Gly-(Arg)₅-Gln-(Arg)₃-NH₂;

(SEQ ID NO: 148)
Ac-Nle-c(Cys-D-Ala-His-D-Phe-Arg-Trp-Cys)-(β-Ala)₂-(Arg)₅-Gln-(Arg)₃-NH₂;

(SEQ ID NO: 149)
Ac-Nle-c(Cys-D-Ala-His-D-Phe-Arg-Trp-Cys)-(β-Ala)₂-Gly-(Arg)₅-Gln-(Arg)₃-NH₂;

(SEQ ID NO: 149)
Ac-Nle-c(Cys-D-Ala-His-D-Phe-Arg-Trp-Cys)-(β-Ala)₂-Tyr-Gly-(Arg)₅-Gln-(Arg)₃-NH₂;

(SEQ ID NO: 151)
Ac-Nle-c(Cys-D-Ala-His-D-Phe-Arg-Trp-Cys)-Doc-(Arg)₅-Gln-(Arg)₃-NH₂;

(SEQ ID NO: 150)
Ac-Nle-c(Cys-D-Ala-His-D-Phe-Arg-Trp-Cys)-Doc-Gly-(Arg)₅-Gln-(Arg)₃-NH₂;

(SEQ ID NO: 150)
Ac-Nle-c(Cys-D-Ala-His-D-Phe-Arg-Trp-Cys)-Doc-Tyr-Gly-(Arg)₅-Gln-(Arg)₃-NH₂;

(SEQ ID NO: 151)
Ac-Nle-c(Cys-D-Ala-His-D-Phe-Arg-Trp-Cys)-(Doc)₂-(Arg)₅-Gln-(Arg)₃-NH₂;

(SEQ ID NO: 152)
Ac-Nle-c(Cys-D-Ala-His-D-Phe-Arg-Trp-Cys)-(Doc)₂-Gly-(Arg)₅-Gln-(Arg)₃-NH₂;

(SEQ ID NO: 152)
Ac-Nle-c(Cys-D-Ala-His-D-Phe-Arg-Trp-Cys)-(Doc)₂-Tyr-Gly-(Arg)₅-Gln-(Arg)₃-NH₂;

(SEQ ID NO: 154)
Ac-Nle-c(Cys-D-Ala-His-D-Phe-Arg-Trp-Cys)-β-Ala-(Arg)₅-Gln-(Arg)₄-NH₂;

(SEQ ID NO: 153)
Ac-Nle-c(Cys-D-Ala-His-D-Phe-Arg-Trp-Cys)-β-Ala-Gly-(Arg)₅-Gln-(Arg)₄-NH₂;

(SEQ ID NO: 153)
Ac-Nle-c(Cys-D-Ala-His-D-Phe-Arg-Trp-Cys)-β-Ala-Tyr-Gly-(Arg)₅-Gln-(Arg)₄-NH₂;

(SEQ ID NO: 154)
Ac-Nle-c(Cys-D-Ala-His-D-Phe-Arg-Trp-Cys)-(β-Ala)₂-(Arg)₅-Gln-(Arg)₄-NH₂;

(SEQ ID NO: 155)
Ac-Nle-c(Cys-D-Ala-His-D-Phe-Arg-Trp-Cys)-(β-Ala)₂-Gly-(Arg)₅-Gln-(Arg)₄-NH₂;

(SEQ ID NO: 155)
Ac-Nle-c(Cys-D-Ala-His-D-Phe-Arg-Trp-Cys)-(β-Ala)₂-Tyr-Gly-(Arg)₅-Gln-(Arg)₄-NH₂;

(SEQ ID NO: 157)
Ac-Nle-c(Cys-D-Ala-His-D-Phe-Arg-Trp-Cys)-Doc-(Arg)₅-Gln-(Arg)₄-NH₂;

(SEQ ID NO: 156)
Ac-Nle-c(Cys-D-Ala-His-D-Phe-Arg-Trp-Cys)-Doc-Gly-(Arg)₅-Gln-(Arg)₄-NH₂;
```

-continued

Ac-Nle-c(Cys-D-Ala-His-D-Phe-Arg-Trp-Cys)-Doc-Tyr-Gly-(Arg)$_5$-Gln-(Arg)$_4$-NH$_2$; (SEQ ID NO: 156)

Ac-Nle-c(Cys-D-Ala-His-D-Phe-Arg-Trp-Cys)-(Doc)$_2$-(Arg)$_5$-Gln-(Arg)$_4$-NH$_2$; (SEQ ID NO: 157)

Ac-Nle-c(Cys-D-Ala-His-D-Phe-Arg-Trp-Cys)-(Doc)$_2$-Gly-(Arg)$_5$-Gln-(Arg)$_4$-NH$_2$; (SEQ ID NO: 158)

Ac-Nle-c(Cys-D-Ala-His-D-Phe-Arg-Trp-Cys)-(Doc)$_2$-Tyr-Gly-(Arg)$_5$-Gln-(Arg)$_4$-NH$_2$; (SEQ ID NO: 158)

Ac-Nle-c(Cys-His-D-Phe-Arg-Trp-Gaba-Cys)-β-Ala-Tyr-Gly-(Arg)$_5$-Gln-(Arg)$_3$-NH$_2$; (SEQ ID NO: 159)

Ac-Nle-c(Cys-His-D-Phe-Arg-Trp-Gaba-Cys)-β-Ala-(Arg)$_5$-Gln-(Arg)$_3$-NH$_2$; (SEQ ID NO: 160)

Ac-Nle-c(Asp-His-D-Phe-Arg-Trp-Ala-Lys)-β-Ala-Tyr-Gly-(Arg)$_5$-Gln-(Arg)$_3$-NH$_2$; (SEQ ID NO: 161)

Ac-Nle-c(Asp-His-D-Phe-Arg-Trp-Ala-Lys)-β-Ala-(Arg)$_5$-Gln-(Arg)$_3$-NH$_2$; (SEQ ID NO: 162)

Ac-Nle-c(Asp-His-D-Phe-Arg-Trp-Lys)-β-Ala-Tyr-Gly-(Arg)$_5$-Gln-(Arg)$_3$-NH$_2$; (SEQ ID NO: 164)

Ac-Nle-c(Asp-His-D-Phe-Arg-Trp-Lys)-β-Ala-Gly-(Arg)$_5$-Gln-(Arg)$_3$-NH$_2$; (SEQ ID NO: 163)

Ac-Nle-c(Asp-His-D-Phe-Arg-Trp-Lys)-β-Ala-(Arg)$_5$-Gln-(Arg)$_3$-NH$_2$; (SEQ ID NO: 163)

Ac-Nle-c(Asp-His-D-Phe-Arg-Trp-Lys)-(β-Ala)$_2$-Tyr-Gly-(Arg)$_5$-Gln-(Arg)$_3$-NH$_2$; (SEQ ID NO: 164)

Ac-Nle-c(Asp-His-D-Phe-Arg-Trp-Lys)-(β-Ala)$_2$-Gly-(Arg)$_5$-Gln-(Arg)$_3$-NH$_2$; (SEQ ID NO: 165)

Ac-Nle-c(Asp-His-D-Phe-Arg-Trp-Lys)-(β-Ala)$_2$-(Arg)$_5$-Gln-(Arg)$_3$-NH$_2$; (SEQ ID NO: 165)

Ac-Nle-c(Asp-His-D-Phe-Arg-Trp-Lys)-Doc-Tyr-Gly-(Arg)$_5$-Gln-(Arg)$_3$-NH$_2$; (SEQ ID NO: 166)

Ac-Nle-c(Asp-His-D-Phe-Arg-Trp-Lys)-Doc-Gly-(Arg)$_5$-Gln-(Arg)$_3$-NH$_2$; (SEQ ID NO: 166)

Ac-Nle-c(Asp-His-D-Phe-Arg-Trp-Lys)-Doc-(Arg)$_5$-Gln-(Arg)$_3$-NH$_2$; (SEQ ID NO: 168)

Ac-Nle-c(Asp-His-D-Phe-Arg-Trp-Lys)-(Doc)$_2$-Tyr-Gly-(Arg)$_5$-Gln-(Arg)$_3$-NH$_2$; (SEQ ID NO: 167)

Ac-Nle-c(Asp-His-D-Phe-Arg-Trp-Lys)-(Doc)$_2$-Gly-(Arg)$_5$-Gln-(Arg)$_3$-NH$_2$; (SEQ ID NO: 167)

Ac-Nle-c(Asp-His-D-Phe-Arg-Trp-Lys)-(Doc)$_2$-(Arg)$_5$-Gln-(Arg)$_3$-NH$_2$; (SEQ ID NO: 168)

Ac-Nle-c(Asp-His-D-Phe-Arg-Trp-Lys)-β-Ala-Tyr-Gly-(Arg)$_5$-Gln-(Arg)$_4$-NH$_2$; (SEQ ID NO: 170)

Ac-Nle-c(Asp-His-D-Phe-Arg-Trp-Lys)-β-Ala-Gly-(Arg)$_5$-Gln-(Arg)$_4$-NH$_2$; (SEQ ID NO: 169)

Ac-Nle-c(Asp-His-D-Phe-Arg-Trp-Lys)-β-Ala-(Arg)$_5$-Gln-(Arg)$_4$-NH$_2$; (SEQ ID NO: 169)

Ac-Nle-c(Asp-His-D-Phe-Arg-Trp-Lys)-(β-Ala)$_2$-Tyr-Gly-(Arg)$_5$-Gln-(Arg)$_4$-NH$_2$; (SEQ ID NO: 170)

Ac-Nle-c(Asp-His-D-Phe-Arg-Trp-Lys)-(β-Ala)$_2$-Gly-(Arg)$_5$-Gln-(Arg)$_4$-NH$_2$; (SEQ ID NO: 171)

Ac-Nle-c(Asp-His-D-Phe-Arg-Trp-Lys)-(β-Ala)$_2$-(Arg)$_5$-Gln-(Arg)$_4$-NH$_2$; (SEQ ID NO: 171)

Ac-Nle-c(Asp-His-D-Phe-Arg-Trp-Lys)-Doc-Tyr-Gly-(Arg)$_5$-Gln-(Arg)$_4$-NH$_2$; (SEQ ID NO: 173)

-continued (SEQ ID NO: 172)
Ac-Nle-c(Asp-His-D-Phe-Arg-Trp-Lys)-Doc-Gly-(Arg)$_5$-Gln-(Arg)$_4$-NH$_2$;

(SEQ ID NO: 172)
Ac-Nle-c(Asp-His-D-Phe-Arg-Trp-Lys)-Doc-(Arg)$_5$-Gln-(Arg)$_4$-NH$_2$;

(SEQ ID NO: 173)
Ac-Nle-c(Asp-His-D-Phe-Arg-Trp-Lys)-(Doc)$_2$-Tyr-Gly-(Arg)$_5$-Gln-(Arg)$_4$-NH$_2$;

(SEQ ID NO: 174)
Ac-Nle-c(Asp-His-D-Phe-Arg-Trp-Lys)-(Doc)$_2$-Gly-(Arg)$_5$-Gln-(Arg)$_4$-NH$_2$;

(SEQ ID NO: 174)
Ac-Nle-c(Asp-His-D-Phe-Arg-Trp-Lys)-(Doc)$_2$-(Arg)$_5$-Gln-(Arg)$_4$-NH$_2$;

(SEQ ID NO: 175)
Ac-Nle-c(Asp-His-D-Phe-Arg-Trp-β-Ala-Lys)-β-Ala-Tyr-Gly-(Arg)$_5$-Gln-(Arg)$_3$-NH$_2$;

(SEQ ID NO: 176)
Ac-Nle-c(Asp-His-D-Phe-Arg-Trp-β-Ala-Lys)-β-Ala-(Arg)$_5$-Gln-(Arg)$_3$-NH$_2$;

(SEQ ID NO: 177)
Ac-Nle-c(Cys-His-D-Phe-Arg-Trp-Ahx-Cys)-β-Ala-Tyr-Gly-(Arg)$_5$-Gln-(Arg)$_3$-NH$_2$;

(SEQ ID NO: 178)
Ac-Nle-c(Cys-His-D-Phe-Arg-Trp-Ahx-Cys)-β-Ala-(Arg)$_5$-Gln-(Arg)$_3$-NH$_2$;

(SEQ ID NO: 179)
D-Phe-c(Cys-His-D-Phe-Arg-Trp-β-Ala-D-Cys)-Thr-β-Ala-Tyr-Gly-(Arg)$_5$-Gln-(Arg)$_3$-NH$_2$;

(SEQ ID NO: 180)
D-Phe-c(Cys-His-D-Phe-Arg-Trp-β-Ala-D-Cys)-Thr-β-Ala-(Arg)$_5$-Gln-(Arg)$_3$-NH$_2$;

(SEQ ID NO: 181)
Ac-Nle-c(Cys-His-D-Phe-Arg-Trp-Apn-Cys)-β-Ala-Tyr-Gly-(Arg)$_5$-Gln-(Arg)$_3$-NH$_2$;

(SEQ ID NO: 182)
Ac-Nle-c(Cys-His-D-Phe-Arg-Trp-Apn-Cys)-β-Ala-(Arg)$_5$-Gln-(Arg)$_3$-NH$_2$;

(SEQ ID NO: 183)
Ac-Cha-c(Asp-His-D-Phe-Arg-Trp-Gaba-Lys)-β-Ala-Tyr-Gly-(Arg)$_5$-Gln-(Arg)$_3$-NH$_2$;

(SEQ ID NO: 184)
Ac-Cha-c(Asp-His-D-Phe-Arg-Trp-Gaba-Lys)-β-Ala-(Arg)$_5$-Gln-(Arg)$_3$-NH$_2$;

(SEQ ID NO: 183)
Ac-Nle-c(Asp-His-D-Phe-Arg-Trp-Gaba-Lys)-β-Ala-Tyr-Gly-(Arg)$_5$-Gln-(Arg)$_3$-NH$_2$;

(SEQ ID NO: 185)
Ac-Nle-c(Asp-His-D-Phe-Arg-Trp-Gaba-Lys)-β-Ala-(Arg)$_5$-Gln-(Arg)$_3$-NH$_2$;

(SEQ ID NO: 186)
Ac-Chg-c(Asp-His-D-Phe-Arg-Trp-Gaba-Lys)-β-Ala-Tyr-Gly-(Arg)$_5$-Gln-(Arg)$_3$-NH$_2$;

(SEQ ID NO: 185)
Ac-Chg-c(Asp-His-D-Phe-Arg-Trp-Gaba-Lys)-β-Ala-(Arg)$_5$-Gln-(Arg)$_3$-NH$_2$;

(SEQ ID NO: 186)
Ac-hCha-c(Asp-His-D-Phe-Arg-Trp-Gaba-Lys)-β-Ala-Tyr-Gly-(Arg)$_5$-Gln-(Arg)$_3$-NH$_2$;

(SEQ ID NO: 188)
Ac-hCha-c(Asp-His-D-Phe-Arg-Trp-Gaba-Lys)-β-Ala-(Arg)$_5$-Gln-(Arg)$_3$-NH$_2$;

(SEQ ID NO: 187)
Ac-hCha-c(Asp-His-D-Phe-Arg-Trp-Gaba-Lys)-(β-Ala)$_2$-Tyr-Gly-(Arg)$_5$-Gln-(Arg)$_3$-NH$_2$;

(SEQ ID NO: 188)
Ac-hCha-c(Asp-His-D-Phe-Arg-Trp-Gaba-Lys)-(β-Ala)$_2$-(Arg)$_5$-Gln-(Arg)$_3$-NH$_2$;

(SEQ ID NO: 189)
Ac-hCha-c(Asp-His-D-Phe-Arg-Trp-Gaba-Lys)-Doc-Tyr-Gly-(Arg)$_5$-Gln-(Arg)$_3$-NH$_2$;

(SEQ ID NO: 190)
Ac-hCha-c(Asp-His-D-Phe-Arg-Trp-Gaba-Lys)-Doc-(Arg)$_5$-Gln-(Arg)$_3$-NH$_2$;

(SEQ ID NO: 189)
Ac-hCha-c(Asp-His-D-Phe-Arg-Trp-Gaba-Lys)-(Doc)$_2$-Tyr-Gly-(Arg)$_5$-Gln-(Arg)$_3$-NH$_2$;

Ac-hCha-c(Asp-His-D-Phe-Arg-Trp-Gaba-Lys)-(Doc)₂-(Arg)₅-Gln-(Arg)₃-NH₂;  (SEQ ID NO: 190)

Ac-hCha-c(Asp-His-D-Phe-Arg-Trp-Gaba-Lys)-β-Ala-Tyr-Gly-(Arg)₅-Gln-(Arg)₄-NH₂;  (SEQ ID NO: 191)

Ac-hCha-c(Asp-His-D-Phe-Arg-Trp-Gaba-Lys)-β-Ala-(Arg)₅-Gln-(Arg)₄-NH₂;  (SEQ ID NO: 192)

Ac-hCha-c(Asp-His-D-Phe-Arg-Trp-Gaba-Lys)-(β-Ala)₂-Tyr-Gly-(Arg)₅-Gln-(Arg)₄-NH₂;  (SEQ ID NO: 191)

Ac-hCha-c(Asp-His-D-Phe-Arg-Trp-Gaba-Lys)-(β-Ala)₂-(Arg)₅-Gln-(Arg)₄-NH₂;  (SEQ ID NO: 192)

Ac-hCha-c(Asp-His-D-Phe-Arg-Trp-Gaba-Lys)-Doc-Tyr-Gly-(Arg)₅-Gln-(Arg)₄-NH₂;  (SEQ ID NO: 193)

Ac-hCha-c(Asp-His-D-Phe-Arg-Trp-Gaba-Lys)-Doc-(Arg)₅-Gln-(Arg)₄-NH₂;  (SEQ ID NO: 194)

Ac-hCha-c(Asp-His-D-Phe-Arg-Trp-Gaba-Lys)-(Doc)₂-Tyr-Gly-(Arg)₅-Gln-(Arg)₄-NH₂;  (SEQ ID NO: 193)

Ac-hCha-c(Asp-His-D-Phe-Arg-Trp-Gaba-Lys)-(Doc)₂-(Arg)₅-Gln-(Arg)₄-NH₂;  (SEQ ID NO: 194)

Ac-D-Chg-c(Asp-His-D-Phe-Arg-Trp-Gaba-Lys)-β-Ala-Tyr-Gly-(Arg)₅-Gln-(Arg)₃-NH₂;  (SEQ ID NO: 195)

Ac-D-Chg-c(Asp-His-D-Phe-Arg-Trp-Gaba-Lys)-β-Ala-(Arg)₅-Gln-(Arg)₃-NH₂;  (SEQ ID NO: 196)

Ac-hPhe-c(Asp-His-D-Phe-Arg-Trp-Gaba-Lys)-β-Ala-Tyr-Gly-(Arg)₅-Gln-(Arg)₃-NH₂;  (SEQ ID NO: 197)

Ac-hPhe-c(Asp-His-D-Phe-Arg-Trp-Gaba-Lys)-β-Ala-(Arg)₅-Gln-(Arg)₃-NH₂;  (SEQ ID NO: 198)

Ac-Nle-c(Cys-His-D-Phe-Arg-D-Trp-Apn-Cys)-β-Ala-Tyr-Gly-(Arg)₅-Gln-(Arg)₃-NH₂;  (SEQ ID NO: 199)

Ac-Nle-c(Cys-His-D-Phe-Arg-D-Trp-Apn-Cys)-β-Ala-(Arg)₅-Gln-(Arg)₃-NH₂;  (SEQ ID NO: 200)

Ac-Nle-c(Cys-His-D-Phe-Arg-D-Trp-Ahx-Cys)-β-Ala-Tyr-Gly-(Arg)₅-Gln-(Arg)₃-NH₂;  (SEQ ID NO: 199)

Ac-Nle-c(Cys-His-D-Phe-Arg-D-Trp-Ahx-Cys)-β-Ala-(Arg)₅-Gln-(Arg)₃-NH₂;  (SEQ ID NO: 200)

Ac-Nle-c(Cys-His-D-Phe-Arg-D-Trp-β-Ala-Cys)-β-Ala-Tyr-Gly-(Arg)₅-Gln-(Arg)₃-NH₂;  (SEQ ID NO: 201)

Ac-Nle-c(Cys-His-D-Phe-Arg-D-Trp-β-Ala-Cys)-β-Ala-(Arg)₅-Gln-(Arg)₃-NH₂;  (SEQ ID NO: 202)

Ac-Nle-c(Cys-D-Ala-His-D-Phe-Arg-Trp-Pen)-β-Ala-Tyr-Gly-(Arg)₅-Gln-(Arg)₃-NH₂;  (SEQ ID NO: 203)

Ac-Nle-c(Cys-D-Ala-His-D-Phe-Arg-Trp-Pen)-β-Ala-Gly-(Arg)₅-Gln-(Arg)₃-NH₂;  (SEQ ID NO: 203)

Ac-Nle-c(Cys-D-Ala-His-D-Phe-Arg-Trp-Pen)-β-Ala-(Arg)₅-Gln-(Arg)₃-NH₂;  (SEQ ID NO: 205)

Ac-Nle-c(Cys-D-Ala-His-D-Phe-Arg-Trp-Pen)-(β-Ala)₂-Tyr-Gly-(Arg)₅-Gln-(Arg)₃-NH₂;  (SEQ ID NO: 204)

Ac-Nle-c(Cys-D-Ala-His-D-Phe-Arg-Trp-Pen)-(β-Ala)₂-Gly-(Arg)₅-Gln-(Arg)₃-NH₂;  (SEQ ID NO: 204)

Ac-Nle-c(Cys-D-Ala-His-D-Phe-Arg-Trp-Pen)-(β-Ala)₂-(Arg)₅-Gln-(Arg)₃-NH₂;  (SEQ ID NO: 205)

Ac-Nle-c(Cys-D-Ala-His-D-Phe-Arg-Trp-Pen)-Doc-Tyr-Gly-(Arg)₅-Gln-(Arg)₃-NH₂;  (SEQ ID NO: 207)

Ac-Nle-c(Cys-D-Ala-His-D-Phe-Arg-Trp-Pen)-Doc-Gly-(Arg)₅-Gln-(Arg)₃-NH₂;  (SEQ ID NO: 206)

```
                                                                      (SEQ ID NO: 206)
Ac-Nle-c(Cys-D-Ala-His-D-Phe-Arg-Trp-Pen)-Doc-(Arg)5-Gln-(Arg)3-NH2;

(SEQ ID NO: 207)
Ac-Nle-c(Cys-D-Ala-His-D-Phe-Arg-Trp-Pen)-(Doc)2-Tyr-Gly-(Arg)5-Gln-(Arg)3-NH2;

(SEQ ID NO: 208)
Ac-Nle-c(Cys-D-Ala-His-D-Phe-Arg-Trp-Pen)-(Doc)2-Gly-(Arg)5-Gln-(Arg)3-NH2;

(SEQ ID NO: 208)
Ac-Nle-c(Cys-D-Ala-His-D-Phe-Arg-Trp-Pen)-(Doc)2-(Arg)5-Gln-(Arg)3-NH2;

(SEQ ID NO: 209)
D-Phe-c(Cys-His-D-(Et)Tyr-Arg-Trp-β-Ala-D-Cys)-β-Ala-Tyr-Gly-(Arg)5-Gln-(Arg)3-
NH2;

(SEQ ID NO: 210)
D-Phe-c(Cys-His-D-(Et)Tyr-Arg-Trp-β-Ala-D-Cys)-β-Ala-(Arg)5-Gln-(Arg)3-NH2;

(SEQ ID NO: 209)
D-Phe-c(Cys-His-D-(Et)Tyr-Arg-Trp-β-Ala-D-Cys)-β-Ala-Gly-(Arg)5-Gln-(Arg)3-NH2;

(SEQ ID NO: 211)
D-Phe-c(Cys-His-D-(Et)Tyr-Arg-Trp-β-Ala-D-Cys)-β-Ala-(Arg)5-Gln-(Arg)4-NH2;

(SEQ ID NO: 212)
D-Phe-c(Cys-His-D-(Et)Tyr-Arg-Trp-β-Ala-D-Cys)-(β-Ala)2-Tyr-Gly-(Arg)5-Gln-(Arg)3-
NH2;

(SEQ ID NO: 213)
D-Phe-c(Cys-His-D-(Et)Tyr-Arg-Trp-β-Ala-D-Cys)-(β-Ala)2-(Arg)5-Gln-(Arg)3-NH2;

(SEQ ID NO: 213)
D-Phe-c(Cys-His-D-(Et)Tyr-Arg-Trp-β-Ala-D-Cys)-(β-Ala)2-Gly-(Arg)5-Gln-(Arg)3-NH2;

(SEQ ID NO: 267)
D-Phe-c(Cys-His-D-(Et)Tyr-Arg-Trp-β-Ala-D-Cys)-(β-Ala)2-(Arg)5-Gln-(Arg)4-NH2;

(SEQ ID NO: 214)
D-Phe-c(Cys-His-D-(Et)Tyr-Arg-Trp-β-Ala-D-Cys)-Doc-Tyr-Gly-(Arg)5-Gln-(Arg)3-NH2;

(SEQ ID NO: 216)
D-Phe-c(Cys-His-D-(Et)Tyr-Arg-Trp-β-Ala-D-Cys)-Doc-(Arg)5-Gln-(Arg)3-NH2;

(SEQ ID NO: 214)
D-Phe-c(Cys-His-D-(Et)Tyr-Arg-Trp-β-Ala-D-Cys)-Doc-Gly-(Arg)5-Gln-(Arg)3-NH2;

(SEQ ID NO: 217)
D-Phe-c(Cys-His-D-(Et)Tyr-Arg-Trp-β-Ala-D-Cys)-Doc-(Arg)5-Gln-(Arg)4-NH2;

(SEQ ID NO: 215)
D-Phe-c(Cys-His-D-(Et)Tyr-Arg-Trp-β-Ala-D-Cys)-(Doc)2-Tyr-Gly-(Arg)5-Gln-(Arg)3-
NH2;

(SEQ ID NO: 216)
D-Phe-c(Cys-His-D-(Et)Tyr-Arg-Trp-β-Ala-D-Cys)-(Doc)2-(Arg)5-Gln-(Arg)3-NH2;

(SEQ ID NO: 215)
D-Phe-c(Cys-His-D-(Et)Tyr-Arg-Trp-β-Ala-D-Cys)-(Doc)2-Gly-(Arg)5-Gln-(Arg)3-NH2;

(SEQ ID NO: 217)
D-Phe-c(Cys-His-D-(Et)Tyr-Arg-Trp-β-Ala-D-Cys)-(Doc)2-(Arg)5-Gln-(Arg)4-NH2;

(SEQ ID NO: 218)
D-Phe-c(Cys-His-D-(Et)Tyr-hArg-Trp-β-Ala-D-Cys)-Thr-β-Ala-Tyr-Gly-(Arg)5-Gln-
(Arg)3-NH2;

(SEQ ID NO: 219)
D-Phe-c(Cys-His-D-(Et)Tyr-hArg-Trp-β-Ala-D-Cys)-Thr-β-Ala-(Arg)5-Gln-(Arg)3-NH2;

(SEQ ID NO: 218)
D-Phe-c(Cys-His-D-(Et)Tyr-hArg-Trp-β-Ala-D-Cys)-Thr-(β-Ala)2-Tyr-Gly-(Arg)5-Gln-
(Arg)3-NH2;
```

-continued (SEQ ID NO: 219)
D-Phe-c(Cys-His-D-(Et)Tyr-hArg-Trp-β-Ala-D-Cys)-Thr-(β-Ala)$_2$-(Arg)$_5$-Gln-(Arg)$_3$-NH$_2$;

(SEQ ID NO: 221)
D-Phe-c(Cys-His-D-(Et)Tyr-hArg-Trp-β-Ala-D-Cys)-Thr-Doc-Tyr-Gly-(Arg)$_5$-Gln-(Arg)$_3$-NH$_2$;

(SEQ ID NO: 220)
D-Phe-c(Cys-His-D-(Et)Tyr-hArg-Trp-β-Ala-D-Cys)-Thr-Doc-(Arg)$_5$-Gln-(Arg)$_3$-NH$_2$;

(SEQ ID NO: 221)
D-Phe-c(Cys-His-D-(Et)Tyr-hArg-Trp-β-Ala-D-Cys)-Thr-(Doc)$_2$-Tyr-Gly-(Arg)$_5$-Gln-(Arg)$_3$-NH$_2$;

(SEQ ID NO: 222)
D-Phe-c(Cys-His-D-(Et)Tyr-hArg-Trp-β-Ala-D-Cys)-Thr-β-Ala-Tyr-Gly-(Arg)$_5$-Gln-(Arg)$_4$-NH$_2$;

(SEQ ID NO: 223)
D-Phe-c(Cys-His-D-(Et)Tyr-hArg-Trp-β-Ala-D-Cys)-Thr-β-Ala-(Arg)$_5$-Gln-(Arg)$_4$-NH$_2$;

(SEQ ID NO: 222)
D-Phe-c(Cys-His-D-(Et)Tyr-hArg-Trp-β-Ala-D-Cys)-Thr-(β-Ala)$_2$-Tyr-Gly-(Arg)$_5$-Gln-(Arg)$_4$-NH$_2$;

(SEQ ID NO: 223)
D-Phe-c(Cys-His-D-(Et)Tyr-hArg-Trp-β-Ala-D-Cys)-Thr-(β-Ala)$_2$-(Arg)$_5$-Gln-(Arg)$_4$-NH$_2$;

(SEQ ID NO: 224)
D-Phe-c(Cys-His-D-(Et)Tyr-hArg-Trp-β-Ala-D-Cys)-Thr-Doc-Tyr-Gly-(Arg)$_5$-Gln-(Arg)$_4$-NH$_2$;

(SEQ ID NO: 225)
D-Phe-c(Cys-His-D-(Et)Tyr-hArg-Trp-β-Ala-D-Cys)-Thr-Doc-(Arg)$_5$-Gln-(Arg)$_4$-NH$_2$;

(SEQ ID NO: 224)
D-Phe-c(Cys-His-D-(Et)Tyr-hArg-Trp-β-Ala-D-Cys)-Thr-(Doc)$_2$-Tyr-Gly-(Arg)$_5$-Gln-(Arg)$_4$-NH$_2$;

(SEQ ID NO: 225)
D-Phe-c(Cys-His-D-(Et)Tyr-hArg-Trp-β-Ala-D-Cys)-Thr-(Doc)$_2$-(Arg)$_5$-Gln-(Arg)$_4$-NH$_2$;

(SEQ ID NO: 227)
D-Phe-c(Cys-His-D-(Et)Tyr-hArg-Bip-β-Ala-D-Cys)-Thr-β-Ala-Tyr-Gly-(Arg)$_5$-Gln-(Arg)$_3$-NH$_2$;

(SEQ ID NO: 226)
D-Phe-c(Cys-His-D-(Et)Tyr-hArg-Bip-β-Ala-D-Cys)-Thr-β-Ala-Tyr-Gly-(Arg)$_5$-Gln-(Arg)$_4$-NH$_2$;

(SEQ ID NO: 228)
D-Phe-c(Cys-His-D-(Et)Tyr-hArg-Bip-β-Ala-D-Cys)-Thr-β-Ala-(Arg)$_5$-Gln-(Arg)$_3$-NH$_2$;

(SEQ ID NO: 227)
D-Phe-c(Cys-His-D-(Et)Tyr-hArg-Bip-β-Ala-D-Cys)-Thr-(β-Ala)$_2$-Tyr-Gly-(Arg)$_5$-Gln-(Arg)$_3$-NH$_2$;

(SEQ ID NO: 228)
D-Phe-c(Cys-His-D-(Et)Tyr-hArg-Bip-β-Ala-D-Cys)-Thr-(β-Ala)$_2$-(Arg)$_5$-Gln-(Arg)$_3$-NH$_2$;

(SEQ ID NO: 229)
D-Phe-c(Cys-His-D-(Et)Tyr-hArg-Bip-β-Ala-D-Cys)-Thr-Doc-Tyr-Gly-(Arg)$_5$-Gln-(Arg)$_3$-NH$_2$;

(SEQ ID NO: 230)
D-Phe-c(Cys-His-D-(Et)Tyr-hArg-Bip-β-Ala-D-Cys)-Thr-Doc-Tyr-Gly-(Arg)$_5$-Gln-(Arg)$_4$-NH$_2$;

-continued

D-Phe-c(Cys-His-D-(Et)Tyr-hArg-Bip-β-Ala-D-Cys)-Thr-Doc-(Arg)$_5$-Gln-(Arg)$_3$-NH$_2$; (SEQ ID NO: 232)

D-Phe-c(Cys-His-D-(Et)Tyr-hArg-Bip-β-Ala-D-Cys)-Thr-(Doc)$_2$-Tyr-Gly-(Arg)$_5$-Gln-(Arg)$_3$-NH$_2$; (SEQ ID NO: 231)

D-Phe-c(Cys-His-D-(Et)Tyr-hArg-Bip-β-Ala-D-Cys)-Thr-(Doc)$_2$-(Arg)$_5$-Gln-(Arg)$_3$-NH$_2$; (SEQ ID NO: 232)

Ac-Nle-c(Cys-D-Ala-His-D-Phe-Arg-Trp-Gly-Cys)-β-Ala-Tyr-Gly-(Arg)$_5$-Gln-(Arg)$_3$-NH$_2$; (SEQ ID NO: 233)

Ac-Nle-c(Cys-D-Ala-His-D-Phe-Arg-Trp-Gly-Cys)-β-Ala-(Arg)$_5$-Gln-(Arg)$_3$-NH$_2$; (SEQ ID NO: 234)

Nle-c(Cys-His-D-Phe-Arg-Trp-Apn-Cys)-β-Ala-Tyr-Gly-(Arg)$_5$-Gln-(Arg)$_3$-NH$_2$; (SEQ ID NO: 235)

Nle-c(Cys-His-D-Phe-Arg-Trp-Apn-Cys)-β-Ala-(Arg)$_5$-Gln-(Arg)$_3$-NH$_2$; (SEQ ID NO: 236)

Nle-c(Cys-His-D-Phe-Arg-Trp-Apn-Cys)-(β-Ala)$_2$-Tyr-Gly-(Arg)$_5$-Gln-(Arg)$_3$-NH$_2$; (SEQ ID NO: 235)

Nle-c(Cys-His-D-Phe-Arg-Trp-Apn-Cys)-(β-Ala)$_2$-(Arg)$_5$-Gln-(Arg)$_3$-NH$_2$; (SEQ ID NO: 236)

Nle-c(Cys-His-D-Phe-Arg-Trp-Apn-Cys)-β-Ala-Tyr-Gly-(Arg)$_5$-Gln-(Arg)$_4$-NH$_2$; (SEQ ID NO: 237)

Nle-c(Cys-His-D-Phe-Arg-Trp-Apn-Cys)-β-Ala-(Arg)$_5$-Gln-(Arg)$_4$-NH$_2$; (SEQ ID NO: 238)

Nle-c(Cys-His-D-Phe-Arg-Trp-Apn-Cys)-(β-Ala)$_2$-Tyr-Gly-(Arg)$_5$-Gln-(Arg)$_4$-NH$_2$; (SEQ ID NO: 237)

Nle-c(Cys-His-D-Phe-Arg-Trp-Apn-Cys)-(β-Ala)$_2$-(Arg)$_5$-Gln-(Arg)$_4$-NH$_2$; (SEQ ID NO: 238)

Nle-c(Cys-His-D-Phe-Arg-Trp-Apn-Cys)-Doc-Tyr-Gly-(Arg)$_5$-Gln-(Arg)$_3$-NH$_2$; (SEQ ID NO: 239)

Nle-c(Cys-His-D-Phe-Arg-Trp-Apn-Cys)-Doc-(Arg)$_5$-Gln-(Arg)$_3$-NH$_2$; (SEQ ID NO: 240)

Nle-c(Cys-His-D-Phe-Arg-Trp-Apn-Cys)-(Doc)$_2$-Tyr-Gly-(Arg)$_5$-Gln-(Arg)$_3$-NH$_2$; (SEQ ID NO: 239)

Nle-c(Cys-His-D-Phe-Arg-Trp-Apn-Cys)-(Doc)$_2$-(Arg)$_5$-Gln-(Arg)$_3$-NH$_2$; (SEQ ID NO: 240)

Nle-c(Cys-His-D-Phe-Arg-Trp-Apn-Cys)-Doc-Tyr-Gly-(Arg)$_5$-Gln-(Arg)$_4$-NH$_2$; (SEQ ID NO: 241)

Nle-c(Cys-His-D-Phe-Arg-Trp-Apn-Cys)-Doc-(Arg)$_5$-Gln-(Arg)$_4$-NH$_2$; (SEQ ID NO: 242)

Nle-c(Cys-His-D-Phe-Arg-Trp-Apn-Cys)-(Doc)$_2$-Tyr-Gly-(Arg)$_5$-Gln-(Arg)$_4$-NH$_2$; (SEQ ID NO: 241)

Nle-c(Cys-His-D-Phe-Arg-Trp-Apn-Cys)-(Doc)$_2$-(Arg)$_5$-Gln-(Arg)$_4$-NH$_2$; (SEQ ID NO: 242)

Ac-Nle-c(Cys-D-Leu-His-D-Phe-Arg-Trp-Cys)-β-Ala-Tyr-Gly-(Arg)$_5$-Gln-(Arg)$_3$-NH$_2$; (SEQ ID NO: 243)

Ac-Nle-c(Cys-D-Leu-His-D-Phe-Arg-Trp-Cys)-β-Ala-(Arg)$_5$-Gln-(Arg)$_3$-NH$_2$; (SEQ ID NO: 244)

Ac-Nle-c(Cys-D-Leu-His-D-Phe-Arg-Trp-Cys)-(β-Ala)$_2$-Tyr-Gly-(Arg)$_5$-Gln-(Arg)$_3$-NH$_2$; (SEQ ID NO: 243)

Ac-Nle-c(Cys-D-Leu-His-D-Phe-Arg-Trp-Cys)-(β-Ala)$_2$-(Arg)$_5$-Gln-(Arg)$_3$-NH$_2$; (SEQ ID NO: 244)

Ac-Nle-c(Cys-D-Leu-His-D-Phe-Arg-Trp-Cys)-Doc-Tyr-Gly-(Arg)$_5$-Gln-(Arg)$_3$-NH$_2$; (SEQ ID NO: 245)

-continued

```
                                                      (SEQ ID NO: 246)
Ac-Nle-c(Cys-D-Leu-His-D-Phe-Arg-Trp-Cys)-Doc-(Arg)5-Gln-(Arg)3-NH2;

(SEQ ID NO: 245)
Ac-Nle-c(Cys-D-Leu-His-D-Phe-Arg-Trp-Cys)-(Doc)2-Tyr-Gly-(Arg)5-Gln-(Arg)3-NH2;

(SEQ ID NO: 246)
Ac-Nle-c(Cys-D-Leu-His-D-Phe-Arg-Trp-Cys)-(Doc)2-(Arg)5-Gln-(Arg)3-NH2;

(SEQ ID NO: 247)
Ac-Nle-c(Cys-D-Leu-His-D-Phe-Arg-Trp-Cys)-β-Ala-Tyr-Gly-(Arg)5-Gln-(Arg)4-NH2;

(SEQ ID NO: 248)
Ac-Nle-c(Cys-D-Leu-His-D-Phe-Arg-Trp-Cys)-β-Ala-(Arg)5-Gln-(Arg)4-NH2;

(SEQ ID NO: 247)
Ac-Nle-c(Cys-D-Leu-His-D-Phe-Arg-Trp-Cys)-(β-Ala)2-Tyr-Gly-(Arg)5-Gln-(Arg)4-NH2;

(SEQ ID NO: 248)
Ac-Nle-c(Cys-D-Leu-His-D-Phe-Arg-Trp-Cys)-(β-Ala)2-(Arg)5-Gln-(Arg)4-NH2;

(SEQ ID NO: 249)
Ac-Nle-c(Cys-D-Leu-His-D-Phe-Arg-Trp-Cys)-Doc-Tyr-Gly-(Arg)5-Gln-(Arg)4-NH2;

(SEQ ID NO: 250)
Ac-Nle-c(Cys-D-Leu-His-D-Phe-Arg-Trp-Cys)-Doc-(Arg)5-Gln-(Arg)4-NH2;

(SEQ ID NO: 249)
Ac-Nle-c(Cys-D-Leu-His-D-Phe-Arg-Trp-Cys)-(Doc)2-Tyr-Gly-(Arg)5-Gln-(Arg)4-NH2;

(SEQ ID NO: 250)
Ac-Nle-c(Cys-D-Leu-His-D-Phe-Arg-Trp-Cys)-(Doc)2-(Arg)5-Gln-(Arg)4-NH2;

(SEQ ID NO: 251)
Ac-Nle-c(Cys-D-Cha-His-D-Phe-Arg-Trp-Cys)-β-Ala-Tyr-Gly-(Arg)5-Gln-(Arg)3-NH2;

(SEQ ID NO: 252)
Ac-Nle-c(Cys-D-Cha-His-D-Phe-Arg-Trp-Cys)-β-Ala-(Arg)5-Gln-(Arg)3-NH2;

(SEQ ID NO: 251)
Ac-Nle-c(Cys-D-Cha-His-D-Phe-Arg-Trp-Cys)-(β-Ala)2-Tyr-Gly-(Arg)5-Gln-(Arg)3-NH2;

(SEQ ID NO: 252)
Ac-Nle-c(Cys-D-Cha-His-D-Phe-Arg-Trp-Cys)-(β-Ala)2-(Arg)5-Gln-(Arg)3-NH2;

(SEQ ID NO: 253)
Ac-Nle-c(Cys-D-Cha-His-D-Phe-Arg-Trp-Cys)-Doc-Tyr-Gly-(Arg)5-Gln-(Arg)3-NH2;

(SEQ ID NO: 254)
Ac-Nle-c(Cys-D-Cha-His-D-Phe-Arg-Trp-Cys)-Doc-(Arg)5-Gln-(Arg)3-NH2;

(SEQ ID NO: 253)
Ac-Nle-c(Cys-D-Cha-His-D-Phe-Arg-Trp-Cys)-(Doc)2-Tyr-Gly-(Arg)5-Gln-(Arg)3-NH2;

(SEQ ID NO: 254)
Ac-Nle-c(Cys-D-Cha-His-D-Phe-Arg-Trp-Cys)-(Doc)2-(Arg)5-Gln-(Arg)3-NH2;

(SEQ ID NO: 255)
Ac-Nle-c(Cys-D-Cha-His-D-Phe-Arg-Trp-Cys)-β-Ala-Tyr-Gly-(Arg)5-Gln-(Arg)4-NH2;

(SEQ ID NO: 256)
Ac-Nle-c(Cys-D-Cha-His-D-Phe-Arg-Trp-Cys)-β-Ala-(Arg)5-Gln-(Arg)4-NH2;

(SEQ ID NO: 255)
Ac-Nle-c(Cys-D-Cha-His-D-Phe-Arg-Trp-Cys)-(β-Ala)2-Tyr-Gly-(Arg)5-Gln-(Arg)4-NH2;

(SEQ ID NO: 256)
Ac-Nle-c(Cys-D-Cha-His-D-Phe-Arg-Trp-Cys)-(β-Ala)2-(Arg)5-Gln-(Arg)4-NH2;

(SEQ ID NO: 257)
Ac-Nle-c(Cys-D-Cha-His-D-Phe-Arg-Trp-Cys)-Doc-Tyr-Gly-(Arg)5-Gln-(Arg)4-NH2;

(SEQ ID NO: 258)
Ac-Nle-c(Cys-D-Cha-His-D-Phe-Arg-Trp-Cys)-Doc-(Arg)5-Gln-(Arg)4-NH2;

(SEQ ID NO: 257)
Ac-Nle-c(Cys-D-Cha-His-D-Phe-Arg-Trp-Cys)-(Doc)2-Tyr-Gly-(Arg)5-Gln-(Arg)4-NH2;

(SEQ ID NO: 258)
Ac-Nle-c(Cys-D-Cha-His-D-Phe-Arg-Trp-Cys)-(Doc)2-(Arg)5-Gln-(Arg)4-NH2;
```

Nle-c(Cys-His-D-Phe-Arg-Trp-Gaba-Cys)-β-Ala-Tyr-Gly-(Arg)₅-Gln-(Arg)₃-NH₂; (SEQ ID NO: 259)

Nle-c(Cys-His-D-Phe-Arg-Trp-Gaba-Cys)-β-Ala-(Arg)₅-Gln-(Arg)₃-NH₂; (SEQ ID NO: 260)

Nle-c(Cys-His-D-Phe-Arg-Trp-Gaba-Cys)-(β-Ala)₂-Tyr-Gly-(Arg)₅-Gln-(Arg)₃-NH₂; (SEQ ID NO: 259)

Nle-c(Cys-His-D-Phe-Arg-Trp-Gaba-Cys)-(β-Ala)₂-(Arg)₅-Gln-(Arg)₃-NH₂; (SEQ ID NO: 260)

Nle-c(Cys-His-D-Phe-Arg-Trp-Gaba-Cys)-β-Ala-Tyr-Gly-(Arg)₅-Gln-(Arg)₄-NH₂; (SEQ ID NO: 261)

Nle-c(Cys-His-D-Phe-Arg-Trp-Gaba-Cys)-β-Ala-(Arg)₅-Gln-(Arg)₄-NH₂; (SEQ ID NO: 262)

Nle-c(Cys-His-D-Phe-Arg-Trp-Gaba-Cys)-(β-Ala)₂-Tyr-Gly-(Arg)₅-Gln-(Arg)₄-NH₂; (SEQ ID NO: 261)

Nle-c(Cys-His-D-Phe-Arg-Trp-Gaba-Cys)-(β-Ala)₂-(Arg)₅-Gln-(Arg)₄-NH₂; (SEQ ID NO: 262)

Nle-c(Cys-His-D-Phe-Arg-Trp-Gaba-Cys)-Doc-Tyr-Gly-(Arg)₅-Gln-(Arg)₃-NH₂; (SEQ ID NO: 263)

Nle-c(Cys-His-D-Phe-Arg-Trp-Gaba-Cys)-Doc-(Arg)₅-Gln-(Arg)₃-NH₂; (SEQ ID NO: 264)

Nle-c(Cys-His-D-Phe-Arg-Trp-Gaba-Cys)-(Doc)₂-Tyr-Gly-(Arg)₅-Gln-(Arg)₃-NH₂; (SEQ ID NO: 263)

Nle-c(Cys-His-D-Phe-Arg-Trp-Gaba-Cys)-(Doc)₂-(Arg)₅-Gln-(Arg)₃-NH₂; (SEQ ID NO: 264)

Nle-c(Cys-His-D-Phe-Arg-Trp-Gaba-Cys)-Doc-Tyr-Gly-(Arg)₅-Gln-(Arg)₄-NH₂; (SEQ ID NO: 265)

Nle-c(Cys-His-D-Phe-Arg-Trp-Gaba-Cys)-Doc-(Arg)₅-Gln-(Arg)₄-NH₂; (SEQ ID NO: 266)

Nle-c(Cys-His-D-Phe-Arg-Trp-Gaba-Cys)-(Doc)₂-Tyr-Gly-(Arg)₅-Gln-(Arg)₄-NH₂; (SEQ ID NO: 265)
or Nle-c(Cys-His-D-Phe-Arg-Trp-Gaba-Cys)-(Doc)₂-(Arg)₅-Gln-(Arg)₄-NH₂;; (SEQ ID NO: 266)

or pharmaceutically acceptable salts thereof.

In a fourth embodiment, the invention provides a method to treat insulin resistance in a mammalian subject, with or without weight loss, by the administration of a therapeutically effective amount of a melanocortin receptor compound according to Formula (IV), and pharmaceutically acceptable salts, hydrates, solvates and prodrugs thereof, with a compound having the following formula (formula (IV)):

Ac-c(Cys-Glu-His-A¹-Arg-A²-A³-Cys)-(Pro)₂-Lys-Asp-NH₂ (IV)

wherein:
A¹ is the D-isomer of X-Phe or 2-Nal where X is halogen;
A² is Bal, 1-Nal, 2-Nal, or Trp; and
A³ is Aib, Ala, β-Ala or Gly,
or pharmaceutically acceptable salts thereof.

Preferred compounds of the immediately foregoing formula discovered to treat insulin resistance in a mammalian subject, with or without weight loss, include the following:

Ac-c(Cys-Glu-His-D-4-Br-Phe-Arg-Trp-Gly-Cys)-(Pro)₂-Lys-Asp-NH₂; (SEQ ID NO: 268)

Ac-c(Cys-Glu-His-D-2-Nal-Arg-Trp-Ala-Cys)-(Pro)₂-Lys-Asp-NH₂; (SEQ ID NO: 269)

Ac-c(Cys-Glu-His-D-2-Nal-Arg-2-Nal-Ala-Cys)-(Pro)₂-Lys-Asp-NH₂; (SEQ ID NO: 269)

Ac-c(Cys-Glu-His-D-2-Nal-Arg-1-Nal-Ala-Cys)-(Pro)₂-Lys-Asp-NH₂; (SEQ ID NO: 269)

Ac-c(Cys-Glu-His-D-2-Nal-Arg-Bal-Ala-Cys)-(Pro)₂-Lys-Asp-NH₂; (SEQ ID NO: 2690)

-continued (SEQ ID NO: 270)
Ac-c(Cys-Glu-His-D-2-Nal-Arg-2-Nal-β-Ala-Cys)-

(Pro)₂-Lys-Asp-NH₂;
or (SEQ ID NO: 270)
Ac-c(Cys-Glu-His-D-2-Nal-Arg-2-Nal-Aib-Cys)-

(Pro)₂-Lys-Asp-NH₂;

or pharmaceutically acceptable salts thereof.

The invention additionally provides a method to treat insulin resistance in a mammalian subject, with or without weight loss, by the administration of a therapeutically effective amount of a melanocortin receptor compound modified with a hydantoin moiety according to Formula (V), (VI) or (VII), and pharmaceutically acceptable salts, hydrates, solvates or prodrugs thereof.

According to a fifth embodiment, the invention provides a method to treat insulin resistance in a mammalian subject, with or without weight loss, by the administration of a therapeutically effective amount of a melanocortin receptor ligand according to the following formula (Formula (V)), pharmaceutically-acceptable salts, hydrates, solvates and/or prodrugs thereof (see International Patent Application Number PCT/US08/06675 incorporated herein by reference in its entirety):

(V)

wherein

X is selected from the group consisting of —CH₂—S—S—CH₂—, —C(CH₃)₂—S—S—CH₂—, —CH₂—S—S—C(CH₃)₂—, —C(CH₃)₂—S—S—C(CH₃)₂—, —(CH₂)₂—S—S—CH₂—, —CH₂—S—S—(CH₂)₂—, —(CH₂)₂—S—S—(CH₂)₂—, —C(CH₃)₂—S—S—(CH₂)₂—, —(CH₂)₂—S—S—C(CH₃)₂—, —(CH₂)ᵣ—C(O)—NR⁸—(CH₂)ᵣ— and —(CH₂)ᵣ—NR⁸—C(O)—(CH₂)ᵣ—;

R¹ and R² each is, independently, H, (C₁-C₁₀)alkyl or substituted (C₁-C₁₀)alkyl;

R³ is —OH or —NH₂;

R⁴ and R⁵ each is, independently, H, (C₁-C₁₀)alkyl or substituted (C₁-C₁₀)alkyl;

X¹ is

A¹ is His, 2-Pal, 3-Pal, 4-Pal, (X¹,X²,X³,X⁴,X⁵)Phe, Taz, 2-Thi, 3-Thi or is deleted;

A² is D-Bal, D-1-Nal, D-2-Nal, D-Phe or D-(X¹,X²,X³,X⁴,X⁵)Phe;

A³ is Arg, hArg, Dab, Dap, Lys or Orn;

A⁴ is Bal, 1-Nal, 2-Nal, (X¹,X²,X³,X⁴,X⁵)Phe or Trp;

R⁶ and R⁷ each is, independently for each occurrence thereof, H, (C₁-C₁₀)alkyl, (C₁-C₁₀)heteroalkyl, aryl(C₁-C₅)alkyl, substituted (C₁-C₁₀)alkyl, substituted (C₁-C₁₀)heteroalkyl or substituted aryl(C₁-C₅)alkyl provided that R⁶ and R⁷ may be joined together to form a ring;

R⁸ is H, (C₁-C₁₀)alkyl or substituted (C₁-C₁₀)alkyl;

r is, independently for each occurrence thereof, 1, 2, 3, 4 or 5; and t is, independently for each occurrence thereof, 1 or 2.

Preferably, a compound according the foregoing formula found useful to treat insulin resistance in a mammalian subject, with or without weight loss, include compounds wherein X¹ is selected from the group consisting of:

Representative embodiments of the foregoing class of compounds useful to treat insulin resistance in a mammalian subject, with or without weight loss, are as follows:

(SEQ ID NO: 271)
c[Hydantoin(C(O)-(Cys-D-Ala))-His-D-Phe-Arg-Trp-

Cys]-NH₂;

(SEQ ID NO: 271)
c[Hydantoin(C(O)-(hCys-D-Ala))-His-D-Phe-Arg-Trp-

Cys]-NH₂;

(SEQ ID NO: 272)
c[Hydantoin(C(O)-(Cys-D-Ala))-His-D-2-Nal-Arg-Trp-

Cys]-NH₂;
or (SEQ ID NO: 272)
c[Hydantoin(C(O)-(hCys-D-Ala))-His-D-2-Nal-Arg-

Trp-Cys]-NH₂;

(SEQ ID NO: 273)
c[Hydantoin(C(O)-(Asp-D-Ala))-His-D-Phe-Arg-Trp-

Lys]-NH₂;

c[Hydantoin(C(O)-(Asp-D-Ala))-His-D-Phe-Arg-Trp-Orn]-NH$_2$; (SEQ ID NO: 273)

c[Hydantoin(C(O)-(Asp-D-Ala))-His-D-Phe-Arg-Trp-Dab]-NH$_2$; (SEQ ID NO: 273)
or c[Hydantoin(C(O)-(Asp-D-Ala))-His-D-Phe-Arg-Trp-Dap]-NH$_2$; (SEQ ID NO: 273)

c[Hydantoin(C(O)-(Asp-His))-D-2-Nal-Arg-Trp-Lys]-NH$_2$; (SEQ ID NO: 275)

c[Hydantoin(C(O)-(Asp-His))-D-Phe-Arg-Trp-Lys]-NH$_2$ (SEQ ID NO: 274)

c[Hydantoin(C(O)-(Asp-A3c))-D-Phe-Arg-Trp-Lys]-NH$_2$; (SEQ ID NO: 274)

c[Hydantoin(C(O)-(Asp-A5c))-D-Phe-Arg-Trp-Lys]-NH$_2$; (SEQ ID NO: 274)

c[Hydantoin(C(O)-(Asp-A6c))-D-Phe-Arg-Trp-Lys]-NH$_2$; (SEQ ID NO: 274)

c[Hydantoin(C(O)-(Asp-A3c))-D-2-Nal-Arg-Trp-Lys]-NH$_2$; (SEQ ID NO: 275)

c[Hydantoin(C(O)-(Asp-A5c))-D-2-Nal-Arg-Trp-Lys]-NH$_2$; (SEQ ID NO: 275)

c[Hydantoin(C(O)-(Asp-A6c))-D-2-Nal-Arg-Trp-Lys]-NH$_2$; (SEQ ID NO: 275)

c[Hydantoin(C(O)-(Asp-Aic))-D-Phe-Arg-Trp-Lys]-NH$_2$; (SEQ ID NO: 274)

c[Hydantoin(C(O)-(Asp-Apc))-D-Phe-Arg-Trp-Lys]-NH$_2$; (SEQ ID NO: 274)

c[Hydantoin(C(O)-(Asp-Aic))-D-2-Nal-Arg-Trp-Lys]-NH$_2$; (SEQ ID NO: 275)

c[Hydantoin(C(O)-(Asp-Apc))-D-2-Nal-Arg-Trp-Lys]-NH$_2$; (SEQ ID NO: 275)

c[Hydantoin-(C(O)-(Asp-Aic))-D-2-Nal-Arg-Trp-Lys]-NH$_2$ (SEQ ID NO: 275)

c[Hydantoin-(C(O)-(Asp-Apc))-D-2-Nal-Arg-Trp-Lys]-NH$_2$ (SEQ ID NO: 275)

c[Hydantoin(C(O)-(Glu-D-Ala))-His-D-Phe-Arg-Trp-Orn]-NH$_2$; (SEQ ID NO: 276)

c[Hydantoin(C(O)-(Glu-D-Ala))-His-D-Phe-Arg-Trp-Dab]-NH$_2$; (SEQ ID NO: 276)
or c[Hydantoin(C(O)-(Glu-D-Ala))-His-D-Phe-Arg-Trp-Dap]-NH$_2$, (SEQ ID NO: 276)

c[Hydantoin(C(O)-(Glu-His))-D-Phe-Arg-Trp-Dap]-NH$_2$ (SEQ ID NO: 277)

According to a sixth embodiment, the invention provides a method to treat insulin resistance in a mammalian subject, with or without weight loss, by the administration of a therapeutically effective amount of a melanocortin receptor compound according to Formula (VI), pharmaceutically-acceptable salts, hydrates, solvates and/or prodrugs thereof (see International Patent Application Number PCT/US08/06675 which is incorporated herein by reference in its entirety):

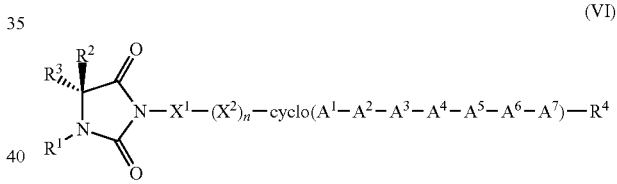

(VI)

wherein
X$^1$ is

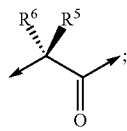

X$^2$ is

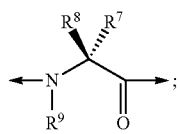

A$^1$ is Asp, Cys, D-Cys, Dab, Dap, Glu, Lys, Orn, Pen or D-Pen;
A$^2$ is an L- or D-amino acid;
A$^3$ is His, 2-Pal, 3-Pal, 4-Pal, (X$^1$,X$^2$,X$^3$,X$^4$,X$^5$)Phe, Taz, 2-Thi or 3-Thi;

A⁴ is D-Bal, D-1-Nal, D-2-Nal, D-Phe or D-(X¹,X²,X³,X⁴,X⁵)Phe;

A⁵ is Arg, hArg, Dab, Dap, Lys or Orn;

A⁶ is Bal, 1-Nal, 2-Nal, (X¹,X²,X³,X⁴,X⁵)Phe or Trp;

A⁷ is Asp, Cys, D-Cys, Dab, Dap, Glu, Lys, Orn, Pen or D-Pen;

R¹ is H, $(C_1-C_{10})$alkyl or substituted $(C_1-C_{10})$alkyl;

R² and R³ each is, independently, H, $(C_1-C_{10})$alkyl, $(C_1-C_{10})$heteroalkyl, aryl$(C_1-C_5)$alkyl, substituted $(C_1-C_{10})$alkyl, substituted $(C_1-C_{10})$heteroalkyl or substituted aryl $(C_1-C_5)$alkyl or R² and R³ may be fused together form a cyclic moiety;

R⁴ is $CO_2H$ or $C(O)NH_2$;

R⁵ and R⁶ each is, independently, H, $(C_1-C_{10})$alkyl, $(C_1-C_{10})$heteroalkyl, aryl$(C_1-C_5)$alkyl, substituted $(C_1-C_{10})$alkyl, substituted $(C_1-C_{10})$heteroalkyl or substituted aryl $(C_1-C_5)$alkyl or R⁵ and R⁶ may be fused together form a cyclic moiety;

R⁷ and R⁸ each is, independently, H, $(C_1-C_{10})$alkyl, $(C_1-C_{10})$heteroalkyl, aryl$(C_1-C_5)$alkyl, substituted $(C_1-C_{10})$alkyl, substituted $(C_1-C_{10})$heteroalkyl or substituted aryl $(C_1-C_5)$alkyl; or R⁷ and R⁸ may be fused together form a cyclic moiety;

R⁹ is H, $(C_1-C_{10})$alkyl or substituted $(C_1-C_{10})$alkyl; and n is, independently for each occurrence thereof, 1, 2, 3, 4, 5, 6 or 7; or a pharmaceutically acceptable salt thereof.

A preferred class of compounds according to Formula (VI) useful to treat insulin resistance in a mammalian subject, with or without weight loss, are those compounds wherein:

A¹ is Cys;

A² is D-Ala, Asn, Asp, Gln, Glu or D-Phe;

A³ is His;

A⁴ is D-2-Nal or D-Phe;

A⁵ is Arg;

A⁶ is Trp; and

A⁷ is Cys or Pen;

each of R¹, R², R³, and R⁹ is, independently, H;

R⁴ is $C(O)NH_2$;

each of R⁵ and R⁶ is, independently, H, $(C_1-C_{10})$alkyl, $(C_1-C_{10})$heteroalkyl, substituted $(C_1-C_{10})$alkyl or substituted $(C_1-C_{10})$heteroalkyl or R⁵ and R⁶ may be fused together form a cyclic moiety; and each of R⁷ and R⁸ is, independently, H, $(C_1-C_{10})$alkyl, $(C_1-C_{10})$heteroalkyl, substituted $(C_1-C_{10})$alkyl or substituted $(C_1-C_{10})$heteroalkyl;

or pharmaceutically acceptable salts thereof.

Preferred compounds of the immediately foregoing formula (Formula (VI)) useful to treat insulin resistance in a mammalian subject, with or without weight loss, include:

```
                                        (SEQ ID NO: 278)
Hydantoin(C(O)-(Arg-Gly))-c(Cys-Glu-His-D-Phe-Arg-
Trp-Cys)-NH2;

(SEQ ID NO: 278)
Hydantoin(C(O)-(Nle-Gly))-c(Cys-Glu-His-D-Phe-Arg-
Trp-Cys)-NH2;

(SEQ ID NO: 278)
Hydantoin(C(O)-(Gly-Gly))-c(Cys-Glu-His-D-Phe-Arg-
Trp-Cys)-NH2;

(SEQ ID NO: 279)
Hydantoin(C(O)-(Nle-Gly))-c(Cys-D-Ala-His-D-Phe-
Arg-Trp-Cys)-NH2;

(SEQ ID NO: 279)
Hydantoin(C(O)-(Gly-Gly))-c(Cys-D-Ala-His-D-
Phe-Arg-Trp-Cys)-NH2;

(SEQ ID NO: 280)
Hydantoin(C(O)-(Nle-Gly))-c(Cys-D-Ala-His-D-Phe-
Arg-Trp-Pen)-NH2;

(SEQ ID NO: 280)
Hydantoin(C(O)-(Gly-Gly))-c(Cys-D-Ala-His-D-Phe-
Arg-Trp-Pen)-NH2;

(SEQ ID NO: 279)
Hydantoin(C(O)-(Ala-Gly))-c(Cys-D-Ala-His-D-Phe-
Arg-Trp-Cys)-NH2;

(SEQ ID NO: 279)
Hydantoin(C(O)-(D-Ala-Gly))-c(Cys-D-Ala-His-D-Phe-
Arg-Trp-Cys)-NH2;

(SEQ ID NO: 279)
Hydantoin(C(O)-(Aib-Gly))-c(Cys-D-Ala-His-D-Phe-
Arg-Trp-Cys)-NH2;

(SEQ ID NO: 279)
Hydantoin(C(O)-(Val-Gly))-c(Cys-D-Ala-His-D-Phe-
Arg-Trp-Cys)-NH2;

(SEQ ID NO: 279)
Hydantoin(C(O)-(Ile-Gly))-c(Cys-D-Ala-His-D-Phe-
Arg-Trp-Cys)-NH2;

(SEQ ID NO: 279)
Hydantoin(C(O)-(Leu-Gly))-c(Cys-D-Ala-His-D-Phe-
Arg-Trp-Cys)-NH2;

(SEQ ID NO: 281)
Hydantoin(C(O)-(Gly-Gly))-c(Cys-Glu-His-D-2-Nal-
Arg-Trp-Cys)-NH2;

(SEQ ID NO: 281)
Hydantoin(C(O)-(Nle-Gly))-c(Cys-Glu-His-D-2-Nal-
Arg-Trp-Cys)-NH2;

(SEQ ID NO: 278)
Hydantoin(C(O)-(D-Arg-Gly))-c(Cys-Glu-His-D-Phe-
Arg-Trp-Cys)-NH2;

(SEQ ID NO: 278)
Hydantoin(C(O)-(Arg-Gly))-c(Cys-Glu-His-D-Phe-
Arg-Trp-Cys)-NH2;

(SEQ ID NO: 279)
Hydantoin(C(O)-(D-Arg-Gly))-c(Cys-D-Ala-His-D-Phe-
Arg-Trp-Cys)-NH2;

(SEQ ID NO: 279)
Hydantoin(C(O)-(Arg-Gly))-c(Cys-D-Ala-His-D-Phe-
Arg-Trp-Cys)-NH2;
```

-continued

Hydantoin(C(O)-(D-Arg-Gly))-c(Cys-D-Ala-His-D-2-Nal-Arg-Trp-Cys)-NH$_2$; (SEQ ID NO: 282)

Hydantoin(C(O)-(Arg-Gly))-c(Cys-D-Ala-His-D-2-Nal-Arg-Trp-Cys)-NH$_2$; (SEQ ID NO: 282)

Hydantoin(C(O)-(Nle-Gly))-c(Cys-Glu-His-D-Phe-Arg-Trp-Cys)-NH$_2$; (SEQ ID NO: 278)

Hydantoin(C(O)-(Gly-Gly))-c(Cys-Glu-His-D-Phe-Arg-Trp-Cys)-NH$_2$; (SEQ ID NO: 278)

Hydantoin(C(O)-(Nle-Gly))-c(Cys-D-Ala-His-D-Phe-Arg-Trp-Cys)-NH$_2$; (SEQ ID NO: 279)

Hydantoin(C(O)-(Gly-Gly))-c(Cys-D-Ala-His-D-Phe-Arg-Trp-Cys)-NH$_2$; (SEQ ID NO: 279)

Hydantoin(C(O)-(Nle-Gly))-c(Cys-D-Ala-His-D-Phe-Arg-Trp-Pen)-NH$_2$; (SEQ ID NO: 280)

Hydantoin(C(O)-(Gly-Gly))-c(Cys-D-Ala-His-D-Phe-Arg-Trp-Pen)-NH$_2$; (SEQ ID NO: 280)

Hydantoin(C(O)-(Ala-Gly))-c(Cys-D-Ala-His-D-Phe-Arg-Trp-Cys)-NH$_2$; (SEQ ID NO: 279)

Hydantoin(C(O)-(D-Ala-Gly))-c(Cys-D-Ala-His-D-Phe-Arg-Trp-Cys)-NH$_2$; (SEQ ID NO: 279)

Hydantoin(C(O)-(Aib-Gly))-c(Cys-D-Ala-His-D-Phe-Arg-Trp-Cys)-NH$_2$; (SEQ ID NO: 279)

Hydantoin(C(O)-(Val-Gly))-c(Cys-D-Ala-His-D-Phe-Arg-Trp-Cys)-NH$_2$; (SEQ ID NO: 279)

Hydantoin(C(O)-(Ile-Gly))-c(Cys-D-Ala-His-D-Phe-Arg-Trp-Cys)-NH$_2$; (SEQ ID NO: 279)

Hydantoin(C(O)-(Leu-Gly))-c(Cys-D-Ala-His-D-Phe-Arg-Trp-Cys)-NH$_2$; (SEQ ID NO: 279)

Hydantoin(C(O)-(D-Arg-Gly))-c(Cys-Glu-His-D-Phe-Arg-Trp-Cys)-NH$_2$; (SEQ ID NO: 278)

Hydantoin(C(O)-(Arg-Gly))-c(Cys-Glu-His-D-Phe-Arg-Trp-Cys)-NH$_2$; (SEQ ID NO: 278)

Hydantoin(C(O)-(Arg-Gly))-c(Cys-D-Ala-His-D-Phe-Arg-Trp-Cys)-NH$_2$; (SEQ ID NO: 279)
or Hydantoin(C(O)-(D-Arg-Gly))-c(Cys-D-Ala-His-D-Phe-Arg-Trp-Cys)-NH$_2$; (SEQ ID NO: 279)

Hydantoin(C(O)-(Ala-Nle))-c(Cys-Glu-His-D-Phe-Arg-Trp-Cys)-NH$_2$; (SEQ ID NO: 283)

Hydantoin(C(O)-(Val-Nle))-c(Cys-Glu-His-D-Phe-Arg-Trp-Cys)-NH$_2$; (SEQ ID NO: 283)

Hydantoin(C(O)-(Gly-Nle))-c(Cys-Glu-His-D-Phe-Arg-Trp-Cys)-NH$_2$; (SEQ ID NO: 283)

Hydantoin(C(O)-(A6c-Nle))-c(Cys-D-Ala-His-D-Phe-Arg-Trp-Cys)-NH$_2$; (SEQ ID NO: 284)

Hydantoin(C(O)-(Gly-Nle))-c(Cys-D-Ala-His-D-Phe-Arg-Trp-Cys)-NH$_2$; (SEQ ID NO: 284)

Hydantoin(C(O)-(Ala-Nle))-c(Cys-D-Ala-His-D-Phe-Arg-Trp-Cys)-NH$_2$; (SEQ ID NO: 284)

Hydantoin(C(O)-(D-Ala-Nle))-c(Cys-D-Ala-His-D-Phe-Arg-Trp-Cys)-NH$_2$; (SEQ ID NO: 284)

Hydantoin(C(O)-(Val-Nle))-c(Cys-D-Ala-His-D-Phe-Arg-Trp-Cys)-NH$_2$; (SEQ ID NO: 284)

Hydantoin(C(O)-(Leu-Nle))-c(Cys-D-Ala-His-D-Phe-Arg-Trp-Cys)-NH$_2$; (SEQ ID NO: 284)

Hydantoin(C(O)-(Cha-Nle))-c(Cys-D-Ala-His-D-Phe-Arg-Trp-Cys)-NH$_2$; (SEQ ID NO: 284)
or Hydantoin(C(O)-(Aib-Nle))-c(Cys-D-Ala-His-D-Phe-Arg-Trp-Cys)-NH$_2$; (SEQ ID NO: 284)

Hydantoin(C(O)-(Gly-Arg))-c(Cys-Glu-His-D-Phe-Arg-Trp-Cys)-NH$_2$; (SEQ ID NO: 285)

Hydantoin(C(O)-(Gly-Arg))-c(Cys-Glu-His-D-2-Nal-Arg-Trp-Cys)-NH$_2$; (SEQ ID NO: 285)

```
                                                      (SEQ ID NO: 286)
Hydantoin(C(O)-(Gly-Arg))-c(Cys-D-Ala-His-D-Phe- Arg-Trp-Cys)-NH2;

(SEQ ID NO: 286)
Hydantoin(C(O)-(Gly-Arg))-c(Cys-D-Ala-His-D-2-Nal-

Arg-Trp-Cys)-NH2;

(SEQ ID NO: 287)
Hydantoin(C(O)-(Gly-D-Arg))-c(Cys-Glu-His-D-Phe-

Arg-Trp-Cys)-NH2;

(SEQ ID NO: 287)
Hydantoin(C(O)-(Gly-D-Arg))-c(Cys-Glu-His-D-Phe-

Arg-Trp-Cys)-NH2;

(SEQ ID NO: 288)
Hydantoin(C(O)-(Gly-D-Arg))-c(Cys-D-Ala-His-D-

Phe-Arg-Trp-Cys)-NH2;
and (SEQ ID NO: 288)
Hydantoin(C(O)-(Gly-D-Arg))-c(Cys-D-Ala-His-D-2-

Nal-Arg-Trp-Cys)-NH2;

(SEQ ID NO: 289);
Hydantoin(C(O)-(Nle-Ala))-c(Cys-Glu-His-D-Phe-Arg-

Trp-Cys)-NH2
``` or pharmaceutically acceptable salts thereof.

In a seventh embodiment, the invention provides a method to treat insulin resistance in a mammalian subject, with or without weight loss, by the administration of a therapeutically effective amount of a melanocortin receptor ligand belonging to a class of cyclic peptide analogs that are ligands for the melanocortin receptors having a structure according to Formula (VII) as depicted below (see International Patent Application Number PCT/US08/06675 which is incorporated herein by reference in its entirety):

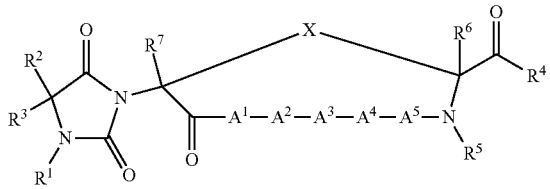

(VII)

wherein

X is selected from the group consisting of —CH$_2$—S—S—CH$_2$—, —C(CH$_3$)$_2$—S—S—CH$_2$—, —CH$_2$—S—S—C(CH$_3$)$_2$—, —C(CH$_3$)$_2$—S—S—C(CH$_3$)$_2$—, —(CH$_2$)$_2$—S—S—CH$_2$—, —CH$_2$—S—S—(CH$_2$)$_2$—, —(CH$_2$)$_2$—S—S—(CH$_2$)$_2$—, —C(CH$_3$)$_2$—S—S—(CH$_2$)$_2$—, —(CH$_2$)$_2$—S—S—C(CH$_3$)$_2$—, —(CH$_2$)$_r$—C(O)—NR$^8$—(CH$_2$)$_t$— and —(CH$_2$)$_r$—NR$^8$—C(O)—(CH$_2$)$_t$—;

each of R$^1$ and R$^5$ is, independently, H, (C$_1$-C$_{10}$)alkyl or substituted (C$_1$-C$_{10}$)alkyl;

each of R$^2$ and R$^3$ is, independently, H, (C$_1$-C$_{10}$)alkyl, (C$_1$-C$_{10}$)heteroalkyl, aryl(C$_1$-C$_5$)alkyl, substituted (C$_1$-C$_{10}$)alkyl, substituted (C$_1$-C$_{10}$)heteroalkyl or substituted aryl (C$_1$-C$_5$)alkyl or R$^2$ and R$^3$ may be fused together to form a ring;

R$^4$ is OH or NH$_2$;

each of R$^6$ and R$^7$ is, independently, H, (C$_1$-C$_{10}$)alkyl or substituted (C$_1$-C$_{10}$)alkyl;

A$^1$ is an L- or D-amino acid or deleted;

A$^2$ is His, 2-Pal, 3-Pal, 4-Pal, (X$^1$,X$^2$,X$^3$,X$^4$,X$^5$)Phe, Taz, 2-Thi or 3-Thi;

A$^3$ is D-Bal, D-1-Nal, D-2-Nal, D-Phe or D-(X$^1$,X$^2$,X$^3$,X$^4$,X$^5$)Phe;

A$^4$ is Arg, hArg, Dab, Dap, Lys or Orn;

A$^5$ is Bal, 1-Nal, 2-Nal, (X$^1$,X$^2$,X$^3$,X$^4$,X$^5$)Phe or Trp;

r is, independently for each occurrence thereof, 1, 2, 3, 4 or 5; and t is, independently for each occurrence thereof, 1 or 2;

or pharmaceutically acceptable salts thereof.

In the preferred aspect of the compounds according to Formula (VII) useful to treat insulin resistance in a mammalian subject, with or without weight loss, A$^1$ is Ala, D-Ala, Asn, Asp, Gln, Glu or Gly;

or pharmaceutically acceptable salts thereof.

Preferred compounds according to Formula (VII) useful in the treatment of insulin resistance in a mammalian subject, include the following compounds:

```
                                                      (SEQ ID NO: 290)
c[Hydantoin(C(O)-(Nle-Cys))-D-Ala-His-D-Phe-Arg- Trp-Cys]-NH2;

(SEQ ID NO: 290)
c[Hydantoin(C(O)-(Ala-Cys))-D-Ala-His-D-Phe-Arg-

Trp-Cys]-NH2;

(SEQ ID NO: 290)
c[Hydantoin(C(O)-(D-Ala-Cys))-D-Ala-His-D-Phe-Arg-

Trp-Cys]-NH2;

(SEQ ID NO: 290)
c[Hydantoin(C(O)-(Aib-Cys))-D-Ala-His-D-Phe-Arg-

Trp-Cys]-NH2;

(SEQ ID NO: 290)
c[Hydantoin(C(O)-(Val-Cys))-D-Ala-His-D-Phe-Arg-

Trp-Cys]-NH2;

(SEQ ID NO: 290)
c[Hydantoin(C(O)-(Abu-Cys))-D-Ala-His-D-Phe-Arg-

Trp-Cys]-NH2;

(SEQ ID NO: 290)
c[Hydantoin(C(O)-(Leu-Cys))-D-Ala-His-D-Phe-Arg-

Trp-Cys]-NH2;

(SEQ ID NO: 290)
c[Hydantoin(C(O)-(Ile-Cys))-D-Ala-His-D-Phe-Arg-

Trp-Cys]-NH2;

(SEQ ID NO: 290)
c[Hydantoin(C(O)-(Cha-Cys))-D-Ala-His-D-Phe-

Arg-Trp-Cys]-NH2;

(SEQ ID NO: 290)
c[Hydantoin(C(O)-(A6c-Cys))-D-Ala-His-D-Phe-

Arg-Trp-Cys]-NH2;
```

-continued c[Hydantoin(C(O)-(Phe-Cys))-D-Ala-His-D-Phe-Arg-Trp-Cys]-NH$_2$; (SEQ ID NO: 290)

c[Hydantoin(C(O)-(Gly-Cys))-D-Ala-His-D-Phe-Arg-Trp-Cys]-NH$_2$; (SEQ ID NO: 290)
or c[Hydantoin(C(O)-(Gly-Cys))-Glu-His-D-Phe-Arg-Trp-Cys]-NH$_2$; (SEQ ID NO: 291)
or c[Hydantoin(C(O)-(Gly-Cys))-Glu-His-D-Phe-Arg-Trp-Cys]-NH$_2$; (SEQ ID NO: 291)

or pharmaceutically acceptable salts thereof.

In an eighth embodiment, the present invention is directed to a method to treat insulin resistance in a mammalian subject, with or without weight loss, by the administration of a therapeutically effective amount of a melanocortin receptor ligand according to Formula (VIII) (see International Patent Application Number PCT/US08/07411, incorporated herein by reference in its entirety):

$$(R^2R^3)\text{-}A^0\text{-}A^1\text{-}c(A^2\text{-}A^3\text{-}A^4\text{-}A^5\text{-}A^6\text{-}A^7\text{-}A^8\text{-}A^9)\text{-}A^{10}\text{-}R^1 \quad (VIII)$$

wherein:
$A^0$ is an aromatic amino acid
$A^1$ is Acc, HN—(CH$_2$)$_m$—C(O), an L- or D-amino acid;
$A^2$ is Asp, Cys, D-Cys, hCys, D-hCys, Glu, Pen, or D-Pen;
$A^3$ is Aib, Ala, β-Ala, Gaba, Gly or a D-amino acid;
$A^4$ is His, 2-Pal, 3-Pal, 4-Pal, (X$^1$,X$^2$,X$^3$,X$^4$,X$^5$)Phe, Taz, 2-Thi, or 3-Thi;
$A^5$ is D-Bal, D-1-Nal, D-2-Nal, D-Phe, L-Phe, D-(X$^1$,X$^2$,X$^3$,X$^4$,X$^5$)Phe, L-Phe, D-Trp or D-(Et)Tyr;
$A^6$ is Arg, hArg, Dab, Dap, Lys, Orn, or HN—CH((CH$_2$)$_n$—N(R$^4$R$^5$))—C(O);
$A^7$ is Bal, D-Bal, Bip, D-Bip, 1-Nal, D-1-Nal, 2-Nal, D-2-Nal, or D-Trp;
$A^8$ is Acc, Aha, Ahx, Ala, D-Ala, β-Ala, Apn, Gaba, Gly, HN—(CH$_2$)$_s$—C(O), or deleted;
$A^9$ is Cys, D-Cys, hCys, D-hCys, Dab, Dap, Lys, Orn, Pen, or D-Pen;
$A^{10}$ is Acc, HN—(CH$_2$)$_t$—C(O), L- or D-amino acid, or deleted;
$R^1$ is OH, or NH$_2$;
each of $R^2$ and $R^3$ is, independently for each occurrence selected from the group consisting of H, (C$_1$-C$_{30}$)alkyl, (C$_1$-C$_{30}$)heteroalkyl, (C$_1$-C$_{30}$)acyl, (C$_2$-C$_{30}$)alkenyl, (C$_2$-C$_{30}$)alkynyl, aryl(C$_1$-C$_{30}$)alkyl, aryl(C$_1$-C$_{30}$)acyl, substituted (C$_1$-C$_{30}$)alkyl, substituted (C$_1$-C$_{30}$)heteroalkyl, substituted (C$_1$-C$_{30}$)acyl, substituted (C$_2$-C$_{30}$)alkenyl, substituted (C$_2$-C$_{30}$)alkynyl, substituted aryl(C$_1$-C$_{30}$)alkyl, and substituted aryl(C$_1$-C$_{30}$)acyl;
each of $R^4$ and $R^5$ is, independently for each occurrence, H, (C$_1$-C$_{40}$)alkyl, (C$_1$-C$_{40}$)heteroalkyl, (C$_1$-C$_{40}$)acyl, (C$_2$-C$_{40}$)alkenyl, (C$_2$-C$_{40}$)alkynyl, aryl(C$_1$-C$_{40}$)alkyl, aryl(C$_1$-C$_{40}$)acyl, substituted (C$_1$-C$_{40}$)alkyl, substituted (C$_1$-C$_{40}$)heteroalkyl, substituted (C$_1$-C$_{40}$)acyl, substituted (C$_2$-C$_{40}$)alkenyl, substituted (C$_2$-C$_{40}$)alkynyl, substituted aryl(C$_1$-C$_{40}$)alkyl, substituted aryl(C$_1$-C$_{40}$)acyl, (C$_1$-C$_{40}$)alkylsulfonyl, or —C(NH)—NH$_2$;

m is, independently for each occurrence, 1, 2, 3, 4, 5, 6 or 7;
n is, independently for each occurrence, 1, 2, 3, 4 or 5;
s is, independently for each occurrence, 1, 2, 3, 4, 5, 6, or 7;
t is, independently for each occurrence, 1, 2, 3, 4, 5, 6, or 7;
$X^1$, $X^2$, $X^3$, $X^4$, and $X^5$ each is, independently for each occurrence, H, F, Cl, Br, I, (C$_{1-10}$)alkyl, substituted (C$_{1-10}$)alkyl, (C$_{2-10}$)alkenyl, substituted (C$_{2-10}$)alkenyl, (C$_{2-10}$)alkynyl, substituted (C$_{2-10}$)alkynyl, aryl, substituted aryl, OH, NH$_2$, NO$_2$, or CN; provided that (I). when $R^4$ is (C$_1$-C$_{40}$)acyl, aryl(C$_1$-C$_{40}$)acyl, substituted (C$_1$-C$_{40}$)acyl, substituted aryl(C$_1$-C$_{40}$)acyl, (C$_1$-C$_{40}$)alkylsulfonyl, or —C(NH)—NH$_2$, then $R^5$ is H or (C$_1$-C$_{40}$)alkyl, (C$_1$-C$_{40}$)heteroalkyl, (C$_2$-C$_{40}$)alkenyl, (C$_2$-C$_{40}$)alkynyl, aryl(C$_1$-C$_{40}$)alkyl, substituted (C$_1$-C$_{40}$)alkyl, substituted (C$_1$-C$_{40}$)heteroalkyl, substituted (C$_2$-C$_{40}$)alkenyl, substituted (C$_2$-C$_{40}$)alkynyl, or substituted aryl(C$_1$-C$_{40}$)alkyl;

(II). when $R^2$ is (C$_1$-C$_{30}$)acyl, aryl(C$_1$-C$_{30}$)acyl, substituted (C$_1$-C$_{30}$)acyl, or substituted aryl(C$_1$-C$_{30}$)acyl, then $R^3$ is H, (C$_1$-C$_{30}$)alkyl, (C$_1$-C$_{30}$)heteroalkyl, (C$_2$-C$_{30}$)alkenyl, (C$_2$-C$_{30}$)alkynyl, aryl(C$_1$-C$_{30}$)alkyl, substituted (C$_1$-C$_{30}$)alkyl, substituted (C$_1$-C$_{30}$)heteroalkyl, substituted (C$_2$-C$_{30}$)alkenyl, substituted (C$_2$-C$_{30}$)alkynyl, or substituted aryl(C$_1$-C$_{30}$)alkyl;

(III). when $A^2$ is Cys, D-Cys, hCys, D-hCys, Pen, or D-Pen, then $A^9$ is Cys, D-Cys, hCys, D-hCys, Pen, or D-Pen;

(IV). when $A^2$ is Asp or Glu, then $A^9$ is Dab, Dap, Orn, or Lys;

(V). when $A^8$ is Ala or Gly, then $A^1$ is not Nle; or pharmaceutically acceptable salts thereof.

A preferred group of compounds of the immediate foregoing formula useful to treat insulin resistance in a mammalian subject, with or without weight loss, is wherein
$A^0$ is 1-Nal, 2-Nal, His, Pff, Phe, Trp, or Tyr;
$A^1$ is Arg;
$A^2$ is Cys;
$A^3$ is D-Ala;
$A^4$ is His;
$A^5$ is D-Phe;
$A^6$ is Arg;
$A^7$ is Trp
$A^8$ is deleted;
$A^9$ is Cys; and
$A^{10}$ is deleted;
or pharmaceutically acceptable salts thereof.

Preferred compounds of the immediately foregoing group of compounds is which are useful to treat insulin resistance in a mammalian subject, with or without weight loss, of the formula:

Ac-Tyr-Arg-c(Cys-D-Ala-His-D-Phe-Arg-Trp-Cys)-NH$_2$; (SEQ ID NO: 292)

Ac-2-Nal-Arg-c(Cys-D-Ala-His-D-Phe-Arg-Trp-Cys)-NH$_2$; (SEQ ID NO: 292)

Ac-1-Nal-Arg-c(Cys-D-Ala-His-DPhe-Arg-Trp-Cys)-NH$_2$; (SEQ ID NO: 292)

Ac-Phe-Arg-c(Cys-D-Ala-His-D-Phe-Arg-Trp-Cys)-NH$_2$; (SEQ ID NO: 292)

-continued

Ac-Trp-Arg-c(Cys-D-Ala-His-D-Phe-Arg-Trp-Cys)-NH$_2$;  (SEQ ID NO: 292)

Ac-Pff-Arg-c(Cys-D-Ala-His-D-Phe-Arg-Trp-Cys)-NH$_2$;  (SEQ ID NO: 292)

H-His-Arg-c(Cys-D-Ala-His-D-Phe-Arg-Trp-Cys)-NH$_2$;  (SEQ ID NO: 293)

or

Ac-His-Arg-c(Cys-D-Ala-His-D-Phe-Arg-Trp-Cys)-NH$_2$;  (SEQ ID NO: 292)

or pharmaceutically acceptable salts thereof.

In yet another preferred embodiment, the compound or compounds of Formula (I), (II), (III), (IV), (V), (VI), (VII) or (VIII) as defined hereinabove, which are useful to treat insulin resistance in a mammalian subject, with or without weight loss, or a pharmaceutically acceptable salt thereof, are provided to said subject in need in a composition with a pharmaceutically acceptable carrier or diluent.

In preferred embodiment, the invention provides a method of treating insulin resistance in a subject in need thereof, comprising peripheral administration of an effective amount of a melanocortin receptor 4 agonist to treat the insulin resistance in the subject in need thereof.

In one aspect, the melanocortin receptor 4 agonist useful to treat insulin resistance with or without an accompanying reduction in body weight in the subject in need thereof, is selected from the group consisting of:

Ac-Nle-c(Asp-His-D-Phe-Arg-Trp-β-Ala-Lys)-NH$_2$;  SEQ ID NO: 1

Ac-Nle-c(Asp-His-D-Phe-Arg-Trp-A6c-Lys)-NH$_2$;  SEQ ID NO: 1

Ac-Nle-c(Cys-His-D-Phe-Arg-Trp-Ahx-Cys)-NH$_2$;  SEQ ID NO: 2

D-Phe-c(Cys-His-D-Phe-Arg-Trp-Ala-D-Cys)-Thr-NH$_2$;  SEQ ID NO: 3

D-Phe-c(Cys-His-D-Phe-Arg-Trp-β-Ala-D-Cys)-Thr-NH$_2$;  SEQ ID NO: 3

D-Phe-c(Cys-His-D-Phe-Arg-Trp-Gaba-D-Cys)-Thr-NH$_2$;  SEQ ID NO: 3

Ac-Nle-c(Cys-His-D-Phe-Arg-Trp-Apn-Cys)-NH$_2$;  SEQ ID NO: 2

Ac-Nle-c(Asp-His-D-Phe-Arg-Trp-Apn-Lys)-NH$_2$;  SEQ ID NO: 4

Ac-A6c-c(Asp-His-D-Phe-Arg-Trp-Gaba-Lys)-NH$_2$;  SEQ ID NO: 5

Ac-D-2-Nal-c(Asp-His-D-Phe-Arg-Trp-Gaba-Lys)-NH$_2$;  SEQ ID NO: 6

Ac-Cha-c(Asp-His-D-Phe-Arg-Trp-Gaba-Lys)-NH$_2$;  SEQ ID NO: 6

Ac-Nle-c(Asp-His-D-Phe-Arg-Trp-Gaba-Lys)-NH$_2$;  SEQ ID NO: 6

Ac-Nle-c(Cys-D-Ala-His-D-Phe-Arg-Trp-Cys)-NH$_2$;  SEQ ID NO: 7

Ac-Nle-c(Cys-β-Ala-His-D-Phe-Arg-Trp-Cys)-NH$_2$;  SEQ ID NO: 7

Ac-Nle-c(Cys-Gaba-His-D-Phe-Arg-Trp-Cys)-NH$_2$;  SEQ ID NO: 7

Ac-Nle-c(Cys-Aib-His-D-Phe-Arg-Trp-Cys)-NH$_2$;  SEQ ID NO: 7

Ac-Nle-c(Cys-Gly-His-D-Phe-Arg-Trp-Cys)-NH$_2$;  SEQ ID NO: 7

Ac-Nle-c(D-Cys-Ala-His-D-Phe-Arg-Trp-Cys)-NH$_2$;  SEQ ID NO: 8

Ac-Nle-c(D-Cys-D-Ala-His-D-Phe-Arg-Trp-Cys)-NH$_2$;  SEQ ID NO: 8

Ac-Nle-c(D-Cys-β-Ala-His-D-Phe-Arg-Trp-Cys)-NH$_2$;  SEQ ID NO: 8

-continued

| | |
|---|---|
| Ac-Nle-c(D-Cys-Gaba-His-D-Phe-Arg-Trp-Cys)-NH₂; | SEQ ID NO: 8 |
| Ac-Nle-c(D-Cys-Aib-His-D-Phe-Arg-Trp-Cys)-NH₂; | SEQ ID NO: 8 |
| Ac-Nle-c(D-Cys-Gly-His-D-Phe-Arg-Trp-Cys)-NH₂; | SEQ ID NO: 8 |
| Ac-Nle-c(Cys-D-Ala-His-D-Phe-Arg-Trp-D-Cys)-NH₂; | SEQ ID NO: 9 |
| Ac-Nle-c(Cys-β-Ala-His-D-Phe-Arg-Trp-D-Cys)-NH₂; | SEQ ID NO: 9 |
| Ac-Nle-c(Cys-Gaba-His-D-Phe-Arg-Trp-D-Cys)-NH₂; | SEQ ID NO: 9 |
| Ac-Nle-c(Cys-Aib-His-D-Phe-Arg-Trp-D-Cys)-NH₂; | SEQ ID NO: 9 |
| Ac-Nle-c(Cys-Gly-His-D-Phe-Arg-Trp-D-Cys)-NH₂; | SEQ ID NO: 9 |
| Ac-Nle-c(D-Cys-Ala-His-D-Phe-Arg-Trp-D-Cys)-NH₂; | SEQ ID NO: 10 |
| Ac-Nle-c(D-Cys-D-Ala-His-D-Phe-Arg-Trp-D-Cys)-NH₂; | SEQ ID NO: 10 |
| Ac-Nle-c(D-Cys-β-Ala-His-D-Phe-Arg-Trp-D-Cys)-NH₂; | SEQ ID NO: 10 |
| Ac-Nle-c(D-Cys-Gaba-His-D-Phe-Arg-Trp-D-Cys)-NH₂; | SEQ ID NO: 10 |
| Ac-Nle-c(D-Cys-Aib-His-D-Phe-Arg-Trp-D-Cys)-NH₂; | SEQ ID NO: 10 |
| Ac-Oic-c(Asp-His-D-Phe-Arg-Trp-Gaba-Lys)-NH₂; | SEQ ID NO: 11 |
| Ac-Chg-c(Asp-His-D-Phe-Arg-Trp-Gaba-Lys)-NH₂; | SEQ ID NO: 11 |
| Ac-hCha-c(Asp-His-D-Phe-Arg-Trp-Gaba-Lys)-NH₂; | SEQ ID NO: 11 |
| Ac-D-Cha-c(Asp-His-D-Phe-Arg-Trp-Gaba-Lys)-NH₂; | SEQ ID NO: 11 |
| Ac-Nip-c(Asp-His-D-Phe-Arg-Trp-Gaba-Lys)-NH₂; | SEQ ID NO: 11 |
| Ac-hPro-c(Asp-His-D-Phe-Arg-Trp-Gaba-Lys)-NH₂; | SEQ ID NO: 11 |
| Ac-hLeu-c(Asp-His-D-Phe-Arg-Trp-Gaba-Lys)-NH₂; | SEQ ID NO: 11 |
| Ac-Phe-c(Asp-His-D-Phe-Arg-Trp-Gaba-Lys)-NH₂; | SEQ ID NO: 11 |
| Ac-D-Phe-c(Asp-His-D-Phe-Arg-Trp-Gaba-Lys)-NH₂; | SEQ ID NO: 11 |
| Ac-D-Chg-c(Asp-His-D-Phe-Arg-Trp-Gaba-Lys)-NH₂; | SEQ ID NO: 11 |
| n-butanoyl-Cha-c(Asp-His-D-Phe-Arg-Trp-Gaba-Lys)-NH₂; | SEQ ID NO: 12 |
| Ac-hPhe-c(Asp-His-D-Phe-Arg-Trp-Gaba-Lys)-NH₂; | SEQ ID NO: 11 |
| Ac-β-hMet-c(Asp-His-D-Phe-Arg-Trp-Gaba-Lys)-NH₂; | SEQ ID NO: 11 |
| Ac-Gaba-c(Asp-His-D-Phe-Arg-Trp-Gaba-Lys)-NH₂; | SEQ ID NO: 11 |

-continued

| | |
|---|---|
| Ac-Cha-c(Asp-His-D-Phe-Arg-D-Trp-Ala-Lys)-NH$_2$; | SEQ ID NO: 13 |
| Ac-hCha-c(Asp-His-D-Phe-Arg-D-Trp-Ala-Lys)-NH$_2$; | SEQ ID NO: 13 |
| Ac-Leu-c(Asp-His-D-Phe-Arg-D-Trp-Ala-Lys)-NH$_2$; | SEQ ID NO: 13 |
| Ac-hLeu-c(Asp-His-D-Phe-Arg-D-Trp-Ala-Lys)-NH$_2$; | SEQ ID NO: 13 |
| Ac-Phe-c(Asp-His-D-Phe-Arg-D-Trp-Ala-Lys)-NH$_2$; | SEQ ID NO: 13 |
| Ac-Nle-c(Asp-His-D-Phe-Arg-D-Trp-D-Ala-Lys)-NH$_2$; | SEQ ID NO: 14 |
| Ac-Nle-c(Asp-His-D-Phe-Arg-D-Trp-β-Ala-Lys)-NH$_2$; | SEQ ID NO: 14 |
| Ac-Nle-c(Asp-His-D-Phe-Arg-D-Trp-Gaba-Lys)-NH$_2$; | SEQ ID NO: 14 |
| Ac-Nle-c(Asp-His-D-Phe-Arg-D-Trp-Aha-Lys)-NH$_2$; | SEQ ID NO: 14 |
| Ac-Nle-c(Asp-His-D-Phe-Arg-D-Trp-Apn-Lys)-NH$_2$; | SEQ ID NO: 14 |
| Ac-Nle-c(Cys-His-D-Phe-Arg-D-Trp-Apn-Cys)-NH$_2$; | SEQ ID NO: 15 |
| Ac-Nle-c(Cys-His-D-Phe-Arg-D-Trp-Gaba-Cys)-NH$_2$; | SEQ ID NO: 15 |
| Ac-Nle-c(Cys-His-D-Phe-Arg-D-Trp-Ahx-Cys)-NH$_2$; | SEQ ID NO: 15 |
| Ac-Nle-c(Cys-His-D-Phe-Arg-D-Trp-β-Ala-Cys)-NH$_2$; | SEQ ID NO: 15 |
| Ac-Nle-c(Cys-His-D-Phe-Arg-D-Trp-D-Ala-Cys)-NH$_2$; | SEQ ID NO: 15 |
| Ac-Nle-c(Cys-D-Ala-His-D-2-Nal-Arg-Trp-Cys)-NH$_2$; | SEQ ID NO: 16 |
| Ac-Nle-c(Cys-D-Ala-His-D-2-Nal-Arg-2-Nal-Cys)-NH$_2$; | SEQ ID NO: 16 |
| Ac-Nle-c(Cys-D-Ala-His-D-2-Nal-Arg-1-Nal-Cys)-NH$_2$; | SEQ ID NO: 16 |
| n-butanoyl-Nle-c(Cys-D-Ala-His-D-Phe-Arg-2-Nal-Cys)-NH$_2$; | SEQ ID NO: 17 |
| n-butanoyl-Nle-c(Cys-D-Ala-His-D-Phe-Arg-Trp-Cys)-NH$_2$; | SEQ ID NO: 17 |
| Ac-Nle-c(Cys-D-Ala-His-D-Phe-Arg-2-Nal-Cys)-NH$_2$; | SEQ ID NO: 18 |
| Ac-Nle-c(Cys-D-Ala-His-D-Phe-Arg-1-Nal-Cys)-NH$_2$; | SEQ ID NO: 18 |
| Ac-Nle-c(Cys-D-Ala-His-D-Phe-Arg-Bal-Cys)-NH$_2$; | SEQ ID NO: 18 |
| Ac-Nle-c(Cys-D-Glu-His-D-Phe-Arg-Trp-Cys)-NH$_2$; | SEQ ID NO: 61 |
| Ac-Nle-c(Asp-His-D-Phe-Arg-Trp-D-Ala-Lys)-NH$_2$; | SEQ ID NO: 19 |
| Ac-Nle-c(Cys-D-Ala-His-D-2-Nal-Arg-Bal-Cys)-NH$_2$; | SEQ ID NO: 20 |
| Ac-Nle-c(Pen-D-Ala-His-D-Phe-Arg-Trp-Cys)-NH$_2$; | SEQ ID NO: 21 |

| | |
|---|---|
| Ac-Nle-c(Cys-D-Ala-His-D-Phe-Arg-Trp-Pen)-NH$_2$; | SEQ ID NO: 22 |
| Ac-Nle-c(Pen-D-Ala-His-D-Phe-Arg-Trp-Pen)-NH$_2$; | SEQ ID NO: 22 |
| D-Phe-c(Cys-His-D-Phe-hArg-Trp-β-Ala-D-Cys)-Thr-NH$_2$; | SEQ ID NO: 23 |
| D-Phe-c(Cys-His-D-(Et)Tyr-Arg-Trp-β-Ala-D-Cys)-Thr-NH$_2$; | SEQ ID NO: 24 |
| D-Phe-c(Cys-His-D-Phe-Arg-Bip-β-Ala-D-Cys)-Thr-NH$_2$; | SEQ ID NO: 25 |
| D-Phe-c(Cys-His-D-(Et)Tyr-hArg-Trp-β-Ala-D-Cys)-Thr-NH$_2$; | SEQ ID NO: 24 |
| D-Phe-c(Cys-His-D-Phe-hArg-Bip-β-Ala-D-Cys)-Thr-NH$_2$; | SEQ ID NO: 26 |
| D-Phe-c(Cys-His-D-(Et)Tyr-hArg-Bip-β-Ala-D-Cys)-Thr-NH$_2$; | SEQ ID NO: 26 |
| Nle-c(Cys-His-D-Phe-Arg-Trp-Apn-Cys)-NH$_2$; | SEQ ID NO: 27 |
| Ac-Nle-c(Asp-D-Ala-His-D-Phe-Arg-Trp-Lys)-NH$_2$; | SEQ ID NO: 28 |
| Ac-Nle-c(Asp-D-Ala-His-D-Phe-Arg-Bal-Lys)-NH$_2$; | SEQ ID NO: 28 |
| Ac-Nle-c(Cys-D-Ala-His-D-Phe-Arg-Trp-Pen)-OH; | SEQ ID NO: 29 |
| Ac-Nle-c(Cys-D-Abu-His-D-Phe-Arg-Trp-Cys)-NH$_2$; | SEQ ID NO: 30 |
| Ac-Nle-c(Cys-D-Val-His-D-Phe-Arg-Trp-Cys)-NH$_2$; | SEQ ID NO: 30 |
| Ac-Nle-c(Cys-D-Ile-His-D-Phe-Arg-Trp-Cys)-NH$_2$; | SEQ ID NO: 30 |
| Ac-Nle-c(Cys-D-Leu-His-D-Phe-Arg-Trp-Cys)-NH$_2$; | SEQ ID NO: 30 |
| Ac-Nle-c(Cys-D-Tle-His-D-Phe-Arg-Trp-Cys)-NH$_2$; | SEQ ID NO: 30 |
| Ac-Nle-c(Cys-D-Cha-His-D-Phe-Arg-Trp-Cys)-NH$_2$; | SEQ ID NO: 30 |
| Ac-Nle-c(Pen-His-D-Phe-Arg-Trp-Gaba-Cys)-NH$_2$; | SEQ ID NO: 31 |
| Ac-Nle-c(Cys-His-D-Phe-Arg-Trp-Gaba-Pen)-NH$_2$; | SEQ ID NO: 32 |
| Ac-Nle-c(Pen-His-D-Phe-Arg-Trp-Gaba-Pen)-NH$_2$; | SEQ ID NO: 32 |
| Ac-Leu-c(Cys-His-D-Phe-Arg-Trp-Gaba-Cys)-NH$_2$; | SEQ ID NO: 33 |
| Ac-Cha-c(Cys-His-D-Phe-Arg-Trp-Gaba-Cys)-NH$_2$; | SEQ ID NO: 33 |
| Ac-Ile-c(Cys-His-D-Phe-Arg-Trp-Gaba-Cys)-NH$_2$; | SEQ ID NO: 33 |
| Ac-Phe-c(Cys-His-D-Phe-Arg-Trp-Gaba-Cys)-NH$_2$; | SEQ ID NO: 33 |
| Ac-Val-c(Cys-His-D-Phe-Arg-Trp-Gaba-Cys)-NH$_2$; | SEQ ID NO: 33 |
| Ac-2-Nal-c(Cys-His-D-Phe-Arg-Trp-Gaba-Cys)-NH$_2$; | SEQ ID NO: 33 |

-continued

| | |
|---|---|
| Nle-c(Cys-His-D-Phe-Arg-Trp-Gaba-Cys)-NH$_2$; | SEQ ID NO: 34 |
| Phe-c(Cys-His-D-Phe-Arg-Trp-Gaba-Cys)-NH$_2$; | SEQ ID NO: 34 |
| Ac-Nle-c(Cys-3-Pal-D-Phe-Arg-Trp-Gaba-Cys)-NH$_2$; | SEQ ID NO: 35 |
| Ac-Nle-c(Cys-D-Ala-His-D-Phe-Arg-Trp-Cys)-OH; | SEQ ID NO: 36 |
| Ac-Nle-c(Cys-His-Phe-Arg-D-Trp-Gaba-Cys)-NH$_2$; | SEQ ID NO: 37 |
| Ac-Nle-c(Asp-His-D-2-Nal-Arg-Trp-Ala-Lys)-NH$_2$; | SEQ ID NO: 38 |
| Ac-Nle-c(Asp-His-D-2-Nal-Arg-Trp-β-Ala-Lys)-NH$_2$; | SEQ ID NO: 38 |
| Ac-Nle-c(Cys-His-D-2-Nal-Arg-Trp-Gaba-Cys)-NH$_2$; | SEQ ID NO: 39 |
| Ac-Nle-c(Cys-His-D-2-Nal-Arg-Trp-Ahx-Cys)-NH$_2$; | SEQ ID NO: 39 |
| Ac-hPhe-c(Asp-His-D-2-Nal-Arg-Trp-Gaba-Lys)-NH$_2$; | SEQ ID NO: 40 |
| Ac-Cha-c(Asp-His-D-2-Nal-Arg-Trp-Gaba-Lys)-NH$_2$; | SEQ ID NO: 40 |
| Ac-Nle-c(Asp-His-D-Phe-Arg-Trp-β-Ala-Lys)-OH; | SEQ ID NO: 41 |
| Ac-Nle-c(Cys-His-D-Phe-Arg-Trp-Ahx-Cys)-OH; | SEQ ID NO: 42 |
| D-Phe-c(Cys-His-D-Phe-Arg-Trp-Ala-D-Cys)-Thr-OH; | SEQ ID NO: 43 |
| D-Phe-c(Cys-His-D-Phe-Arg-Trp-β-Ala-D-Cys)-Thr-OH; | SEQ ID NO: 43 |
| D-Phe-c(Cys-His-D-Phe-Arg-Trp-Gaba-D-Cys)-Thr-OH; | SEQ ID NO: 43 |
| Ac-Nle-c(Cys-His-D-Phe-Arg-Trp-Apn-Cys)-OH; | SEQ ID NO: 42 |
| Ac-Nle-c(Asp-His-D-Phe-Arg-Trp-Apn-Lys)-OH; | SEQ ID NO: 41 |
| Ac-Cha-c(Asp-His-D-Phe-Arg-Trp-Gaba-Lys)-OH; | SEQ ID NO: 44 |
| Ac-Nle-c(Asp-His-D-Phe-Arg-Trp-Gaba-Lys)-OH; | SEQ ID NO: 44 |
| Ac-Chg-c(Asp-His-D-Phe-Arg-Trp-Gaba-Lys)-OH; | SEQ ID NO: 44 |
| Ac-D-Cha-c(Asp-His-D-Phe-Arg-Trp-Gaba-Lys)-OH; | SEQ ID NO: 44 |
| Ac-hCha-c(Asp-His-D-Phe-Arg-Trp-Gaba-Lys)-OH; | SEQ ID NO: 44 |
| Ac-D-Chg-c(Asp-His-D-Phe-Arg-Trp-Gaba-Lys)-OH; | SEQ ID NO: 44 |
| Ac-hPhe-c(Asp-His-D-Phe-Arg-Trp-Gaba-Lys)-OH; | SEQ ID NO: 44 |
| Ac-Nle-c(Cys-His-D-Phe-Arg-D-Trp-Gaba-Cys)-OH; | SEQ ID NO: 45 |
| Ac-Nle-c(Cys-His-D-Phe-Arg-D-Trp-Ahx-Cys)-OH; | SEQ ID NO: 45 |

-continued

| | |
|---|---|
| Ac-Nle-c(Cys-His-D-Phe-Arg-D-Trp-β-Ala-Cys)-OH; | SEQ ID NO: 45 |
| Ac-Nle-c(Cys-His-D-Phe-Arg-D-Trp-D-Ala-Cys)-OH; | SEQ ID NO: 45 |
| Ac-Nle-c(Cys-D-Ala-His-D-2-Nal-Arg-Trp-Cys)-OH; | SEQ ID NO: 46 |
| Ac-Nle-c(Cys-D-Ala-His-D-2-Nal-Arg-2-Nal-Cys)-OH; | SEQ ID NO: 46 |
| Ac-Nle-c(Cys-D-Ala-His-D-2-Nal-Arg-1-Nal-Cys)-OH; | SEQ ID NO: 46 |
| Ac-Nle-c(Cys-D-Ala-His-D-2-Nal-Arg-Bal-Cys)-OH; | SEQ ID NO: 46 |
| Ac-Nle-c(Pen-D-Ala-His-D-Phe-Arg-Trp-Cys)-OH; | SEQ ID NO: 47 |
| Ac-Nle-c(Cys-His-D-Phe-Arg-Trp-Gaba-Pen)-OH; | SEQ ID NO: 48 |
| Ac-Arg-c(Cys-D-Ala-His-D-2-Nal-Arg-Trp-Cys)-NH$_2$; | SEQ ID NO: 49 |
| Ac-Arg-c(Cys-D-Ala-His-D-Phe-Arg-Trp-Cys)-NH$_2$; | SEQ ID NO: 50 |
| Ac-D-Arg-c(Cys-D-Ala-His-D-Phe-Arg-Trp-Cys)-NH$_2$; | SEQ ID NO: 50 |
| Ac-D-Arg-c(Cys-D-Ala-His-D-Phe-Arg-Trp-Pen)-NH$_2$; | SEQ ID NO: 51 |
| Ac-D-Arg-c(Cys-His-D-Phe-Arg-Trp-Gaba-Pen)-NH$_2$; | SEQ ID NO: 52 |
| Ac-Arg-c(Cys-His-D-Phe-Arg-Trp-Gaba-Pen)-NH$_2$; | SEQ ID NO: 52 |
| Ac-Arg-c(Cys-D-Ala-His-D-Phe-Arg-Trp-Pen)-NH$_2$; | SEQ ID NO: 51 |
| Ac-D-Arg-c(Asp-His-D-Phe-Arg-Trp-Ala-Lys)-NH$_2$; | SEQ ID NO: 53 |
| Ac-Arg-c(Asp-His-D-Phe-Arg-Trp-Ala-Lys)-NH$_2$; | SEQ ID NO: 53 |
| Ac-Nle-c(Cys-3-Pal-D-Phe-Arg-Trp-Gaba-Cys)-NH$_2$; | SEQ ID NO: 35 |
| Ac-Nle-c(Cys-D-Ala-His-D-Phe-Arg-Trp-Gly-Cys)-NH$_2$; | SEQ ID NO: 54 |
| Ac-Nle-c(Cys-D-Ala-His-D-Phe-Arg-Trp-D-Ala-Cys)-NH$_2$; | SEQ ID NO: 54 |
| Ac-Nle-c(Cys-D-Ala-His-D-Phe-Arg-Trp-β-Ala-Cys)-NH$_2$; | SEQ ID NO: 54 |
| Ac-Nle-c(Cys-D-Ala-His-D-Phe-Arg-Trp-Gaba-Cys)-NH$_2$; | SEQ ID NO: 54 |
| Ac-Nle-c(Cys-D-Ala-His-D-Phe-Arg-Trp-Apn-Cys)-NH$_2$; | SEQ ID NO: 54 |
| Ac-c(Cys-Glu-His-D-Phe-Arg-Trp-Ala-Cys)-NH$_2$; | SEQ ID NO: 55 |
| Ac-c(Cys-Glu-His-D-Phe-Arg-2-Nal-Ala-Cys)-NH$_2$; | SEQ ID NO: 55 |
| Ac-c(Cys-D-Ala-His-D-Phe-Arg-Trp-Ala-Cys)-NH$_2$; | SEQ ID NO: 56 |
| Ac-c(Cys-D-Ala-His-D-Phe-Arg-2-Nal-Ala-Cys)-NH$_2$; | SEQ ID NO: 56 |

```
                                                             SEQ ID NO: 57
Ac-Nle-c(Cys-D-Ala-His-D-Phe-Arg-Trp-Ala-Cys)-NH2;

SEQ ID NO: 57
Ac-Nle-c(Cys-D-Ala-His-D-Phe-Arg-Trp-β-Ala-Cys)-NH2;

SEQ ID NO: 58
Ac-Nle-c(Asp-D-Ala-His-D-Phe-Arg-Bal-Ala-Lys)-NH2;

(SEQ ID NO: 60)
Tyr-Gly-Arg-(Lys)2-(Arg)2-Gln-(Arg)3-Nle-c(Asp-His-D-2-Nal-Arg-Trp-Lys)-NH2;

(SEQ ID NO: 61)
Tyr-Gly-Arg-(Lys)2-(Arg)2-Gln-(Arg)3-Doc-Nle-c(Asp-His-D-2-Nal-Arg-Trp-Lys)-NH2;

(SEQ ID NO: 62)
Nle-c(Asp-His-D-2-Nal-Arg-Trp-Lys)-β-Ala-Tyr-Gly-Arg-(Lys)2-(Arg)2-Gln-(Arg)3-NH2;

(SEQ ID NO: 62)
Ac-Nle-c(Asp-His-D-2-Nal-Arg-Trp-Lys)-β-Ala-Tyr-Gly-Arg-(Lys)2-(Arg)2-Gln-(Arg)3-
NH2;

(SEQ ID NO: 63)
Nle-c(Asp-His-D-2-Nal-Arg-Trp-Lys)-(Doc)2-Tyr-Gly-Arg-(Lys)2-(Arg)2-Gln-(Arg)3-NH2;

(SEQ ID NO: 64)
Ac-Nle-c(Asp-His-D-2-Nal-Arg-Trp-Lys)-(Pro)2-Lys-Asp-Tyr-Gly-Arg-(Lys)2-(Arg)2-Gln-
(Arg)3-NH2;

(SEQ ID NO: 65)
Ac-c(Cys-Glu-His-D-2-Nal-Arg-Trp-Gly-Cys)-(Pro)2-Lys-Asp-Tyr-Gly-Arg-(Lys)2-(Arg)2-
Gln-(Arg)3-NH2;

(SEQ ID NO 66)
Ac-Nle-c(Asp-His-D-2-Nal-Arg-Trp-Lys)-(β-Ala)2-Tyr-Gly-Arg-(Lys)2-(Arg)2-Gln-(Arg)3-
NH2;

(SEQ ID NO: 67)
Ac-Nle-c(Asp-His-D-2-Nal-Arg-Trp-Lys)-(Pro)2-Lys-Asp-Doc-Tyr-Gly-Arg-(Lys)2-(Arg)2-
Gln-(Arg)3-NH2;

(SEQ ID NO: 68)
Ac-c(Cys-Glu-His-D-2-Nal-Arg-Trp-Gly-Cys)-(Pro)2-Lys-Asp-Doc-Tyr-Gly-Arg-(Lys)2-
(Arg)2-Gln-(Arg)3-NH2;

(SEQ ID NO: 69)
Ac-c(Cys-Glu-His-D-2-Nal-Arg-Trp-Ala-Cys)-(Pro)2-Lys-Asp-β-Ala-Tyr-Gly-Arg-(Lys)2-
(Arg)2-Gln-(Arg)3-NH2;

(SEQ ID NO: 69)
Ac-c(Cys-Glu-His-D-2-Nal-Arg-Trp-Ala-Cys)-(Pro)2-Lys-Asp-Doc-Tyr-Gly-Arg-(Lys)2-
(Arg)2-Gln-(Arg)3-NH2;

(SEQ ID NO: 70)
Ac-Nle-c(Asp-His-D-2-Nal-Arg-Trp-Lys)-(Doc)2-Tyr-Gly-Arg-(Lys)2-(Arg)2-Gln-(Arg)3-
NH2;

(SEQ ID NO: 71)
Ac-c(Cys-Glu-His-D-2-Nal-Arg-2-Nal-Ala-Cys)-(Pro)2-Lys-Asp-β-Ala-Tyr-Gly-Arg-
(Lys)2-(Arg)2-Gln-(Arg)3-NH2;

(SEQ ID NO: 72)
Ac-c(Cys-Glu-His-D-2-Nal-Arg-Bal-Ala-Cys)-(Pro)2-Lys-Asp-β-Ala-(Arg)5-Gln-(Arg)3-
NH2;

(SEQ ID NO: 73)
Ac-c(Cys-Glu-His-D-2-Nal-Arg-Bal-Ala-Cys)-(Pro)2-Lys-Asp-β-Ala-Gly-(Arg)5-Gln-
(Arg)3-NH2;
```

-continued (SEQ ID NO: 74)
Ac-c(Cys-Glu-His-D-2-Nal-Arg-Bal-Ala-Cys)-(Pro)$_2$-Lys-Asp-β-Ala-Tyr-Gly-(Arg)$_5$-Gln-(Arg)$_3$-NH$_2$;

(SEQ ID NO: 75)
Ac-c(Cys-Glu-His-D-2-Nal-Arg-Trp-Ala-Cys)-(Pro)$_2$-Lys-Asp-β-Ala-Tyr-Gly-Arg-(Lys)$_2$-Arg-Gln-(Arg)$_4$-NH$_2$;

(SEQ ID NO: 76)
Ac-c(Cys-Glu-His-D-2-Nal-Arg-Trp-Ala-Cys)-(Pro)$_2$-Lys-Asp-β-Ala-Tyr-Gly-Arg-(Lys)$_2$-Gln-(Arg)$_5$-NH$_2$;

(SEQ ID NO: 77)
Ac-c(Cys-Glu-His-D-2-Nal-Arg-Trp-Ala-Cys)-(Pro)$_2$-Lys-Asp-β-Ala-Tyr-Gly-Arg-Lys-Gln-Lys-(Arg)$_5$-NH$_2$;

(SEQ ID NO: 78)
Ac-c(Cys-Glu-His-D-2-Nal-Arg-Trp-Ala-Cys)-(Pro)$_2$-Lys-Asp-β-Ala-Tyr-Gly-Arg-(Lys)$_2$-(Arg)$_4$-Gln-Arg-NH$_2$;

(SEQ ID NO: 79)
Ac-c(Cys-Glu-His-D-2-Nal-Arg-Bal-Ala-Cys)-(Pro)$_2$-Lys-Asp-β-Ala-Tyr-Aib-Arg-(Lys)$_2$-(Arg)$_2$-Gln-(Arg)$_3$-NH$_2$;

(SEQ ID NO: 80)
Ac-c(Cys-Glu-His-D-2-Nal-Arg-1-Nal-Ala-Cys)-(Pro)$_2$-Arg-Asp-β-Ala-(Arg)$_5$-Gln-(Arg)$_3$-NH$_2$;

(SEQ ID NO: 80)
Ac-c(Cys-Glu-His-D-2-Nal-Arg-1-Nal-Ala-Cys)-(Pro)$_2$-Lys-Asp-β-Ala-(Arg)$_5$-Gln-(Arg)$_3$-NH$_2$;

(SEQ ID NO: 81)
Ac-c(Cys-Glu-His-D-2-Nal-Arg-1-Nal-Ala-Cys)-(Pro)$_2$-Lys-Asp-β-Ala-(Arg)$_6$-Gln-(Arg)$_3$-NH$_2$;

(SEQ ID NO: 82)
Ac-c(Cys-Glu-His-D-2-Nal-Arg-2-Nal-Ala-Cys)-(Pro)$_2$-Arg-Asp-β-Ala-(Arg)$_5$-Gln-(Arg)$_3$-NH$_2$;

(SEQ ID NO: 82)
Ac-c(Cys-Glu-His-D-2-Nal-Arg-2-Nal-Ala-Cys)-(Pro)$_2$-Lys-Asp-β-Ala-(Arg)$_5$-Gln-(Arg)$_3$-NH$_2$;

(SEQ ID NO: 81)
Ac-c(Cys-Glu-His-D-2-Nal-Arg-2-Nal-Ala-Cys)-(Pro)$_2$-Lys-Asp-β-Ala-(Arg)$_6$-Gln-(Arg)$_3$-NH$_2$;

(SEQ ID NO: 83)
Ac-c(Cys-Glu-His-D-2-Nal-Arg-Bal-Ala-Cys)-(Pro)$_2$-Arg-Asp-β-Ala-(Arg)$_6$-Gln-(Arg)$_3$-NH$_2$;

(SEQ ID NO: 84)
Ac-c(Cys-Glu-His-D-2-Nal-Arg-Bal-Ala-Cys)-(Pro)$_2$-Arg-Asp-β-Ala-(Arg)$_5$-Gln-(Arg)$_3$-NH$_2$;

(SEQ ID NO: 83)
Ac-c(Cys-Glu-His-D-2-Nal-Arg-Bal-Ala-Cys)-(Pro)$_2$-Lys-Asp-β-Ala-(Arg)$_6$-Gln-(Arg)$_3$-NH$_2$;

(SEQ ID NO: 85)
Ac-c(Cys-Glu-His-D-2-Nal-Arg-Trp-Ala-Cys)-(Pro)$_2$-Lys-Asp-β-Ala-Tyr-Gly-Arg-(Lys)$_2$-(Arg)$_3$-Gln-(Arg)$_2$-NH$_2$;

(SEQ ID NO: 86)
Ac-c(Cys-Glu-His-D-2-Nal-Arg-Trp-Ala-Cys)-(Pro)$_2$-Lys-Asp-β-Ala-Tyr-Gly-Arg-Gln-(Lys)$_2$-(Arg)$_5$-NH$_2$;

(SEQ ID NO: 87)
Ac-c(Cys-Glu-His-D-2-Nal-Arg-Trp-Ala-Cys)-(Pro)$_2$-Lys-Asp-β-Ala-Tyr-Gly-Arg-(Lys)$_2$-(Arg)$_5$-Gln-NH$_2$;

(SEQ ID NO: 71)
Ac-c(Cys-Glu-His-D-2-Nal-Arg-1-Nal-Ala-Cys)-(Pro)$_2$-Lys-Asp-β-Ala-Tyr-Gly-Arg-(Lys)$_2$-(Arg)$_2$-Gln-(Arg)$_3$-NH$_2$;

(SEQ ID NO: 71)
Ac-c(Cys-Glu-His-D-2-Nal-Arg-Bal-Ala-Cys)-(Pro)$_2$-Lys-Asp-β-Ala-Tyr-Gly-Arg-(Lys)$_2$-(Arg)$_2$-Gln-(Arg)$_3$-NH$_2$;

(SEQ ID NO: 88)
Ac-c(Cys-Glu-His-D-2-Nal-Arg-1-Nal-Ala-Cys)-(Pro)$_2$-Lys-Asp-β-Ala-(Arg)$_2$-Lys-(Arg)$_2$-Gln-(Arg)$_3$-NH$_2$;

(SEQ ID NO: 89)
Ac-c(Cys-Glu-His-D-2-Nal-Arg-1-Nal-Ala-Cys)-(Pro)$_2$-Lys-Asp-β-Ala-Arg-Lys-(Arg)$_3$-Gln-(Arg)$_3$-NH$_2$;

(SEQ ID NO: 88)
Ac-c(Cys-Glu-His-D-2-Nal-Arg-2-Nal-Ala-Cys)-(Pro)$_2$-Lys-Asp-β-Ala-(Arg)$_2$-Lys-(Arg)$_2$-Gln-(Arg)$_3$-NH$_2$;

(SEQ ID NO: 90)
Ac-c(Cys-Glu-His-D-2-Nal-Arg-2-Nal-Ala-Cys)-(Pro)$_2$-Lys-Asp-β-Ala-Tyr-Gly-(Arg)$_2$-Lys-(Arg)$_2$-Gln-(Arg)$_3$-NH$_2$;

(SEQ ID NO: 91)
Ac-c(Cys-Glu-His-D-2-Nal-Arg-2-Nal-Ala-Cys)-(Pro)$_2$-Lys-Asp-β-Ala-Gly-(Arg)$_2$-Lys-(Arg)$_2$-Gln-(Arg)$_3$-NH$_2$;

(SEQ ID NO: 92)
Ac-c(Cys-Glu-His-D-2-Nal-Arg-2-Nal-Ala-Cys)-(Pro)$_2$-Lys-Asp-β-Ala-Gly-Arg-Lys-(Arg)$_3$-Gln-(Arg)$_3$-NH$_2$;

(SEQ ID NO: 95)
Ac-c(Cys-Glu-His-D-2-Nal-Arg-1-Nal-Ala-Cys)-(Pro)$_2$-Lys-Asp-β-Ala-Tyr-Gly-(Arg)$_2$-Lys-(Arg)$_2$-Gln-(Arg)$_3$-NH$_2$;

(SEQ ID NO: 96)
Ac-c(Cys-Glu-His-D-2-Nal-Arg-1-Nal-Ala-Cys)-(Pro)$_2$-Lys-Asp-β-Ala-Tyr-Gly-Arg-Lys-(Arg)$_3$-Gln-(Arg)$_3$-NH$_2$;

(SEQ ID NO: 97)
Ac-c(Cys-Glu-His-D-2-Nal-Arg-1-Nal-Ala-Cys)-(Pro)$_2$-Lys-Asp-β-Ala-Gly-(Arg)$_2$-Lys-(Arg)$_2$-Gln-(Arg)$_3$-NH$_2$;

(SEQ ID NO: 92)
Ac-c(Cys-Glu-His-D-2-Nal-Arg-1-Nal-Ala-Cys)-(Pro)$_2$-Lys-Asp-β-Ala-Gly-Arg-Lys-(Arg)$_3$-Gln-(Arg)$_3$-NH$_2$;

(SEQ ID NO: 98)
Ac-c(Cys-Glu-His-D-2-Nal-Arg-2-Nal-Ala-Cys)-(Pro)$_2$-Lys-Asp-β-Ala-(Arg)$_2$-Lys-(Arg)$_2$-Gln-(Arg)$_3$-NH$_2$;

(SEQ ID NO: 99)
Ac-c(Cys-Glu-His-D-2-Nal-Arg-2-Nal-Ala-Cys)-(Pro)$_2$-Lys-Asp-β-Ala-Arg-Lys-(Arg)$_3$-Gln-(Arg)$_3$-NH$_2$;

```
                                                                 (SEQ ID NO: 101)
Ac-c(Cys-Glu-His-D-2-Nal-Arg-2-Nal-Ala-Cys)-(Pro)$_2$-Lys-Asp-β-Ala-Tyr-Gly-Arg-Lys-
(Arg)$_3$-Gln-(Arg)$_3$-NH$_2$;

(SEQ ID NO: 104)
Ac-c(Cys-Glu-His-D-2-Nal-Arg-Bal-Ala-Cys)-(Pro)$_2$-Lys-Asp-β-Ala-(Arg)$_2$-Lys-(Arg)$_2$-
Gln-(Arg)$_3$-NH$_2$;

(SEQ ID NO: 105)
Ac-c(Cys-Glu-His-D-2-Nal-Arg-Bal-Ala-Cys)-(Pro)$_2$-Lys-Asp-β-Ala-Arg-Lys-(Arg)$_3$-Gln-
(Arg)$_3$-NH$_2$;

(SEQ ID NO: 100)
Ac-c(Cys-Glu-His-D-2-Nal-Arg-Bal-Ala-Cys)-(Pro)$_2$-Lys-Asp-β-Ala-Tyr-Gly-(Arg)$_2$-Lys-
(Arg)$_2$-Gln-(Arg)$_3$-NH$_2$;

(SEQ ID NO: 101)
Ac-c(Cys-Glu-His-D-2-Nal-Arg-Bal-Ala-Cys)-(Pro)$_2$-Lys-Asp-β-Ala-Tyr-Gly-Arg-Lys-
(Arg)$_3$-Gln-(Arg)$_3$-NH$_2$;

(SEQ ID NO: 102)
Ac-c(Cys-Glu-His-D-2-Nal-Arg-Bal-Ala-Cys)-(Pro)$_2$-Lys-Asp-β-Ala-Gly-(Arg)$_2$-Lys-
(Arg)$_2$-Gln-(Arg)$_3$-NH$_2$;

(SEQ ID NO: 103)
Ac-c(Cys-Glu-His-D-2-Nal-Arg-Bal-Ala-Cys)-(Pro)$_2$-Lys-Asp-β-Ala-Gly-Arg-Lys-(Arg)$_3$-
Gln-(Arg)$_3$-NH$_2$;

(SEQ ID NO: 113)
Ac-c(Cys-Glu-His-D-2-Nal-Arg-Trp-Ala-Cys)-(Pro)$_2$-Lys-Asp-β-Ala-(Arg)$_5$-Gln-(Arg)$_3$-
NH$_2$;

(SEQ ID NO: 113)
Ac-c(Cys-Glu-His-D-2-Nal-Arg-Trp-Ala-Cys)-(Pro)$_2$-Arg-Asp-β-Ala-(Arg)$_5$-Gln-(Arg)$_3$-
NH$_2$;

(SEQ ID NO: 114)
Ac-c(Cys-Glu-His-D-2-Nal-Arg-Trp-Ala-Cys)-(Pro)$_2$-Lys-Asp-β-Ala-Tyr-Gly-(Arg)$_5$-Gln-
(Arg)$_3$-NH$_2$;

(SEQ ID NO: 114)
Ac-c(Cys-Glu-His-D-2-Nal-Arg-Trp-Ala-Cys)-(Pro)$_2$-Arg-Asp-β-Ala-Tyr-Gly-(Arg)$_5$-Gln-
(Arg)$_3$-NH$_2$;

(SEQ ID NO: 115)
Ac-c(Cys-Glu-His-D-2-Nal-Arg-Trp-Ala-Cys)-(Pro)$_2$-Lys-Asp-β-Ala-(Arg)$_5$-Gln-(Arg)$_4$-
NH$_2$;

(SEQ ID NO: 115)
Ac-c(Cys-Glu-His-D-2-Nal-Arg-Trp-Ala-Cys)-(Pro)$_2$-Arg-Asp-β-Ala-(Arg)$_5$-Gln-(Arg)$_4$-
NH$_2$;

(SEQ ID NO: 116)
Ac-c(Cys-Glu-His-D-2-Nal-Arg-Trp-Ala-Cys)-(Pro)$_2$-Lys-Asp-β-Ala-Tyr-Gly-(Arg)$_5$-Gln-
(Arg)$_4$-NH$_2$;

(SEQ ID NO: 116)
Ac-c(Cys-Glu-His-D-2-Nal-Arg-Trp-Ala-Cys)-(Pro)$_2$-Arg-Asp-β-Ala-Tyr-Gly-(Arg)$_5$-Gln-
(Arg)$_4$-NH$_2$;

(SEQ ID NO: 118)
Ac-c(Cys-Glu-His-D-2-Nal-Arg-1-Nal-Ala-Cys)-(Pro)$_2$-Lys-Asp-β-Ala-(Arg)$_5$-Gln-(Arg)$_4$-
NH$_2$;
```

-continued (SEQ ID NO: 118)
Ac-c(Cys-Glu-His-D-2-Nal-Arg-1-Nal-Ala-Cys)-(Pro)$_2$-Arg-Asp-β-Ala-(Arg)$_5$-Gln-(Arg)$_4$-NH$_2$;

(SEQ ID NO: 119)
Ac-c(Cys-Glu-His-D-2-Nal-Arg-1-Nal-Ala-Cys)-(Pro)$_2$-Arg-Asp-β-Ala-(Arg)$_6$-Gln-(Arg)$_3$-NH$_2$;

(SEQ ID NO: 120)
Ac-c(Cys-Glu-His-D-2-Nal-Arg-1-Nal-Ala-Cys)-(Pro)$_2$-Lys-Asp-β-Ala-Tyr-Gly-(Arg)$_5$-Gln-(Arg)$_3$-NH$_2$;

(SEQ ID NO: 120)
Ac-c(Cys-Glu-His-D-2-Nal-Arg-1-Nal-Ala-Cys)-(Pro)$_2$-Arg-Asp-β-Ala-Tyr-Gly-(Arg)$_5$-Gln-(Arg)$_3$-NH$_2$;

(SEQ ID NO: 121)
Ac-c(Cys-Glu-His-D-2-Nal-Arg-1-Nal-Ala-Cys)-(Pro)$_2$-Lys-Asp-β-Ala-Tyr-Gly-(Arg)$_5$-Gln-(Arg)$_4$-NH$_2$;

(SEQ ID NO: 121)
Ac-c(Cys-Glu-His-D-2-Nal-Arg-1-Nal-Ala-Cys)-(Pro)$_2$-Arg-Asp-β-Ala-Tyr-Gly-(Arg)$_5$-Gln-(Arg)$_4$-NH$_2$;

(SEQ ID NO: 122)
Ac-c(Cys-Glu-His-D-2-Nal-Arg-1-Nal-Ala-Cys)-(Pro)$_2$-Lys-Asp-β-Ala-Tyr-Gly-(Arg)$_6$-Gln-(Arg)$_3$-NH$_2$;

(SEQ ID NO: 122)
Ac-c(Cys-Glu-His-D-2-Nal-Arg-1-Nal-Ala-Cys)-(Pro)$_2$-Arg-Asp-β-Ala-Tyr-Gly-(Arg)$_6$-Gln-(Arg)$_3$-NH$_2$;

(SEQ ID NO: 124)
Ac-c(Cys-Glu-His-D-2-Nal-Arg-2-Nal-Ala-Cys)-(Pro)$_2$-Arg-Asp-β-Ala-(Arg)$_6$-Gln-(Arg)$_3$-NH$_2$;

(SEQ ID NO: 125)
Ac-c(Cys-Glu-His-D-2-Nal-Arg-2-Nal-Ala-Cys)-(Pro)$_2$-Lys-Asp-β-Ala-(Arg)$_5$-Gln-(Arg)$_4$-NH$_2$;

(SEQ ID NO: 125)
Ac-c(Cys-Glu-His-D-2-Nal-Arg-2-Nal-Ala-Cys)-(Pro)$_2$-Arg-Asp-β-Ala-(Arg)$_5$-Gln-(Arg)$_4$-NH$_2$;

(SEQ ID NO: 126)
Ac-c(Cys-Glu-His-D-2-Nal-Arg-2-Nal-Ala-Cys)-(Pro)$_2$-Lys-Asp-β-Ala-Tyr-Gly-(Arg)$_5$-Gln-(Arg)$_3$-NH$_2$;

(SEQ ID NO: 126)
Ac-c(Cys-Glu-His-D-2-Nal-Arg-2-Nal-Ala-Cys)-(Pro)$_2$-Arg-Asp-β-Ala-Tyr-Gly-(Arg)$_5$-Gln-(Arg)$_3$-NH$_2$;

(SEQ ID NO: 127)
Ac-c(Cys-Glu-His-D-2-Nal-Arg-2-Nal-Ala-Cys)-(Pro)$_2$-Lys-Asp-β-Ala-Tyr-Gly-(Arg)$_6$-Gln-(Arg)$_3$-NH$_2$;

(SEQ ID NO: 127)
Ac-c(Cys-Glu-His-D-2-Nal-Arg-2-Nal-Ala-Cys)-(Pro)$_2$-Arg-Asp-β-Ala-Tyr-Gly-(Arg)$_6$-Gln-(Arg)$_3$-NH$_2$;

(SEQ ID NO: 128)
Ac-c(Cys-Glu-His-D-2-Nal-Arg-2-Nal-Ala-Cys)-(Pro)$_2$-Lys-Asp-β-Ala-Tyr-Gly-(Arg)$_5$-Gln-(Arg)$_4$-NH$_2$;

```
                                                                  (SEQ ID NO: 128)
Ac-c(Cys-Glu-His-D-2-Nal-Arg-2-Nal-Ala-Cys)-(Pro)₂-Arg-Asp-β-Ala-Tyr-Gly-(Arg)₅-

Gln-(Arg)₄-NH₂;

(SEQ ID NO: 130)
Ac-c(Cys-Glu-His-D-2-Nal-Arg-Bal-Ala-Cys)-(Pro)₂-Lys-Asp-β-Ala-(Arg)₅-Gln-(Arg)₄-

NH₂;

(SEQ ID NO: 130)
Ac-c(Cys-Glu-His-D-2-Nal-Arg-Bal-Ala-Cys)-(Pro)₂-Arg-Asp-β-Ala-(Arg)₅-Gln-(Arg)₄-

NH₂;

(SEQ ID NO: 133)
Ac-c(Cys-Glu-His-D-2-Nal-Arg-Bal-Ala-Cys)-(Pro)₂-Arg-Asp-β-Ala-Tyr-Gly-(Arg)₅-Gln- (Arg)₃-NH₂;

(SEQ ID NO: 134)
Ac-c(Cys-Glu-His-D-2-Nal-Arg-Bal-Ala-Cys)-(Pro)₂-Lys-Asp-β-Ala-Tyr-Gly-(Arg)₅-Gln- (Arg)₄-NH₂;

(SEQ ID NO: 134)
Ac-c(Cys-Glu-His-D-2-Nal-Arg-Bal-Ala-Cys)-(Pro)₂-Arg-Asp-β-Ala-Tyr-Gly-(Arg)₅-Gln- (Arg)₄-NH₂;

(SEQ ID NO: 135)
Ac-c(Cys-Glu-His-D-2-Nal-Arg-Bal-Ala-Cys)-(Pro)₂-Lys-Asp-β-Ala-Tyr-Gly-(Arg)₆-Gln- (Arg)₃-NH₂;

(SEQ ID NO: 135)
Ac-c(Cys-Glu-His-D-2-Nal-Arg-Bal-Ala-Cys)-(Pro)₂-Arg-Asp-β-Ala-Tyr-Gly-(Arg)₆-Gln- (Arg)₃-NH₂;

(SEQ ID NO: 136)
Ac-Nle-c(Cys-D-Ala-His-D-Phe-Arg-Trp-Cys)-(Doc)₂-Tyr-Gly-Arg-(Lys)₂-(Arg)₂-Gln- (Arg)₃-NH₂;

(SEQ ID NO: 137)
Ac-Nle-c(Cys-D-Ala-His-D-Phe-Arg-Trp-Cys)-β-Ala-Tyr-Gly-Arg-(Lys)₂-Arg-Gln-(Arg)₄-

NH₂;

(SEQ ID NO: 136)
Ac-Nle-c(Cys-D-Ala-His-D-Phe-Arg-Trp-Cys)-Doc-Tyr-Gly-Arg-(Lys)₂-(Arg)₂-Gln- (Arg)₃-NH₂;

(SEQ ID NO: 138)
Ac-Nle-c(Cys-D-Ala-His-D-Phe-Arg-Trp-Cys)-β-Ala-(Arg)₅-Gln-(Arg)₃-NH₂;

(SEQ ID NO: 138)
Ac-Nle-c(Cys-D-Ala-His-D-Phe-Arg-Trp-Cys)-β-Ala-Gly-(Arg)₅-Gln-(Arg)₃-NH₂;

(SEQ ID NO: 139)
Ac-Nle-c(Cys-D-Ala-His-D-Phe-Arg-Trp-Cys)-β-Ala-Tyr-Gly-(Arg)₅-Gln-(Arg)₃-NH₂;

(SEQ ID NO: 140)
Ac-Nle-c(Cys-D-Ala-His-D-Phe-Arg-Trp-Cys)-β-Ala-Gly-(Arg)₅-Gln-(Arg)₄-NH₂;

(SEQ ID NO: 141)
Ac-Nle-c(Cys-D-Ala-His-D-Phe-Arg-Trp-Cys)-β-Ala-Tyr-Gly-(Arg)₂-Lys-(Arg)₂-Gln- (Arg)₃-NH₂;

(SEQ ID NO: 142)
Ac-Nle-c(Cys-D-Ala-His-D-Phe-Arg-Trp-Cys)-β-Ala-Tyr-Gly-Arg-Lys-(Arg)₃-Gln-(Arg)₃-

NH₂;
```

(SEQ ID NO: 141)
Ac-Nle-c(Cys-D-Ala-His-D-Phe-Arg-Trp-Cys)-β-Ala-Gly-(Arg)$_2$-Lys-(Arg)$_2$-Gln-(Arg)$_3$-NH$_2$;

(SEQ ID NO: 142)
Ac-Nle-c(Cys-D-Ala-His-D-Phe-Arg-Trp-Cys)-β-Ala-Gly-Arg-Lys-(Arg)$_3$-Gln-(Arg)$_3$-NH$_2$;

(SEQ ID NO: 143)
Ac-Nle-c(Cys-D-Ala-His-D-Phe-Arg-Trp-Cys)-β-Ala-(Arg)$_2$-Lys-(Arg)$_2$-Gln-(Arg)$_3$-NH$_2$;

(SEQ ID NO: 144)
Ac-Nle-c(Cys-D-Ala-His-D-Phe-Arg-Trp-Cys)-β-Ala-Arg-Lys-(Arg)$_3$-Gln-(Arg)$_3$-NH$_2$;

(SEQ ID NO: 148)
Ac-Nle-c(Cys-D-Ala-His-D-Phe-Arg-Trp-Cys)-β-Ala-(Arg)$_5$-Gln-(Arg)$_3$-NH$_2$;

(SEQ ID NO: 148)
Ac-Nle-c(Cys-D-Ala-His-D-Phe-Arg-Trp-Cys)-(β-Ala)$_2$-(Arg)$_5$-Gln-(Arg)$_3$-NH$_2$;

(SEQ ID NO: 149)
Ac-Nle-c(Cys-D-Ala-His-D-Phe-Arg-Trp-Cys)-(β-Ala)$_2$-Gly-(Arg)$_5$-Gln-(Arg)$_3$-NH$_2$;;

(SEQ ID NO: 149)
Ac-Nle-c(Cys-D-Ala-His-D-Phe-Arg-Trp-Cys)-(β-Ala)$_2$-Tyr-Gly-(Arg)$_5$-Gln-(Arg)$_3$-NH$_2$;

(SEQ ID NO: 151)
Ac-Nle-c(Cys-D-Ala-His-D-Phe-Arg-Trp-Cys)-Doc-(Arg)$_5$-Gln-(Arg)$_3$-NH$_2$;

(SEQ ID NO: 150)
Ac-Nle-c(Cys-D-Ala-His-D-Phe-Arg-Trp-Cys)-Doc-Gly-(Arg)$_5$-Gln-(Arg)$_3$-NH$_2$;

(SEQ ID NO: 150)
Ac-Nle-c(Cys-D-Ala-His-D-Phe-Arg-Trp-Cys)-Doc-Tyr-Gly-(Arg)$_5$-Gln-(Arg)$_3$-NH$_2$;

(SEQ ID NO: 151)
Ac-Nle-c(Cys-D-Ala-His-D-Phe-Arg-Trp-Cys)-(Doc)$_2$-(Arg)$_5$-Gln-(Arg)$_3$-NH$_2$;

(SEQ ID NO: 152)
Ac-Nle-c(Cys-D-Ala-His-D-Phe-Arg-Trp-Cys)-(Doc)$_2$-Gly-(Arg)$_5$-Gln-(Arg)$_3$-NH$_2$;

(SEQ ID NO: 152)
Ac-Nle-c(Cys-D-Ala-His-D-Phe-Arg-Trp-Cys)-(Doc)$_2$-Tyr-Gly-(Arg)$_5$-Gln-(Arg)$_3$-NH$_2$;

(SEQ ID NO: 154)
Ac-Nle-c(Cys-D-Ala-His-D-Phe-Arg-Trp-Cys)-β-Ala-(Arg)$_5$-Gln-(Arg)$_4$-NH$_2$;

(SEQ ID NO: 153)
Ac-Nle-c(Cys-D-Ala-His-D-Phe-Arg-Trp-Cys)-β-Ala-Tyr-Gly-(Arg)$_5$-Gln-(Arg)$_4$-NH$_2$;

(SEQ ID NO: 154)
Ac-Nle-c(Cys-D-Ala-His-D-Phe-Arg-Trp-Cys)-(β-Ala)$_2$-(Arg)$_5$-Gln-(Arg)$_4$-NH$_2$;

(SEQ ID NO: 155)
Ac-Nle-c(Cys-D-Ala-His-D-Phe-Arg-Trp-Cys)-(β-Ala)$_2$-Gly-(Arg)$_5$-Gln-(Arg)$_4$-NH$_2$;

(SEQ ID NO: 155)
Ac-Nle-c(Cys-D-Ala-His-D-Phe-Arg-Trp-Cys)-(β-Ala)$_2$-Tyr-Gly-(Arg)$_5$-Gln-(Arg)$_4$-NH$_2$;

(SEQ ID NO: 157)
Ac-Nle-c(Cys-D-Ala-His-D-Phe-Arg-Trp-Cys)-Doc-(Arg)$_5$-Gln-(Arg)$_4$-NH$_2$;

(SEQ ID NO: 156)
Ac-Nle-c(Cys-D-Ala-His-D-Phe-Arg-Trp-Cys)-Doc-Gly-(Arg)$_5$-Gln-(Arg)$_4$-NH$_2$;

(SEQ ID NO: 156)
Ac-Nle-c(Cys-D-Ala-His-D-Phe-Arg-Trp-Cys)-Doc-Tyr-Gly-(Arg)$_5$-Gln-(Arg)$_4$-NH$_2$;

(SEQ ID NO: 157)
Ac-Nle-c(Cys-D-Ala-His-D-Phe-Arg-Trp-Cys)-(Doc)$_2$-(Arg)$_5$-Gln-(Arg)$_4$-NH$_2$;

(SEQ ID NO: 158)
Ac-Nle-c(Cys-D-Ala-His-D-Phe-Arg-Trp-Cys)-(Doc)$_2$-Gly-(Arg)$_5$-Gln-(Arg)$_4$-NH$_2$;

(SEQ ID NO: 158)
Ac-Nle-c(Cys-D-Ala-His-D-Phe-Arg-Trp-Cys)-(Doc)$_2$-Tyr-Gly-(Arg)$_5$-Gln-(Arg)$_4$-NH$_2$;

-continued

```
                                                        (SEQ ID NO: 159)
Ac-Nle-c(Cys-His-D-Phe-Arg-Trp-Gaba-Cys)-β-Ala-Tyr-Gly-(Arg)5-Gln-(Arg)3-NH2;

(SEQ ID NO: 160)
Ac-Nle-c(Cys-His-D-Phe-Arg-Trp-Gaba-Cys)-β-Ala-(Arg)5-Gln-(Arg)3-NH2;

(SEQ ID NO: 161)
Ac-Nle-c(Asp-His-D-Phe-Arg-Trp-Ala-Lys)-β-Ala-Tyr-Gly-(Arg)5-Gln-(Arg)3-NH2;

(SEQ ID NO: 162)
Ac-Nle-c(Asp-His-D-Phe-Arg-Trp-Ala-Lys)-β-Ala-(Arg)5-Gln-(Arg)3-NH2;

(SEQ ID NO: 164)
Ac-Nle-c(Asp-His-D-Phe-Arg-Trp-Lys)-β-Ala-Tyr-Gly-(Arg)5-Gln-(Arg)3-NH2;

(SEQ ID NO: 163)
Ac-Nle-c(Asp-His-D-Phe-Arg-Trp-Lys)-β-Ala-Gly-(Arg)5-Gln-(Arg)3-NH2;

(SEQ ID NO: 163)
Ac-Nle-c(Asp-His-D-Phe-Arg-Trp-Lys)-β-Ala-(Arg)5-Gln-(Arg)3-NH2;

(SEQ ID NO: 164)
Ac-Nle-c(Asp-His-D-Phe-Arg-Trp-Lys)-(β-Ala)2-Tyr-Gly-(Arg)5-Gln-(Arg)3-NH2;

(SEQ ID NO: 165)
Ac-Nle-c(Asp-His-D-Phe-Arg-Trp-Lys)-(β-Ala)2-Gly-(Arg)5-Gln-(Arg)3-NH2;

(SEQ ID NO: 165)
Ac-Nle-c(Asp-His-D-Phe-Arg-Trp-Lys)-(β-Ala)2-(Arg)5-Gln-(Arg)3-NH2;

(SEQ ID NO: 166)
Ac-Nle-c(Asp-His-D-Phe-Arg-Trp-Lys)-Doc-Tyr-Gly-(Arg)5-Gln-(Arg)3-NH2;

(SEQ ID NO: 166)
Ac-Nle-c(Asp-His-D-Phe-Arg-Trp-Lys)-Doc-Gly-(Arg)5-Gln-(Arg)3-NH2;

(SEQ ID NO: 168)
Ac-Nle-c(Asp-His-D-Phe-Arg-Trp-Lys)-Doc-(Arg)5-Gln-(Arg)3-NH2;

(SEQ ID NO: 167)
Ac-Nle-c(Asp-His-D-Phe-Arg-Trp-Lys)-(Doc)2-Tyr-Gly-(Arg)5-Gln-(Arg)3-NH2;

(SEQ ID NO: 167)
Ac-Nle-c(Asp-His-D-Phe-Arg-Trp-Lys)-(Doc)2-Gly-(Arg)5-Gln-(Arg)3-NH2;

(SEQ ID NO: 168)
Ac-Nle-c(Asp-His-D-Phe-Arg-Trp-Lys)-(Doc)2-(Arg)5-Gln-(Arg)3-NH2;

(SEQ ID NO: 170)
Ac-Nle-c(Asp-His-D-Phe-Arg-Trp-Lys)-β-Ala-Tyr-Gly-(Arg)5-Gln-(Arg)4-NH2;

(SEQ ID NO: 169)
Ac-Nle-c(Asp-His-D-Phe-Arg-Trp-Lys)-β-Ala-Gly-(Arg)5-Gln-(Arg)4-NH2;

(SEQ ID NO: 169)
Ac-Nle-c(Asp-His-D-Phe-Arg-Trp-Lys)-β-Ala-(Arg)5-Gln-(Arg)4-NH2;

(SEQ ID NO: 170)
Ac-Nle-c(Asp-His-D-Phe-Arg-Trp-Lys)-(β-Ala)2-Tyr-Gly-(Arg)5-Gln-(Arg)4-NH2;

(SEQ ID NO: 171)
Ac-Nle-c(Asp-His-D-Phe-Arg-Trp-Lys)-(β-Ala)2-Gly-(Arg)5-Gln-(Arg)4-NH2;

(SEQ ID NO: 171)
Ac-Nle-c(Asp-His-D-Phe-Arg-Trp-Lys)-(β-Ala)2-(Arg)5-Gln-(Arg)4-NH2;

(SEQ ID NO: 173)
Ac-Nle-c(Asp-His-D-Phe-Arg-Trp-Lys)-Doc-Tyr-Gly-(Arg)5-Gln-(Arg)4-NH2;

(SEQ ID NO: 172)
Ac-Nle-c(Asp-His-D-Phe-Arg-Trp-Lys)-Doc-Gly-(Arg)5-Gln-(Arg)4-NH2;

(SEQ ID NO: 172)
Ac-Nle-c(Asp-His-D-Phe-Arg-Trp-Lys)-Doc-(Arg)5-Gln-(Arg)4-NH2;

(SEQ ID NO: 173)
Ac-Nle-c(Asp-His-D-Phe-Arg-Trp-Lys)-(Doc)2-Tyr-Gly-(Arg)5-Gln-(Arg)4-NH2;

(SEQ ID NO: 174)
Ac-Nle-c(Asp-His-D-Phe-Arg-Trp-Lys)-(Doc)2-Gly-(Arg)5-Gln-(Arg)4-NH2;
```

-continued

Ac-Nle-c(Asp-His-D-Phe-Arg-Trp-Lys)-(Doc)$_2$-(Arg)$_5$-Gln-(Arg)$_4$-NH$_2$; (SEQ ID NO: 174)

Ac-Nle-c(Asp-His-D-Phe-Arg-Trp-β-Ala-Lys)-β-Ala-Tyr-Gly-(Arg)$_5$-Gln-(Arg)$_3$-NH$_2$; (SEQ ID NO: 175)

Ac-Nle-c(Asp-His-D-Phe-Arg-Trp-β-Ala-Lys)-β-Ala-(Arg)$_5$-Gln-(Arg)$_3$-NH$_2$; (SEQ ID NO: 176)

Ac-Nle-c(Cys-His-D-Phe-Arg-Trp-Ahx-Cys)-β-Ala-Tyr-Gly-(Arg)$_5$-Gln-(Arg)$_3$-NH$_2$; (SEQ ID NO: 177)

Ac-Nle-c(Cys-His-D-Phe-Arg-Trp-Ahx-Cys)-β-Ala-(Arg)$_5$-Gln-(Arg)$_3$-NH$_2$; (SEQ ID NO: 178)

D-Phe-c(Cys-His-D-Phe-Arg-Trp-β-Ala-D-Cys)-Thr-β-Ala-Tyr-Gly-(Arg)$_5$-Gln-(Arg)$_3$-NH$_2$; (SEQ ID NO: 179)

D-Phe-c(Cys-His-D-Phe-Arg-Trp-β-Ala-D-Cys)-Thr-β-Ala-(Arg)$_5$-Gln-(Arg)$_3$-NH$_2$; (SEQ ID NO: 180)

Ac-Nle-c(Cys-His-D-Phe-Arg-Trp-Apn-Cys)-β-Ala-Tyr-Gly-(Arg)$_5$-Gln-(Arg)$_3$-NH$_2$; (SEQ ID NO: 181)

Ac-Nle-c(Cys-His-D-Phe-Arg-Trp-Apn-Cys)-β-Ala-(Arg)$_5$-Gln-(Arg)$_3$-NH$_2$; (SEQ ID NO: 182)

Ac-Cha-c(Asp-His-D-Phe-Arg-Trp-Gaba-Lys)-β-Ala-Tyr-Gly-(Arg)$_5$-Gln-(Arg)$_3$-NH$_2$; (SEQ ID NO: 183)

Ac-Cha-c(Asp-His-D-Phe-Arg-Trp-Gaba-Lys)-β-Ala-(Arg)$_5$-Gln-(Arg)$_3$-NH$_2$; (SEQ ID NO: 184)

Ac-Nle-c(Asp-His-D-Phe-Arg-Trp-Gaba-Lys)-β-Ala-Tyr-Gly-(Arg)$_5$-Gln-(Arg)$_3$-NH$_2$; (SEQ ID NO: 183)

Ac-Nle-c(Asp-His-D-Phe-Arg-Trp-Gaba-Lys)-β-Ala-(Arg)$_5$-Gln-(Arg)$_3$-NH$_2$; (SEQ ID NO: 185)

Ac-Chg-c(Asp-His-D-Phe-Arg-Trp-Gaba-Lys)-β-Ala-Tyr-Gly-(Arg)$_5$-Gln-(Arg)$_3$-NH$_2$; (SEQ ID NO: 186)

Ac-Chg-c(Asp-His-D-Phe-Arg-Trp-Gaba-Lys)-β-Ala-(Arg)$_5$-Gln-(Arg)$_3$-NH$_2$; (SEQ ID NO: 185)

Ac-hCha-c(Asp-His-D-Phe-Arg-Trp-Gaba-Lys)-β-Ala-Tyr-Gly-(Arg)$_5$-Gln-(Arg)$_3$-NH$_2$; (SEQ ID NO: 186)

Ac-hCha-c(Asp-His-D-Phe-Arg-Trp-Gaba-Lys)-β-Ala-(Arg)$_5$-Gln-(Arg)$_3$-NH$_2$; (SEQ ID NO: 188)

Ac-hCha-c(Asp-His-D-Phe-Arg-Trp-Gaba-Lys)-(β-Ala)$_2$-Tyr-Gly-(Arg)$_5$-Gln-(Arg)$_3$-NH$_2$; (SEQ ID NO: 187)

Ac-hCha-c(Asp-His-D-Phe-Arg-Trp-Gaba-Lys)-(β-Ala)$_2$-(Arg)$_5$-Gln-(Arg)$_3$-NH$_2$; (SEQ ID NO: 188)

Ac-hCha-c(Asp-His-D-Phe-Arg-Trp-Gaba-Lys)-Doc-Tyr-Gly-(Arg)$_5$-Gln-(Arg)$_3$-NH$_2$; (SEQ ID NO: 189)

Ac-hCha-c(Asp-His-D-Phe-Arg-Trp-Gaba-Lys)-Doc-(Arg)$_5$-Gln-(Arg)$_3$-NH$_2$; (SEQ ID NO: 190)

Ac-hCha-c(Asp-His-D-Phe-Arg-Trp-Gaba-Lys)-(Doc)$_2$-Tyr-Gly-(Arg)$_5$-Gln-(Arg)$_3$-NH$_2$; (SEQ ID NO: 189)

Ac-hCha-c(Asp-His-D-Phe-Arg-Trp-Gaba-Lys)-(Doc)$_2$-(Arg)$_5$-Gln-(Arg)$_3$-NH$_2$; (SEQ ID NO: 190)

Ac-hCha-c(Asp-His-D-Phe-Arg-Trp-Gaba-Lys)-β-Ala-Tyr-Gly-(Arg)$_5$-Gln-(Arg)$_4$-NH$_2$; (SEQ ID NO: 191)

Ac-hCha-c(Asp-His-D-Phe-Arg-Trp-Gaba-Lys)-β-Ala-(Arg)$_5$-Gln-(Arg)$_4$-NH$_2$; (SEQ ID NO: 192)

Ac-hCha-c(Asp-His-D-Phe-Arg-Trp-Gaba-Lys)-(β-Ala)$_2$-Tyr-Gly-(Arg)$_5$-Gln-(Arg)$_4$-NH$_2$; (SEQ ID NO: 191)

-continued

Ac-hCha-c(Asp-His-D-Phe-Arg-Trp-Gaba-Lys)-(β-Ala)$_2$-(Arg)$_5$-Gln-(Arg)$_4$-NH$_2$;  (SEQ ID NO: 192)

Ac-hCha-c(Asp-His-D-Phe-Arg-Trp-Gaba-Lys)-Doc-Tyr-Gly-(Arg)$_5$-Gln-(Arg)$_4$-NH$_2$;  (SEQ ID NO: 193)

Ac-hCha-c(Asp-His-D-Phe-Arg-Trp-Gaba-Lys)-Doc-(Arg)$_5$-Gln-(Arg)$_4$-NH$_2$;  (SEQ ID NO: 194)

Ac-hCha-c(Asp-His-D-Phe-Arg-Trp-Gaba-Lys)-(Doc)$_2$-Tyr-Gly-(Arg)$_5$-Gln-(Arg)$_4$-NH$_2$;  (SEQ ID NO: 193)

Ac-hCha-c(Asp-His-D-Phe-Arg-Trp-Gaba-Lys)-(Doc)$_2$-(Arg)$_5$-Gln-(Arg)$_4$-NH$_2$;  (SEQ ID NO: 194)

Ac-D-Chg-c(Asp-His-D-Phe-Arg-Trp-Gaba-Lys)-β-Ala-Tyr-Gly-(Arg)$_5$-Gln-(Arg)$_3$-NH$_2$;  (SEQ ID NO: 195)

Ac-D-Chg-c(Asp-His-D-Phe-Arg-Trp-Gaba-Lys)-β-Ala-(Arg)$_5$-Gln-(Arg)$_3$-NH$_2$;  (SEQ ID NO: 196)

Ac-hPhe-c(Asp-His-D-Phe-Arg-Trp-Gaba-Lys)-β-Ala-Tyr-Gly-(Arg)$_5$-Gln-(Arg)$_3$-NH$_2$;  (SEQ ID NO: 197)

Ac-hPhe-c(Asp-His-D-Phe-Arg-Trp-Gaba-Lys)-β-Ala-(Arg)$_5$-Gln-(Arg)$_3$-NH$_2$;  (SEQ ID NO: 198)

Ac-Nle-c(Cys-His-D-Phe-Arg-D-Trp-Apn-Cys)-β-Ala-Tyr-Gly-(Arg)$_5$-Gln-(Arg)$_3$-NH$_2$;  (SEQ ID NO: 199)

Ac-Nle-c(Cys-His-D-Phe-Arg-D-Trp-Apn-Cys)-β-Ala-(Arg)$_5$-Gln-(Arg)$_3$-NH$_2$;  (SEQ ID NO: 200)

Ac-Nle-c(Cys-His-D-Phe-Arg-D-Trp-Ahx-Cys)-β-Ala-Tyr-Gly-(Arg)$_5$-Gln-(Arg)$_3$-NH$_2$;  (SEQ ID NO: 199)

Ac-Nle-c(Cys-His-D-Phe-Arg-D-Trp-Ahx-Cys)-β-Ala-(Arg)$_5$-Gln-(Arg)$_3$-NH$_2$;  (SEQ ID NO: 200)

Ac-Nle-c(Cys-His-D-Phe-Arg-D-Trp-β-Ala-Cys)-β-Ala-Tyr-Gly-(Arg)$_5$-Gln-(Arg)$_3$-NH$_2$;  (SEQ ID NO: 201)

Ac-Nle-c(Cys-His-D-Phe-Arg-D-Trp-β-Ala-Cys)-β-Ala-(Arg)$_5$-Gln-(Arg)$_3$-NH$_2$;  (SEQ ID NO: 202)

Ac-Nle-c(Cys-D-Ala-His-D-Phe-Arg-Trp-Pen)-β-Ala-Tyr-Gly-(Arg)$_5$-Gln-(Arg)$_3$-NH$_2$;  (SEQ ID NO: 203)

Ac-Nle-c(Cys-D-Ala-His-D-Phe-Arg-Trp-Pen)-β-Ala-Gly-(Arg)$_5$-Gln-(Arg)$_3$-NH$_2$;  (SEQ ID NO: 203)

Ac-Nle-c(Cys-D-Ala-His-D-Phe-Arg-Trp-Pen)-β-Ala-(Arg)$_5$-Gln-(Arg)$_3$-NH$_2$;  (SEQ ID NO: 205)

Ac-Nle-c(Cys-D-Ala-His-D-Phe-Arg-Trp-Pen)-(β-Ala)$_2$-Tyr-Gly-(Arg)$_5$-Gln-(Arg)$_3$-NH$_2$;  (SEQ ID NO: 204)

Ac-Nle-c(Cys-D-Ala-His-D-Phe-Arg-Trp-Pen)-(β-Ala)$_2$-Gly-(Arg)$_5$-Gln-(Arg)$_3$-NH$_2$;  (SEQ ID NO: 204)

Ac-Nle-c(Cys-D-Ala-His-D-Phe-Arg-Trp-Pen)-(β-Ala)$_2$-(Arg)$_5$-Gln-(Arg)$_3$-NH$_2$;  (SEQ ID NO: 205)

Ac-Nle-c(Cys-D-Ala-His-D-Phe-Arg-Trp-Pen)-Doc-Tyr-Gly-(Arg)$_5$-Gln-(Arg)$_3$-NH$_2$;  (SEQ ID NO: 207)

Ac-Nle-c(Cys-D-Ala-His-D-Phe-Arg-Trp-Pen)-Doc-Gly-(Arg)$_5$-Gln-(Arg)$_3$-NH$_2$;  (SEQ ID NO: 206)

Ac-Nle-c(Cys-D-Ala-His-D-Phe-Arg-Trp-Pen)-Doc-(Arg)$_5$-Gln-(Arg)$_3$-NH$_2$;  (SEQ ID NO: 206)

Ac-Nle-c(Cys-D-Ala-His-D-Phe-Arg-Trp-Pen)-(Doc)$_2$-Tyr-Gly-(Arg)$_5$-Gln-(Arg)$_3$-NH$_2$;  (SEQ ID NO: 207)

Ac-Nle-c(Cys-D-Ala-His-D-Phe-Arg-Trp-Pen)-(Doc)$_2$-Gly-(Arg)$_5$-Gln-(Arg)$_3$-NH$_2$;  (SEQ ID NO: 208)

Ac-Nle-c(Cys-D-Ala-His-D-Phe-Arg-Trp-Pen)-(Doc)$_2$-(Arg)$_5$-Gln-(Arg)$_3$-NH$_2$;  (SEQ ID NO: 208)

-continued (SEQ ID NO: 209)
D-Phe-c(Cys-His-D-(Et)Tyr-Arg-Trp-β-Ala-D-Cys)-β-Ala-Tyr-Gly-(Arg)₅-Gln-(Arg)₃-NH₂;

(SEQ ID NO: 210)
D-Phe-c(Cys-His-D-(Et)Tyr-Arg-Trp-β-Ala-D-Cys)-β-Ala-(Arg)₅-Gln-(Arg)₃-NH₂;

(SEQ ID NO: 209)
D-Phe-c(Cys-His-D-(Et)Tyr-Arg-Trp-β-Ala-D-Cys)-β-Ala-Gly-(Arg)₅-Gln-(Arg)₃-NH₂;

(SEQ ID NO: 211)
D-Phe-c(Cys-His-D-(Et)Tyr-Arg-Trp-β-Ala-D-Cys)-β-Ala-(Arg)₅-Gln-(Arg)₄-NH₂;

(SEQ ID NO: 212)
D-Phe-c(Cys-His-D-(Et)Tyr-Arg-Trp-β-Ala-D-Cys)-(β-Ala)₂-Tyr-Gly-(Arg)₅-Gln-(Arg)₃-NH₂;

(SEQ ID NO: 213)
D-Phe-c(Cys-His-D-(Et)Tyr-Arg-Trp-β-Ala-D-Cys)-(β-Ala)₂-(Arg)₅-Gln-(Arg)₃-NH₂;

(SEQ ID NO: 213)
D-Phe-c(Cys-His-D-(Et)Tyr-Arg-Trp-β-Ala-D-Cys)-(β-Ala)₂-Gly-(Arg)₅-Gln-(Arg)₃-NH₂;

(SEQ ID NO: 267)
D-Phe-c(Cys-His-D-(Et)Tyr-Arg-Trp-β-Ala-D-Cys)-(β-Ala)₂-(Arg)₅-Gln-(Arg)₄-NH₂;

(SEQ ID NO: 214)
D-Phe-c(Cys-His-D-(Et)Tyr-Arg-Trp-β-Ala-D-Cys)-Doc-Tyr-Gly-(Arg)₅-Gln-(Arg)₃-NH₂;

(SEQ ID NO: 216)
D-Phe-c(Cys-His-D-(Et)Tyr-Arg-Trp-β-Ala-D-Cys)-Doc-(Arg)₅-Gln-(Arg)₃-NH₂;

(SEQ ID NO: 214)
D-Phe-c(Cys-His-D-(Et)Tyr-Arg-Trp-β-Ala-D-Cys)-Doc-Gly-(Arg)₅-Gln-(Arg)₃-NH₂;

(SEQ ID NO: 217)
D-Phe-c(Cys-His-D-(Et)Tyr-Arg-Trp-β-Ala-D-Cys)-Doc-(Arg)₅-Gln-(Arg)₄-NH₂;

(SEQ ID NO: 215)
D-Phe-c(Cys-His-D-(Et)Tyr-Arg-Trp-β-Ala-D-Cys)-(Doc)₂-Tyr-Gly-(Arg)₅-Gln-(Arg)₃-NH₂;

(SEQ ID NO: 216)
D-Phe-c(Cys-His-D-(Et)Tyr-Arg-Trp-β-Ala-D-Cys)-(Doc)₂-(Arg)₅-Gln-(Arg)₃-NH₂;

(SEQ ID NO: 215)
D-Phe-c(Cys-His-D-(Et)Tyr-Arg-Trp-β-Ala-D-Cys)-(Doc)₂-Gly-(Arg)₅-Gln-(Arg)₃-NH₂;

(SEQ ID NO: 217)
D-Phe-c(Cys-His-D-(Et)Tyr-Arg-Trp-β-Ala-D-Cys)-(Doc)₂-(Arg)₅-Gln-(Arg)₄-NH₂;

(SEQ ID NO: 218)
D-Phe-c(Cys-His-D-(Et)Tyr-hArg-Trp-β-Ala-D-Cys)-Thr-β-Ala-Tyr-Gly-(Arg)₅-Gln-(Arg)₃-NH₂;

(SEQ ID NO: 219)
D-Phe-c(Cys-His-D-(Et)Tyr-hArg-Trp-β-Ala-D-Cys)-Thr-β-Ala-(Arg)₅-Gln-(Arg)₃-NH₂;

(SEQ ID NO: 218)
D-Phe-c(Cys-His-D-(Et)Tyr-hArg-Trp-β-Ala-D-Cys)-Thr-(β-Ala)₂-Tyr-Gly-(Arg)₅-Gln-(Arg)₃-NH₂;

(SEQ ID NO: 219)
D-Phe-c(Cys-His-D-(Et)Tyr-hArg-Trp-β-Ala-D-Cys)-Thr-(β-Ala)₂-(Arg)₅-Gln-(Arg)₃-NH₂;

(SEQ ID NO: 221)
D-Phe-c(Cys-His-D-(Et)Tyr-hArg-Trp-β-Ala-D-Cys)-Thr-Doc-Tyr-Gly-(Arg)₅-Gln-(Arg)₃-NH₂;

(SEQ ID NO: 220)
D-Phe-c(Cys-His-D-(Et)Tyr-hArg-Trp-β-Ala-D-Cys)-Thr-Doc-(Arg)₅-Gln-(Arg)₃-NH₂;

```
                                                                (SEQ ID NO: 221)
D-Phe-c(Cys-His-D-(Et)Tyr-hArg-Trp-β-Ala-D-Cys)-Thr-(Doc)₂-Tyr-Gly-(Arg)₅-Gln-
(Arg)₃-NH₂;

(SEQ ID NO: 222)
D-Phe-c(Cys-His-D-(Et)Tyr-hArg-Trp-β-Ala-D-Cys)-Thr-β-Ala-Tyr-Gly-(Arg)₅-Gln-
(Arg)₄-NH₂;

(SEQ ID NO: 223)
D-Phe-c(Cys-His-D-(Et)Tyr-hArg-Trp-β-Ala-D-Cys)-Thr-β-Ala-(Arg)₅-Gln-(Arg)₄-NH₂;

(SEQ ID NO: 222)
D-Phe-c(Cys-His-D-(Et)Tyr-hArg-Trp-β-Ala-D-Cys)-Thr-(β-Ala)₂-Tyr-Gly-(Arg)₅-Gln-
(Arg)₄-NH₂;

(SEQ ID NO: 223)
D-Phe-c(Cys-His-D-(Et)Tyr-hArg-Trp-β-Ala-D-Cys)-Thr-(β-Ala)₂-(Arg)₅-Gln-(Arg)₄-NH₂;

(SEQ ID NO: 224)
D-Phe-c(Cys-His-D-(Et)Tyr-hArg-Trp-β-Ala-D-Cys)-Thr-Doc-Tyr-Gly-(Arg)₅-Gln-(Arg)₄-
NH₂;

(SEQ ID NO: 225)
D-Phe-c(Cys-His-D-(Et)Tyr-hArg-Trp-β-Ala-D-Cys)-Thr-Doc-(Arg)₅-Gln-(Arg)₄-NH₂;

(SEQ ID NO: 224)
D-Phe-c(Cys-His-D-(Et)Tyr-hArg-Trp-β-Ala-D-Cys)-Thr-(Doc)₂-Tyr-Gly-(Arg)₅-Gln-
(Arg)₄-NH₂;

(SEQ ID NO: 225)
D-Phe-c(Cys-His-D-(Et)Tyr-hArg-Trp-β-Ala-D-Cys)-Thr-(Doc)₂-(Arg)₅-Gln-(Arg)₄-NH₂;

(SEQ ID NO: 227)
D-Phe-c(Cys-His-D-(Et)Tyr-hArg-Bip-β-Ala-D-Cys)-Thr-β-Ala-Tyr-Gly-(Arg)₅-Gln-
(Arg)₃-NH₂;

(SEQ ID NO: 226)
D-Phe-c(Cys-His-D-(Et)Tyr-hArg-Bip-β-Ala-D-Cys)-Thr-β-Ala-Tyr-Gly-(Arg)₅-Gln-
(Arg)₄-NH₂;

(SEQ ID NO: 228)
D-Phe-c(Cys-His-D-(Et)Tyr-hArg-Bip-β-Ala-D-Cys)-Thr-β-Ala-(Arg)₅-Gln-(Arg)₃-NH₂;

(SEQ ID NO: 227)
D-Phe-c(Cys-His-D-(Et)Tyr-hArg-Bip-β-Ala-D-Cys)-Thr-(β-Ala)₂-Tyr-Gly-(Arg)₅-Gln-
(Arg)₃-NH₂;

(SEQ ID NO: 228)
D-Phe-c(Cys-His-D-(Et)Tyr-hArg-Bip-β-Ala-D-Cys)-Thr-(β-Ala)₂-(Arg)₅-Gln-(Arg)₃-NH₂;

(SEQ ID NO: 229)
D-Phe-c(Cys-His-D-(Et)Tyr-hArg-Bip-β-Ala-D-Cys)-Thr-Doc-Tyr-Gly-(Arg)₅-Gln-(Arg)₃-
NH₂;

(SEQ ID NO: 230)
D-Phe-c(Cys-His-D-(Et)Tyr-hArg-Bip-β-Ala-D-Cys)-Thr-Doc-Tyr-Gly-(Arg)₅-Gln-(Arg)₄-
NH₂;

(SEQ ID NO: 232)
D-Phe-c(Cys-His-D-(Et)Tyr-hArg-Bip-β-Ala-D-Cys)-Thr-Doc-(Arg)₅-Gln-(Arg)₃-NH₂;

(SEQ ID NO: 231)
D-Phe-c(Cys-His-D-(Et)Tyr-hArg-Bip-β-Ala-D-Cys)-Thr-(Doc)₂-Tyr-Gly-(Arg)₅-Gln-
(Arg)₃-NH₂;

(SEQ ID NO: 232)
D-Phe-c(Cys-His-D-(Et)Tyr-hArg-Bip-β-Ala-D-Cys)-Thr-(Doc)₂-(Arg)₅-Gln-(Arg)₃-NH₂;
```

-continued (SEQ ID NO: 233)
Ac-Nle-c(Cys-D-Ala-His-D-Phe-Arg-Trp-Gly-Cys)-β-Ala-Tyr-Gly-(Arg)$_5$-Gln-(Arg)$_3$-NH$_2$;

(SEQ ID NO: 234)
Ac-Nle-c(Cys-D-Ala-His-D-Phe-Arg-Trp-Gly-Cys)-β-Ala-(Arg)$_5$-Gln-(Arg)$_3$-NH$_2$;

(SEQ ID NO: 235)
Nle-c(Cys-His-D-Phe-Arg-Trp-Apn-Cys)-β-Ala-Tyr-Gly-(Arg)$_5$-Gln-(Arg)$_3$-NH$_2$;

(SEQ ID NO: 236)
Nle-c(Cys-His-D-Phe-Arg-Trp-Apn-Cys)-β-Ala-(Arg)$_5$-Gln-(Arg)$_3$-NH$_2$;

(SEQ ID NO: 235)
Nle-c(Cys-His-D-Phe-Arg-Trp-Apn-Cys)-(β-Ala)$_2$-Tyr-Gly-(Arg)$_5$-Gln-(Arg)$_3$-NH$_2$;

(SEQ ID NO: 236)
Nle-c(Cys-His-D-Phe-Arg-Trp-Apn-Cys)-(β-Ala)$_2$-(Arg)$_5$-Gln-(Arg)$_3$-NH$_2$;

(SEQ ID NO: 237)
Nle-c(Cys-His-D-Phe-Arg-Trp-Apn-Cys)-β-Ala-Tyr-Gly-(Arg)$_5$-Gln-(Arg)$_4$-NH$_2$;

(SEQ ID NO: 238)
Nle-c(Cys-His-D-Phe-Arg-Trp-Apn-Cys)-β-Ala-(Arg)$_5$-Gln-(Arg)$_4$-NH$_2$;

(SEQ ID NO: 237)
Nle-c(Cys-His-D-Phe-Arg-Trp-Apn-Cys)-(β-Ala)$_2$-Tyr-Gly-(Arg)$_5$-Gln-(Arg)$_4$-NH$_2$;

(SEQ ID NO: 238)
Nle-c(Cys-His-D-Phe-Arg-Trp-Apn-Cys)-(β-Ala)$_2$-(Arg)$_5$-Gln-(Arg)$_4$-NH$_2$;

(SEQ ID NO: 239)
Nle-c(Cys-His-D-Phe-Arg-Trp-Apn-Cys)-Doc-Tyr-Gly-(Arg)$_5$-Gln-(Arg)$_3$-NH$_2$;

(SEQ ID NO: 240)
Nle-c(Cys-His-D-Phe-Arg-Trp-Apn-Cys)-Doc-(Arg)$_5$-Gln-(Arg)$_3$-NH$_2$;

(SEQ ID NO: 239)
Nle-c(Cys-His-D-Phe-Arg-Trp-Apn-Cys)-(Doc)$_2$-Tyr-Gly-(Arg)$_5$-Gln-(Arg)$_3$-NH$_2$;

(SEQ ID NO: 240)
Nle-c(Cys-His-D-Phe-Arg-Trp-Apn-Cys)-(Doc)$_2$-(Arg)$_5$-Gln-(Arg)$_3$-NH$_2$;

(SEQ ID NO: 241)
Nle-c(Cys-His-D-Phe-Arg-Trp-Apn-Cys)-Doc-Tyr-Gly-(Arg)$_5$-Gln-(Arg)$_4$-NH$_2$;

(SEQ ID NO: 242)
Nle-c(Cys-His-D-Phe-Arg-Trp-Apn-Cys)-Doc-(Arg)$_5$-Gln-(Arg)$_4$-NH$_2$;

(SEQ ID NO: 241)
Nle-c(Cys-His-D-Phe-Arg-Trp-Apn-Cys)-(Doc)$_2$-Tyr-Gly-(Arg)$_5$-Gln-(Arg)$_4$-NH$_2$;

(SEQ ID NO: 242)
Nle-c(Cys-His-D-Phe-Arg-Trp-Apn-Cys)-(Doc)$_2$-(Arg)$_5$-Gln-(Arg)$_4$-NH$_2$;

(SEQ ID NO: 243)
Ac-Nle-c(Cys-D-Leu-His-D-Phe-Arg-Trp-Cys)-β-Ala-Tyr-Gly-(Arg)$_5$-Gln-(Arg)$_3$-NH$_2$;

(SEQ ID NO: 244)
Ac-Nle-c(Cys-D-Leu-His-D-Phe-Arg-Trp-Cys)-β-Ala-(Arg)$_5$-Gln-(Arg)$_3$-NH$_2$;

(SEQ ID NO: 243)
Ac-Nle-c(Cys-D-Leu-His-D-Phe-Arg-Trp-Cys)-(β-Ala)$_2$-Tyr-Gly-(Arg)$_5$-Gln-(Arg)$_3$-NH$_2$;

(SEQ ID NO: 244)
Ac-Nle-c(Cys-D-Leu-His-D-Phe-Arg-Trp-Cys)-(β-Ala)$_2$-(Arg)$_5$-Gln-(Arg)$_3$-NH$_2$;

(SEQ ID NO: 245)
Ac-Nle-c(Cys-D-Leu-His-D-Phe-Arg-Trp-Cys)-Doc-Tyr-Gly-(Arg)$_5$-Gln-(Arg)$_3$-NH$_2$;

(SEQ ID NO: 246)
Ac-Nle-c(Cys-D-Leu-His-D-Phe-Arg-Trp-Cys)-Doc-(Arg)$_5$-Gln-(Arg)$_3$-NH$_2$;

(SEQ ID NO: 245)
Ac-Nle-c(Cys-D-Leu-His-D-Phe-Arg-Trp-Cys)-(Doc)$_2$-Tyr-Gly-(Arg)$_5$-Gln-(Arg)$_3$-NH$_2$;

(SEQ ID NO: 246)
Ac-Nle-c(Cys-D-Leu-His-D-Phe-Arg-Trp-Cys)-(Doc)$_2$-(Arg)$_5$-Gln-(Arg)$_3$-NH$_2$;

-continued

```
                                                                     (SEQ ID NO: 247)
Ac-Nle-c(Cys-D-Leu-His-D-Phe-Arg-Trp-Cys)-β-Ala-Tyr-Gly-(Arg)5-Gln-(Arg)4-NH2;

(SEQ ID NO: 248)
Ac-Nle-c(Cys-D-Leu-His-D-Phe-Arg-Trp-Cys)-β-Ala-(Arg)5-Gln-(Arg)4-NH2;

(SEQ ID NO: 247)
Ac-Nle-c(Cys-D-Leu-His-D-Phe-Arg-Trp-Cys)-(β-Ala)2-Tyr-Gly-(Arg)5-Gln-(Arg)4-NH2;

(SEQ ID NO: 248)
Ac-Nle-c(Cys-D-Leu-His-D-Phe-Arg-Trp-Cys)-(β-Ala)2-(Arg)5-Gln-(Arg)4-NH2;

(SEQ ID NO: 249)
Ac-Nle-c(Cys-D-Leu-His-D-Phe-Arg-Trp-Cys)-Doc-Tyr-Gly-(Arg)5-Gln-(Arg)4-NH2;

(SEQ ID NO: 250)
Ac-Nle-c(Cys-D-Leu-His-D-Phe-Arg-Trp-Cys)-Doc-(Arg)5-Gln-(Arg)4-NH2;

(SEQ ID NO: 249)
Ac-Nle-c(Cys-D-Leu-His-D-Phe-Arg-Trp-Cys)-(Doc)2-Tyr-Gly-(Arg)5-Gln-(Arg)4-NH2;

(SEQ ID NO: 250)
Ac-Nle-c(Cys-D-Leu-His-D-Phe-Arg-Trp-Cys)-(Doc)2-(Arg)5-Gln-(Arg)4-NH2;

(SEQ ID NO: 251)
Ac-Nle-c(Cys-D-Cha-His-D-Phe-Arg-Trp-Cys)-β-Ala-Tyr-Gly-(Arg)5-Gln-(Arg)3-NH2;

(SEQ ID NO: 252)
Ac-Nle-c(Cys-D-Cha-His-D-Phe-Arg-Trp-Cys)-β-Ala-(Arg)5-Gln-(Arg)3-NH2;

(SEQ ID NO: 251)
Ac-Nle-c(Cys-D-Cha-His-D-Phe-Arg-Trp-Cys)-(β-Ala)2-Tyr-Gly-(Arg)5-Gln-(Arg)3-NH2;

(SEQ ID NO: 252)
Ac-Nle-c(Cys-D-Cha-His-D-Phe-Arg-Trp-Cys)-(β-Ala)2-(Arg)5-Gln-(Arg)3-NH2;

(SEQ ID NO: 253)
Ac-Nle-c(Cys-D-Cha-His-D-Phe-Arg-Trp-Cys)-Doc-Tyr-Gly-(Arg)5-Gln-(Arg)3-NH2;

(SEQ ID NO: 254)
Ac-Nle-c(Cys-D-Cha-His-D-Phe-Arg-Trp-Cys)-Doc-(Arg)5-Gln-(Arg)3-NH2;

(SEQ ID NO: 253)
Ac-Nle-c(Cys-D-Cha-His-D-Phe-Arg-Trp-Cys)-(Doc)2-Tyr-Gly-(Arg)5-Gln-(Arg)3-NH2;

(SEQ ID NO: 254)
Ac-Nle-c(Cys-D-Cha-His-D-Phe-Arg-Trp-Cys)-(Doc)2-(Arg)5-Gln-(Arg)3-NH2;

(SEQ ID NO: 255)
Ac-Nle-c(Cys-D-Cha-His-D-Phe-Arg-Trp-Cys)-β-Ala-Tyr-Gly-(Arg)5-Gln-(Arg)4-NH2;

(SEQ ID NO: 256)
Ac-Nle-c(Cys-D-Cha-His-D-Phe-Arg-Trp-Cys)-β-Ala-(Arg)5-Gln-(Arg)4-NH2;

(SEQ ID NO: 255)
Ac-Nle-c(Cys-D-Cha-His-D-Phe-Arg-Trp-Cys)-(β-Ala)2-Tyr-Gly-(Arg)5-Gln-(Arg)4-NH2;

(SEQ ID NO: 256)
Ac-Nle-c(Cys-D-Cha-His-D-Phe-Arg-Trp-Cys)-(β-Ala)2-(Arg)5-Gln-(Arg)4-NH2;

(SEQ ID NO: 257)
Ac-Nle-c(Cys-D-Cha-His-D-Phe-Arg-Trp-Cys)-Doc-Tyr-Gly-(Arg)5-Gln-(Arg)4-NH2;

(SEQ ID NO: 258)
Ac-Nle-c(Cys-D-Cha-His-D-Phe-Arg-Trp-Cys)-Doc-(Arg)5-Gln-(Arg)4-NH2;

(SEQ ID NO: 257)
Ac-Nle-c(Cys-D-Cha-His-D-Phe-Arg-Trp-Cys)-(Doc)2-Tyr-Gly-(Arg)5-Gln-(Arg)4-NH2;

(SEQ ID NO: 258)
Ac-Nle-c(Cys-D-Cha-His-D-Phe-Arg-Trp-Cys)-(Doc)2-(Arg)5-Gln-(Arg)4-NH2;

(SEQ ID NO: 259)
Nle-c(Cys-His-D-Phe-Arg-Trp-Gaba-Cys)-β-Ala-Tyr-Gly-(Arg)5-Gln-(Arg)3-NH2;

(SEQ ID NO: 260)
Nle-c(Cys-His-D-Phe-Arg-Trp-Gaba-Cys)-β-Ala-(Arg)5-Gln-(Arg)3-NH2;

(SEQ ID NO: 259)
Nle-c(Cys-His-D-Phe-Arg-Trp-Gaba-Cys)-(β-Ala)2-Tyr-Gly-(Arg)5-Gln-(Arg)3-NH2;
```

Nle-c(Cys-His-D-Phe-Arg-Trp-Gaba-Cys)-(β-Ala)₂-(Arg)₅-Gln-(Arg)₃-NH₂; (SEQ ID NO: 260)

Nle-c(Cys-His-D-Phe-Arg-Trp-Gaba-Cys)-β-Ala-Tyr-Gly-(Arg)₅-Gln-(Arg)₄-NH₂; (SEQ ID NO: 261)

Nle-c(Cys-His-D-Phe-Arg-Trp-Gaba-Cys)-β-Ala-(Arg)₅-Gln-(Arg)₄-NH₂; (SEQ ID NO: 262)

Nle-c(Cys-His-D-Phe-Arg-Trp-Gaba-Cys)-(β-Ala)₂-Tyr-Gly-(Arg)₅-Gln-(Arg)₄-NH₂; (SEQ ID NO: 261)

Nle-c(Cys-His-D-Phe-Arg-Trp-Gaba-Cys)-(β-Ala)₂-(Arg)₅-Gln-(Arg)₄-NH₂; (SEQ ID NO: 262)

Nle-c(Cys-His-D-Phe-Arg-Trp-Gaba-Cys)-Doc-Tyr-Gly-(Arg)₅-Gln-(Arg)₃-NH₂; (SEQ ID NO: 263)

Nle-c(Cys-His-D-Phe-Arg-Trp-Gaba-Cys)-Doc-(Arg)₅-Gln-(Arg)₃-NH₂; (SEQ ID NO: 264)

Nle-c(Cys-His-D-Phe-Arg-Trp-Gaba-Cys)-(Doc)₂-Tyr-Gly-(Arg)₅-Gln-(Arg)₃-NH₂; (SEQ ID NO: 263)

Nle-c(Cys-His-D-Phe-Arg-Trp-Gaba-Cys)-(Doc)₂-(Arg)₅-Gln-(Arg)₃-NH₂; (SEQ ID NO: 264)

Nle-c(Cys-His-D-Phe-Arg-Trp-Gaba-Cys)-Doc-Tyr-Gly-(Arg)₅-Gln-(Arg)₄-NH₂; (SEQ ID NO: 265)

Nle-c(Cys-His-D-Phe-Arg-Trp-Gaba-Cys)-Doc-(Arg)₅-Gln-(Arg)₄-NH₂; (SEQ ID NO: 266)

Nle-c(Cys-His-D-Phe-Arg-Trp-Gaba-Cys)-(Doc)₂-Tyr-Gly-(Arg)₅-Gln-(Arg)₄-NH₂; (SEQ ID NO: 265)

Nle-c(Cys-His-D-Phe-Arg-Trp-Gaba-Cys)-(Doc)₂-(Arg)₅-Gln-(Arg)₄-NH₂; (SEQ ID NO: 266)

Ac-c(Cys-Glu-His-D-4-Br-Phe-Arg-Trp-Gly-Cys)-(Pro)₂-Lys-Asp-NH₂; (SEQ ID NO: 268)

Ac-c(Cys-Glu-His-D-2-Nal-Arg-Trp-Ala-Cys)-(Pro)₂-Lys-Asp-NH₂; (SEQ ID NO: 269)

Ac-c(Cys-Glu-His-D-2-Nal-Arg-2-Nal-Ala-Cys)-(Pro)₂-Lys-Asp-NH₂; (SEQ ID NO: 269)

Ac-c(Cys-Glu-His-D-2-Nal-Arg-1-Nal-Ala-Cys)-(Pro)₂-Lys-Asp-NH₂; (SEQ ID NO: 269)

Ac-c(Cys-Glu-His-D-2-Nal-Arg-Bal-Ala-Cys)-(Pro)₂-Lys-Asp-NH₂; (SEQ ID NO: 269)

Ac-c(Cys-Glu-His-D-2-Nal-Arg-2-Nal-β-Ala-Cys)-(Pro)₂-Lys-Asp-NH₂; (SEQ ID NO: 270)

Ac-c(Cys-Glu-His-D-2-Nal-Arg-2-Nal-Aib-Cys)-(Pro)₂-Lys-Asp-NH₂; (SEQ ID NO: 270)

c[Hydantoin(C(O)-(Cys-D-Ala))-His-D-Phe-Arg-Trp-Cys]-NH₂; (SEQ ID NO: 271)

c[Hydantoin(C(O)-(hCys-D-Ala))-His-D-Phe-Arg-Trp-Cys]-NH₂; (SEQ ID NO: 271)

c[Hydantoin(C(O)-(Cys-D-Ala))-His-D-2-Nal-Arg-Trp-Cys]-NH₂; (SEQ ID NO: 272)

c[Hydantoin(C(O)-(hCys-D-Ala))-His-D-2-Nal-Arg-Trp-Cys]-NH₂; (SEQ ID NO: 272)

c[Hydantoin(C(O)-(Asp-D-Ala))-His-D-Phe-Arg-Trp-Lys]NH₂; (SEQ ID NO: 273)

c[Hydantoin(C(O)-(Asp-D-Ala))-His-D-Phe-Arg-Trp-Orn]-NH₂; (SEQ ID NO: 273)

c[Hydantoin(C(O)-(Asp-D-Ala))-His-D-Phe-Arg-Trp-Dab]-NH₂; (SEQ ID NO: 273)

-continued

| Sequence | SEQ ID NO |
|---|---|
| c[Hydantoin(C(O)-(Asp-D-Ala))-His-D-Phe-Arg-Trp-Dap]-NH$_2$; | (SEQ ID NO: 273) |
| c[Hydantoin(C(O)-(Asp-His))-D-2-Nal-Arg-Trp-Lys]-NH$_2$; | (SEQ ID NO: 275) |
| c[Hydantoin(C(O)-(Asp-His))-D-Phe-Arg-Trp-Lys]-NH$_2$; | (SEQ ID NO: 274) |
| c[Hydantoin(C(O)-(Asp-A3c))-D-Phe-Arg-Trp-Lys]-NH$_2$; | (SEQ ID NO: 274) |
| c[Hydantoin(C(O)-(Asp-A5c))-D-Phe-Arg-Trp-Lys]-NH$_2$; | (SEQ ID NO: 274) |
| c[Hydantoin(C(O)-(Asp-A6c))-D-Phe-Arg-Trp-Lys]-NH$_2$; | (SEQ ID NO: 274) |
| c[Hydantoin(C(O)-(Asp-A3c))-D-2-Nal-Arg-Trp-Lys]-NH$_2$; | (SEQ ID NO: 275) |
| c[Hydantoin(C(O)-(Asp-A5c))-D-2-Nal-Arg-Trp-Lys]-NH$_2$; | (SEQ ID NO: 275) |
| c[Hydantoin(C(O)-(Asp-A6c))-D-2-Nal-Arg-Trp-Lys]-NH$_2$; | (SEQ ID NO: 275) |
| c[Hydantoin (C(O)-(Asp-A5c))-D-2-Nal-Arg-Trp-Lys]-NH$_2$; | (SEQ ID NO: 275) |
| c[Hydantoin(C(O)-(Asp-Aic))-D-Phe-Arg-Trp-Lys]-NH$_2$; | (SEQ ID NO: 274) |
| c[Hydantoin(C(O)-(Asp-Apc))-D-Phe-Arg-Trp-Lys]-NH$_2$; | (SEQ ID NO: 274) |
| c[Hydantoin(C(O)-(Asp-Aic))-D-2-Nal-Arg-Trp-Lys]-NH$_2$; | (SEQ ID NO: 275) |
| c[Hydantoin(C(O)-(Asp-Apc))-D-2-Nal-Arg-Trp-Lys]-NH$_2$; | (SEQ ID NO: 275) |
| c[Hydantoin-(C(O)-(Asp-Aic))-D-2-Nal-Arg-Trp-Lys]-NH$_2$; | (SEQ ID NO: 275) |
| c[Hydantoin-(C(O)-(Asp-Apc))-D-2-Nal-Arg-Trp-Lys]-NH$_2$; | (SEQ ID NO: 275) |
| c[Hydantoin(C(O)-(Glu-D-Ala))-His-D-Phe-Arg-Trp-Orn]-NH$_2$; | (SEQ ID NO: 276) |
| c[Hydantoin(C(O)-(Glu-D-Ala))-His-D-Phe-Arg-Trp-Dab]-NH$_2$; | (SEQ ID NO: 276) |
| c[Hydantoin(C(O)-(Glu-D-Ala))-His-D-Phe-Arg-Trp-Dap]-NH$_2$; | (SEQ ID NO: 276) |
| c[Hydantoin(C(O)-(Glu-His))-D-Phe-Arg-Trp-Dap]-NH$_2$; | (SEQ ID NO: 277) |
| Hydantoin(C(O)-(Arg-Gly))-c(Cys-Glu-His-D-Phe-Arg-Trp-Cys)-NH$_2$; | (SEQ ID NO: 278) |
| Hydantoin(C(O)-(Nle-Gly))-c(Cys-Glu-His-D-Phe-Arg-Trp-Cys)-NH$_2$; | (SEQ ID NO: 278) |
| Hydantoin(C(O)-(Gly-Gly))-c(Cys-Glu-His-D-Phe-Arg-Trp-Cys)-NH$_2$; | (SEQ ID NO: 278) |
| Hydantoin(C(O)-(Nle-Gly))-c(Cys-D-Ala-His-D-Phe-Arg-Trp-Cys)-NH$_2$; | (SEQ ID NO: 279) |
| Hydantoin(C(O)-(Gly-Gly))-c(Cys-D-Ala-His-D-Phe-Arg-Trp-Cys)-NH$_2$; | (SEQ ID NO: 279) |
| Hydantoin(C(O)-(Nle-Gly))-c(Cys-D-Ala-His-D-Phe-Arg-Trp-Pen)-NH$_2$; | (SEQ ID NO: 280) |
| Hydantoin(C(O)-(Gly-Gly))-c(Cys-D-Ala-His-D-Phe-Arg-Trp-Pen)-NH$_2$; | (SEQ ID NO: 280) |

-continued

Hydantoin(C(O)-(Ala-Gly))-c(Cys-D-Ala-His-D-Phe-Arg-Trp-Cys)-NH$_2$; (SEQ ID NO: 279)

Hydantoin(C(O)-(D-Ala-Gly))-c(Cys-D-Ala-His-D-Phe-Arg-Trp-Cys)-NH$_2$; (SEQ ID NO: 279)

Hydantoin(C(O)-(Aib-Gly))-c(Cys-D-Ala-His-D-Phe-Arg-Trp-Cys)-NH$_2$; (SEQ ID NO: 279)

Hydantoin(C(O)-(Val-Gly))-c(Cys-D-Ala-His-D-Phe-Arg-Trp-Cys)-NH$_2$; (SEQ ID NO: 279)

Hydantoin(C(O)-(Ile-Gly))-c(Cys-D-Ala-His-D-Phe-Arg-Trp-Cys)-NH$_2$; (SEQ ID NO: 279)

Hydantoin(C(O)-(Leu-Gly))-c(Cys-D-Ala-His-D-Phe-Arg-Trp-Cys)-NH$_2$; (SEQ ID NO: 279)

Hydantoin(C(O)-(Gly-Gly))-c(Cys-Glu-His-D-2-Nal-Arg-Trp-Cys)-NH$_2$; (SEQ ID NO: 281)

Hydantoin(C(O)-(Nle-Gly))-c(Cys-Glu-His-D-2-Nal-Arg-Trp-Cys)-NH$_2$; (SEQ ID NO: 281)

Hydantoin(C(O)-(D-Arg-Gly))-c(Cys-Glu-His-D-Phe-Arg-Trp-Cys)-NH$_2$; (SEQ ID NO: 278)

Hydantoin(C(O)-(D-Arg-Gly))-c(Cys-D-Ala-His-D-Phe-Arg-Trp-Cys)-NH$_2$; (SEQ ID NO: 279)

Hydantoin(C(O)-(Arg-Gly))-c(Cys-D-Ala-His-D-Phe-Arg-Trp-Cys)-NH$_2$; (SEQ ID NO: 279)

Hydantoin(C(O)-(D-Arg-Gly))-c(Cys-D-Ala-His-D-2-Nal-Arg-Trp-Cys)-NH$_2$; (SEQ ID NO: 282)

Hydantoin(C(O)-(Arg-Gly))-c(Cys-D-Ala-His-D-2-Nal-Arg-Trp-Cys)-NH$_2$; (SEQ ID NO: 282)

Hydantoin(C(O)-(Ala-Nle))-c(Cys-Glu-His-D-Phe-Arg-Trp-Cys)-NH$_2$; (SEQ ID NO: 283)

Hydantoin(C(O)-(Val-Nle))-c(Cys-Glu-His-D-Phe-Arg-Trp-Cys)-NH$_2$; (SEQ ID NO: 283)

Hydantoin(C(O)-(Gly-Nle))-c(Cys-Glu-His-D-Phe-Arg-Trp-Cys)-NH$_2$; (SEQ ID NO: 283)

Hydantoin(C(O)-(A6c-Nle))-c(Cys-D-Ala-His-D-Phe-Arg-Trp-Cys)-NH$_2$; (SEQ ID NO: 284)

Hydantoin(C(O)-(Gly-Nle))-c(Cys-D-Ala-His-D-Phe-Arg-Trp-Cys)-NH$_2$; (SEQ ID NO: 284)

Hydantoin(C(O)-(Ala-Nle))-c(Cys-D-Ala-His-D-Phe-Arg-Trp-Cys)-NH$_2$; (SEQ ID NO: 284)

Hydantoin(C(O)-(D-Ala-Nle))-c(Cys-D-Ala-His-D-Phe-Arg-Trp-Cys)-NH$_2$; (SEQ ID NO: 284)

Hydantoin(C(O)-(Val-Nle))-c(Cys-D-Ala-His-D-Phe-Arg-Trp-Cys)-NH$_2$; (SEQ ID NO: 284)

Hydantoin(C(O)-(Leu-Nle))-c(Cys-D-Ala-His-D-Phe-Arg-Trp-Cys)-NH$_2$; (SEQ ID NO: 284)

Hydantoin(C(O)-(Cha-Nle))-c(Cys-D-Ala-His-D-Phe-Arg-Trp-Cys)-NH$_2$; (SEQ ID NO: 284)

Hydantoin(C(O)-(Aib-Nle))-c(Cys-D-Ala-His-D-Phe-Arg-Trp-Cys)-NH$_2$; (SEQ ID NO: 284)

Hydantoin(C(O)-(Gly-Arg))-c(Cys-Glu-His-D-Phe-Arg-Trp-Cys)-NH$_2$; (SEQ ID NO: 285)

-continued

```
                                                                  (SEQ ID NO: 285)
Hydantoin(C(O)-(Gly-Arg))-c(Cys-Glu-His-D-2-Nal-Arg-Trp-Cys)-NH2;

(SEQ ID NO: 286)
Hydantoin(C(O)-(Gly-Arg))-c(Cys-D-Ala-His-D-Phe-Arg-Trp-Cys)-NH2;

(SEQ ID NO: 286)
Hydantoin(C(O)-(Gly-Arg))-c(Cys-D-Ala-His-D-2-Nal-Arg-Trp-Cys)-NH2;

(SEQ ID NO: 287)
Hydantoin(C(O)-(Gly-D-Arg))-c(Cys-Glu-His-D-Phe-Arg-Trp-Cys)-NH2;

(SEQ ID NO: 288)
Hydantoin(C(O)-(Gly-D-Arg))-c(Cys-D-Ala-His-D-Phe-Arg-Trp-Cys)-NH2;

(SEQ ID NO: 288)
Hydantoin(C(O)-(Gly-D-Arg))-c(Cys-D-Ala-His-D-2-Nal-Arg-Trp-Cys)-NH2;

(SEQ ID NO: 289)
Hydantoin(C(O)-(Nle-Ala))-c(Cys-Glu-His-D-Phe-Arg-Trp-Cys)-NH2;

(SEQ ID NO: 290)
c[Hydantoin(C(O)-(Ala-Cys))-D-Ala-His-D-Phe-Arg-Trp-Cys]-NH2, (SEQ ID NO: 290)
c[Hydantoin(C(O)-(Nle-Cys))-D-Ala-His-D-Phe-Arg-Trp-Cys]-NH2;

(SEQ ID NO: 290)
c[Hydantoin(C(O)-(D-Ala-Cys))-D-Ala-His-D-Phe-Arg-Trp-Cys]-NH2;

(SEQ ID NO: 290)
c[Hydantoin(C(O)-(Aib-Cys))-D-Ala-His-D-Phe-Arg-Trp-Cys]-NH2;

(SEQ ID NO: 290)
c[Hydantoin(C(O)-(Val-Cys))-D-Ala-His-D-Phe-Arg-Trp-Cys]-NH2;

(SEQ ID NO: 290)
c[Hydantoin(C(O)-(Abu-Cys))-D-Ala-His-D-Phe-Arg-Trp-Cys]-NH2;

(SEQ ID NO: 290)
c[Hydantoin(C(O)-(Leu-Cys))-D-Ala-His-D-Phe-Arg-Trp-Cys]-NH2;

(SEQ ID NO: 290)
c[Hydantoin(C(O)-(Ile-Cys))-D-Ala-His-D-Phe-Arg-Trp-Cys]-NH2;

(SEQ ID NO: 290)
c[Hydantoin(C(O)-(Cha-Cys))-D-Ala-His-D-Phe-Arg-Trp-Cys]-NH2;

(SEQ ID NO: 290)
c[Hydantoin(C(O)-(A6c-Cys))-D-Ala-His-D-Phe-Arg-Trp-Cys]-NH2;

(SEQ ID NO: 290)
c[Hydantoin(C(O)-(Phe-Cys))-D-Ala-His-D-Phe-Arg-Trp-Cys]-NH2;

(SEQ ID NO: 290)
c[Hydantoin(C(O)-(Gly-Cys))-D-Ala-His-D-Phe-Arg-Trp-Cys]-NH2;

(SEQ ID NO: 291)
c[Hydantoin(C(O)-(Gly-Cys))-Glu-His-D-Phe-Arg-Trp-Cys]-NH2;

(SEQ ID NO: 292)
Ac-Tyr-Arg-c(Cys-D-Ala-His-D-Phe-Arg-Trp-Cys)-NH2;

(SEQ ID NO: 292)
Ac-2-Nal-Arg-c(Cys-D-Ala-His-D-Phe-Arg-Trp-Cys)-NH2;

(SEQ ID NO: 292)
Ac-1-Nal-Arg-c(Cys-D-Ala-His-DPhe-Arg-Trp-Cys)-NH2;

(SEQ ID NO: 292)
Ac-Phe-Arg-c(Cys-D-Ala-His-D-Phe-Arg-Trp-Cys)-NH2;

(SEQ ID NO: 292)
Ac-Trp-Arg-c(Cys-D-Ala-His-D-Phe-Arg-Trp-Cys)-NH2;

(SEQ ID NO: 292)
Ac-Pff-Arg-c(Cys-D-Ala-His-D-Phe-Arg-Trp-Cys)-NH2;
```

H-His-Arg-c(Cys-D-Ala-His-D-Phe-Arg-Trp-Cys)-NH$_2$;
and

Ac-His-Arg-c(Cys-D-Ala-His-D-Phe-Arg-Trp-Cys)-NH$_2$; (SEQ ID NO: 292)

(SEQ ID NO: 293)

or a pharmaceutically acceptable salt thereof.

In one preferred aspect, the melanocortin receptor 4 agonist useful to treat insulin resistance in the subject in need thereof, is Ac-Arg-c(Cys-D-Ala-His-D-Phe-Arg-Trp-Cys)-NH$_2$ (SEQ ID NO:50) or a pharmaceutically acceptable salt thereof. In another preferred aspect, the melanocortin receptor 4 agonist useful to treat insulin resistance in the subject in need thereof, is Hydantoin(C(O)-(Arg-Gly))-c(Cys-Glu-His-D-Phe-Arg-Trp-Cys)-NH$_2$ (SEQ ID NO:278) or a pharmaceutically acceptable salt thereof.

In other aspects of the invention, administration of a compound or composition comprising a compound or pharmaceutical salt of a compound of the invention useful to treat insulin resistance, is continuous, hourly, four times daily, three time daily, twice daily, once daily, once every other day, twice weekly, once weekly, once every two weeks, once a month, or once every two months, or longer. The subject in need of treatment may be obese, overweight, of normal weight or lean. The obese, overweight, normal weight or lean subject may suffer from type II diabetes. The preferred administration of a compound or composition comprising a compound or pharmaceutical salt of a compound of the invention useful to treat insulin resistance, is peripheral administration. Examples of peripheral administration include oral, subcutaneous, intraperitoneal, intramuscular, intravenous, rectal, transdermal or intranasal forms of administration.

BRIEF DESCRIPTION OF THE DRAWINGS

FIG. 2B. Effect of subcutaneous administration of 75, 300 or 1200 nmole/kg/day of Compound A upon cumulative food intake in rats.

FIG. 4. Effect of subcutaneous administration of 200, 600 or 1800 nmole/kg/day of Compound A upon blood glucose levels in mice.

DETAILED DESCRIPTION OF THE INVENTION

Figure 1:
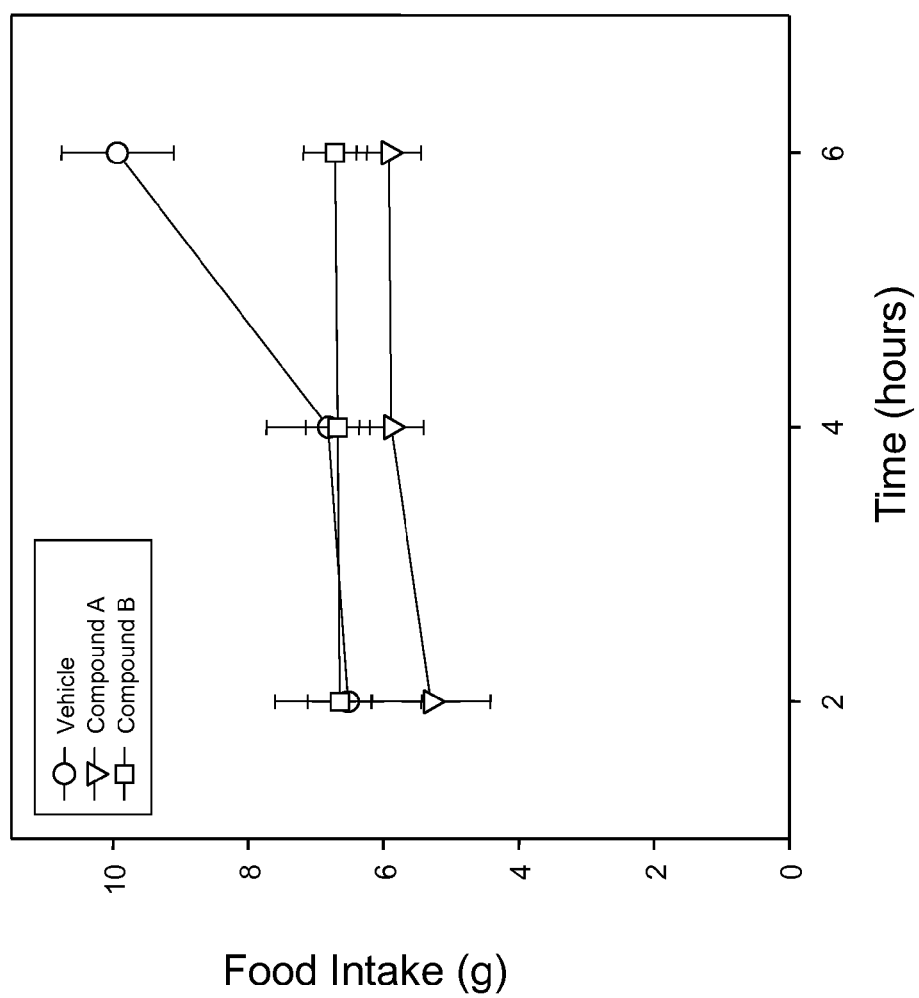
FIG. 1: Food consumed in fasted rats 6 hours after administration of 100 nmole/Kg of selected compounds.
Figure 2A:
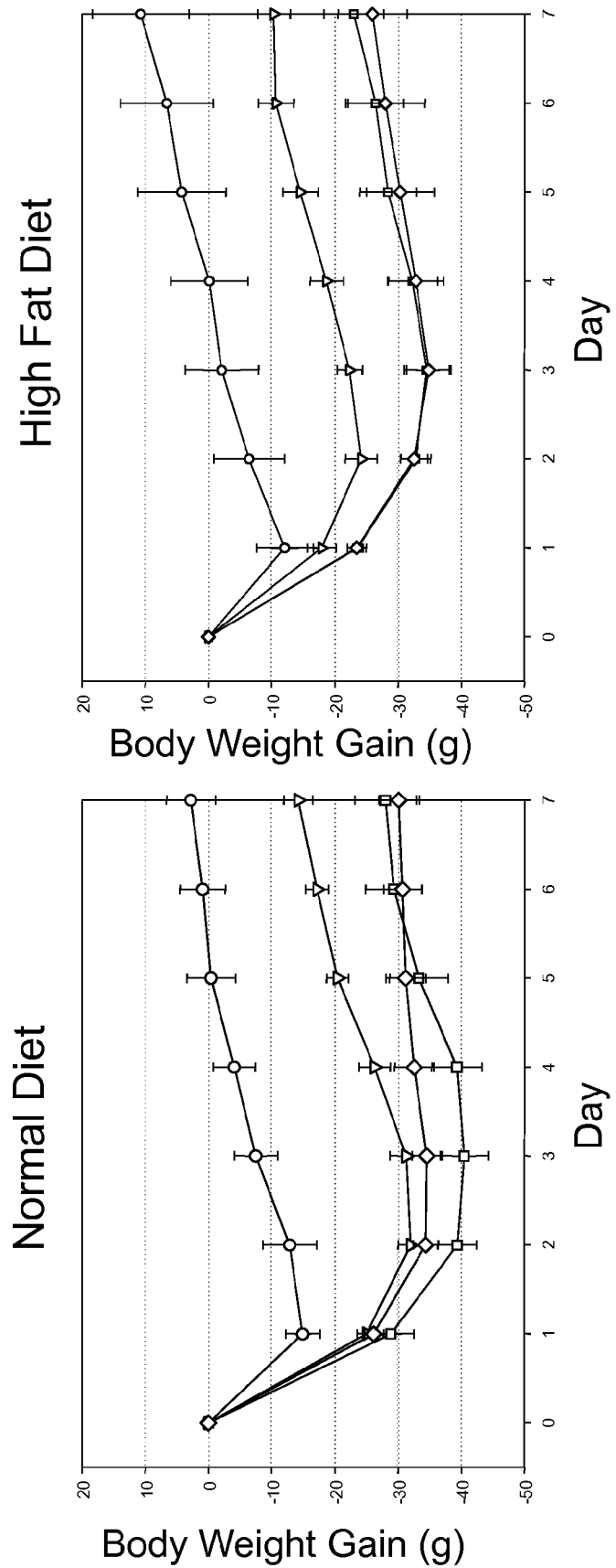
FIG. 2A. Effect of subcutaneous administration of 75, 300 or 1200 nmole/kg/day of Compound A upon body weight in rats.
Figure 2C:
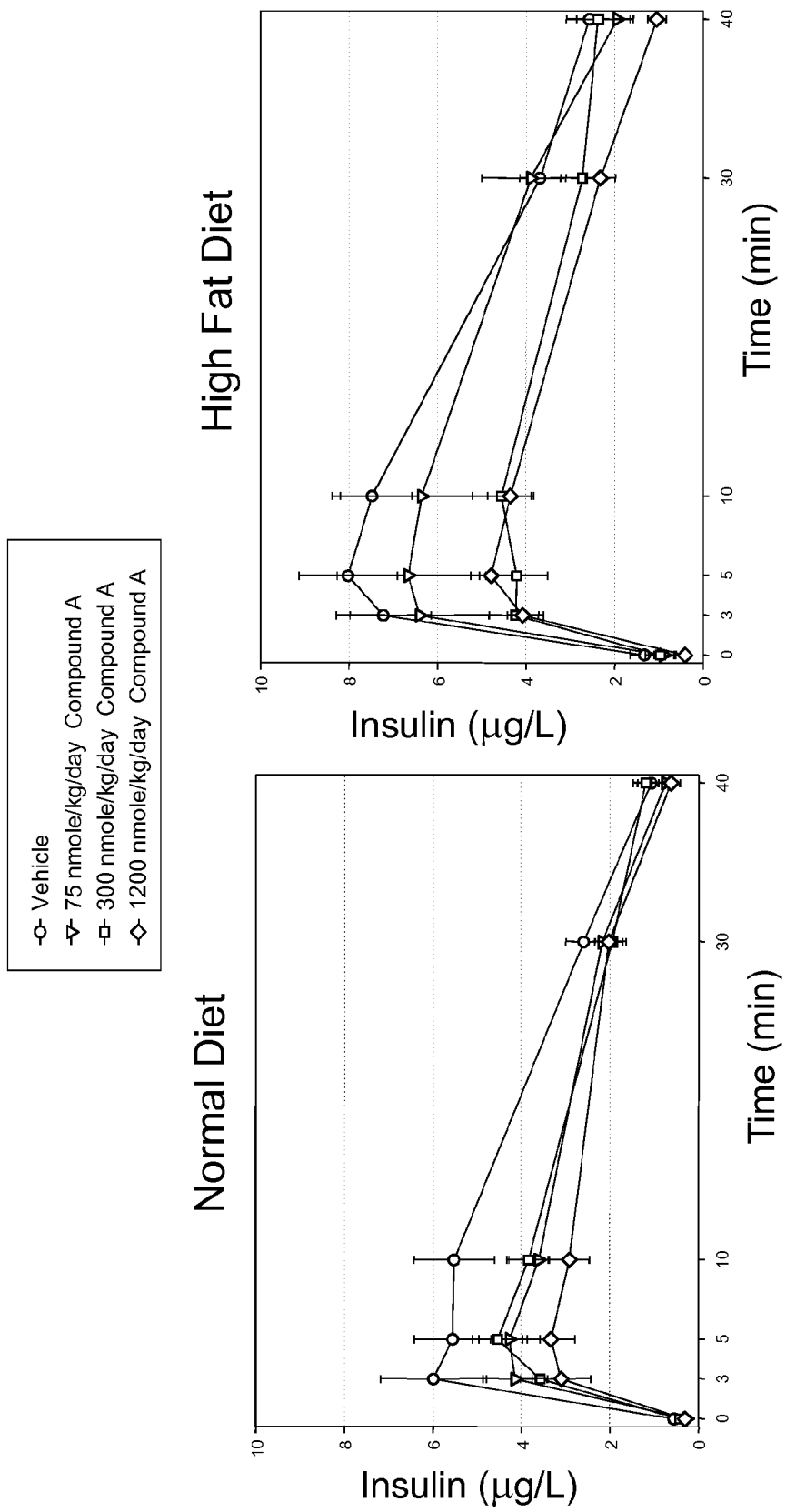
FIG. 2C. Effect of subcutaneous administration of 75, 300 or 1200 nmole/kg/day of Compound A upon insulin levels in rats.
Figure 2D:
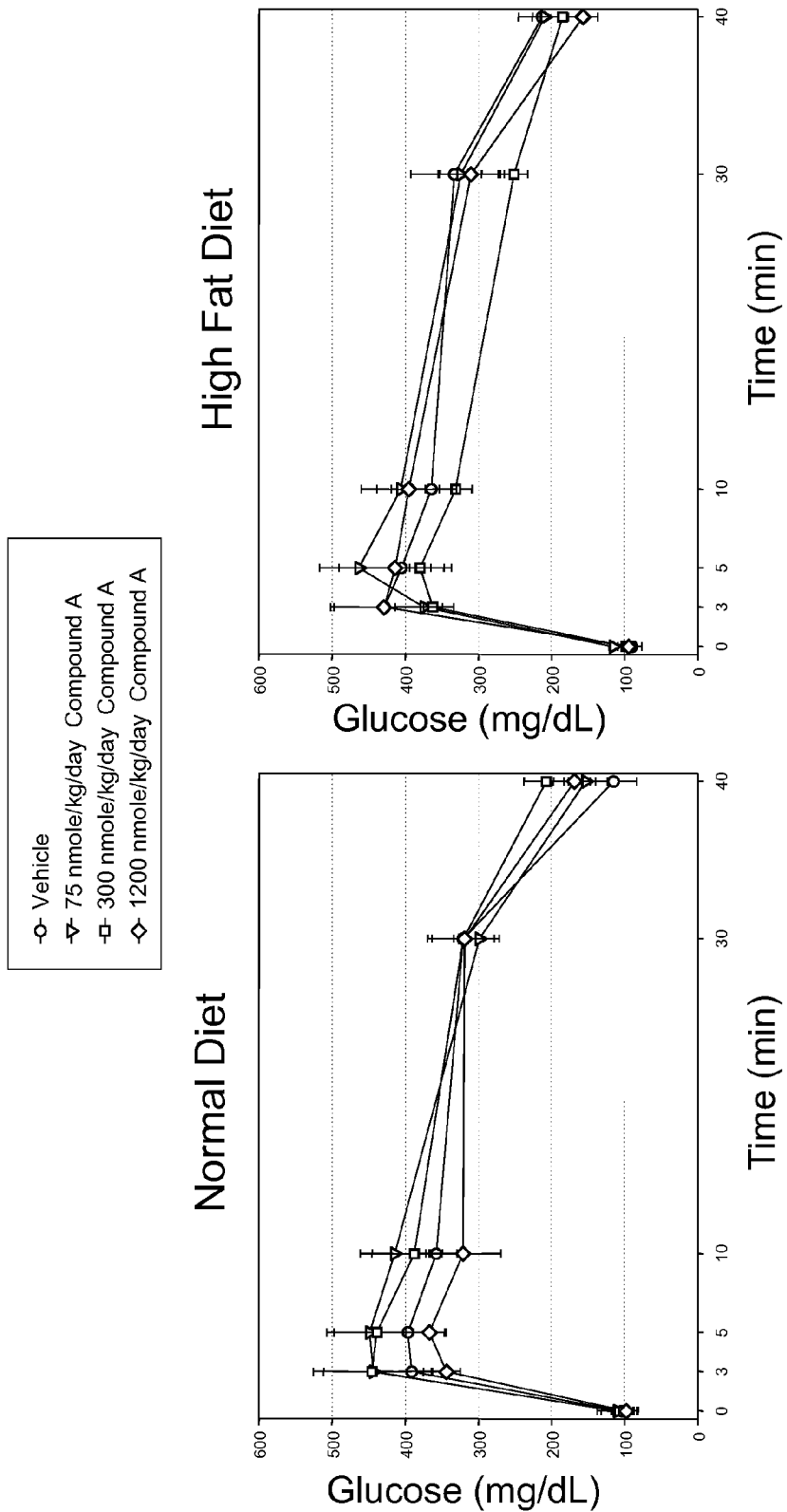
FIG. 2D. Effect of subcutaneous administration of 75, 300 or 1200 nmole/kg/day of Compound A upon glucose levels in rats.
Figure 3A:
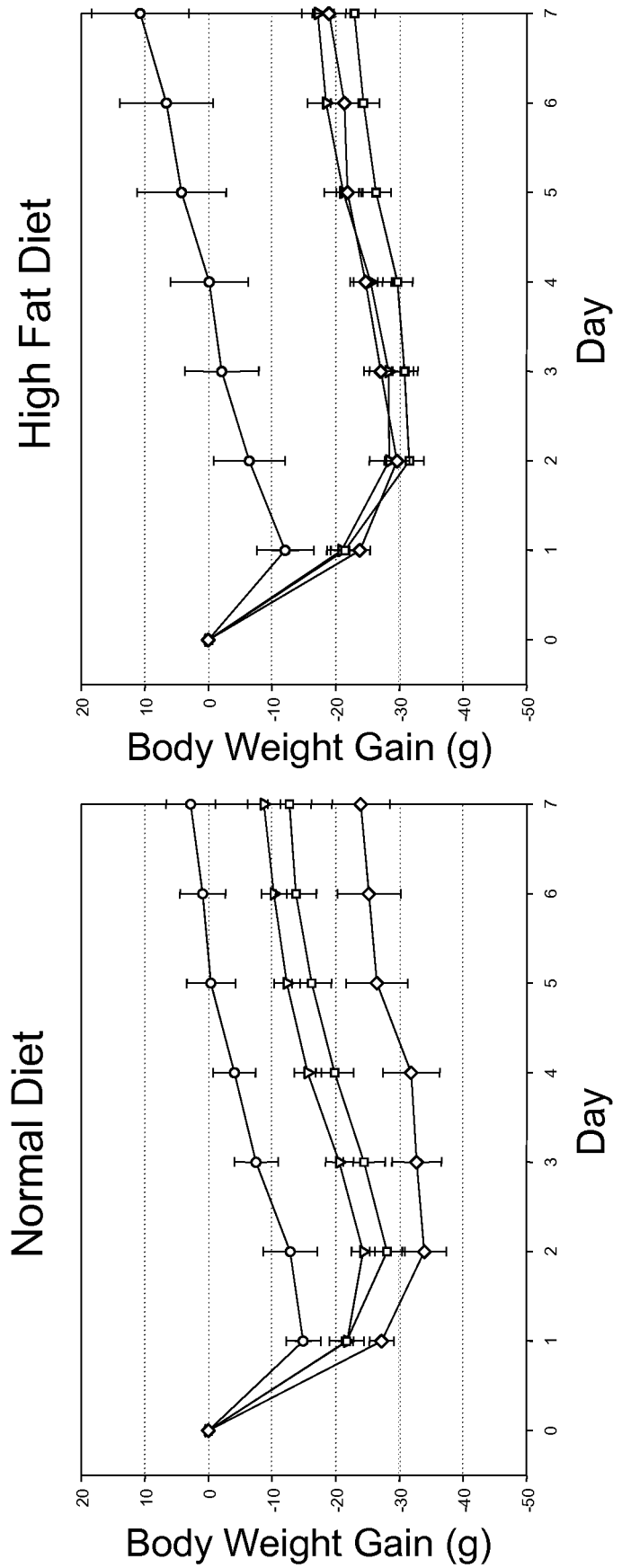
FIG. 3A. Effect of subcutaneous administration of 75, 300 or 1200 nmole/kg/day of Compound B upon body weight in rats.
Figure 3B:
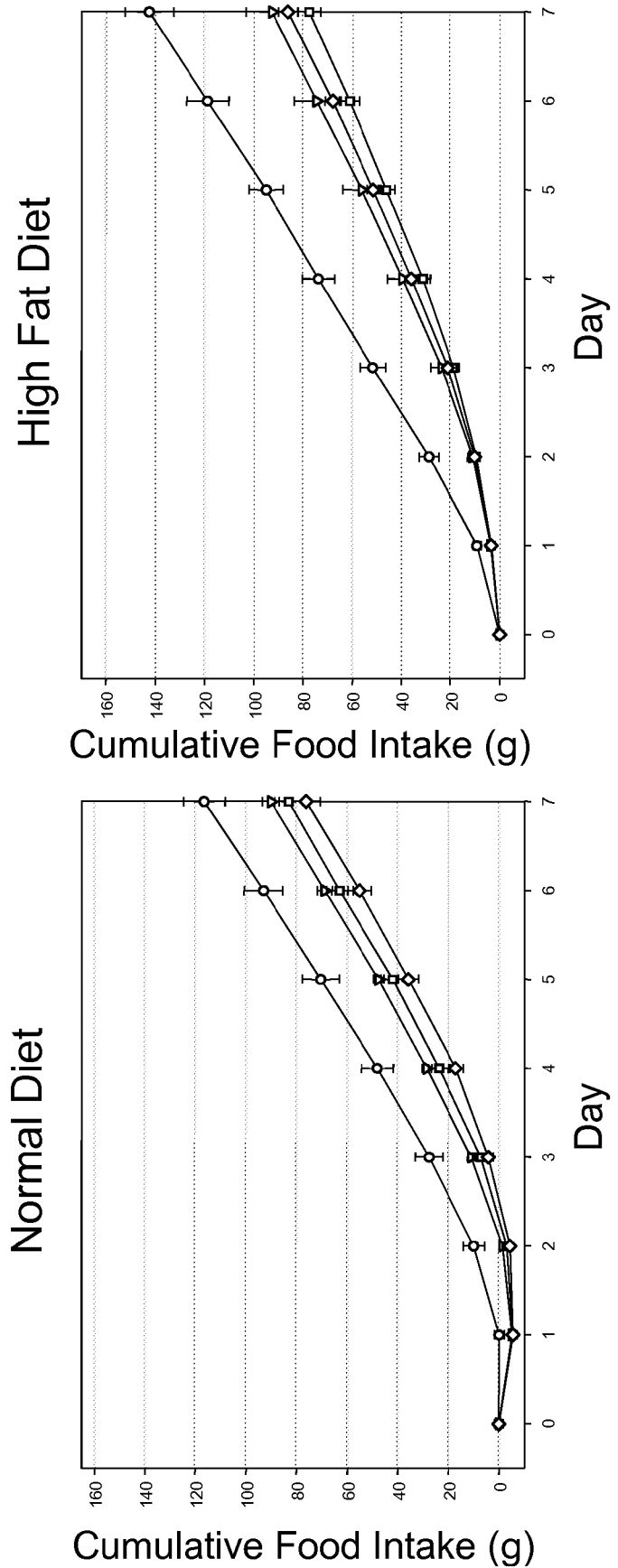
FIG. 3B. Effect of subcutaneous administration of 75, 300 or 1200 nmole/kg/day of Compound B upon cumulative food intake in rats.
Figure 3C:
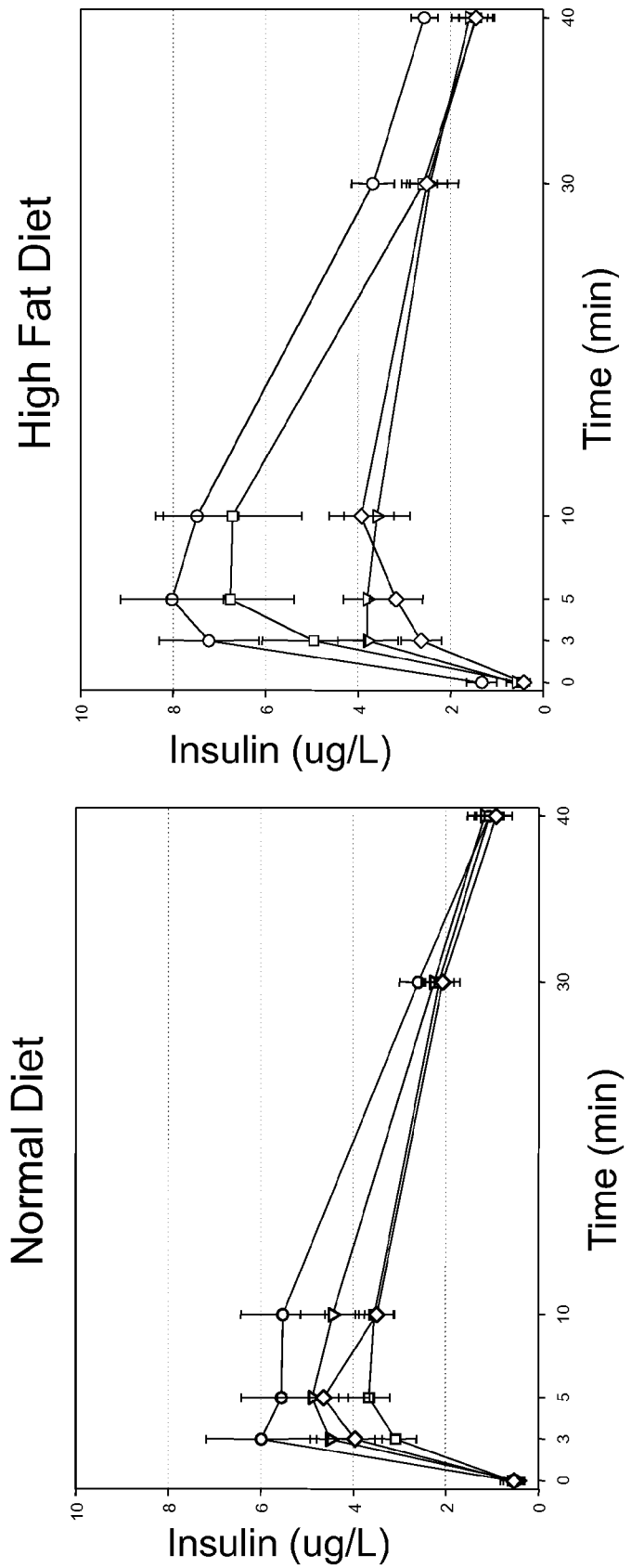
FIG. 3C. Effect of subcutaneous administration of 75, 300 or 1200 nmole/kg/day of Compound B upon insulin levels in rats.
Figure 3D:
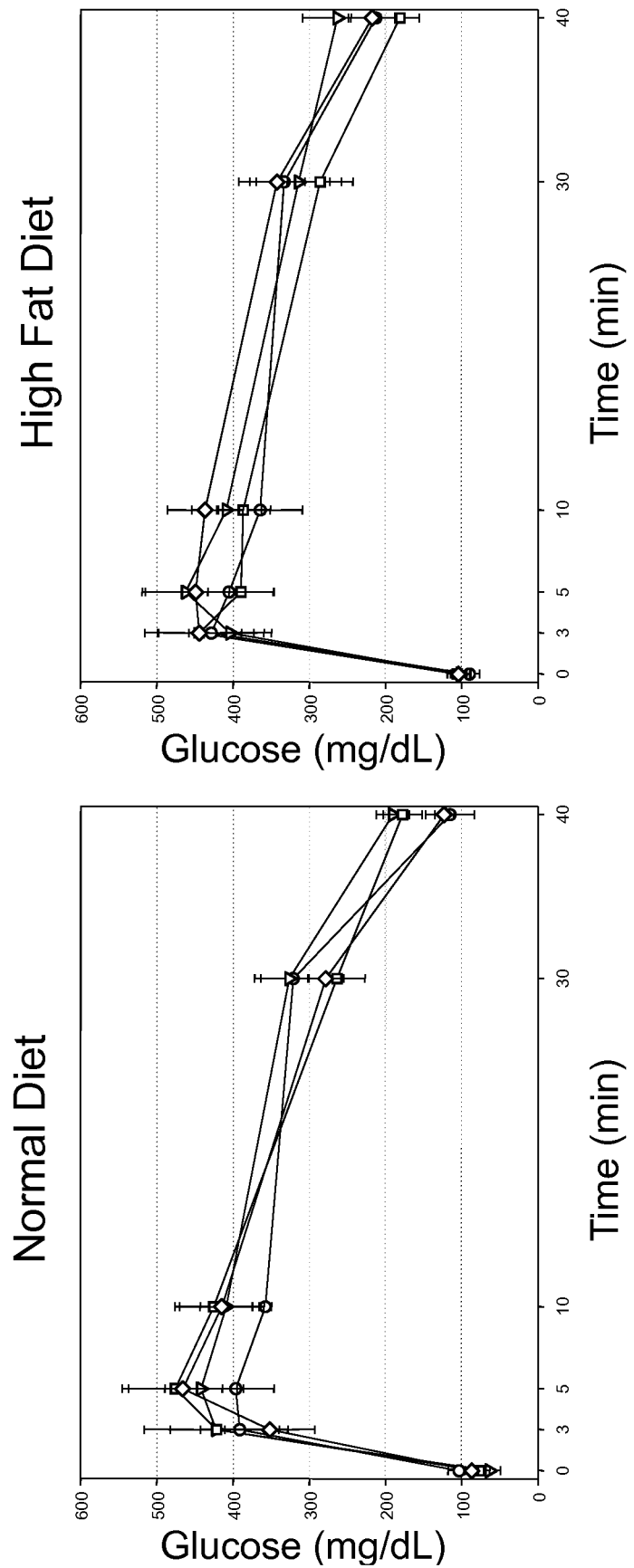
FIG. 3D. Effect of subcutaneous administration of 75, 300 or 1200 nmole/kg/day of Compound B upon glucose levels in rats.

Recent studies have reported that staggering numbers of people world wide are overweight and suffering a wide variety of serious and expensive health problems. According the World Health Organization (as reported in Kouris-Blazos et al., Asia Pac. J. Clin. Nutr., 2007, 16:329-338), an estimated 1 billion people throughout the world are overweight and an estimated 300 million of these are obese. An estimated 22 million children under the age of 5 are severely overweight and in the European Union alone, the number of children who are overweight is expected to rise by 1.3 million children per year (Kosti et al., 2006, Cent. Eur. J. Public Health, 14:151-159). Obesity, as defined by the Statistical Bulletin provided by the Metropolitan Life Insurance Co., (1959, 40:1), is a condition in which a person is approximately 20-25% over normal body weight. Alternatively, an individual is considered obese if the person has a body mass index of greater than 25% over normal or greater than 30% over normal with risk factors (see Bray et al., Diabetes/Metabolism Review, 1988, 4:653-679 or Flynn et al., Proc. Nutritional Society, 1991, 50:413). One of the main causes for obesity is the consumption of a high caloric diet (Riccardi et al., Clin. Nutr., 2004, 23:447-456).

Diabetes is a chronic, debilitating disease afflicting many overweight and obese people. It is estimated that 20.8 million people in the United States alone have diabetes and more than 6 million more additional cases remain undiagnosed (Cornell, Manag. Care Pharm., 2007, 13:S11-5). Type 2 diabetes (also referred to herein as type II diabetes) is a chronic disease characterized by insulin resistance, impaired insulin secretion and hyperglycemia. Worldwide, type II diabetes is believed to affect approximately 171 million people, imparting numerous microvascular and macrovascular complications resulting in morbidity and mortality (Mudaliar, Indian J. Med. Res., 2007, 125:275-296). Mudaliar further notes that despite the availability of anti-hyperglycaemic agents available, control of glucose remains elusive in many patients.

Insulin resistance, also referred to as reduced insulin sensitivity, is a condition in which the amount of insulin needed to clear glucose from the blood of a subject is increased as compared to the amount of insulin needed to clear the same amount of glucose from the blood of a normal, non-insulin sensitive subject. Insulin resistance is regarded as the main link between obesity and type II diabetes (see Obici et al., J. Clin. Inv., 2001, 108:1079-1085 and references therein). It is known that rats fed a high fat diet show an increase in body weight (diet-induced obesity or DIO) and a decrease in insulin sensitivity. Such DIO rats provide an animal model in which to study the mechanisms of insulin resistance due to obesity (see for example Banno et al., FEBS letters, 2007, 581:1131-1136). The size and weight of adipose tissues are increased in DIO rats and it is thought that the accompanying hypertrophy of adipocytes leads to changes in the release of adipocytokines such as leptin and adiponectin which are known to regulate insulin sensitivity; it is thought that morphological changes in adipose tissue as well as changes in plasma levels of adipocytokines are among the causes of insulin resistance in DIO rats (summarized in Banno, et al., FEBS letters, 2007, 581:1131-1136 and references therein).

Melanocortins are proposed to play a large role in energy metabolism and homeostasis. Melanocortins cleaved from the POMC precursor exert their effects by binding to members of the melanocortin receptor family located in the brain. The major effect of melanocortin in the brain is to reduce food intake however, it has also been shown that melanocortin agonists or antagonists injected directly into the cerebral ventricle affect insulin actions in the periphery while food was withdrawn or while food intake was kept constant (see Schwartz et al., Nature, 2000, 404:661-671; Seeley et al., Ann. Rev. Nutr., 2004, 24:133-149; Cone et al., Recent Prog. Horm. Res., 1996, 51:287-317; Heijbor et al., Diabetologia, 2005, 48:1621-1626; Obici et al., J. Clin. Inv., 2001, 108:1079-1085). Taken together, these data suggest that central administration of melanocortins affects insulin sensitivity and may do so independently of energy balance. Banno et al., (FEBS letters, 2007, 581:1131-1136) demonstrated that intracerebral injections of a melanocortin agonist to DIO rats ameliorated insulin sensitivity in the periphery, decreased the size of and increased the number of adipocytes in white adipose tissue and decreased triglycerides content in the liver.

Considering the large numbers of overweight and/or insulin resistant subjects in need of treatment, intracerebral administration is an unlikely means to disperse medicaments to patients. There is a need in the art, therefore, to identify melanocortin agonists and antagonists suitable for peripheral administration to affect parameters of insulin action and energy metabolism such as insulin sensitivity, cellular characteristics of white adipose tissue, triglyceride levels and the like.

Nomenclature and Abbreviations

As used herein, an "obese subject" or mammal is characterized as having a body weight approximately 20% or greater than the normal body weight for said subject. Normal body weight may be determined by a comparison of the weight of the subject at a prior point in time, such as when insulin metabolism was normal, or by a comparison of the weight of the subject as compared to averages of other subjects of a similar age and/or condition.

As used herein, an "overweight subject" or mammal is characterized as having a body weight approximately 5% greater to approximately 20% greater than the normal body weight for said subject. Normal body weight may be determined by a comparison of the weight of the subject at a prior point in time, such as when insulin metabolism was normal, or by a comparison of the weight of the subject as compared to averages of other subjects of a similar age and/or condition.

As used herein, a "normal subject" or mammal is characterized as having a body weight up to approximately 5% greater than to approximately 5% less than the normal body weight for said subject. Normal body weight may be determined by a comparison of the weight of the subject at a prior point in time, such as when insulin metabolism was normal, or by a comparison of the weight of the subject as compared to averages of other subjects of a similar age and/or condition.

As used herein, a "lean subject" or mammal is characterized as having a body weight approximately 5% to 30% or even to 50% less than the normal body weight for said subject. Normal body weight may be determined by a comparison of the weight of the subject at a prior point in time, such as when insulin metabolism was normal, or by a comparison of the weight of the subject as compared to averages of other subjects of a similar age and/or condition.

As used herein, the terms "treat", "treating" and "treatment" include palliative, curative and prophylactic treatment.

As used herein, "measurable" means the biologic effect is both reproducible and significantly different from the baseline variability of the assay.

As used herein, peripheral administration includes all forms of administration of a compound or a composition comprising a compound of the instant invention which excludes intracranial administration. Examples of peripheral administration include, but are not limited to, oral, parenteral (e.g., intramuscular, intraperitoneal, intravenous or subcutaneous injection, implant and the like), nasal, vaginal, rectal, sublingual or topical routes of administration, including transdermal patch applications and the like.

A "subject", as used herein and throughout this application, refers to a mammalian or non-mammalian animal including, for example and without limitation, a human, a rat, a mouse or farm animal. Reference to a subject does not necessarily indicate the presence of a disease or disorder. The term "subject" includes, for example, a mammalian or non-mammalian animal being dosed with a melanocortin analog as part of an experiment, a mammalian or non-mammalian animal being treated to help alleviate a disease or disorder, and a mammalian or non-mammalian animal being treated prophylactically to retard or prevent the onset of a disease or disorder. Subject mammals may be human subjects of any age, such as an infant, a child, an adult or an elderly adult.

A "therapeutically acceptable amount" of a compound or composition of the invention, regardless of the formulation or route of administration, is that amount which elicits a desired biological response in a subject. The biological effect of the therapeutic amount may occur at and be measured at many levels in an organism. For example, the biological effect of the therapeutic amount may occur at and be measured at the cellular level by measuring the response at a receptor which binds melanocortin and/or a melanocortin analog, or the biological effect of the therapeutic amount may occur at and be measured at the system level, such as effecting an increase/decrease in the levels of insulin. The biological effect of the therapeutic amount may occur at and be measured at the organism level, such as the alleviation of a symptom(s) or progression of a disease or condition in a subject. A therapeutically acceptable amount of a compound or composition of the invention, regardless of the formulation or route of administration, may result in one or more biological responses in a subject. In the event that the compound or composition of the invention is subject to testing in an in vitro system, a therapeutically acceptable amount of the compound or composition may be viewed as that amount which gives a measurable response in the in vitro system of choice.

The nomenclature used to define the peptides is that typically used in the art wherein the amino group at the N-terminus appears to the left and the carboxyl group at the C-terminus appears to the right. Where the amino acid has D and L isomeric forms, it is the L form of the amino acid that is represented unless otherwise explicitly indicated.

The compounds of the invention useful for the treatment of insulin resistance, with or without weight loss, may possess one or more chiral centers and so exist in a number of stereoisomeric forms. All stereoisomers and mixtures thereof are included in the scope of the present invention. Racemic compounds may either be separated using preparative HPLC and a column with a chiral stationary phase or resolved to yield individual enantiomers utilizing methods known to those skilled in the art. In addition, chiral intermediate compounds may be resolved and used to prepare chiral compounds of the invention.

The compounds of the invention useful for the treatment of insulin resistance, with or without weight loss, may exist in one or more tautomeric forms. All tautomers and mixtures thereof are included in the scope of the present invention. For example, a claim to 2-hydroxypyridinyl would also cover its tautomeric form, α-pyridonyl.

Unless defined otherwise, all technical and scientific terms used herein have the same meaning as commonly understood by one of ordinary skill in the art to which this invention belongs. Also, all publications, patent applications, patents and other references mentioned herein are incorporated by reference in their entirety.

| Symbol | Meaning |
|---|---|
| Abu | α-aminobutyric acid |
| Ac | acyl group |
| Acc | 1-amino-1-cyclo($C_3$-$C_6$)alkyl carboxylic acid |
| A3c | 1-amino-1-cyclopropanecarboxylic acid |
| A4c | 1-amino-1-cyclobutanecarboxylic acid |
| A5c | 1-amino-1-cyclopentanecarboxylic acid |
| A6c | 1-amino-1-cyclohexanecarboxylic acid |
| Aha | 7-aminoheptanoic acid |
| Ahx | 6-aminohexanoic acid |
| Aib | α-aminoisobutyric acid |
| Aic | 2-aminoindan-2-carboxylic acid |
| Ala or A | alanine |
| β-Ala | βalanine |
| Apc | denotes the structure: 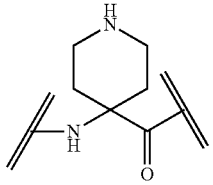 |
| Apn | 5-aminopentanoic acid (HN—($CH2)_4$—C(O) |
| Arg or R | arginine |
| hArg | homoarginine |
| Asn or N | asparagine |
| Asp or D | aspartic acid |
| Bal | 3-benzothienylalanine |
| Bip | 4,4'-biphenylalanine, represented by the structure 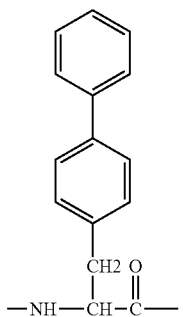 |

| Symbol | Meaning |
|---|---|
| Bpa | 4-benzoylphenylalanine |
| 4-Br-Phe | 4-bromo-phenylalanine |
| Cha | β-cyclohexylalanine |
| hCha | homo-cyclohexylalanine |
| Chg | cyclohexylglycine |
| Cys or C | cysteine |
| hCys | homocysteine |
| Dab | 2,4-diaminobutyric acid |
| Dap | 2,3-diaminopropionic acid |
| Dip | β,β-diphenylalanine |
| Doc | 8-amino-3,6-dioxaoctanoic acid with the structure of: |
| 2-Fua | β-(2-furyl)-alanine |
| Gaba | 4-aminobutyric acid |
| Gln or Q | glutamine |
| Glu or E | glutamic acid |
| Gly or G | glycine |
| His or H | histidine |
| 3-Hyp | trans-3-hydroxy-L-proline, i.e., (2S,3S)-hydroxypyrrolidine-2-carboxylic acid |
| 4-Hyp | 4-hydroxyproline, i.e, (2S,4R)-4-hydroxypyrrolidine-2-carboxylic acid |
| Ile or I | isoleucine |
| Leu or L | leucine |
| hLeu | homoleucine |
| Lys or K | lysine |
| Met or M | methionine |
| β-hMet | β-homomethionine |
| 1-Nal | β-(1-naphthyl)alanine: |
| 2-Nal | β-(2-naphthyl)alanine |
| Nip | nipecotic acid |
| Nle | norleucine |
| Oic | octahydroindole-2-carboxylic acid |
| Orn | ornithine |
| 2-Pal | β-(2-pyridyl)alanine |
| 3-Pal | β-(3-pyridiyl)alanine |
| 4-Pal | β-(4-pyridiyl)alanine |
| Pen | pencillamine |
| Pff | (S)-pentafluorophenylalanine |
| Phe or F | phenylalanine |
| hPhe | homophenylalanine |
| Pro or P | proline |
| hPro | homoproline |
| Ser or S | serine |
| Tle | tert-Leucine |
| Taz | β-(4-thiazolyl)alanine |
| 2-Thi | β-(2-thienyl)alanine |
| 3-Thi | β-(3-thienyl)alanine |
| Thr or T | threonine |
| Trp or W | tryptophan |
| Tyr or Y | tyrosine |
| D-(Et)Tyr | has a structure of |
| Val or V | valine |

Certain other abbreviations used herein are defined as follows:
Boc: tert-butyloxycarbonyl
Bzl: benzyl DCM: dichloromethane
DIC: N, N-diisopropylcarbodiimide
DIEA: diisopropylethyl amine
Dmab: 4-{N-(1-(4,4-dimethyl-2,6-dioxocyclohexylidene)-3-methylbutyl)-amino}benzyl
DMAP: 4-(dimethylamino)pyridine
DMF dimethylformamide
DNP: 2,4-dinitrophenyl
Fm: fluorenylmethyl
Fmoc: fluorenylmethyloxycarbonyl
For: formyl
HBTU: 2-(1H-benzotriazole-1-yl)-1,1,3,3-tetramethyluronium hexafluorophosphate
cHex cyclohexyl
HOAT: O-(7-azabenzotriazol-1-yl)-1,1,3,3-tetramethyluronium hexafluorophosphate
HOBt: 1-hydroxy-benzotriazole
MBHA 4-methylbenzhydrylamine
Mmt: 4-methoxytrityl
NMP: N-methylpyrrolidone
O-tBu oxy-tert-butyl
Pbf: 2,2,4,6,7-pentamethyldihydrobenzofuran-5-sulfonyl
PyBroP bromo-tris-pyrrolidino-phosphonium hexafluorophosphate
tBu: tert-butyl
TIS: triisopropylsilane
TOS: tosyl
Trt trityl
TFA: trifluoro acetic acid
TFFH: tetramethylfluoroforamidinium hexafluorophosphate
Z: benzyloxycarbonyl Unless otherwise indicated, with the exception of the N-terminal amino acid, all abbreviations (e.g. Ala) of amino acids in this disclosure stand for the structure of —NH—C(R)(R')—CO—, wherein R and R' each is, independently, hydrogen or the side chain of an amino acid (e.g., R=CH$_3$ and R'=H for Ala), or R and R' may be joined to form a ring system.

For the N-terminal amino acid, the abbreviation stands for the structure of:

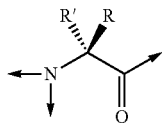

The designation "NH$_2$" in e.g., Ac-Nle-c(Cys-D-Ala-His-D-Phe-Arg-Trp-Cys)-NH$_2$ (SEQ ID NO:7), indicates that the C-terminus of the peptide is amidated. Ac-Nle-c(Cys-D-Ala-His-D-Phe-Arg-Trp-Cys) (SEQ ID NO:36), or alternatively Ac-Nle-c(Cys-D-Ala-His-D-Phe-Arg-Trp-Cys)-OH (SEQ ID NO:36), indicates that the C-terminus is the free acid.

"-c(Cys-Cys)-" or "-cyclo(Cys-Cys)-" denotes the structure:

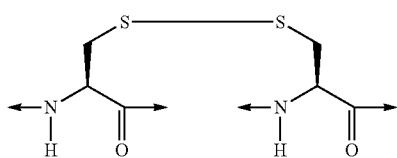

"-c(Cys-Pen)-" or "-cyclo(Cys-Pen)-" denotes the structure:

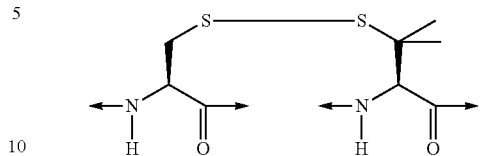

"-c(Asp-Lys)-" or "-cyclo(Asp-Lys)-" denotes the structure:

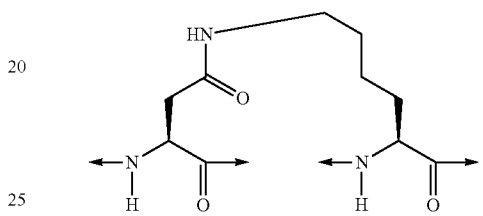

Applicants have devised the following shorthand used in naming the specific embodiments and/or species:

"HydantoinC(O)-(A$^a$-A$^b$)" denotes the structure:

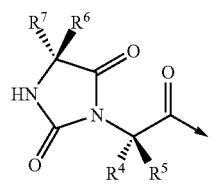

wherein amino acid "A$^a$" has the structure:

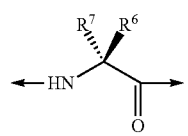

and
amino acid "A$^b$" the structure:

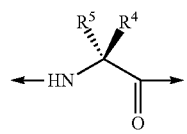

For example, a compound represented as "c[Hydantoin(C(O)-(Cys-A$^b$))-A$^1$-A$^2$-A$^3$-A$^4$-Cys]-" would have the following the structure:

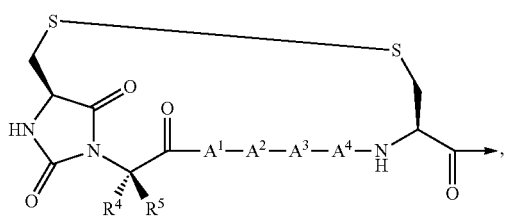

whereas a compound represented as "c[Hydantoin(C(O)-(A$^b$-Cys))-A$^1$-A$^2$-A$^3$-A$^4$-Cys]-" would have the structure:

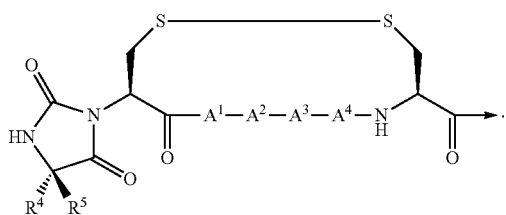

For further guidance, "c[Hydantoin(C(O)-(Asp-A$^b$))-A$^1$-A$^2$-A$^3$-A$^4$-Lys]-" represents the following compound:

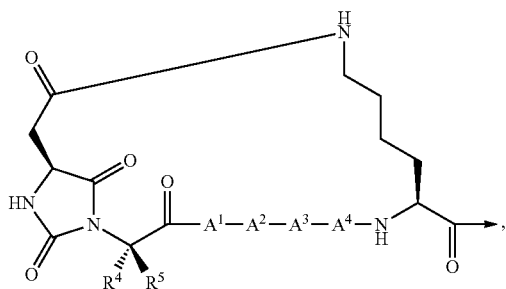

whereas "c[Hydantoin(C(O)-(Dap-A$^b$))-A$^1$-A$^2$-A$^3$-A$^4$-Asp]-" has the following formula:

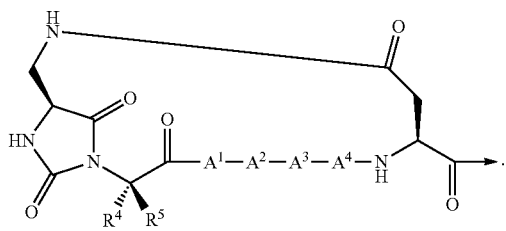

"Acyl" refers to R"—C(O)—, where R" is H, alkyl, substituted alkyl, heteroalkyl, substituted heteroalkyl, alkenyl, substituted alkenyl, aryl, alkylaryl, or substituted alkylaryl, and is indicated in the general formula of a particular embodiment as "Ac".

"Alkyl" refers to a hydrocarbon group containing one or more carbon atoms, where multiple carbon atoms if present are joined by single bonds. The alkyl hydrocarbon group may be straight-chain or contain one or more branches or cyclic groups.

"Hydroxyalkyl" refers to an alkyl group wherein one or more hydrogen atoms of the hydrocarbon group are substituted with one or more hydroxy radicals, such as hydroxymethyl, hydroxyethyl, hydroxypropyl, hydroxybutyl, hydroxypentyl, hydroxyhexyl and the like.

"Substituted alkyl" refers to an alkyl wherein one or more hydrogen atoms of the hydrocarbon group are replaced with one or more substituents selected from the group consisting of halogen, (i.e., fluorine, chlorine, bromine, and iodine), —OH, —CN, —SH, —NH$_2$, —NHCH$_3$, —NO$_2$, and —C$_{1-20}$ alkyl, wherein said —C$_{1-20}$ alkyl optionally may be substituted with one or more substituents selected, independently for each occurrence, from the group consisting of halogens, —CF$_3$, —OCH$_3$, —OCF$_3$, and —(CH$_2$)$_{0-20}$—COOH. In different embodiments 1, 2, 3 or 4 substituents are present. The presence of —(CH$_2$)$_{0-20}$—COOH results in the production of an alkyl acid. Non-limiting examples of alkyl acids containing, or consisting of, —(CH$_2$)$_{0-20}$—COOH include 2-norbornane acetic acid, tert-butyric acid, 3-cyclopentyl propionic acid, and the like.

The term "halo" encompasses fluoro, chloro, bromo and iodo.

"Heteroalkyl" refers to an alkyl wherein one of more of the carbon atoms in the hydrocarbon group is replaced with one or more of the following groups: amino, amido, —O—, —S— or carbonyl. In different embodiments 1 or 2 heteroatoms are present.

"Substituted heteroalkyl" refers to a heteroalkyl wherein one or more hydrogen atoms of the hydrocarbon group are replaced with one or more substituents selected from the group consisting of halogen, (i.e., fluorine, chlorine, bromine, and iodine), —OH, —CN, —SH, —NH$_2$, —NHCH$_3$, —NO$_2$, and —C$_{1-20}$ alkyl, wherein said —C$_{1-20}$ alkyl optionally may be substituted with one or more substituents selected, independently for each occurrence, from the group consisting of halogens, —CF$_3$, —OCH$_3$, —OCF$_3$, and —(CH$_2$)$_{0-20}$—COOH. In different embodiments 1, 2, 3 or 4 substituents are present.

"Alkenyl" refers to a hydrocarbon group made up of two or more carbons where one or more carbon-carbon double bonds are present. The alkenyl hydrocarbon group may be straight-chain or contain one or more branches or cyclic groups.

"Substituted alkenyl" refers to an alkenyl wherein one or more hydrogens are replaced with one or more substituents selected from the group consisting of halogen (i.e., fluorine, chlorine, bromine, and iodine), —OH, —CN, —SH, —NH$_2$, —NHCH$_3$, —NO$_2$, and —C$_{1-20}$ alkyl, wherein said —C$_{1-20}$ alkyl optionally may be substituted with one or more substituents selected, independently for each occurrence, from the group consisting of halogens, —CF$_3$, —OCH$_3$, —OCF$_3$, and —(CH$_2$)$_{0-20}$—COOH. In different embodiments 1, 2, 3 or 4 substituents are present.

"Aryl" refers to an optionally substituted aromatic group with at least one ring having a conjugated pi-electron system, containing up to three conjugated or fused ring systems. Aryl includes carbocyclic aryl, heterocyclic aryl and biaryl groups. Preferably, the aryl is a 5- or 6-membered ring. Preferred atoms for a heterocyclic aryl are one or more sulfur, oxygen, and/or nitrogen. Non-limiting examples of aryl include phenyl, 1-naphthyl, 2-naphthyl, indole, quinoline, 2-imidazole, 9-anthracene, and the like. Aryl substituents are selected from the group consisting of —C$_{1-20}$ alkyl, —C$_{1-20}$ alkoxy, halogen (i.e., fluorine, chlorine, bromine, and iodine), —OH, —CN, —SH, —NH$_2$, —NO$_2$, —C$_{1-20}$ alkyl substituted with halogens, —CF$_3$, —OCF$_3$, and —(CH$_2$)$_{0-20}$—COOH. In different embodiments the aryl contains 0, 1, 2, 3, or 4 substituents.

"Alkylaryl" refers to an "alkyl" joined to an "aryl".

The term "($C_1$-$C_{12}$)hydrocarbon moiety" encompasses alkyl, alkenyl and alkynyl and in the case of alkenyl and alkynyl there is $C_2$-$C_{12}$.

For the avoidance of doubt, unless otherwise indicated, the term substituted means substituted by one or more defined groups. In the case where groups may be selected from a number of alternative groups, the selected groups may be the same or different. For the avoidance of doubt, the term independently means that where more than one substituent is selected from a number of possible substituents, those substituents may be the same or different.

The pharmaceutically acceptable salts of the compounds of the invention which contain a basic centre are, for example, non-toxic acid addition salts formed with inorganic acids such as hydrochloric, hydrobromic, hydroiodic, sulfuric and phosphoric acid, with carboxylic acids or with organo-sulfonic acids. Examples include the HCl, HBr, HI, sulfate or bisulfate, nitrate, phosphate or hydrogen phosphate, acetate, benzoate, succinate, saccharate, fumarate, maleate, lactate, citrate, tartrate, gluconate, camsylate, methanesulfonate, ethanesulfonate, benzenesulfonate, p-toluenesulfonate and pamoate salts. Compounds of the invention can also provide pharmaceutically acceptable metal salts, in particular non-toxic alkali and alkaline earth metal salts, with bases. Examples include the sodium, potassium, aluminum, calcium, magnesium, zinc and diethanolamine salts (Berge, S. M. et al., *J. Pharm. Sci.*, 66:1-19 (1977); Gould, P. L., *Intl J. Pharmaceutics*, 33:201-17 (1986); and Bighley, L. D. et al., *Encyclo. Pharma. Tech.*, Marcel Dekker Inc, New York, 13:453-97 (1996).

The pharmaceutically acceptable solvates of the compounds of the invention include the hydrates thereof. Also included within the scope of the invention and various salts of the invention are polymorphs thereof. Hereinafter, compounds their pharmaceutically acceptable salts, their solvates or polymorphs, defined in any aspect of the invention (except intermediate compounds in chemical processes) are referred to as "compounds of the invention".

In Vitro Studies

Compounds of the present invention can be and were tested for activity as ligands of one or more of the melanocortin receptors according to the following procedures. One skilled in the art would know that procedures similar to those described herein may be used to assay the binding activities of the compounds of the invention to melanocortin receptor molecules.

Radioligand Binding Assays

Cellular membranes used for the in vitro receptor binding assays were obtained from transgenic CHO-K1 cells stably expressing hMC-R receptor subtypes 1, 3, 4 or 5. The CHO-K1 cells expressing the desired hMC-R receptor type were sonicated (Branson® setting 7, approximately 30 sec) in ice-cold 50 mM Tris-HCl at pH 7.4 and then centrifuged at 39,000 g for 10 minutes at approximately 4° C. The pellets were resuspended in the same buffer and centrifuged at 50,000 g for 10 minutes at approximately 4° C. The washed pellets containing the cellular membranes were stored at approximately −80° C.

Competitive inhibition of $[^{125}I](Tyr^2)$-$(Nle^4$-D-$Phe^7)\alpha$-MSH ($[^{125}I]$-NDP-$\alpha$-MSH, Amersham Biosciences®) binding was carried out in polypropylene 96 well plates. Cell membranes (1-10 g protein/well) prepared as described above were incubated in 50 mM Tris-HCl at pH 7.4 containing 0.2% bovine serum albumin (BSA), 5 mM $MgCl_2$, 1 mM $CaCl_2$ and 0.1 mg/mL bacitracin, with increasing concentrations of the test compound and 0.1-0.3 nM $[^{125}I]$-NDP-$\alpha$-MSH for approximately 90-120 minutes at approximately 37° C. Bound $[^{125}I]$-NDP-$\alpha$-MSH ligand was separated from free $[^{125}I]$-NDP-$\alpha$-MSH by filtration through GF/C glass fiber filter plates (Unifilter®; Packard) pre-soaked with 0.1% (w/v) polyethylenimine (PEI), using a Packard Filtermate® harvester. Filters were washed three times with 50 mM Tris-HCl at pH 7.4 at a temperature of approximately 0-4° C. and then assayed for radioactivity using a Packard Topcount® scintillation counter. Binding data were analyzed by computer-assisted non-linear regression analysis (XL fit; IDBS). A selection of the preferred embodiments was tested using the above-discussed assay and the binding constants (Ki in nM) are reported in Tables 5, 6, 7 and 8.

TABLE 5

Radioligand Binding Assay Data for Selected Compounds

Table 5A

| Compound | Ki hMC1-R | Ki hMC3-R | Ki hMC4-R | Ki hMC5-R | Ki hMC1-R/ MC4-R | SEQ ID NO: |
|---|---|---|---|---|---|---|
| Ac-Arg-c(Cys-D-Ala-His-D-Phe-Arg-Trp-Cys)-$NH_2$ | 3.87 | 10.1 | 2.09 | 430 | 1.9 | SEQ ID NO: 50 |
| Ac-D-Arg-c(Cys-D-Ala-His-D-Phe-Arg-Trp-Cys)-$NH_2$ | 4.01 | 12.1 | 1.76 | 352 | 2.3 | SEQ ID NO: 50 |
| Ac-D-Arg-c(Cys-D-Ala-His-D-Phe-Arg-Trp-Pen)-$NH_2$ | 8.29 | 13.3 | 2.78 | 816 | 3.0 | SEQ ID NO: 51 |
| Ac-D-Arg-c(Cys-His-D-Phe-Arg-Trp-Gaba-Pen)-$NH_2$ | 3.93 | 172 | 11.0 | 538 | 0.36 | SEQ ID NO: 52 |
| Ac-Arg-c(Cys-His-D-Phe-Arg-Trp-Gaba-Pen)-$NH_2$ | 1.81 | 20.5 | 4.57 | 502 | 0.4 | SEQ ID NO: 52 |
| Ac-Arg-c(Cys-D-Ala-His-D-Phe-Arg-Trp-Pen)-$NH_2$ | 9.67 | 22.0 | 4.2 | 1900 | 2.3 | SEQ ID NO: 51 |

TABLE 5-continued

Radioligand Binding Assay Data for Selected Compounds

| Compound | | | | | | |
|---|---|---|---|---|---|---|
| Ac-D-Arg-c(Asp-His-D-Phe-Arg-Trp-Ala-Lys)-NH$_2$ | 0.79 | 45.5 | 1.21 | 493 | 0.6 | SEQ ID NO: 53 |
| Ac-Arg-c(Asp-His-D-Phe-Arg-Trp-Ala-Lys)-NH$_2$ | 0.68 | 20.7 | 1.01 | 783 | 0.7 | SEQ ID NO: 53 |

Table 5B

| Compound | Ki hMC1-R | Ki hMC3-R | Ki hMC4-R | Ki hMC5-R | Ki hMC1-R/ MC4-R | SEQ ID NO: |
|---|---|---|---|---|---|---|
| Ac-Nle-c(Cys-D-Ala-His-D-2-Nal-Arg-1-Nal-Cys)-NH$_2$ | 114 | 63.9 | 3.07 | 1657 | 37.1 | SEQ ID NO: 16 |
| Ac-Nle-c(Cys-D-Ala-His-D-Phe-Arg-Trp-Cys)-NH$_2$ | 11 | 26 | 7.6 | 1800 | 1.4 | SEQ ID NO: 7 |
| D-Phe-c(Cys-His-D-(Et)Tyr-Arg-Trp-β-Ala-D-Cys)-Thr-NH$_2$ | 0.05 | 9.3 | 1.1 | 2.9 | 0.0 | SEQ ID NO: 24 |
| Nle-c(Cys-His-D-Phe-Arg-Trp-Apn-Cys)-NH$_2$ | 0.07 | 4.1 | 0.85 | 8.8 | 0.1 | SEQ ID NO: 27 |
| Ac-Nle-c(Cys-His-D-Phe-Arg-Trp-Gaba-Pen)-NH$_2$ | 0.12 | 10 | 0.43 | 0.42 | 0.3 | SEQ ID NO: 32 |
| Nle-c(Cys-His-D-Phe-Arg-Trp-Gaba-Cys)-NH$_2$ | 0.05 | 1.3 | 0.47 | 0.2 | 0.1 | SEQ ID NO: 34 |
| Ac-Nle-c(Asp-His-D-Phe-Arg-Trp-β-Ala-Lys)-NH$_2$ | 0.0996 | 9318 | 0.617 | 10.9 | 0.16 | SEQ ID NO: 1 |
| Ac-Nle-c(Cys-His-D-Phe-Arg-Trp-Ahx-Cys)-NH$_2$ | .0132 | 16.1 | 1.23 | 0.359 | 0.11 | SEQ ID NO: 2 |
| D-Phe-c(Cys-His-D-Phe-Arg-Trp-β-Ala-D-Cys)-Thr-NH$_2$ | 0.207 | 43.2 | 2.58 | 344 | 0.08 | SEQ ID NO: 3 |
| D-Phe-c(Cys-His-D-Phe-Arg-Trp-Gaba-D-Cys)-Thr-NH$_2$ | 0.420 | 106 | 4.75 | 1260 | 0.09 | SEQ ID NO: 3 |
| Ac-Nle-c(Cys-His-D-Phe-Arg-Trp-Apn-Cys)-NH$_2$ | 0.0951 | 9.33 | 0.894 | 13.4 | 0.11 | SEQ ID NO: 2 |
| Ac-Nle-c(Asp-His-D-Phe-Arg-Trp-Apn-Lys)-NH$_2$ | 0.999 | 300 | 11.1 | 431 | 0.09 | SEQ ID NO: 4 |
| Ac-Cha-c(Asp-His-D-Phe-Arg-Trp-Gaba-Lys)-NH$_2$ | 0.106 | 11.8 | 1.49 | 110 | 0.07 | SEQ ID NO: 6 |
| Ac-Nle-c(Asp-His-D-Phe-Arg-Trp-Gaba-Lys)-NH$_2$ | 0.0506 | 9.89 | 1.04 | 16.3 | 0.05 | SEQ ID NO: 6 |
| Ac-Chg-c(Asp-His-D-Phe-Arg-Trp-Gaba-Lys)-NH$_2$ | 0.884 | 223 | 22.5 | 609 | 0.04 | SEQ ID NO: 11 |
| Ac-hCha-c(Asp-His-D-Phe-Arg-Trp-Gaba-Lys)-NH$_2$ | 0.721 | 93.5 | 56.0 | 747 | 0.01 | SEQ ID NO: 11 |
| Ac-D-Chg-c(Asp-His-D-Phe-Arg-Trp-Gaba-Lys)-NH$_2$ | 0.227 | 14.5 | 2.99 | 164 | 0.08 | SEQ ID NO: 11 |
| Ac-hPhe-c(Asp-His-D-Phe-Arg-Trp-Gaba-Lys)-NH$_2$ | 0.277 | 25.2 | 3.37 | 203 | 0.08 | SEQ ID NO: 11 |
| Ac-Nle-c(Cys-His-D-Phe-Arg-D-Trp-β-Ala-Cys)-NH$_2$ | 0.323 | 14.1 | 1.96 | 24.0 | 0.16 | SEQ ID NO: 15 |
| Ac-Nle-c(Pen-D-Ala-His-D-Phe-Arg-Trp-Cys)-NH$_2$ | 34.1 | 118 | 17.0 | 5560 | 2.01 | SEQ ID NO: 21 |
| Ac-Nle-c(Cys-D-Ala-His-D-Phe-Arg-Trp-Pen)-NH$_2$ | 29.1 | 22.8 | 3.84 | 2550 | 7.58 | SEQ ID NO: 22 |

TABLE 5-continued

Radioligand Binding Assay Data for Selected Compounds

| Compound | | | | | | |
|---|---|---|---|---|---|---|
| D-Phe-c(Cys-His-D-Phe-hArg-Trp-β-Ala-D-Cys)-Thr-NH₂ | 0.442 | 123 | 10.3 | 521 | 0.04 | SEQ ID NO: 23 |
| D-Phe-c(Cys-His-D-Phe-Arg-Bip-β-Ala-D-Cys)-Thr-NH₂ | 5.80 | 3370 | 583 | 1130 | 0.01 | SEQ ID NO: 25 |
| D-Phe-c(Cys-His-D-(Et)Tyr-hArg-Trp-β-Ala-D-Cys)-Thr-NH₂ | 0.0567 | 31.4 | 14.7 | 9.27 | 0 | SEQ ID NO: 24 |
| D-Phe-c(Cys-His-D-Phe-hArg-Bip-β-Ala-D-Cys)-Thr-NH₂ | 1.68 | 1260 | 172 | 1220 | 0.01 | SEQ ID NO: 26 |
| D-Phe-c(Cys-His-D-(Et)Tyr-hArg-Bip-β-Ala-D-Cys)-Thr-NH₂ | 0.128 | 85.6 | 36.9 | 38.0 | 0 | SEQ ID NO: 26 |
| Ac-Nle-c(Cys-D-Ala-His-D-Phe-Arg-Trp-Gly-Cys)-NH₂ | 0.352 | 149 | 3.01 | 339 | 0.12 | SEQ ID NO: 54 |
| Ac-Nle-c(Cys-D-Ala-His-D-Phe-Arg-Trp-D-Ala-Cys)-NH₂ | 3.93 | 876 | 48.0 | 4940 | 0.08 | SEQ ID NO: 54 |
| Ac-Nle-c(Cys-D-Ala-His-D-Phe-Arg-Trp-β-Ala-Cys)-NH₂ | 0.995 | 287 | 4.80 | 766 | 0.21 | SEQ ID NO: 54 |
| Ac-Nle-c(Cys-D-Ala-His-D-Phe-Arg-Trp-Gaba-Cys)-NH₂ | 0.848 | 184 | 3.76 | 956 | 0.23 | SEQ ID NO: 54 |
| Ac-Nle-c(Cys-D-Ala-His-D-Phe-Arg-Trp-Apn-Cys)-NH₂ | 1.10 | 228 | 7.58 | 859 | 0.15 | SEQ ID NO: 54 |
| Ac-Nle-c(Asp-D-Ala-His-D-Phe-Arg-Trp-Lys)-NH₂ | 0.659 | 98.9 | 2.55 | 4.19 | 0.26 | SEQ ID NO: 28 |
| Ac-Nle-c(Asp-D-Ala-His-D-Phe-Arg-Bal-Lys)-NH₂ | 4.12 | 445 | 50.6 | 4300 | 0.08 | SEQ ID NO: 28 |
| Ac-c(Cys-Glu-His-D-Phe-Arg-Trp-Ala-Cys)-NH₂ | 111 | 1710 | 47.7 | 694 | 2.33 | SEQ ID NO: 55 |
| Ac-c(Cys-Glu-His-D-Phe-Arg-2-Nal-Ala-Cys)-NH₂ | 262 | 2500 | 96.4 | 1460 | 2.72 | SEQ ID NO: 55 |
| Ac-c(Cys-D-Ala-His-D-Phe-Arg-Trp-Ala-Cys)-NH₂ | 199 | 5990 | 96.7 | >10000 | 2.06 | SEQ ID NO: 56 |
| Ac-c(Cys-D-Ala-His-D-Phe-Arg-2-Nal-Ala-Cys)-NH₂ | 132 | 4560 | 40.7 | 8810 | 3.24 | SEQ ID NO: 56 |
| Ac-Nle-c(Cys-D-Ala-His-D-Phe-Arg-Trp-Ala-Cys)-NH₂ | 9.12 | 1130 | 22.1 | 2860 | 0.41 | SEQ ID NO: 57 |
| Ac-Nle-c(Cys-D-Ala-His-D-Phe-Arg-Trp-β-Ala-Cys)-NH₂ | 1.00 | 227 | 5.55 | 496 | 0.18 | SEQ ID NO: 57 |
| Ac-Nle-c(Cys-D-Ala-His-D-Phe-Arg-Trp-Gaba-Cys)-NH₂ | 0.536 | 169 | 3.12 | 358 | 0.17 | SEQ ID NO: 57 |
| Ac-Nle-c(Cys-D-Ala-His-D-Phe-Arg-Trp-Pen)-OH | 32.1 | 330 | 17.4 | 165 | 1.84 | SEQ ID NO: 29 |
| Ac-Nle-c(Cys-D-Abu-His-D-Phe-Arg-Trp-Cys)-NH₂ | 10.6 | 41.1 | 7.69 | 54.9 | 1.38 | SEQ ID NO: 30 |
| Ac-Nle-c(Cys-D-Val-His-D-Phe-Arg-Trp-Cys)-NH₂ | 13.0 | 104 | 10.1 | 40 | 1.29 | SEQ ID NO: 30 |

TABLE 5-continued

Radioligand Binding Assay Data for Selected Compounds

| Compound | | | | | | |
|---|---|---|---|---|---|---|
| Ac-Nle-c(Cys-D-Ile-His-D-Phe-Arg-Trp-Cys)-NH$_2$ | 4.28 | 38.5 | 9.0 | 12.5 | 0.48 | SEQ ID NO: 30 |
| Ac-Nle-c(Cys-D-Leu-His-D-Phe-Arg-Trp-Cys)-NH$_2$ | 1.60 | 6.82 | 4.13 | 5.57 | 0.39 | SEQ ID NO: 30 |
| Ac-Nle-c(Cys-D-Tle-His-D-Phe-Arg-Trp-Cys)-NH$_2$ | 12.0 | 85.8 | 11.2 | 40 | 1.07 | SEQ ID NO: 30 |
| Ac-Nle-c(Cys-D-Cha-His-D-Phe-Arg-Trp-Cys)-NH$_2$ | 0.353 | 2.08 | 1.41 | 0.857 | 0.25 | SEQ ID NO: 30 |
| Ac-Nle-c(Pen-His-D-Phe-Arg-Trp-Gaba-Cys)-NH$_2$ | 0.537 | 86.1 | 5.89 | 2.56 | 0.09 | SEQ ID NO: 31 |
| Ac-Nle-c(Pen-His-D-Phe-Arg-Trp-Gaba-Pen)-NH$_2$ | 0.744 | 178 | 3.51 | 2.69 | 0.21 | SEQ ID NO: 32 |
| Ac-Leu-c(Cys-His-D-Phe-Arg-Trp-Gaba-Cys)-NH$_2$ | 0.216 | 17.4 | 0.995 | 0.486 | 0.22 | SEQ ID NO: 33 |
| Ac-Cha-c(Cys-His-D-Phe-Arg-Trp-Gaba-Cys)-NH$_2$ | 0.107 | 9.11 | 0.884 | 0.354 | 0.12 | SEQ ID NO: 33 |
| Ac-Ile-c(Cys-His-D-Phe-Arg-Trp-Gaba-Cys)-NH$_2$ | 0.148 | 13.9 | 1.06 | 0.423 | 0.14 | SEQ ID NO: 33 |
| Ac-Phe-c(Cys-His-D-Phe-Arg-Trp-Gaba-Cys)-NH$_2$ | 0.254 | 18.5 | 2.13 | 0.714 | 0.12 | SEQ ID NO: 33 |
| Ac-Val-c(Cys-His-D-Phe-Arg-Trp-Gaba-Cys)-NH$_2$ | 0.256 | 29.9 | 1.98 | 0.864 | 0.13 | SEQ ID NO: 33 |
| Ac-2-Nal-c(Cys-His-D-Phe-Arg-Trp-Gaba-Cys)-NH$_2$ | 0.560 | 39.2 | 2.94 | 2.73 | 0.19 | SEQ ID NO: 33 |
| Phe-c(Cys-His-D-Phe-Arg-Trp-Gaba-Cys)-NH$_2$ | 0.186 | 15.2 | 4.93 | 0.537 | 0.04 | SEQ ID NO: 34 |
| Ac-Nle-c(Cys-3-Pal-D-Phe-Arg-Trp-Gaba-Cys)-NH$_2$ | 21.1 | 151 | 10.4 | 92.6 | 2.03 | SEQ ID NO: 35 |
| Ac-Nle-c(Cys-D-Ala-His-D-Phe-Arg-Trp-Cys)-OH | 30.7 | 152 | 15.6 | 114 | 1.97 | SEQ ID NO: 36 |
| Ac-Nle-c(Cys-His-Phe-Arg-D-Trp-Gaba-Cys)-NH$_2$ | 5.20 | 150 | 138 | 20.3 | 0.04 | SEQ ID NO: 37 |
| Ac-Nle-c(Asp-D-Ala-His-D-Phe-Arg-Bal-Ala-Lys)-NH$_2$ | 4.89 | 290 | 21.3 | 11.1 | 0.23 | SEQ ID NO: 58 |
| Ac-Nle-c(Cys-D-Ala-His-D-2-Nal-Arg-Trp-Cys)-NH$_2$ | 25.5 | 3.82 | 7.61 | 102 | 3.35 | SEQ ID NO: 16 |
| Ac-Nle-c(Cys-D-Ala-His-D-2-Nal-Arg-2-Nal-Cys)-NH$_2$ | 32.5 | 5.85 | 2.53 | 94.6 | 12.85 | SEQ ID NO: 16 |
| Ac-Nle-c(Cys-D-Ala-His-D-2-Nal-Arg-Bal-Cys)-NH$_2$ | 22.2 | 12.7 | 16.6 | 125 | 1.34 | SEQ ID NO: 20 |
| Ac-Nle-c(Asp-His-D-2-Nal-Arg-Trp-Ala-Lys)-NH$_2$ | 1.17 | 1.56 | 0.277 | 3.24 | 4.22 | SEQ ID NO: 38 |
| Ac-Nle-c(Asp-His-D-2-Nal-Arg-Trp-β-Ala-Lys)-NH$_2$ | 0.648 | 2.78 | 0.329 | 1.4 | 1.97 | SEQ ID NO: 38 |
| Ac-Nle-c(Cys-His-D-2-Nal-Arg-Trp-Gaba-Cys)-NH$_2$ | 0.393 | 1.86 | 0.375 | 1.11 | 1.05 | SEQ ID NO: 39 |
| Ac-Nle-c(Cys-His-D-2-Nal-Arg-Trp-Ahx-Cys)-NH$_2$ | 0.333 | 2.91 | 0.998 | 0.366 | 0.33 | SEQ ID NO: 39 |

TABLE 5-continued

Radioligand Binding Assay Data for Selected Compounds

| Compound | | | | | | |
|---|---|---|---|---|---|---|
| Ac-hPhe-c(Asp-His-D-2-Nal-Arg-Trp-Gaba-Lys)-NH$_2$ | 0.461 | 2.45 | 0.931 | 1.37 | 0.50 | SEQ ID NO: 40 |
| Ac-Cha-c(Asp-His-D-2-Nal-Arg-Trp-Gaba-Lys)-NH$_2$ | 0.576 | 3.98 | 2.82 | 3.91 | 0.20 | SEQ ID NO: 40 |

Table 5C

| Compound | Ki hMC1-R | Ki hMC3-R | Ki hMC4-R | Ki hMC5-R | Ki hMC1-R/ MC4-R | SEQ ID NO: |
|---|---|---|---|---|---|---|
| Ac-Arg-c(Cys-D-Ala-His-D-2-Nal-Arg-Trp-Cys)-NH$_2$ | 17.9 | 1.68 | 0.256 | 23.4 | 69.9 | SEQ ID NO: 49 |

TABLE 6

Radioligand Binding Assay Data for Selected Compounds

Table 6A

| Compound | Ki hMC1-R | Ki hMC3-R | Ki hMC4-R | Ki hMC5-R |
|---|---|---|---|---|
| Ac-c(Cys-Glu-His-D-2-Nal-Arg-Trp-Ala-Cys)-Pro-Pro-Lys-Asp-NH$_2$ (SEQ ID NO: 269) | 49.9 | 9.00 | 0.569 | 218 |
| Tyr-Gly-Arg-Lys-Lys-Arg-Arg-Gln-Arg-Arg-Nle-c(Asp-His-D-2-Nal-Arg-Trp-Lys)-NH$_2$ (SEQ ID NO: 60) | 11.9 | 38.1 | 5.70 | 11.8 |
| Tyr-Gly-Arg-Lys-Lys-Arg-Arg-Gln-Arg-Arg-Doc-Nle-c(Asp-His-D-2-Nal-Arg-Trp-Lys)-NH$_2$ (SEQ ID NO: 61) | 3.46 | 16.6 | 6.65 | 4.88 |
| Nle-c(Asp-His-D-2-Nal-Arg-Trp-Lys)-β-Ala-Tyr-Gly-Arg-Lys-Lys-Arg-Arg-Gln-Arg-Arg-NH$_2$ (SEQ ID NO: 62) | 0.614 | 5.09 | 2.31 | 3.23 |
| Ac-Nle-c(Asp-His-D-2-Nal-Arg-Trp-Lys)-β-Ala-Tyr-Gly-Arg-Lys-Lys-Arg-Arg-Gln-Arg-Arg-NH$_2$ (SEQ ID NO: 62) | 1.56 | 14.1 | 5.17 | 7.12 |
| H-Nle-c(Asp-His-D-2-Nal-Arg-Trp-Lys)-Doc-Doc-Tyr-Gly-Arg-Lys-Lys-Arg-Arg-Gln-Arg-Arg-NH$_2$ (SEQ ID NO: 63) | 1.10 | 1.58 | 6.00 | 0.629 |
| Ac-Nle-c(Asp-His-D-2-Nal-Arg-Trp-Lys)-Pro-Pro-Lys-Asp-Tyr-Gly-Arg-Lys-Lys-Arg-Arg-Gln-Arg-Arg-Arg-NH$_2$ (SEQ ID NO: 64) | 0.0868 | 0.751 | 0.0944 | 0.147 |
| Ac-c(Cys-Glu-His-D-2-Nal-Arg-Trp-Gly-Cys)-Pro-Pro-Lys-Asp-Tyr-Gly-Arg-Lys-Lys-Arg-Arg-Gln-Arg-Arg-Arg-NH$_2$ (SEQ ID NO: 65) | 1.66 | 4.80 | 0.250 | 9.62 |
| Ac-Nle-c(Asp-His-D-2-Nal-Arg-Trp-Lys)-β-Ala-β-Ala-Tyr-Gly-Arg-Lys-Lys-Arg-Arg-Gln-Arg-Arg-Arg-NH$_2$ (SEQ ID NO: 66) | 0.0452 | 0.298 | 0.169 | 0.386 |
| Ac-Nle-c(Asp-His-D-2-Nal-Arg-Trp-Lys)-Pro-Pro-Lys-Asp-Doc-Tyr-Gly-Arg-Lys-Lys-Arg-Arg-Gln-Arg-Arg-Arg-NH$_2$ (SEQ ID NO: 67) | 0.0808 | 0.396 | 0.0747 | 0.311 |
| Ac-c(Cys-Glu-His-D-2-Nal-Arg-Trp-Gly-Cys)-Pro-Pro-Lys-Asp-Doc-Tyr-Gly-Arg-Lys-Lys-Arg-Arg-Gln-Arg-Arg-Arg-NH$_2$ (SEQ ID NO: 68) | 4.41 | 4.23 | 0.455 | 12.9 |
| Ac-c(Cys-Glu-His-D-2-Nal-Arg-Trp-Ala-Cys)-Pro-Pro-Lys-Asp-β-Ala-Tyr-Gly-Arg-Lys-Lys-Arg-Arg-Gln-Arg-Arg-Arg-NH$_2$ (SEQ ID NO: 71) | 1.25 | 0.661 | 0.292 | 5.94 |

TABLE 6-continued

Radioligand Binding Assay Data for Selected Compounds

| Compound | | | | |
|---|---|---|---|---|
| Ac-c(Cys-Glu-His-D-2-Nal-Arg-Trp-Ala-Cys)-Pro-Pro-Lys-Asp-Doc-Tyr-Gly-Arg-Lys-Lys-Arg-Gln-Arg-Arg-Arg-NH$_2$ (SEQ ID NO: 71) | 1.89 | 0.546 | 0.166 | 6.06 |
| Ac-c(Cys-Glu-His-D-2-Nal-Arg-2-Nal-Ala-Cys)-Pro-Pro-Lys-Asp-NH$_2$ (SEQ ID NO: 269) | 87.8 | 9.08 | 1.20 | 359 |
| Ac-c(Cys-Glu-His-D-2-Nal-Arg-1-Nal-Ala-Cys)-Pro-Pro-Lys-Asp-NH$_2$ (SEQ ID NO: 269) | 124 | 17.8 | 1.11 | 348 |
| Ac-c(Cys-Glu-His-D-2-Nal-Arg-Bal-Ala-Cys)-Pro-Pro-Lys-Asp-NH$_2$ (SEQ ID NO: 269) | 163 | 23.0 | 0.586 | 844 |
| Ac-Nle-c(Asp-His-D-2-Nal-Arg-Trp-Lys)-Doc-Doc-Tyr-Gly-Arg-Lys-Lys-Arg-Arg-Gln-Arg-Arg-Arg-NH$_2$ (SEQ ID NO: 701) | 0.144 | 0.352 | 0.0845 | 0.415 |
| Ac-c(Cys-Glu-His-D-2-Nal-Arg-2-Nal-Ala-Cys)-Pro-Pro-Lys-Asp-β-Ala-Tyr-Gly-Arg-Lys-Lys-Arg-Arg-Gln-Arg-Arg-Arg-NH$_2$ (SEQ ID NO: 71) | 1.74 | 0.590 | 0.170 | 4.38 |
| Ac-c(Cys-Glu-His-D-2-Nal-Arg-Bal-Ala-Cys)-Pro-Pro-Lys-Asp-β-Ala-Arg-Arg-Arg-Arg-Gln-Arg-Arg-Arg-NH$_2$ (SEQ ID NO: 83) | 3.86 | 4.97 | 0.192 | 38.3 |
| Ac-c(Cys-Glu-His-D-2-Nal-Arg-Bal-Ala-Cys)-Pro-Pro-Lys-Asp-β-Ala-Gly-Arg-Arg-Arg-Arg-Gln-Arg-Arg-Arg-NH$_2$ (SEQ ID NO: 73) | 12.8 | 15.9 | 0.950 | 165 |
| Ac-c(Cys-Glu-His-D-2-Nal-Arg-Bal-Ala-Cys)-Pro-Pro-Lys-Asp-β-Ala-Tyr-Gly-Arg-Arg-Arg-Arg-Gln-Arg-Arg-Arg-NH$_2$ (SEQ ID NO: 74) | 3.07 | 4.05 | 0.498 | 31.1 |
| Ac-c(Cys-Glu-His-D-2-Nal-Arg-Trp-Ala-Cys)-Pro-Pro-Lys-Asp-βAla-Tyr-Gly-Arg-Lys-Lys-Arg-Gln-Arg-Arg-Arg-NH$_2$ (SEQ ID NO: 75) | 0.792 | 0.570 | 0.162 | 4.18 |
| Ac-c(Cys-Glu-His-D-2-Nal-Arg-Trp-Ala-Cys)-Pro-Pro-Lys-Asp-β-Ala-Tyr-Gly-Arg-Lys-Lys-Gln-Arg-Arg-Arg-Arg-NH$_2$ (SEQ ID NO: 76) | 0.726 | 0.474 | 0.209 | 5.12 |
| Ac-c(Cys-Glu-His-D-2-Nal-Arg-Trp-Ala-Cys)-Pro-Pro-Lys-Asp-β-Ala-Tyr-Gly-Arg-Lys-Gln-Lys-Arg-Arg-Arg-Arg-NH$_2$ (SEQ ID NO: 77) | 0.857 | 0.580 | 0.209 | 4.42 |
| Ac-c(Cys-Glu-His-D-2-Nal-Arg-Trp-Ala-Cys)-Pro-Pro-Lys-Asp-β-Ala-Tyr-Gly-Arg-Lys-Lys-Arg-Arg-Arg-Gln-Arg-NH$_2$ (SEQ ID NO: 78) | 0.813 | 0.675 | 0.269 | 4.20 |
| Ac-c(Cys-Glu-His-D-2-Nal-Arg-Bal-Ala-Cys)-Pro-Pro-Lys-Asp-β-Ala-Tyr-Aib-Arg-Lys-Lys-Arg-Gln-Arg-Arg-Arg-NH$_2$ (SEQ ID NO: 79) | 7.84 | 10.2 | 0.783 | 91.8 |
| Ac-c(Cys-Glu-His-D-2-Nal-Arg-1-Nal-Ala-Cys)-Pro-Pro-Arg-Asp-β-Ala-Arg-Arg-Arg-Arg-Gln-Arg-Arg-Arg-NH$_2$ (SEQ ID NO: 80) | 2.93 | 9.07 | 0.293 | 59.0 |
| Ac-c(Cys-Glu-His-D-2-Nal-Arg-1-Nal-Ala-Cys)-Pro-Pro-Lys-Asp-β-Ala-Arg-Arg-Arg-Arg-Gln-Arg-Arg-Arg-NH$_2$ (SEQ ID NO: 80) | 2.42 | 6.56 | 0.238 | 41.7 |
| Ac-c(Cys-Glu-His-D-2-Nal-Arg-1-Nal-Ala-Cys)-Pro-Pro-Lys-Asp-β-Ala-Arg-Arg-Arg-Arg-Arg-Gln-Arg-Arg-Arg-NH$_2$ (SEQ ID NO: 81) | 6.66 | 19.3 | 0.819 | 88.8 |

TABLE 6-continued

Radioligand Binding Assay Data for Selected Compounds

| Compound | | | | |
|---|---|---|---|---|
| Ac-c(Cys-Glu-His-D-2-Nal-Arg-2-Nal-Ala-Cys)-Pro-Pro-Arg-Asp-β-Ala-Arg-Arg-Arg-Arg-Arg-Gln-Arg-Arg-Arg-NH$_2$ (SEQ ID NO: 82) | 2.63 | 2.09 | 0.0737 | 11.6 |
| Ac-c(Cys-Glu-His-D-2-Nal-Arg-2-Nal-Ala-Cys)-Pro-Pro-Lys-Asp-β-Ala-Arg-Arg-Arg-Arg-Arg-Gln-Arg-Arg-Arg-NH$_2$ (SEQ ID NO: 82) | 2.48 | 1.21 | 0.209 | 9.17 |
| Ac-c(Cys-Glu-His-D-2-Nal-Arg-2-Nal-Ala-Cys)-Pro-Pro-Lys-Asp-β-Ala-Arg-Arg-Arg-Arg-Arg-Gln-Arg-Arg-Arg-NH$_2$ (SEQ ID NO: 81) | 3.65 | 2.26 | 0.261 | 12.1 |
| Ac-c(Cys-Glu-His-D-2-Nal-Arg-Bal-Ala-Cys)-Pro-Pro-Arg-Asp-β-Ala-Arg-Arg-Arg-Arg-Arg-Gln-Arg-Arg-Arg-NH$_2$ (SEQ ID NO: 83) | 7.32 | 11.0 | 0.659 | 78.0 |
| Ac-c(Cys-Glu-His-D-2-Nal-Arg-Bal-Ala-Cys)-Pro-Pro-Arg-Asp-β-Ala-Arg-Arg-Arg-Arg-Gln-Arg-Arg-Arg-NH$_2$ (SEQ ID NO: 84) | 4.11 | 7.26 | 0.302 | 48.3 |
| Ac-c(Cys-Glu-His-D-2-Nal-Arg-Bal-Ala-Cys)-Pro-Pro-Lys-Asp-β-Ala-Arg-Arg-Arg-Arg-Arg-Gln-Arg-Arg-Arg-NH$_2$ (SEQ ID NO: 283) | 6.77 | 14.3 | 0.781 | 84.0 |
| Ac-c(Cys-Glu-His-D-2-Nal-Arg-Trp-Ala-Cys)-Pro-Pro-Lys-Asp-β-Ala-Tyr-Gly-Arg-Lys-Lys-Arg-Arg-Arg-Arg-Gln-Arg-Arg-NH$_2$ (SEQ ID NO: 2685) | 3.04 | 3.22 | 0.230 | 3.85 |
| Ac-c(Cys-Glu-His-D-2-Nal-Arg-Trp-Ala-Cys)-Pro-Pro-Lys-Asp-β-Ala-Tyr-Gly-Arg-Gln-Lys-Lys-Arg-Arg-Arg-Arg-NH$_2$ (SEQ ID NO: 86) | 3.24 | 2.66 | 0.208 | 5.96 |
| Ac-c(Cys-Glu-His-D-2-Nal-Arg-Trp-Ala-Cys)-Pro-Pro-Lys-Asp-β-Ala-Tyr-Gly-Arg-Lys-Lys-Arg-Arg-Arg-Arg-Gln-NH$_2$ (SEQ ID NO: 87) | 1.58 | 1.43 | 0.275 | 2.97 |
| Ac-c(Cys-Glu-His-D-2-Nal-Arg-1-Nal-Ala-Cys)-Pro-Pro-Lys-Asp-β-Ala-Tyr-Gly-Arg-Lys-Lys-Arg-Arg-Gln-Arg-Arg-NH$_2$ (SEQ ID NO: 71) | 4.59 | 6.28 | 0.588 | 22.6 |
| Ac-c(Cys-Glu-His-D-2-Nal-Arg-Bal-Ala-Cys)-Pro-Pro-Lys-Asp-β-Ala-Tyr-Gly-Arg-Lys-Lys-Arg-Arg-Gln-Arg-Arg-NH$_2$ (SEQ ID NO: 71) | 6.46 | 5.22 | 0.380 | 15.3 |
| Ac-c(Cys-Glu-His-D-2-Nal-Arg-1-Nal-Ala-Cys)-Pro-Pro-Lys-Asp-β-Ala-Arg-Arg-Lys-Arg-Arg-Gln-Arg-Arg-Arg-NH$_2$ (SEQ ID NO: 88) | 4.62 | 5.68 | 0.505 | 45.3 |
| Ac-c(Cys-Glu-His-D-2-Nal-Arg-1-Nal-Ala-Cys)-Pro-Pro-Lys-Asp-β-Ala-Arg-Lys-Arg-Arg-Arg-Gln-Arg-Arg-Arg-NH$_2$ (SEQ ID NO: 89) | 2.12 | 3.99 | 0.352 | 27.5 |
| Ac-c(Cys-Glu-His-D-2-Nal-Arg-2-Nal-Ala-Cys)-Pro-Pro-Lys-Asp-β-Ala-Arg-Arg-Lys-Arg-Arg-Gln-Arg-Arg-Arg-NH$_2$ (SEQ ID NO: 88) | 3.41 | 0.975 | 0.549 | 11.3 |
| Ac-c(Cys-Glu-His-D-2-Nal-Arg-2-Nal-Ala-Cys)-Pro-Pro-Lys-Asp-β-Ala-Tyr-Gly-Arg-Arg-Lys-Arg-Arg-Gln-Arg-Arg-NH$_2$ (SEQ ID NO: 90) | 4.18 | 1.12 | 0.223 | 15.3 |
| Ac-c(Cys-Glu-His-D-2-Nal-Arg-2-Nal-Ala-Cys)-Pro-Pro-Lys-Asp-β-Ala-Gly-Arg-Arg-Lys-Arg-Arg-Gln-Arg-Arg-NH$_2$ (SEQ ID NO: 91) | 2.71 | 0.732 | 0.202 | 5.53 |

TABLE 6-continued

Radioligand Binding Assay Data for Selected Compounds

| Compound | | | | |
|---|---|---|---|---|
| Ac-c(Cys-Glu-His-D-2-Nal-Arg-2-Nal-Ala-Cys)-Pro-Pro-Lys-Asp-β-Ala-Gly-Arg-Lys-Arg-Arg-Arg-Gln-Arg-Arg-Arg-NH$_2$ (SEQ ID NO: 92) | 5.66 | 1.40 | 0.446 | 6.23 |
| Ac-Nle-c(Cys-D-Ala-His-D-Phe-Arg-Trp-Cys)-(Doc)2-Tyr-Gly-Arg-Lys-Lys-Arg-Arg-Gln-Arg-Arg-Arg-NH$_2$ (SEQ ID NO: 136) | 0.211 | 0.665 | 0.635 | 118 |
| Ac-Nle-c(Cys-D-Ala-His-D-Phe-Arg-Trp-Cys)-β-Ala-Tyr-Gly-Arg-Lys-Lys-Arg-Gln-Arg-Arg-Arg-NH$_2$ (SEQ ID NO: 137) | 0.351 | 0.891 | 0.503 | 102 |
| Ac-Nle-c(Cys-D-Ala-His-D-Phe-Arg-Trp-Cys)-Doc-Tyr-Gly-Arg-Lys-Lys-Arg-Arg-Gln-Arg-Arg-Arg-NH$_2$ (SEQ ID NO: 136) | 0.209 | 0.699 | 0.596 | 137 |
| Ac-Nle-c(Cys-D-Ala-His-D-Phe-Arg-Trp-Cys)-β-Ala-Gly-Arg-Arg-Arg-Arg-Gln-Arg-Arg-Arg-NH$_2$ (SEQ ID NO: 138) | 0.439 | 1.52 | 0.476 | 115 |
| Ac-Nle-c(Cys-D-Ala-His-D-Phe-Arg-Trp-Cys)-β-Ala-Arg-Arg-Arg-Arg-Arg-Gln-Arg-Arg-NH$_2$ (SEQ ID NO: 138) | 0.821 | 2.50 | 0.700 | 148 |
| Ac-Nle-c(Cys-D-Ala-His-D-Phe-Arg-Trp-Cys)-β-Ala-Tyr-Gly-Arg-Arg-Arg-Arg-Arg-Gln-Arg-Arg-NH$_2$ (SEQ ID NO: 139) | 0.406 | 1.11 | 0.602 | 131 |
| Ac-Nle-c(Cys-D-Ala-His-D-Phe-Arg-Trp-Cys)-β-Ala-Gly-Arg-Arg-Arg-Arg-Arg-Gln-Arg-Arg-Arg-NH$_2$ (SEQ ID NO: 139) | 1.27 | 4.63 | 1.51 | 220 |

Table 6B

| Compound | Ki hMC1-R | Ki hMC3-R | Ki hMC4-R | Ki hMC5-R |
|---|---|---|---|---|
| Ac-c(Cys-Glu-His-D-2-Nal-Arg-2-Nal-β-Ala-Cys)-Pro-Pro-Lys-Asp-NH$_2$ (SEQ ID NO: 270) | 2058 | 113 | 10.7 | 239 |
| Ac-c(Cys-Glu-His-D-2-Nal-Arg-2-Nal-Aib-Cys)-Pro-Pro-Lys-Asp-NH$_2$ (SEQ ID NO: 270) | 1818 | 306 | 5.87 | 979 |
| Ac-c(Cys-Glu-His-D-2-Nal-Arg-1-Nal-Ala-Cys)-Pro-Pro-Lys-Asp-β-Ala-Tyr-Gly-Arg-Arg-Lys-Arg-Arg-Gln-Arg-Arg-Arg-NH$_2$ (SEQ ID NO: 95) | 1.75 | 1.74 | 0.15 | 16.8 |
| Ac-c(Cys-Glu-His-D-2-Nal-Arg-1-Nal-Ala-Cys)-Pro-Pro-Lys-Asp-β-Ala-Tyr-Gly-Arg-Lys-Arg-Arg-Gln-Arg-Arg-Arg-NH$_2$ (SEQ ID NO: 96) | 1.50 | 1.61 | 0.301 | 10.4 |
| Ac-c(Cys-Glu-His-D-2-Nal-Arg-1-Nal-Ala-Cys)-Pro-Pro-Lys-Asp-β-Ala-Gly-Arg-Arg-Lys-Arg-Arg-Gln-Arg-Arg-Arg-NH$_2$ (SEQ ID NO: 97) | 1.81 | 2.08 | 0.305 | 19.3 |
| Ac-c(Cys-Glu-His-D-2-Nal-Arg-1-Nal-Ala-Cys)-Pro-Pro-Lys-Asp-β-Ala-Gly-Arg-Lys-Arg-Arg-Gln-Arg-Arg-Arg-NH$_2$ (SEQ ID NO: 92) | 2.69 | 2.59 | 0.243 | 19.2 |
| Ac-c(Cys-Glu-His-D-2-Nal-Arg-2-Nal-Ala-Cys)-Pro-Pro-Lys-Asp-β-Ala-Arg-Lys-Arg-Arg-Gln-Arg-Arg-Arg-NH$_2$ (SEQ ID NO: 99) | 2.25 | 0.62 | 0.303 | 2.77 |
| Ac-c(Cys-Glu-His-D-2-Nal-Arg-2-Nal-Ala-Cys)-Pro-Pro-Lys-Asp-β-Ala-Tyr-Gly-Arg-Lys-Arg-Arg-Gln-Arg-Arg-Arg-NH$_2$ (SEQ ID NO: 101) | 1.49 | 0.604 | 0.865 | 3.13 |
| Ac-c(Cys-Glu-His-D-2-Nal-Arg-Bal-Ala-Cys)-Pro-Pro-Lys-Asp-β-Ala-Arg-Lys-Arg-Arg-Gln-Arg-Arg-Arg-NH$_2$ (SEQ ID NO: 105) | 3.28 | 1.95 | 0.575 | 15.5 |

TABLE 6-continued

Radioligand Binding Assay Data for Selected Compounds

| | | | | |
|---|---|---|---|---|
| Ac-c(Cys-Glu-His-D-2-Nal-Arg-Bal-Ala-Cys)-Pro-Pro-Lys-Asp-β-Ala-Tyr-Gly-Arg-Arg-Lys-Arg-Arg-Gln-Arg-Arg-Arg-NH₂ (SEQ ID NO: 100) | 2.24 | 1.57 | 0.437 | 16.4 |
| Ac-c(Cys-Glu-His-D-2-Nal-Arg-Bal-Ala-Cys)-Pro-Pro-Lys-Asp-β-Ala-Tyr-Gly-Arg-Lys-Arg-Arg-Arg-Gln-Arg-Arg-Arg-NH₂ (SEQ ID NO: 101) | 2.14 | 1.12 | 0.624 | 11.9 |
| Ac-c(Cys-Glu-His-D-2-Nal-Arg-Bal-Ala-Cys)-Pro-Pro-Lys-Asp-β-Ala-Gly-Arg-Arg-Lys-Arg-Arg-Gln-Arg-Arg-Arg-NH₂ (SEQ ID NO: 102) | 2.50 | 1.59 | 0.573 | 15.7 |
| Ac-c(Cys-Glu-His-D-2-Nal-Arg-Bal-Ala-Cys)-Pro-Pro-Lys-Asp-β-Ala-Arg-Arg-Lys-Arg-Arg-Gln-Arg-Arg-Arg-NH₂ (SEQ ID NO: 104) | 3.00 | 1.70 | 0.442 | 15.5 |
| Ac-c(Cys-Glu-His-D-2-Nal-Arg-Bal-Ala-Cys)-Pro-Pro-Lys-Asp-β-Ala-Gly-Arg-Lys-Arg-Arg-Gln-Arg-Arg-Arg-NH₂ (SEQ ID NO: 103) | 4.29 | 2.15 | 0.425 | 15.5 |
| Ac-Nle-c(Cys-D-Ala-His-D-Phe-Arg-Trp-Cys)-β-Ala-Tyr-Gly-Arg-Arg-Lys-Arg-Arg-Gln-Arg-Arg-Arg-NH₂ (SEQ ID NO: 141) | 0.410 | 0.837 | 0.246 | 56.3 |
| Ac-Nle-c(Cys-D-Ala-His-D-Phe-Arg-Trp-Cys)-β-Ala-Tyr-Gly-Arg-Lys-Arg-Arg-Arg-Gln-Arg-Arg-Arg-NH₂ (SEQ ID NO: 142) | 0.572 | 1.07 | 0.210 | 63.6 |
| Ac-Nle-c(Cys-D-Ala-His-D-Phe-Arg-Trp-Cys)-β-Ala-Gly-Arg-Arg-Lys-Arg-Arg-Gln-Arg-Arg-Arg-NH₂ (SEQ ID NO: 141) | 0.475 | 0.800 | 0.196 | 53.8 |
| Ac-Nle-c(Cys-D-Ala-His-D-Phe-Arg-Trp-Cys)-β-Ala-Gly-Arg-Lys-Arg-Arg-Arg-Gln-Arg-Arg-Arg-NH₂ (SEQ ID NO: 142) | 0.779 | 1.21 | 0.293 | 56.0 |
| Ac-Nle-c(Cys-D-Ala-His-D-Phe-Arg-Trp-Cys)-β-Ala-Arg-Arg-Lys-Arg-Arg-Gln-Arg-Arg-Arg-NH₂ (SEQ ID NO: 143) | 0.212 | 1.23 | 0.484 | 58.5 |
| Ac-Nle-c(Cys-D-Ala-His-D-Phe-Arg-Trp-Cys)-β-Ala-Arg-Lys-Arg-Arg-Arg-Gln-Arg-Arg-Arg-NH₂ (SEQ ID NO: 144) | 0.778 | 1.22 | 0.468 | 47.0 |

TABLE 7

Binding Constants for Formula (V) Examples
Table 7A

| Formula (V) Compounds | Ki hMC1 | Ki hMC3 | Ki hMC4 | Ki hMC5 |
|---|---|---|---|---|
| c[Hydantoin(C(O)-(Cys-D-Ala))-His-D-Phe-Arg-Trp-Cys]-NH₂ (SEQ ID NO: 271) | 230 | 7590 | 126 | 7020 |
| c[Hydantoin(C(O)-(Glu-D-Ala))-His-D-Phe-Arg-Trp-Lys]-NH₂ (SEQ ID NO: 276) | 72.6 | 1920 | 45.2 | >10000 |
| c[Hydantoin(C(O)-(Glu-D-Ala))-His-D-Phe-Arg-Trp-Orn]-NH₂ (SEQ ID NO: 276) | 60.4 | 2840 | 52.4 | >10000 |
| c[Hydantoin(C(O)-(Glu-D-Ala))-His-D-Phe-Arg-Trp-Dab]-NH₂ (SEQ ID NO: 276) | 28 | 90.5 | 12.7 | 877 |
| c[Hydantoin(C(O)-(Glu-D-Ala))-His-D-Phe-Arg-Trp-Dap]-NH₂ (SEQ ID NO: 276) | 16.4 | 863 | 4.97 | >10000 |
| c[Hydantoin(C(O)-(Asp-D-Ala))-His-D-Phe-Arg-Trp-Orn]-NH₂ (SEQ ID NO: 273) | 37.7 | 576 | 7.81 | 6400 |

TABLE 7-continued

| | | | | |
|---|---|---|---|---|
| c[Hydantoin(C(O)-(Asp-D-Ala))-His-D-Phe-Arg-Trp-Dap]-NH$_2$ (SEQ ID NO: 273) | 66.6 | 1820 | 19.9 | >10000 |
| c[Hydantoin(C(O)-(Asp-His))-D-2-Nal-Arg-Trp-Lys]-NH$_2$ (SEQ ID NO: 275) | 200 | 68.8 | 6.63 | 142 |
| c[Hydantoin(C(O)-(Asp-Aic))-D-2-Nal-Arg-Trp-Lys]-NH$_2$ (SEQ ID NO: 275) | 9028 | 2628 | 35.8 | 1156 |
| c[Hydantoin(C(O)-(Asp-A5c))-D-2-Nal-Arg-Trp-Lys]-NH$_2$ (SEQ ID NO: 275) | 9938 | 2390 | 44.6 | 1103 |
| c[Hydantoin(C(O)-(Asp-A6c))-D-2-Nal-Arg-Trp-Lys]-NH$_2$ (SEQ ID NO: 275) | 2170 | 1479 | 16.5 | 451 |
| c[Hydantoin(C(O)-(Asp-Apc))-D-2-Nal-Arg-Trp-Lys]-NH$_2$ (SEQ ID NO: 275) | 1276 | 2756 | 266 | 1096 |
| c[Hydantoin(C(O)-(Asp-A3c))-D-2-Nal-Arg-Trp-Lys]-NH$_2$ (SEQ ID NO: 275) | 7567 | 1922 | 420 | 2879 |

TABLE 7B - Binding Constants for Formula (VI) Examples

| Formula (VI) Compounds | Ki hMC1 | Ki hMC3 | Ki hMC4 | Ki hMC5 |
|---|---|---|---|---|
| Hydantoin(C(O)-(Nle-Gly))-c(Cys-Glu-His-D-Phe-Arg-Trp-Cys)-NH$_2$ (SEQ ID NO: 278) | 14.3 | 198 | 5.76 | 67.8 |
| Hydantoin(C(O)-(Gly-Gly))-c(Cys-Glu-His-D-Phe-Arg-Trp-Cys)-NH$_2$ (SEQ ID NO: 278) | 11.9 | 311 | 5.41 | 73.9 |
| Hydantoin(C(O)-(A6c-Nle))-c(Cys-D-Ala-His-D-Phe-Arg-Trp-Cys)-NH$_2$ (SEQ ID NO: 284) | 31.6 | 224 | 19.6 | 2500 |
| Hydantoin(C(O)-(D-Ala-Nle))-c(Cys-D-Ala-His-D-Phe-Arg-Trp-Cys)-NH$_2$ (SEQ ID NO: 284) | 16.0 | 63.9 | 8.64 | 1820 |
| Hydantoin(C(O)-(Val-Nle))-c(Cys-D-Ala-His-D-Phe-Arg-Trp-Cys)-NH$_2$ (SEQ ID NO: 284) | 33.7 | 132 | 40.2 | 3210 |
| Hydantoin(C(O)-(Leu-Nle))-c(Cys-D-Ala-His-D-Phe-Arg-Trp-Cys)-NH$_2$ (SEQ ID NO: 284) | 48.3 | 534 | 74.1 | 3290 |
| Hydantoin(C(O)-(Cha-Nle))-c(Cys-D-Ala-His-D-Phe-Arg-Trp-Cys)-NH$_2$ (SEQ ID NO: 284) | 40.8 | 870 | 137 | 3560 |
| Hydantoin(C(O)-(Aib-Nle))-c(Cys-D-Ala-His-D-Phe-Arg-Trp-Cys)-NH$_2$ (SEQ ID NO: 284) | 17.7 | 73.6 | 8.40 | 2120 |
| Hydantoin(C(O)-(Nle-Gly))-c(Cys-D-Ala-His-D-Phe-Arg-Trp-Cys)-NH$_2$ (SEQ ID NO: 279) | 7.92 | 46.4 | 6.70 | 21.3 |
| Hydantoin(C(O)-(Gly-Gly))-c(Cys-D-Ala-His-D-Phe-Arg-Trp-Cys)-NH$_2$ (SEQ ID NO: 279) | 20.9 | 69.7 | 8.32 | 50.0 |
| Hydantoin(C(O)-(Nle-Gly))-c(Cys-D-Ala-His-D-Phe-Arg-Trp-Pen)-NH$_2$ (SEQ ID NO: 280) | 12.9 | 38.5 | 3.53 | 27.1 |
| Hydantoin(C(O)-(Gly-Gly))-c(Cys-D-Ala-His-D-Phe-Arg-Trp-Pen)-NH$_2$ (SEQ ID NO: 280) | 127 | 811 | 10.4 | 381 |
| Hydantoin(C(O)-(Ala-Gly))-c(Cys-D-Ala-His-D-Phe-Arg-Trp-Cys)-NH$_2$ (SEQ ID NO: 279) | 13.9 | 38.4 | 5.73 | 18.9 |
| Hydantoin(C(O)-(D-Ala-Gly))-c(Cys-D-Ala-His-D-Phe-Arg-Trp-Cys)-NH$_2$ (SEQ ID NO: 279) | 11.7 | 73.1 | 4.28 | 34.7 |
| Hydantoin(C(O)-(Aib-Gly))-c(Cys-D-Ala-His-D-Phe-Arg-Trp-Cys)-NH$_2$ (SEQ ID NO: 279) | 36.8 | 290 | 13.7 | 133 |
| Hydantoin(C(O)-(Val-Gly))-c(Cys-D-Ala-His-D-Phe-Arg-Trp-Cys)-NH$_2$ (SEQ ID NO: 279) | 15.3 | 160 | 8.66 | 33.4 |
| Hydantoin(C(O)-(Ile-Gly))-c(Cys-D-Ala-His-D-Phe-Arg-Trp-Cys)-NH$_2$ (SEQ ID NO: 279) | 11.6 | 194 | 11.5 | 28.9 |

TABLE 7-continued

| | | | | |
|---|---|---|---|---|
| Hydantoin(C(O)-(Leu-Gly))-c(Cys-D-Ala-His-D-Phe-Arg-Trp-Cys)-NH₂ (SEQ ID NO: 279) | 19.3 | 331 | 26.7 | 44.6 |
| Hydantoin(C(O)-(D-Arg-Gly))-c(Cys-Glu-His-D-Phe-Arg-Trp-Cys)-NH₂ (SEQ ID NO: 278) | 9.49 | 124 | 2.95 | 2260 |
| Hydantoin(C(O)-(Gly-D-Arg))-c(Cys-Glu-His-D-Phe-Arg-Trp-Cys)-NH₂ (SEQ ID NO: 287) | 4.30 | 78.0 | 1.77 | 4540 |
| Hydantoin(C(O)-(Arg-Gly))-c(Cys-Glu-His-D-Phe-Arg-Trp-Cys)-NH₂ (SEQ ID NO: 278) | 8.59 | 94.1 | 2.44 | 7760 |
| Hydantoin(C(O)-(Gly-Arg))-c(Cys-Glu-His-D-Phe-Arg-Trp-Cys)-NH₂ (SEQ ID NO: 285) | 5.68 | 55.5 | 2.44 | 4220 |
| Hydantoin(C(O)-(Arg-Gly))-c(Cys-D-Ala-His-D-Phe-Arg-Trp-Cys)-NH₂ (SEQ ID NO: 279) | 2.65 | 41.3 | 4.17 | 650 |
| Hydantoin(C(O)-(D-Arg-Gly))-c(Cys-D-Ala-His-D-Phe-Arg-Trp-Cys)-NH₂ (SEQ ID NO: 279) | 3.52 | 48.7 | 5.78 | 872 |
| Hydantoin(C(O)-(Gly-D-Arg))-c(Cys-D-Ala-His-D-Phe-Arg-Trp-Cys)-NH₂ (SEQ ID NO288) | 3.51 | 29.2 | 6.04 | 914 |
| Hydantoin(C(O)-(Gly-Arg))-c(Cys-D-Ala-His-D-Phe-Arg-Trp-Cys)-NH₂ (SEQ ID NO: 286) | 1.14 | 01.7 | 4.53 | 783 |
| Hydantoin(C(O)-(Arg-Gly))-c(Cys-D-Ala-His-D-2-Nal-Arg-Trp-Cys)-NH₂ (SEQ ID NO: 282) | 11.9 | 7.43 | 0.195 | 14.6 |

TABLE 7C -
Binding Constants for Formula (VII) Examples

| Formula (VII) Compounds | Ki hMC1 | Ki hMC3 | Ki hMC4 | Ki hMC5 |
|---|---|---|---|---|
| c[Hydantoin(C(O)-(Aib-Cys))-D-Ala-His-D-Phe-Arg-Trp-Cys]-NH₂ (SEQ ID NO: 290) | 47.6 | 1100 | 47.1 | >10000 |
| c[Hydantoin(C(O)-(Val-Cys))-D-Ala-His-D-Phe-Arg-Trp-Cys]-NH₂ (SEQ ID NO: 290) | 21.2 | 730 | 34.5 | >10000 |
| c[Hydantoin(C(O)-(Leu-Cys))-D-Ala-His-D-Phe-Arg-Trp-Cys]-NH₂ (SEQ ID NO: 290) | 47.4 | 1550 | 27.9 | >10000 |
| c[Hydantoin(C(O)-(Ile-Cys))-D-Ala-His-D-Phe-Arg-Trp-Cys]-NH₂ (SEQ ID NO: 290) | 53.4 | 1760 | 41.6 | >10000 |
| c[Hydantoin(C(O)-(A6c-Cys))-D-Ala-His-D-Phe-Arg-Trp-Cys]-NH₂ (SEQ ID NO: 290) | 38.5 | 1760 | 53.2 | 9270 |
| c[Hydantoin(C(O)-(Gly-Cys))-Glu-His-D-Phe-Arg-Trp-Cys]-NH₂ (SEQ ID NO: 291) | 15.6 | 305 | 8.92 | 3070 |

TABLE 8

Radioligand Binding Assay Data for Selected Compounds

| Compound | Ki hMC1-R | Ki hMC3-R | Ki hMC4-R | Ki hMC5-R |
|---|---|---|---|---|
| Ac-Tyr-Arg-c(Cys-D-Ala-His-D-Phe-Arg-Trp-Cys)-NH₂ (SEQ ID NO: 292) | 8.53 | 21.2 | 3.72 | 714 |
| Ac-2-Nal-Arg-c(Cys-D-Ala-His-D-Phe-Arg-Trp-Cys)-NH₂ (SEQ ID NO: 292) | 6.09 | 34.9 | 2.02 | 864 |
| Ac-1-Nal-Arg-c(Cys-D-Ala-His-D-Phe-Arg-Trp-Cys)-NH₂ (SEQ ID NO: 292) | 6.27 | 36.4 | 1.53 | 888 |
| Ac-Phe-Arg-c(Cys-D-Ala-His-D-Phe-Arg-Trp-Cys)-NH₂ (SEQ ID NO: 292) | 1.48 | 14.8 | 2.34 | 491 |
| Ac-Trp-Arg-c(Cys-D-Ala-His-D-Phe-Arg-Trp-Cys)-NH₂ (SEQ ID NO: 292) | 4.7 | 42 | 2.25 | 1470 |

TABLE 8-continued

Radioligand Binding Assay Data for Selected Compounds

| Compound | Ki hMC1-R | Ki hMC3-R | Ki hMC4-R | Ki hMC5-R |
|---|---|---|---|---|
| Ac-Pff-Arg-c(Cys-D-Ala-His-D-Phe-Arg-Trp-Cys)-NH$_2$ (SEQ ID NO: 292) | 0.323 | 1.33 | 1.95 | 786 |

Melanocortin Functional Activity and Selectivity

The compounds of the present invention will interact preferentially (i.e., selectively) to MC-4 relative to the other melanocortin receptors. Selectivity is particularly important when the compounds are administered to humans or other animals to minimize the number of side effects associated with their administration. MC-4 selectivity of a compound is defined herein as the ratio of the EC$_{50}$ of the compound for an MC-1 receptor (EC$_{50}$-MC-1) over the EC$_{50}$ of the compound for the MC-3 (EC$_{50}$-MC-3)/MC-4 (EC$_{50}$-MC-4) receptor, the EC$_{50}$ values being measured as described above. The formulas are as follows:

MC-3 selectivity=[EC$_{50}$-MC-1]/[EC$_{50}$-MC-3]

MC-4 selectivity=[EC$_{50}$-MC-1]/[EC$_{50}$-MC-4]

A compound is defined herein as being "selective for the MC-3 receptor" when the above mentioned ratio "MC-3-selectivity" is at least about 10, preferably at least about 100, and more preferably at least about 500.

A compound is defined herein as being "selective for the MC-4 receptor" when the above mentioned ratio "MC-4-selectivity" is at least about 10, preferably at least about 100, and more preferably at least about 500.

One skilled in the art would know that procedures similar to those described herein may be used to assay the binding activities of the compounds of the invention to melanocortin receptor molecules.

Cyclic AMP Bioassay

Intracellular cyclic AMP (cAMP) levels were determined by an electrochemiluminescence (ECL) assay (Meso Scale Discovery®, Gaithersburg, Md.; referred to hereinafter as MSD). CHO-K1 cells stably expressing the hMC receptor subtypes were suspended in RMPI 1640 ® assay buffer (RMPI 1640 buffer contains 0.5 mM isobutylmethylxanthine (IBMX), and 0.2% protein cocktail (MSD blocker A)). Transgenic CHO-K1 cells stably expressing hMC receptor subtypes 1, 3, 4 or 5 were dispensed at a density of approximately 7,000 cells/well in 384-well Multi-Array® plates (MSD) containing integrated carbon electrodes and coated with anti-cAMP antibody. Increasing concentrations of the test compounds were added and the cells were incubated for approximately 40 minutes at approximately 37° C. Following this incubation, lysis buffer (HEPES-buffered saline solution with MgCl$_2$ and Triton X-100® at ph 7.3) containing 0.2% protein cocktail and 2.5 nM TAG™ ruthenium-labeled cAMP (MSD) was added and the cells were incubated for approximately 90 minutes at room temperature. At the end of the second incubation period read buffer (Tris-buffered solution containing an ECL co-reactant and Triton X-100 at ph 7.8) was added and the cAMP levels in the cell lysates were immediately determined by ECL detection with a Sector Imager 6000 Reader® (MSD). Data were analyzed using a computer-assisted non-linear regression analysis (XL fit; IDBS) and reported as either an EC$_{50}$ value or a Kb value.

EC$_{50}$ represents the concentration of an agonist compound needed to obtain 50% of the maximum reaction response, e.g., 50% of the maximum level of cAMP as determined using the assay described above. The Kb value reflects the potency of an antagonist and is determined by Schild analysis. In brief, concentration-response curves of an agonist are carried out in the presence of increasing concentrations of an antagonist. The Kb value is the concentration of antagonist which would produce a 2-fold shift in the concentration-response curve for an agonist. It is calculated by extrapolating the line on a Schild plot to zero on the y-axis.

A selection of compounds was tested using the above-discussed assays and the results are reported in Tables 9, 10, 11, and 12.

TABLE 9 cAMP Bioassay Data for Selected Compounds

Table 9A

| Compound | EC$_{50}$ hMC1-R | EC$_{50}$ hMC3-R | EC$_{50}$ hMC4-R | EC$_{50}$ hMC5-R | EC$_{50}$ hMC1-R/ MC4-R | SEQ ID NO: |
|---|---|---|---|---|---|---|
| Ac-Arg-c(Cys-D-Ala-His-D-Phe-Arg-Trp-Cys)-NH$_2$ | 5.79 | 5.25 | 0.313 | 1630 | 18.0 | SEQ ID NO: 50 |
| Ac-D-Arg-c(Cys-D-Ala-His-D-Phe-Arg-Trp-Cys)-NH$_2$ | 6.17 | 5.6 | 0.397 | 1020 | 16.0 | SEQ ID NO: 50 |
| Ac-D-Arg-c(Cys-D-Ala-His-D-Phe-Arg-Trp-Pen)-NH$_2$ | 26.5 | 10.5 | 0.493 | 2440 | 54.0 | SEQ ID NO: 51 |

TABLE 9-continued cAMP Bioassay Data for Selected Compounds

| Compound | | | | | | |
|---|---|---|---|---|---|---|
| Ac-D-Arg-c(Cys-His-D-Phe-Arg-Trp-Gaba-Pen)-NH$_2$ | 8.43 | 32.4 | 0.959 | 2140 | 9.0 | SEQ ID NO: 52 |
| Ac-Arg-c(Cys-His-D-Phe-Arg-Trp-Gaba-Pen)-NH$_2$ | 4.23 | 8.09 | 0.719 | 23.2 | 6.0 | SEQ ID NO: 52 |
| Ac-Arg-c(Cys-D-Ala-His-D-Phe-Arg-Trp-Pen)-NH$_2$ | 48.3 | 13.3 | 0.79 | 10000 | 61.0 | SEQ ID NO: 51 |
| Ac-D-Arg-c(Asp-His-D-Phe-Arg-Trp-Ala-Lys)-NH$_2$ | 1.48 | 5.76 | 0.078 | 297 | 19.0 | SEQ ID NO: 53 |
| Ac-Arg-c(Asp-His-D-Phe-Arg-Trp-Ala-Lys)-NH$_2$ | 1.39 | 2.89 | 0.055 | 467 | 25.0 | SEQ ID NO: 53 |

Table 9B

| Compound | EC$_{50}$ hMC1-R | EC$_{50}$ hMC3-R | EC$_{50}$ hMC4-R | EC$_{50}$ hMC5-R | EC$_{50}$ hMC1-R/MC4-R | SEQ ID NO: |
|---|---|---|---|---|---|---|
| Ac-Nle-c(Cys-D-Ala-His-D-Phe-Arg-Trp-Cys)-NH$_2$ | 2.4 | 0.33 | 0.078 | 420 | 31 | SEQ ID NO: 7 |
| D-Phe-c(Cys-His-D-(Et)Tyr-Arg-Trp-β-Ala-D-Cys)-Thr-NH$_2$ | 0.35 | 1.1 | 0.11 | 0.37 | 3 | SEQ ID NO: 24 |
| Nle-c(Cys-His-D-Phe-Arg-Trp-Apn-Cys)-NH$_2$ | 0.31 | 0.27 | 0.018 | 3.1 | 17 | SEQ ID NO: 27 |
| Ac-Nle-c(Cys-His-D-Phe-Arg-Trp-Gaba-Pen)-NH$_2$ | 0.28 | 0.24 | 0.028 | 3.9 | 10 | SEQ ID NO: 32 |
| Nle-c(Cys-His-D-Phe-Arg-Trp-Gaba-Cys)-NH$_2$ | 0.37 | 0.1 | 0.021 | 1.7 | 18 | SEQ ID NO: 34 |
| Ac-Nle-c(Asp-His-D-Phe-Arg-Trp-β-Ala-Lys)-NH$_2$ | 0.834 | 0.145 | 0.128 | 2.79 | 6.52 | SEQ ID NO: 1 |
| Ac-Nle-c(Cys-His-D-Phe-Arg-Trp-Apn-Cys)-NH$_2$ | 0.76 | 0.199 | 0.0492 | 1.73 | 15.45 | SEQ ID NO: 2 |
| Ac-Cha-c(Asp-His-D-Phe-Arg-Trp-Gaba-Lys)-NH$_2$ | 3.26 | 0.189 | 0.0949 | 30.2 | 34.35 | SEQ ID NO: 6 |
| Ac-Nle-c(Asp-His-D-Phe-Arg-Trp-Gaba-Lys)-NH$_2$ | 1.37 | 0.628 | 0.131 | 3.48 | 10.46 | SEQ ID NO: 6 |
| Ac-hCha-c(Asp-His-D-Phe-Arg-Trp-Gaba-Lys)-NH$_2$ | 2.27 | 3.32 | 7.24 | 415 | 0.31 | SEQ ID NO: 11 |
| Ac-Nle-c(Pen-D-Ala-His-D-Phe-Arg-Trp-Cys)-NH$_2$ | ND | 1.89 | 0.531 | ND | ND | SEQ ID NO: 21 |
| Ac-Nle-c(Cys-D-Ala-His-D-Phe-Arg-Trp-Pen)-NH$_2$ | 14.3 | 2.03 | 0.183 | 2240 | 78.14 | SEQ ID NO: 22 |
| D-Phe-c(Cys-His-D-(Et)Tyr-hArg-Trp-β-Ala-D-Cys)-Thr-NH$_2$ | 0.345 | 2.71 | 5376 | 2.38 | 0.06 | SEQ ID NO: 24 |
| D-Phe-c(Cys-His-D-(Et)Tyr-hArg-Bip-β-Ala-D-Cys)-Thr-NH$_2$ | 0.685 | 81.8 | 86.9 | 31.8 | 0.01 | SEQ ID NO: 26 |

TABLE 9-continued cAMP Bioassay Data for Selected Compounds

| Compound | | | | | |
|---|---|---|---|---|---|
| Ac-Nle-c(Asp-D-Ala-His-D-Phe-Arg-Bal-Lys)-NH$_2$ | 0.931 | 3.22 | 1.65 | >10000 | 0.56 SEQ ID NO: 28 |
| Ac-Nle-c(Cys-D-Leu-His-D-Phe-Arg-Trp-Cys)-NH$_2$ | 3.24 | 0.465 | 0.0915 | 78.5 | 35.41 SEQ ID NO: 30 |
| Ac-Nle-c(Cys-D-Cha-His-D-Phe-Arg-Trp-Cys)-NH$_2$ | 0.819 | 0.541 | 0.453 | 45.3 | 1.81 SEQ ID NO: 30 |

Table 9C

| Compound | EC50 hMC1-R | Kb hMC3-R | Kb MC4-R | EC50 hMC5-R | SEQ ID NO: |
|---|---|---|---|---|---|
| Ac-Nle-c(Cys-D-Ala-His-D-2-Nal-Arg-Trp-Cys)-NH$_2$ | 17.6 | 12.4 | 38.8 | 11.8 | SEQ ID NO: 16 |
| Ac-Nle-c(Asp-His-D-2-Nal-Arg-Trp-Ala-Lys)-NH$_2$ | 0.619 | 2.98 | 0.109 | 0.189 | SEQ ID NO: 38 |
| Ac-Nle-c(Asp-His-D-2-Nal-Arg-Trp-β-Ala-Lys)-NH$_2$ | 0.913 | 0.536 | 0.346 | 0.489 | SEQ ID NO: 38 |
| Ac-Nle-c(Cys-His-D-2-Nal-Arg-Trp-Gaba-Cys)-NH$_2$ | 0.231 | 18.4 | 0.782 | 0.153 | SEQ ID NO: 39 |
| Ac-Nle-c(Cys-His-D-2-Nal-Arg-Trp-Ahx-Cys)-NH$_2$ | 0.581 | 10.8 | 0.967 | 0.126 | SEQ ID NO: 39 |
| Ac-hPhe-c(Asp-His-D-2-Nal-Arg-Trp-Gaba-Lys)-NH$_2$ | 0.413 | 9.32 | 0.824 | 0.307 | SEQ ID NO: 40 |
| Ac-Cha-c(Asp-His-D-2-Nal-Arg-Trp-Gaba-Lys)-NH$_2$ | 1.27 | 3.02 | 0.442 | 0.736 | SEQ ID NO: 40 |
| Ac-Nle-c(Cys-D-Ala-His-D-2-Nal-Arg-1-Nal-Cys)-NH$_2$ | 383 | 61.5 | 53.6 | 2842 | SEQ ID NO: 16 |

Table 9D

| Compound | EC50 hMC1-R | Kb hMC3-R | Kb MC4-R | EC50 hMC5-R | SEQ ID NO: |
|---|---|---|---|---|---|
| Ac-Arg-c(Cys-D-Ala-His-D-2-Nal-Arg-Trp-Cys)-NH$_2$ | 193 | 5.72 | 1.58 | 1111 | SEQ ID NO: 49 |

ND = not determined

Table 10A

| Compound | EC$_{50}$ hMC1-R | Kb hMC3-R | Kb hMC4-R | EC$_{50}$ hMC5-R |
|---|---|---|---|---|
| Ac-c(Cys-Glu-His-D-2-Nal-Arg-Trp-Ala-Cys)-Pro-Pro-Lys-Asp-NH$_2$ (SEQ ID NO: 269) | 66.1 | 33.4 | 0.687 | 6.84 |
| Tyr-Gly-Arg-Lys-Lys-Arg-Arg-Gln-Arg-Arg-Arg-Nle-c(Asp-His-D-2-Nal-Arg-Trp-Lys)-NH$_2$ (SEQ ID NO: 60) | ND | 4500 | 105 | ND |
| Tyr-Gly-Arg-Lys-Lys-Arg-Arg-Gln-Arg-Arg-Arg-Doc-Nle-c(Asp-His-D-2-Nal-Arg-Trp-Lys)-NH$_2$ (SEQ ID NO: 61) | ND | 395 | 16.8 | ND |
| Nle-c(Asp-His-D-2-Nal-Arg-Trp-Lys)-β-Ala-Tyr-Gly-Arg-Lys-Lys-Arg-Arg-Gln-Arg-Arg-Arg-NH$_2$ (SEQ ID NO: 62) | ND | 207 | 18.5 | ND |
| Ac-Nle-c(Asp-His-D-2-Nal-Arg-Trp-Lys)-β-Ala-Tyr-Gly-Arg-Lys-Lys-Arg-Arg-Gln-Arg-Arg-Arg-NH$_2$ (SEQ ID NO: 62) | ND | 220 | 4.07 | ND |

-continued

| Sequence | | | | |
|---|---|---|---|---|
| H-Nle-c(Asp-His-D-2-Nal-Arg-Trp-Lys)-Doc-Doc-Tyr-Gly-Arg-Lys-Lys-Arg-Arg-Gln-Arg-Arg-Arg-NH₂ (SEQ ID NO: 63) | ND | 261 | 3.11 | ND |
| Ac-Nle-c(Asp-His-D-2-Nal-Arg-Trp-Lys)-Pro-Pro-Lys-Asp-Tyr-Gly-Arg-Lys-Lys-Arg-Arg-Gln-Arg-Arg-Arg-NH₂ (SEQ ID NO: 64) | ND | 14.1 | 22.8 | ND |
| Ac-c(Cys-Glu-His-D-2-Nal-Arg-Trp-Gly-Cys)-Pro-Pro-Lys-Asp-Tyr-Gly-Arg-Lys-Lys-Arg-Arg-Gln-Arg-Arg-Arg-NH₂ (SEQ ID NO: 65) | ND | 233 | 26.0 | ND |
| Ac-Nle-c(Asp-His-D-2-Nal-Arg-Trp-Lys)-β-Ala-β-Ala-Tyr-Gly-Arg-Lys-Lys-Arg-Arg-Gln-Arg-Arg-Arg-NH₂ (SEQ ID NO: 66) | 1.39 | 16.2 | 7.94 | 0.839 |
| Ac-Nle-c(Asp-His-D-2-Nal-Arg-Trp-Lys)-Pro-Pro-Lys-Asp-Doc-Tyr-Gly-Arg-Lys-Lys-Arg-Arg-Gln-Arg-Arg-Arg-NH₂ (SEQ ID NO: 67) | 3.65 | 19.4 | 3.73 | 1.61 |
| Ac-c(Cys-Glu-His-D-2-Nal-Arg-Trp-Gly-Cys)-Pro-Pro-Lys-Asp-Doc-Tyr-Gly-Arg-Lys-Lys-Arg-Arg-Gln-Arg-Arg-Arg-NH₂ (SEQ ID NO: 68) | ND | 17.7 | 1.49 | ND |
| Ac-c(Cys-Glu-His-D-2-Nal-Arg-Trp-Ala-Cys)-Pro-Pro-Lys-Asp-β-Ala-Tyr-Gly-Arg-Lys-Lys-Arg-Arg-Gln-Arg-Arg-Arg-NH₂ (SEQ ID NO: 69) | 6.3 | 70.0 | 1.66 | 38.2 |
| Ac-c(Cys-Glu-His-D-2-Nal-Arg-Trp-Ala-Cys)-Pro-Pro-Lys-Asp-Doc-Tyr-Gly-Arg-Lys-Lys-Arg-Arg-Gln-Arg-Arg-Arg-NH₂ (SEQ ID NO: 69) | 12.1 | 30.3 | 1.81 | 70.0 |
| Ac-c(Cys-Glu-His-D-2-Nal-Arg-2-Nal-Ala-Cys)-Pro-Pro-Lys-Asp-NH₂ (SEQ ID NO: 269) | 33.6 | 140 | 12.2 | 66.9 |
| Ac-c(Cys-Glu-His-D-2-Nal-Arg-1-Nal-Ala-Cys)-Pro-Pro-Lys-Asp-NH₂ (SEQ ID NO: 269) | 269 | 105 | 5.92 | 104 |
| Ac-c Cys-Glu-His-D-2-Nal-Arg-Bal-Ala-Cys)-Pro-Pro-Lys-Asp-NH₂ (SEQ ID NO: 269) | 690 | 70.7 | 4.56 | 177 |
| Ac-Nle-c(Asp-His-D-2-Nal-Arg-Trp-Lys)-Doc-Doc-Tyr-Gly-Arg-Lys-Lys-Arg-Arg-Gln-Arg-Arg-Arg-NH₂ (SEQ ID NO: 70) | 3.23 | 8.97 | 4.61 | 2.86 |
| Ac-c(Cys-Glu-His-D-2-Nal-Arg-Bal-Ala-Cys)-Pro-Pro-Lys-Asp-β-Ala-Arg-Arg-Arg-Arg-Arg-Gln-Arg-Arg-Arg-NH₂ (SEQ ID NO: 72) | 52.0 | 170 | 6.14 | 328 |
| Ac-c(Cys-Glu-His-D-2-Nal-Arg-Bal-Ala-Cys)-Pro-Pro-Lys-Asp-β-Ala-Gly-Arg-Arg-Arg-Arg-Arg-Gln-Arg-Arg-Arg-NH₂ (SEQ ID NO: 73) | 146 | 104 | 32.0 | 1400 |
| Ac-c(Cys-Glu-His-D-2-Nal-Arg-Bal-Ala-Cys)-Pro-Pro-Lys-Asp-β-Ala-Tyr-Gly-Arg-Arg-Arg-Arg-Arg-Gln-Arg-Arg-Arg-NH₂ (SEQ ID NO: 74) | 114 | 44.6 | 28.4 | 879 |
| Ac-c(Cys-Glu-His-D-2-Nal-Arg-Bal-Ala-Cys)-Pro-Pro-Lys-Asp-β-Ala-Tyr-Aib-Arg-Lys-Lys-Arg-Arg-Gln-Arg-Arg-Arg-NH₂ (SEQ ID NO: 79) | 67.1 | 439 | 46.5 | 582 |
| Ac-c(Cys-Glu-His-D-2-Nal-Arg-1-Nal-Ala-Cys)-Pro-Pro-Arg-Asp-β-Ala-Arg-Arg-Arg-Arg-Arg-Gln-Arg-Arg-Arg-NH₂ (SEQ ID NO: 80) | 144 | 116 | 8.93 | 819 |

| | | | | |
|---|---|---|---|---|
| Ac-c(Cys-Glu-His-D-2-Nal-Arg-1-Nal-Ala-Cys)-Pro-Pro-Lys-Asp-β-Ala-Arg-Arg-Arg-Arg-Arg-Gln-Arg-Arg-Arg-NH$_2$ (SEQ ID NO: 80) | 36.0 | 46.5 | 11.4 | 56.1 |
| Ac-c(Cys-Glu-His-D-2-Nal-Arg-1-Nal-Ala-Cys)-Pro-Pro-Lys-Asp-β-Ala-Arg-Arg-Arg-Arg-Arg-Gln-Arg-Arg-Arg-NH$_2$ (SEQ ID NO: 81) | 93.0 | 71 | 15.9 | >10000 |
| Ac-c(Cys-Glu-His-D-2-Nal-Arg-2-Nal-Ala-Cys)-Pro-Pro-Arg-Asp-β-Ala-Arg-Arg-Arg-Arg-Arg-Gln-Arg-Arg-Arg-NH$_2$ (SEQ ID NO: 82) | 39.7 | 30.9 | 6.66 | 501 |
| Ac-c(Cys-Glu-His-D-2-Nal-Arg-2-Nal-Ala-Cys)-Pro-Pro-Lys-Asp-β-Ala-Arg-Arg-Arg-Arg-Arg-Gln-Arg-Arg-Arg-NH$_2$ (SEQ ID NO: 82) | 35.2 | 22.9 | 12.6 | 199 |
| Ac-c(Cys-Glu-His-D-2-Nal-Arg-2-Nal-Ala-Cys)-Pro-Pro-Lys-Asp-β-Ala-Arg-Arg-Arg-Arg-Arg-Gln-Arg-Arg-Arg-NH$_2$ (SEQ ID NO: 81) | 29.1 | 13.6 | 13.4 | 204 |
| Ac-c(Cys-Glu-His-D-2-Nal-Arg-Bal-Ala-Cys)-Pro-Pro-Arg-Asp-β-Ala-Arg-Arg-Arg-Arg-Arg-Gln-Arg-Arg-Arg-NH$_2$ (SEQ ID NO: 83) | 86.1 | 41.7 | 19.4 | 2360 |
| Ac-c(Cys-Glu-His-D-2-Nal-Arg-Bal-Ala-Cys)-Pro-Pro-Arg-Asp-β-Ala-Arg-Arg-Arg-Arg-Gln-Arg-Arg-Arg-NH$_2$ (SEQ ID NO: 84) | 38.3 | 20.2 | 21.2 | >10000 |
| Ac-c(Cys-Glu-His-D-2-Nal-Arg-Bal-Ala-Cys)-Pro-Pro-Lys-Asp-β-Ala-Arg-Arg-Arg-Arg-Arg-Gln-Arg-Arg-Arg-NH$_2$ (SEQ ID NO: 83) | 68.6 | 153 | 33.2 | >10000 |
| Ac-c(Cys-Glu-His-D-2-Nal-Arg-1-Nal-Ala-Cys)-Pro-Pro-Lys-Asp-β-Ala-Arg-Arg-Lys-Arg-Arg-Gln-Arg-Arg-Arg-NH$_2$ (SEQ ID NO: 88) | 70.4 | 286 | 18.6 | >10000 |
| Ac-c(Cys-Glu-His-D-2-Nal-Arg-1-Nal-Ala-Cys)-Pro-Pro-Lys-Asp-β-Ala-Arg-Lys-Arg-Arg-Arg-Gln-Arg-Arg-Arg-NH$_2$ (SEQ ID NO: 89) | 33.1 | 65.1 | 15.3 | 1720 |
| Ac-c(Cys-Glu-His-D-2-Nal-Arg-2-Nal-Ala-Cys)-Pro-Pro-Lys-Asp-β-Ala-Arg-Arg-Lys-Arg-Arg-Gln-Arg-Arg-Arg-NH$_2$ (SEQ ID NO: 88) | 88.2 | 10.6 | 17.4 | 514 |
| Ac-c(Cys-Glu-His-D-2-Nal-Arg-2-Nal-Ala-Cys)-Pro-Pro-Lys-Asp-β-Ala-Tyr-Gly-Arg-Lys-Arg-Arg-Gln-Arg-Arg-Arg-NH$_2$ (SEQ ID NO: 90) | 58.7 | 39.3 | 10.3 | 460 |
| Ac-c(Cys-Glu-His-D-2-Nal-Arg-2-Nal-Ala-Cys)-Pro-Pro-Lys-Asp-β-Ala-Gly-Arg-Arg-Lys-Arg-Arg-Gln-Arg-Arg-Arg-NH$_2$ (SEQ ID NO: 91) | 45.4 | 12.7 | 12.7 | 162 |
| Ac-c(Cys-Glu-His-D-2-Nal-Arg-2-Nal-Ala-Cys)-Pro-Pro-Lys-Asp-β-Ala-Gly-Arg-Lys-Arg-Arg-Gln-Arg-Arg-Arg-NH$_2$ (SEQ ID NO: 92) | 309 | 22.8 | 17.1 | 570 |
| Ac-Nle-c(Cys-D-Ala-His-D-Phe-Arg-Trp-Cys)-β-Ala-Tyr-Gly-Arg-Arg-Arg-Arg-Gln-Arg-Arg-Arg-NH$_2$ (SEQ ID NO: 139) | 7.86 | 10.5 | 0.843 | 4900 |
| Ac-c(Cys-Glu-His-D-2-Nal-Arg-2-Nal-Ala-Cys)-Pro-Pro-Lys-Asp-β-Ala-Tyr-Gly-Arg-Lys-Lys-Arg-Arg-Gln-Arg-Arg-Arg-NH$_2$ (SEQ ID NO: 71) | 29.7 | 25.6 | 7.37 | 82.9 |

-continued

| Compound | | | | |
|---|---|---|---|---|
| Ac-c(Cys-Glu-His-D-2-Nal-Arg-Trp-Ala-Cys)-Pro-Pro-Lys-Asp-βAla-Tyr-Gly-Arg-Lys-Lys-Arg-Gln-Arg-Arg-Arg-Arg-NH$_2$ (SEQ ID NO: 75) | 15.2 | 14.6 | 4.52 | 36.8 |
| Ac-c(Cys-Glu-His-D-2-Nal-Arg-Trp-Ala-Cys)-Pro-Pro-Lys-Asp-β-Ala-Tyr-Gly-Arg-Lys-Gln-Arg-Arg-Arg-Arg-Arg-NH$_2$ (SEQ ID NO: 76) | 6.7 | 9.38 | 11.7 | 46.2 |
| Ac-c(Cys-Glu-His-D-2-Nal-Arg-Trp-Ala-Cys)-Pro-Pro-Lys-Asp-β-Ala-Tyr-Gly-Arg-Lys-Gln-Lys-Arg-Arg-Arg-Arg-NH$_2$ (SEQ ID NO: 77) | 7.9 | 41.7 | 10.9 | 62.4 |
| Ac-c(Cys-Glu-His-D-2-Nal-Arg-Trp-Ala-Cys)-Pro-Pro-Lys-Asp-β-Ala-Tyr-Gly-Arg-Lys-Lys-Arg-Arg-Gln-Arg-Arg-NH$_2$ (SEQ ID NO: 78) | 16.9 | 36.0 | 7.12 | 58.9 |
| Ac-c(Cys-Glu-His-D-2-Nal-Arg-Trp-Ala-Cys)-Pro-Pro-Lys-Asp-β-Ala-Tyr-Gly-Arg-Lys-Lys-Arg-Arg-Gln-Arg-Arg-NH$_2$ (SEQ ID NO: 85) | 16.4 | 20.8 | 7.31 | 44.2 |
| Ac-c(Cys-Glu-His-D-2-Nal-Arg-Trp-Ala-Cys)-Pro-Pro-Lys-Asp-β-Ala-Tyr-Gly-Arg-Gln-Lys-Lys-Arg-Arg-Arg-Arg-NH$_2$ (SEQ ID NO: 86) | 12.0 | 13.7 | 9.38 | 54.2 |
| Ac-c(Cys-Glu-His-D-2-Nal-Arg-Trp-Ala-Cys)-Pro-Pro-Lys-Asp-β-Ala-Tyr-Gly-Arg-Lys-Lys-Arg-Arg-Arg-Arg-Gln-NH$_2$ (SEQ ID NO: 87) | 7.5 | 12.2 | 7.61 | 51.7 |
| Ac-c(Cys-Glu-His-D-2-Nal-Arg-1-Nal-Ala-Cys)-Pro-Pro-Lys-Asp-β-Ala-Tyr-Gly-Arg-Lys-Lys-Arg-Arg-Gln-Arg-Arg-NH$_2$ (SEQ ID NO: 71) | 43.3 | 215 | 5.87 | 1286 |
| Ac-c(Cys-Glu-His-D-2-Nal-Arg-Bal-Ala-Cys)-Pro-Pro-Lys-Asp-β-Ala-Tyr-Gly-Arg-Lys-Lys-Arg-Arg-Gln-Arg-Arg-NH$_2$ (SEQ ID NO: 71) | 37.9 | 112 | 41.1 | 1798 |

Table 10B

| Compound | EC50 hMC1-R | EC50 hMC3-R | EC50 hMC4-R | EC50 hMC5-R |
|---|---|---|---|---|
| Ac-Nle-c(Cys-D-Ala-His-D-Phe-Arg-Trp-Cys)-(Doc)2-Tyr-Gly-Arg-Lys-Lys-Arg-Arg-Gln-Arg-Arg-Arg-NH$_2$ (SEQ ID NO: 136) | 4.70 | 4.56 | 0.634 | 147 |
| Ac-Nle-c(Cys-D-Ala-His-D-Phe-Arg-Trp-Cys)-β-Ala-Tyr-Gly-Arg-Lys-Lys-Arg-Gln-Arg-Arg-Arg-Arg-NH$_2$ (SEQ ID NO: 137) | 5.90 | 7.73 | 1.02 | 2890 |
| Ac-Nle-c(Cys-D-Ala-His-D-Phe-Arg-Trp-Cys)-β-Ala-Gly-Arg-Arg-Arg-Arg-Arg-Gln-Arg-Arg-Arg-NH$_2$ (SEQ ID NO: 136) | 0.481 | 7.32 | 0.964 | 2010 |
| Ac-Nle-c(Cys-D-Ala-His-D-Phe-Arg-Trp-Cys)-β-Ala-Arg-Arg-Arg-Arg-Arg-Gln-Arg-Arg-Arg-NH$_2$ (SEQ ID NO: 138) | 7.15 | 9.37 | 1.25 | 1570 |

Table 10C

| Compound | EC$_{50}$ hMC1-R | Kb hMC3-R | Kb hMC4-R | EC$_{50}$ hMC5-R |
|---|---|---|---|---|
| Ac-c(Cys-Glu-His-D-2-Nal-Arg-2-Nal-β-Ala-Cys)-Pro-Pro-Lys-Asp-NH$_2$ (SEQ ID NO: 270) | ND | ND | ND | ND |

| Compound | | | | |
|---|---|---|---|---|
| Ac-c(Cys-Glu-His-D-2-Nal-Arg-2-Nal-Aib-Cys)-Pro-Pro-Lys-Asp-NH$_2$ (SEQ ID NO: 270) | 770 | 221 | 4.52 | 869 |
| Ac-c(Cys-Glu-His-D-2-Nal-Arg-1-Nal-Ala-Cys)-Pro-Pro-Lys-Asp-β-Ala-Tyr-Gly-Arg-Lys-Arg-Arg-Gln-Arg-Arg-Arg-NH$_2$ (SEQ ID NO: 95) | 29 | 22.6 | 16.7 | 173 |
| Ac-c(Cys-Glu-His-D-2-Nal-Arg-1-Nal-Ala-Cys)-Pro-Pro-Lys-Asp-β-Ala-Tyr-Gly-Arg-Lys-Arg-Arg-Gln-Arg-Arg-Arg-NH$_2$ (SEQ ID NO: 96) | 102 | 26.3 | 14.6 | 261 |
| Ac-c(Cys-Glu-His-D-2-Nal-Arg-1-Nal-Ala-Cys)-Pro-Pro-Lys-Asp-β-Ala-Gly-Arg-Arg-Lys-Arg-Arg-Gln-Arg-Arg-Arg-NH$_2$ (SEQ ID NO: 97) | 26.6 | 101 | 9.34 | 351 |
| Ac-c(Cys-Glu-His-D-2-Nal-Arg-1-Nal-Ala-Cys)-Pro-Pro-Lys-Asp-β-Ala-Gly-Arg-Lys-Arg-Arg-Arg-Gln-Arg-Arg-Arg-NH$_2$ (SEQ ID NO: 92) | 45.5 | 181 | 6.35 | 149 |
| Ac-c(Cys-Glu-His-D-2-Nal-Arg-2-Nal-Ala-Cys)-Pro-Pro-Lys-Asp-β-Ala-Arg-Lys-Arg-Arg-Arg-Gln-Arg-Arg-Arg-NH$_2$ (SEQ ID NO: 99) | 23.7 | 9.22 | 5.87 | 39.7 |
| Ac-c(Cys-Glu-His-D-2-Nal-Arg-2-Nal-Ala-Cys)-Pro-Pro-Lys-Asp-β-Ala-Tyr-Gly-Arg-Lys-Arg-Arg-Gln-Arg-Arg-Arg-NH$_2$ (SEQ ID NO: 101) | 34.7 | 15.0 | 8.68 | 28.2 |
| Ac-c(Cys-Glu-His-D-2-Nal-Arg-Bal-Ala-Cys)-Pro-Pro-Lys-Asp-β-Ala-Arg-Lys-Arg-Arg-Arg-Gln-Arg-Arg-Arg-NH$_2$ (SEQ ID NO: 105) | 19.1 | 106 | 4.59 | 100 |
| Ac-c(Cys-Glu-His-D-2-Nal-Arg-Bal-Ala-Cys)-Pro-Pro-Lys-Asp-β-Ala-Tyr-Gly-Arg-Arg-Lys-Arg-Arg-Gln-Arg-Arg-Arg-NH$_2$ (SEQ ID NO: 100) | 19.8 | 37.8 | 8.43 | 158 |
| Ac-c(Cys-Glu-His-D-2-Nal-Arg-Bal-Ala-Cys)-Pro-Pro-Lys-Asp-β-Ala-Tyr-Gly-Arg-Lys-Arg-Arg-Arg-Gln-Arg-Arg-Arg-NH$_2$ (SEQ ID NO: 101) | 11.2 | 52.1 | 9.45 | 95.7 |
| Ac-c(Cys-Glu-His-D-2-Nal-Arg-Bal-Ala-Cys)-Pro-Pro-Lys-Asp-β-Ala-Gly-Arg-Arg-Lys-Arg-Arg-Gln-Arg-Arg-Arg-NH$_2$ (SEQ ID NO: 102) | 33.8 | 93.6 | 4.42 | 89.5 |
| Ac-c(Cys-Glu-His-D-2-Nal-Arg-Bal-Ala-Cys)-Pro-Pro-Lys-Asp-β-Ala-Arg-Arg-Lys-Arg-Arg-Gln-Arg-Arg-Arg-NH$_2$ (SEQ ID NO: 104) | 232 | 68.8 | 10.0 | 250 |
| Ac-c(Cys-Glu-His-D-2-Nal-Arg-Bal-Ala-Cys)-Pro-Pro-Lys-Asp-β-Ala-Gly-Arg-Lys-Arg-Arg-Arg-Gln-Arg-Arg-Arg-NH$_2$ (SEQ ID NO: 103) | 32.2 | 98.3 | 5.23 | 194 |

Table 10D

| Compound | EC50 hMC1-R | EC50 hMC3-R | EC50 hMC4-R | EC50 hMC5-R |
|---|---|---|---|---|
| Ac-Nle-c(Cys-D-Ala-His-D-Phe-Arg-Trp-Cys)-β-Ala-Tyr-Gly-Arg-Arg-Lys-Arg-Arg-Gln-Arg-Arg-Arg-NH$_2$ (SEQ ID NO: 141) | 5.66 | 4.70 | 0.422 | 1551 |
| Ac-Nle-c(Cys-D-Ala-His-D-Phe-Arg-Trp-Cys)-β-Ala-Tyr-Gly-Arg-Lys-Arg-Arg-Arg-Gln-Arg-Arg-Arg-NH$_2$ (SEQ ID NO: 142) | 7.57 | 4.18 | 0.600 | 1792 |

-continued

| | | | | |
|---|---|---|---|---|
| Ac-Nle-c(Cys-D-Ala-His-D-Phe-Arg-Trp-Cys)-β-Ala-Gly-Arg-Arg-Lys-Arg-Arg-Gln-Arg-Arg-Arg-NH$_2$ (SEQ ID NO: 141) | 2.36 | 2.74 | 0.260 | 500 |
| Ac-Nle-c(Cys-D-Ala-His-D-Phe-Arg-Trp-Cys)-β-Ala-Gly-Arg-Lys-Arg-Arg-Arg-Gln-Arg-Arg-Arg-NH$_2$ (SEQ ID NO: 142) | 2.81 | 3.29 | 0.298 | 566 |
| Ac-Nle-c(Cys-D-Ala-His-D-Phe-Arg-Trp-Cys)-β-Ala-Arg-Arg-Lys-Arg-Arg-Gln-Arg-Arg-Arg-NH$_2$ (SEQ ID NO: 143) | 1.86 | 1.39 | 0.367 | 165 |
| Ac-Nle-c(Cys-D-Ala-His-D-Phe-Arg-Trp-Cys)-β-Ala-Arg-Lys-Arg-Arg-Arg-Gln-Arg-Arg-Arg-NH$_2$ (SEQ ID NO: 144) | 2.06 | 1.61 | 0.394 | 199 |

ND = not determined

TABLE 11

Intracellular Cyclic AMP (cAMP) Levels for Formula (I) Examples

Table 11A

| Formula (V) Compounds | EC$_{50}$ hMC1 | EC$_{50}$ hMC3 | EC$_{50}$ hMC4 | EC$_{50}$ hMC5 |
|---|---|---|---|---|
| c[Hydantoin(C(O)-(Cys-D-Ala))-His-D-Phe-Arg-Trp-Cys]-NH$_2$ (SEQ ID NO: 271) | — | 218 | 5.42 | — |
| c[Hydantoin(C(O)-(Glu-D-Ala))-His-D-Phe-Arg-Trp-Lys]-NH$_2$ (SEQ ID NO: 276) | — | 22.3 | 3.62 | — |
| c[Hydantoin(C(O)-(Glu-D-Ala))-His-D-Phe-Arg-Trp-Orn]-NH$_2$ (SEQ ID NO: 276) | — | 39.2 | 4.94 | — |
| c[Hydantoin(C(O)-(Glu-D-Ala))-His-D-Phe-Arg-Trp-Dap]-NH$_2$ (SEQ ID NO: 276) | 56.7 | 18.2 | 0.182 | >10000 |
| c[Hydantoin(C(O)-(Asp-D-Ala))-His-D-Phe-Arg-Trp-Orn]-NH$_2$ (SEQ ID NO: 273) | 56.6 | 88.6 | 4.50 | 9300 |
| c[Hydantoin(C(O)-(Asp-D-Ala))-His-D-Phe-Arg-Trp-Dap]-NH$_2$ (SEQ ID NO: 273) | — | 49.3 | 2.12 | — |

TABLE 11B-

| Formula (VI) Compounds | EC$_{50}$ hMC1 | EC$_{50}$ hMC3 | EC$_{50}$ hMC4 | EC$_{50}$ hMC5 |
|---|---|---|---|---|
| Hydantoin(C(O)-(Nle-Gly))-c(Cys-Glu-His-D-Phe-Arg-Trp-Cys)-NH$_2$ (SEQ ID NO: 278) | 54.3 | 12.2 | 0.177 | >10000 |
| Hydantoin(C(O)-(Gly-Gly))-c(Cys-Glu-His-D-Phe-Arg-Trp-Cys)-NH$_2$ (SEQ ID NO: 278) | 124 | 8.05 | 0.214 | >10000 |
| Hydantoin(C(O)-(A6c-Nle))-c(Cys-D-Ala-His-D-Phe-Arg-Trp-Cys)-NH$_2$ (SEQ ID NO: 284) | — | 4.89 | 1.80 | — |
| Hydantoin(C(O)-(D-Ala-Nle))-c(Cys-D-Ala-His-D-Phe-Arg-Trp-Cys)-NH$_2$ (SEQ ID NO: 284) | — | 2.56 | 1.47 | — |
| Hydantoin(C(O)-(Val-Nle))-c(Cys-D-Ala-His-D-Phe-Arg-Trp-Cys)-NH$_2$ (SEQ ID NO: 284) | — | 4.61 | 0.977 | — |
| Hydantoin(C(O)-(Leu-Nle))-c(Cys-D-Ala-His-D-Phe-Arg-Trp-Cys)-NH$_2$ (SEQ ID NO: 284) | — | 9.68 | 1.83 | — |
| Hydantoin(C(O)-(Cha-Nle))-c(Cys-D-Ala-His-D-Phe-Arg-Trp-Cys)-NH$_2$ (SEQ ID NO: 284) | — | 9.97 | 13.9 | — |

TABLE 11-continued

Intracellular Cyclic AMP (cAMP) Levels for Formula (I) Examples

| | | | | |
|---|---|---|---|---|
| Hydantoin(C(O)-(Gly-Gly))-c(Cys-D-Ala-His-D-Phe-Arg-Trp-Cys)-NH$_2$ (SEQ ID NO: 279) | 14.2 | 2.46 | 0.336 | 201 |
| Hydantoin(C(O)-(Nle-Gly))-c(Cys-D-Ala-His-D-Phe-Arg-Trp-Pen)-NH$_2$ (SEQ ID NO: 280) | 17.0 | 21.5 | 0.584 | 352 |
| Hydantoin(C(O)-(Gly-Gly))-c(Cys-D-Ala-His-D-Phe-Arg-Trp-Pen)-NH$_2$ (SEQ ID NO: 280) | 40.2 | 8.90 | 0.495 | 8300 |
| Hydantoin(C(O)-(Ala-Gly))-c(Cys-D-Ala-His-D-Phe-Arg-Trp-Cys)-NH$_2$ (SEQ ID NO: 279) | 17.6 | 2.23 | 0.241 | 516 |
| Hydantoin(C(O)-(D-Ala-Gly))-c(Cys-D-Ala-His-D-Phe-Arg-Trp-Cys)-NH$_2$ (SEQ ID NO: 279) | 4.70 | 2.22 | 0.309 | 355 |
| Hydantoin(C(O)-(D-Arg-Gly))-c(Cys-Glu-His-D-Phe-Arg-Trp-Cys)-NH$_2$ (SEQ ID NO: 278) | 18.0 | 17.1 | 0.160 | 2710 |
| Hydantoin(C(O)-(Gly-D-Arg))-c(Cys-Glu-His-D-Phe-Arg-Trp-Cys)-NH$_2$ (SEQ ID NO: 287) | 12.9 | 10.3 | 0.125 | 7440 |
| Hydantoin(C(O)-(Arg-Gly))-c(Cys-Glu-His-D-Phe-Arg-Trp-Cys)-NH$_2$ (SEQ ID NO: 278) | 8.83 | 7.86 | 0.0979 | 4010 |
| Hydantoin(C(O)-(Gly-Arg))-c(Cys-Glu-His-D-Phe-Arg-Trp-Cys)-NH$_2$ (SEQ ID NO: 285) | 9.97 | 3.63 | 0.0687 | 335 |
| Hydantoin(C(O)-(Arg-Gly))-c(Cys-D-Ala-His-D-Phe-Arg-Trp-Cys)-NH$_2$ (SEQ ID NO: 279) | 8.81 | 18.2 | 0.503 | 3560 |
| Hydantoin(C(O)-(D-Arg-Gly))-c(Cys-D-Ala-His-D-Phe-Arg-Trp-Cys)-NH$_2$ (SEQ ID NO: 279) | 11.5 | 23.2 | 0.513 | 3950 |
| Hydantoin(C(O)-(Gly-D-Arg))-c(Cys-D-Ala-His-D-Phe-Arg-Trp-Cys)-NH$_2$ (SEQ ID NO: 288) | 7.53 | 11.6 | 0.435 | 9840 |
| Hydantoin(C(O)-(Gly-Arg))-c(Cys-D-Ala-His-D-Phe-Arg-Trp-Cys)-NH$_2$ (SEQ ID NO: 286) | 8.85 | 5.17 | 0.599 | 3610 |
| Hydantoin(C(O)-(Arg-Gly))-c(Cys-D-Ala-His-D-2-Nal-Arg-Trp-Cys)-NH$_2$ (SEQ ID NO: 282) | 96.6 | 13.1 | 21.2 | 103 |

TABLE 11C

| Formula (VII) Compounds | EC$_{50}$ hMC1 | EC$_{50}$ hMC3 | EC$_{50}$ hMC4 | EC$_{50}$ hMC5 |
|---|---|---|---|---|
| c[Hydantoin(C(O)-(Aib-Cys))-D-Ala-His-D-Phe-Arg-Trp-Cys]-NH$_2$ (SEQ ID NO: 290) | — | 6.28 | 0.407 | — |
| c[Hydantoin(C(O)-(Val-Cys))-D-Ala-His-D-Phe-Arg-Trp-Cys]-NH$_2$ (SEQ ID NO: 290) | — | 3.77 | 0.214 | — |
| c[Hydantoin(C(O)-(Leu-Cys))-D-Ala-His-D-Phe-Arg-Trp-Cys]-NH$_2$ (SEQ ID NO: 290) | — | 4.72 | 0.428 | — |
| c[Hydantoin(C(O)-(Ile-Cys))-D-Ala-His-D-Phe-Arg-Trp-Cys]-NH$_2$ (SEQ ID NO: 290) | — | 8.51 | 1.85 | — |
| c[Hydantoin(C(O)-(A6c-Cys))-D-Ala-His-D-Phe-Arg-Trp-Cys]-NH$_2$ (SEQ ID NO: 290) | — | 5.66 | 1.72 | — |
| c[Hydantoin(C(O)-(Gly-Cys))-Glu-His-D-Phe-Arg-Trp-Cys]-NH$_2$ (SEQ ID NO: 291) | 14.5 | 21.8 | 0.576 | 1780 |

TABLE 12 cAMP Bioassay Data for Selected Compounds

| Compound | EC$_{50}$ hMC1-R | EC$_{50}$ hMC3-R | EC$_{50}$ hMC4-R | EC$_{50}$ hMC5-R |
|---|---|---|---|---|
| Ac-Tyr-Arg-c(Cys-D-Ala-His-D-Phe-Arg-Trp-Cys)-NH$_2$ (SEQ ID NO: 292) | 6.42 | 2.39 | 0.194 | 1540 |
| Ac-2-Nal-Arg-c(Cys-D-Ala-His-D-Phe-Arg-Trp-Cys)-NH$_2$ (SEQ ID NO: 292) | 9.66 | 6.11 | 0.275 | 1730 |
| Ac-1-Nal-Arg-c(Cys-D-Ala-His-D-Phe-Arg-Trp-Cys)-NH$_2$ (SEQ ID NO: 292) | 8.67 | 4.21 | 0.363 | 1320 |
| Ac-Trp-Arg-c(Cys-D-Ala-His-D-Phe-Arg-Trp-Cys)-NH$_2$ (SEQ ID NO: 292) | 5.78 | 3.95 | 0.219 | 2580 |

In Vivo Studies

Compounds of the present invention can be and were tested for an effect upon insulin resistance and/or body weight according to the following procedures. One skilled in the art would know that procedures similar to those described herein may be used to assay the effect of the compounds of the invention upon insulin resistance and/or body weight.

Ligand compounds activating melanocortin receptors tested in the in vivo studies were as follows (Table 13):

TABLE 13

| Ligand Code | Structure |
|---|---|
| Compound A | Ac-Arg-c(Cys-D-Ala-His-D-Phe-Arg-Trp-Cys)-NH$_2$ SEQ ID NO: 50 |
| Compound B | Hydantoin(C(O)-(Arg-Gly))-c(Cys-Glu-His-D-Phe-Arg-Trp-Cys)-NH$_2$ (SEQ ID NO: 278) |

Acute Feeding Experiments (Fasting)

Male Sprague Dawley rats (250 g) were housed in individual cages and maintained under 12:12 hour light:dark conditions. The rats were fasted for 18 hours prior to the start of the experiment with water available ad libitum. At time 0, the rats were injected subcutaneously (sc) with selected compounds at doses of 100 nmole/kg, or with vehicle, and were provided with food. Individual food consumption was measured at about 2, 4 and 6 hours after injection. Data for selected compounds of the invention are reported in FIG. 1.

Chronic Feeding Experiments

Male, Sprague Dawley rats that had been fed either a normal diet (300 g; Research Diets 12450) or a high fat diet (400 g; Research Diets 12451) for 10 weeks prior to the start of the experiment were housed in individual cages and maintained under 12:12 hour light:dark conditions with both food and water available ad libitum. The rats were anesthetized and implanted subcutaneously with an osmotic mini pump (Alzet, Cupertino, Calif.). The pumps delivered either Compound A or Compound B at doses of 75, 300 or 1200 nmole/kg/day, or vehicle for 7 days. Individual body weight and food consumption were measured daily.

On day 7 rats were anesthetized and fit with a jugular-right atrial cannula. On day 8 an iv glucose tolerance test was performed and blood samples were withdrawn into heparinized syringes at time −10 and 0. Immediately after the time 0 blood sample, the rats were injected with glucose (1 g/kg) via the indwelling cannula. Subsequent blood samples were withdrawn at 2.5, 5, 10, 20 and 40 minutes later. Plasma levels of glucose (Diagnostic Chemicals Limited) and insulin (Alpco) were determined by commercially available kits. Results are shown in FIGS. 2A-D and 3A-D.

Glucose Tolerance Tests

Male, C57BL/6 mice that had been fed either a normal diet (30 g; Research Diets 12450) or a high fat diet (45 g; Research Diets 12452) for 12 weeks prior to the start of the experiment were housed in individual cages and maintained under 12:12 hour light:dark conditions with both food and water available ad libitum. The mice were anesthetized and implanted subcutaneously with an osmotic mini pump (Alzet, Cupertino, Calif.). The pumps delivered Compound A at doses of 200, 600 or 1800 nmole/kg/day, or vehicle for 14 days. On day 14 the mice were fasted for 18 hours or overnight. On day 15 an glucose tolerance test was performed by injecting the mice with glucose (2 g/kg) ip. Blood samples were taken by tail stick at 0, 15, 30, 60 and 180 minutes after the glucose injection and blood glucose level was measured using an Accu-Chek glucometer. Results are shown in FIG. 4.

Figure 5:
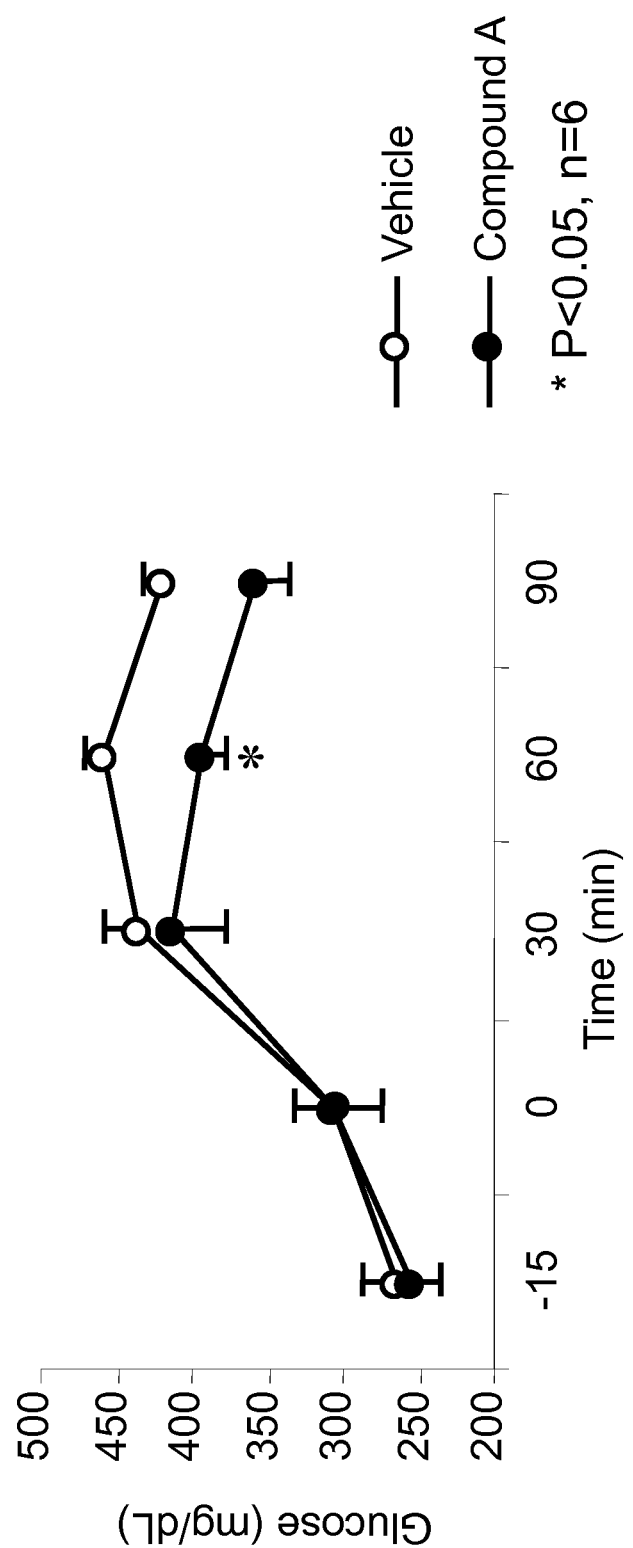
FIG. 5. Effect of intraperitoneal administration of 6.4 µmole/kg of Compound A upon blood glucose levels in obese mice.

Male, Lep$^{ob}$/Lep$^{ob}$ mice (50 g) were group housed maintained under 12:12 hour light:dark conditions with both food and water available ad libitum. The mice were fasted for 18 hours or overnight and an ip glucose tolerance test was performed. Mice were injected with Compound A ip at a dose of 6.4 µmole/kg at −15 minutes and a blood sample was taken by tail stick. At time 0 mice were injected ip with glucose (1 g/kg) and blood samples were taken by tail stick at 0, 15, 30, 60 and 90 minutes later and blood glucose level was measured using Glucometer Elite XL (Bayer Corporation). Results are shown in FIG. 5.

Administration and Use

The peptides of this invention can be provided in the form of pharmaceutically acceptable salts. Examples of such salts include, but are not limited to, those formed with organic acids (e.g., acetic, lactic, maleic, citric, malic, ascorbic, succinic, benzoic, methanesulfonic, toluenesulfonic, or pamoic acid), inorganic acids (e.g., hydrochloric acid, sulfuric acid, or phosphoric acid), and polymeric acids (e.g., tannic acid, carboxymethyl cellulose, polylactic, polyglycolic, or copolymers of polylactic-glycolic acids). A typical method of making a salt of a peptide of the present invention is well known in the art and can be accomplished by standard methods of salt exchange. Accordingly, the TFA salt of a peptide of the present invention (the TFA salt results from the purification of the peptide by using preparative HPLC, eluting with TFA containing buffer solutions) can be converted into another salt, such as an acetate salt, by dissolving the peptide in a small amount of 0.25 N acetic acid aqueous solution. The resulting solution is applied to a semi-prep HPLC column (Zorbax®, 300 SB, C-8). The column is eluted with: (1) 0.1N ammonium acetate aqueous solution for 0.5 hours; (2) 0.25N acetic acid aqueous solution for 0.5 hours; and (3) a linear gradient (20% to 100% of solution B over 30 minutes) at a flow rate of 4 ml/min (solution A is 0.25N acetic acid aqueous solution; solution B is 0.25N acetic acid in acetonitrile/water, 80:20). The fractions containing the peptide are collected and lyophilized to dryness.

As is well known to those skilled in the art, the known and potential uses of peptides with melanocortin receptor (MC-R) agonist or antagonist activity is varied and multitudinous, thus the administration of the compounds of this invention for purposes of eliciting an agonist effect can have the same effects and uses as melanocortin itself.

Accordingly, the present invention includes within its scope pharmaceutical compositions comprising, as an active ingredient, at least one of the compounds of formula (I) in association with a pharmaceutically acceptable carrier.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. In general, an effective dosage for the activities of this invention is in the range of $1 \times 10^{-7}$ to 200 mg/kg/day, preferably $1 \times 10^{-4}$ to 100 mg/kg/day which can be administered as a single dose or divided into multiple doses.

The compounds of this invention can be administered by oral, parenteral (e.g., intramuscular, intraperitoneal, intravenous or subcutaneous injection, or implant), nasal, vaginal, rectal, sublingual or topical routes of administration and can be formulated with pharmaceutically acceptable carriers to provide dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. Preparations may be sterilized by, for example, filtration through a bacteria-retaining filter, by incorporating sterilizing agents into the compositions, by irradiating the compositions, or by heating the compositions. Preparations can also be manufactured in the form of sterile solid compositions which can be dissolved in sterile water or some other sterile injectable medium immediately before use.

Compositions for rectal or vaginal administration are preferably suppositories which may contain, in addition to the active substance, excipients such as cocoa butter or a suppository wax.

Compositions for nasal or sublingual administration are also prepared with standard excipients well known in the art.

Further, a compound of this invention can be administered in a sustained release composition such as those described in the following patents and patent applications. U.S. Pat. No. 5,672,659 teaches sustained release compositions comprising a bioactive agent and a polyester. U.S. Pat. No. 5,595,760 teaches sustained release compositions comprising a bioactive agent in a gelable form. U.S. Pat. No. 5,821,221 teaches polymeric sustained release compositions comprising a bioactive agent and chitosan. U.S. Pat. No. 5,916,883 teaches sustained release compositions comprising a bioactive agent and cyclodextrin. The teachings of the foregoing patents and applications are incorporated herein by reference.

---

What is claimed is:

1. A method of treating insulin resistance in a subject in need thereof, comprising peripheral administration of an effective amount of Hydantoin(C(O)-(Arg-Gly))-c(Cys-Glu-His-D-Phe-Arg-Trp-Cys)-NH$_2$ (SEQ ID NO:278) or a pharmaceutically acceptable salt thereof to treat said insulin resistance in said subject.

2. The method according to claim 1, wherein said subject is obese or overweight.

3. The method according to claim 1, wherein said subject is normal weight or lean.

4. The method according to claim 1, wherein said peripheral administration is oral, subcutaneous, intraperitoneal, intramuscular, intravenous, rectal, transdermal or intranasal.

5. The method according to claim 4, wherein said administration is continuous, hourly, four times daily, three time daily, twice daily, once daily, once every other day, twice weekly, once weekly, once every two weeks, once a month, or once every two months.

6. The method according to claim 5, wherein said administration is once daily.

7. The method according to claim 5, wherein said administration is once every other day.

8. The method according to claim 5, wherein said administration is once weekly.

9. The method according to claim 1, wherein said subject is non-diabetic.

10. The method according to claim 1, wherein said subject suffers from Type II diabetes.

11. The method according to claim 1, wherein said method reduces the body weight of said subject in need thereof.

12. The method according to claim 11, wherein said subject is obese or overweight.

13. The method according to claim 11, wherein said peripheral administration is oral, subcutaneous, intraperitoneal, intramuscular, intravenous, rectal, transdermal or intranasal.

14. The method according to claim 13, wherein said administration is continuous, hourly, four times daily, three time daily, twice daily, once daily, once every other day, twice weekly, once weekly, once every two weeks, once a month, or once every two months.

15. The method according to claim 14, wherein said administration is once daily.

16. The method according to claim 14, wherein said administration is once every other day.

17. The method according to claim 14, wherein said administration is once weekly.

* * * * *

UNITED STATES PATENT AND TRADEMARK OFFICE
CERTIFICATE OF CORRECTION

PATENT NO. : 9,439,943 B2  
APPLICATION NO. : 14/844128  
DATED : September 13, 2016  
INVENTOR(S) : Heather A. Halem et al.

Page 1 of 1

It is certified that error appears in the above-identified patent and that said Letters Patent is hereby corrected as shown below:

On the Title Page

Item (73) add 2nd assignee:
Board of Supervisors of Louisiana State University and Agricultural and Mechanical College
Baton Rouge, LA In the Claims Please replace Lines 16-20 of Column 487 with:
Claim 5: The method according to claim 4, wherein said administration is continuous, hourly, four times daily, three times daily, twice daily, once daily, once every other day, twice weekly, once weekly, once every two weeks, once a month, or once every two months.

Please replace Lines 14-18 of Column 488 with:
Claim 14: The method according to claim 13, wherein said administration is continuous, hourly, four times daily, three times daily, twice daily, once daily, once every other day, twice weekly, once weekly, once every two weeks, once a month, or once every two months.

Signed and Sealed this
Thirty-first Day of October, 2017

Joseph Matal
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 335

<210> SEQ ID NO 1
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
```

```
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = beta-Ala or 1-amino-1-
      cyclohexanecarboxylic acid (A6c)
<220> FEATURE:
<221> NAME/KEY: MOD_RES
<222> LOCATION: (8)..(8)
<223> OTHER INFORMATION: AMIDATION

<400> SEQUENCE: 1

Xaa Asp His Xaa Arg Trp Xaa Lys
1               5

<210> SEQ ID NO 2
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 6-aminohexanoic acid (Ahx) or
      5-aminopentanoic acid (Apn)
<220> FEATURE:
<221> NAME/KEY: MOD_RES
<222> LOCATION: (8)..(8)
<223> OTHER INFORMATION: AMIDATION

<400> SEQUENCE: 2

Xaa Cys His Xaa Arg Trp Xaa Cys
1               5

<210> SEQ ID NO 3
<211> LENGTH: 9
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = Ala, beta-Ala or 4-aminobutyric acid
      (Gaba)
<220> FEATURE:
<221> NAME/KEY: MISC_FEATURE
<222> LOCATION: (8)..(8)
```

```
<223> OTHER INFORMATION: Xaa = D-Cys
<220> FEATURE:
<221> NAME/KEY: MOD_RES
<222> LOCATION: (9)..(9)
<223> OTHER INFORMATION: AMIDATION

<400> SEQUENCE: 3

Xaa Cys His Xaa Arg Trp Xaa Xaa Thr
1               5

<210> SEQ ID NO 4
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 5-aminopentanoic acid (Apn)
<220> FEATURE:
<221> NAME/KEY: MOD_RES
<222> LOCATION: (8)..(8)
<223> OTHER INFORMATION: AMIDATION

<400> SEQUENCE: 4

Xaa Asp His Xaa Arg Trp Xaa Lys
1               5

<210> SEQ ID NO 5
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = 1-amino-1-cyclohexanecarboxylic acid
      (A6c) modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MOD_RES
<222> LOCATION: (8)..(8)
<223> OTHER INFORMATION: AMIDATION

<400> SEQUENCE: 5

Xaa Asp His Xaa Arg Trp Xaa Lys
1               5
```

```
<210> SEQ ID NO 6
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = D-beta-(2-naphthyl)Ala (D-2-Nal), beta-
      cyclohexylAla (Cha) or Nle, all modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MOD_RES
<222> LOCATION: (8)..(8)
<223> OTHER INFORMATION: AMIDATION

<400> SEQUENCE: 6

Xaa Asp His Xaa Arg Trp Xaa Lys
1               5

<210> SEQ ID NO 7
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (3)..(3)
<223> OTHER INFORMATION: Xaa = D-Ala, beta-Ala, 4-aminobutyric acid
      (Gaba), alpha-aminoisobutyric acid (Aib) or Gly
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MOD_RES
<222> LOCATION: (8)..(8)
<223> OTHER INFORMATION: AMIDATION

<400> SEQUENCE: 7

Xaa Cys Xaa His Xaa Arg Trp Cys
1               5

<210> SEQ ID NO 8
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
```

```
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (2)..(2)
<223> OTHER INFORMATION: Xaa = D-Cys
<220> FEATURE:
<221> NAME/KEY: MISC_FEATURE
<222> LOCATION: (3)..(3)
<223> OTHER INFORMATION: Xaa = Ala, D-Ala, beta-Ala, 4-aminobutyric acid
      (Gaba), alpha-aminoisobutyric acid (Aib) or Gly
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MOD_RES
<222> LOCATION: (8)..(8)
<223> OTHER INFORMATION: AMIDATION

<400> SEQUENCE: 8

Xaa Xaa Xaa His Xaa Arg Trp Cys
1               5

<210> SEQ ID NO 9
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (3)..(3)
<223> OTHER INFORMATION: Xaa = D-Ala, beta-Ala, 4-aminobutyric acid
      (Gaba), alpha-aminoisobutyric acid (Aib) or Gly
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (8)..(8)
<223> OTHER INFORMATION: Xaa = D-Cys
<220> FEATURE:
<221> NAME/KEY: MOD_RES
<222> LOCATION: (8)..(8)
<223> OTHER INFORMATION: AMIDATION

<400> SEQUENCE: 9

Xaa Cys Xaa His Xaa Arg Trp Xaa
1               5

<210> SEQ ID NO 10
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
```

```
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (2)..(2)
<223> OTHER INFORMATION: Xaa = D-Cys
<220> FEATURE:
<221> NAME/KEY: MISC_FEATURE
<222> LOCATION: (3)..(3)
<223> OTHER INFORMATION: Xaa = Ala, D-Ala, beta-Ala, 4-aminobutyric acid
      (Gaba) or alpha-aminoisobutyric acid (Aib)
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (8)..(8)
<223> OTHER INFORMATION: Xaa = D-Cys
<220> FEATURE:
<221> NAME/KEY: MOD_RES
<222> LOCATION: (8)..(8)
<223> OTHER INFORMATION: AMIDATION

<400> SEQUENCE: 10

Xaa Xaa Xaa His Xaa Arg Trp Xaa
1               5

<210> SEQ ID NO 11
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = octahydroindole-2-carboxylic acid (Oic),
      cyclohexylGly (Chg), homo-cyclohexylAla (hCha), D-Cha,nipecotic
      acid (Nip), hPro, hLeu, Phe, D-Phe, D-Chg, hPhe, beta-homoMet, or
      4-aminobutyric acid (Gaba), all modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MOD_RES
<222> LOCATION: (8)..(8)
<223> OTHER INFORMATION: AMIDATION

<400> SEQUENCE: 11

Xaa Asp His Xaa Arg Trp Xaa Lys
1               5

<210> SEQ ID NO 12
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
```

```
<220> FEATURE:
<221> NAME/KEY: MISC_FEATURE
<222> LOCATION: (1)..(1)
<223> OTHER INFORMATION: Xaa = beta-cyclohexylAla (Cha) modified with
      n-butanoyl
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MOD_RES
<222> LOCATION: (8)..(8)
<223> OTHER INFORMATION: AMIDATION

<400> SEQUENCE: 12

Xaa Asp His Xaa Arg Trp Xaa Lys
1               5

<210> SEQ ID NO 13
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = beta-cyclohexylAla (Cha), homo-
      cyclohexylAla (hCha), Leu, homo-Leu (hLeu) or Phe, all modified
      with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (6)..(6)
<223> OTHER INFORMATION: Xaa = D-Trp
<220> FEATURE:
<221> NAME/KEY: MOD_RES
<222> LOCATION: (8)..(8)
<223> OTHER INFORMATION: AMIDATION

<400> SEQUENCE: 13

Xaa Asp His Xaa Arg Xaa Ala Lys
1               5

<210> SEQ ID NO 14
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
```

```
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (6)..(6)
<223> OTHER INFORMATION: Xaa = D-Trp
<220> FEATURE:
<221> NAME/KEY: MISC_FEATURE
<222> LOCATION: (7)..(7)
<223> OTHER INFORMATION: Xaa = D-Ala, beta-Ala, 4-aminobutyric acid
      (Gaba), 7-aminoheptanoic acid (Aha) or 5-aminopentanoic acid (Apn)
<220> FEATURE:
<221> NAME/KEY: MOD_RES
<222> LOCATION: (8)..(8)
<223> OTHER INFORMATION: AMIDATION

<400> SEQUENCE: 14

Xaa Asp His Xaa Arg Xaa Xaa Lys
1               5

<210> SEQ ID NO 15
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (6)..(6)
<223> OTHER INFORMATION: Xaa = D-Trp
<220> FEATURE:
<221> NAME/KEY: MISC_FEATURE
<222> LOCATION: (7)..(7)
<223> OTHER INFORMATION: Xaa = 5-aminopentanoic acid (Apn),
      4-aminobutyric acid (Gaba), 6-aminohexanoic acid (Ahx), beta-Ala,
      or D-Ala
<220> FEATURE:
<221> NAME/KEY: MOD_RES
<222> LOCATION: (8)..(8)
<223> OTHER INFORMATION: AMIDATION

<400> SEQUENCE: 15

Xaa Cys His Xaa Arg Xaa Xaa Cys
1               5

<210> SEQ ID NO 16
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
```

```
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-beta-(2-naphthyl)Ala (D-2-Nal)
<220> FEATURE:
<221> NAME/KEY: MISC_FEATURE
<222> LOCATION: (7)..(7)
<223> OTHER INFORMATION: Xaa = Trp, beta-(2-naphthyl)Ala (2-Nal) or
      beta-(1-naphthyl)Ala (1-Nal)
<220> FEATURE:
<221> NAME/KEY: MOD_RES
<222> LOCATION: (8)..(8)
<223> OTHER INFORMATION: AMIDATION

<400> SEQUENCE: 16

Xaa Cys Xaa His Xaa Arg Xaa Cys
1               5

<210> SEQ ID NO 17
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with n-butanoyl
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = beta-(2-naphthyl)Ala (2-Nal) or Trp
<220> FEATURE:
<221> NAME/KEY: MOD_RES
<222> LOCATION: (8)..(8)
<223> OTHER INFORMATION: AMIDATION

<400> SEQUENCE: 17

Xaa Cys Xaa His Xaa Arg Xaa Cys
1               5

<210> SEQ ID NO 18
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
```

```
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = beta-(2-naphthyl)Ala (2-Nal), beta-(1-
      naphthyl)Ala (1-Nal) or 3-benzothienylAla (Bal)
<220> FEATURE:
<221> NAME/KEY: MOD_RES
<222> LOCATION: (8)..(8)
<223> OTHER INFORMATION: AMIDATION

<400> SEQUENCE: 18

Xaa Cys Xaa His Xaa Arg Xaa Cys
1               5

<210> SEQ ID NO 19
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = D-Ala
<220> FEATURE:
<221> NAME/KEY: MOD_RES
<222> LOCATION: (8)..(8)
<223> OTHER INFORMATION: AMIDATION

<400> SEQUENCE: 19

Xaa Asp His Xaa Arg Trp Xaa Lys
1               5

<210> SEQ ID NO 20
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-beta-2-naphthylAla (D-2-Nal)
```

```
<220> FEATURE:
<221> NAME/KEY: MISC_FEATURE
<222> LOCATION: (7)..(7)
<223> OTHER INFORMATION: Xaa = 3-benzothienylAla (Bal)
<220> FEATURE:
<221> NAME/KEY: MOD_RES
<222> LOCATION: (8)..(8)
<223> OTHER INFORMATION: AMIDATION

<400> SEQUENCE: 20

Xaa Cys Xaa His Xaa Arg Xaa Cys
1               5

<210> SEQ ID NO 21
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (2)..(2)
<223> OTHER INFORMATION: Xaa = penicillamine (Pen)
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MOD_RES
<222> LOCATION: (8)..(8)
<223> OTHER INFORMATION: AMIDATION

<400> SEQUENCE: 21

Xaa Xaa Xaa His Xaa Arg Trp Cys
1               5

<210> SEQ ID NO 22
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (2)..(2)
<223> OTHER INFORMATION: Xaa = Cys or penicillamine (Pen)
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
```

```
<223> OTHER INFORMATION: Xaa = D-Phe
<220> FEATURE:
<221> NAME/KEY: MISC_FEATURE
<222> LOCATION: (8)..(8)
<223> OTHER INFORMATION: Xaa = penicillamine (Pen)
<220> FEATURE:
<221> NAME/KEY: MOD_RES
<222> LOCATION: (8)..(8)
<223> OTHER INFORMATION: AMIDATION

<400> SEQUENCE: 22

Xaa Xaa Xaa His Xaa Arg Trp Xaa
1               5

<210> SEQ ID NO 23
<211> LENGTH: 9
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (5)..(5)
<223> OTHER INFORMATION: Xaa = homo-Arg (hArg)
<220> FEATURE:
<221> NAME/KEY: MISC_FEATURE
<222> LOCATION: (7)..(7)
<223> OTHER INFORMATION: Xaa = beta-Ala
<220> FEATURE:
<221> NAME/KEY: MISC_FEATURE
<222> LOCATION: (8)..(8)
<223> OTHER INFORMATION: Xaa = D-Cys
<220> FEATURE:
<221> NAME/KEY: MOD_RES
<222> LOCATION: (9)..(9)
<223> OTHER INFORMATION: AMIDATION

<400> SEQUENCE: 23

Xaa Cys His Xaa Xaa Trp Xaa Xaa Thr
1               5

<210> SEQ ID NO 24
<211> LENGTH: 9
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-(Et)Tyr
<220> FEATURE:
<221> NAME/KEY: MISC_FEATURE
```

```
<222> LOCATION: (5)..(5)
<223> OTHER INFORMATION: Xaa = Arg or homo-Arg (hArg)
<220> FEATURE:
<221> NAME/KEY: MISC_FEATURE
<222> LOCATION: (7)..(7)
<223> OTHER INFORMATION: Xaa = beta-Ala
<220> FEATURE:
<221> NAME/KEY: MISC_FEATURE
<222> LOCATION: (8)..(8)
<223> OTHER INFORMATION: Xaa = D-Cys
<220> FEATURE:
<221> NAME/KEY: MOD_RES
<222> LOCATION: (9)..(9)
<223> OTHER INFORMATION: AMIDATION

<400> SEQUENCE: 24

Xaa Cys His Xaa Xaa Trp Xaa Xaa Thr
1               5

<210> SEQ ID NO 25
<211> LENGTH: 9
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (6)..(6)
<223> OTHER INFORMATION: Xaa = 4,4'-biphenylAla (Bip)
<220> FEATURE:
<221> NAME/KEY: MISC_FEATURE
<222> LOCATION: (7)..(7)
<223> OTHER INFORMATION: Xaa = beta-Ala
<220> FEATURE:
<221> NAME/KEY: MISC_FEATURE
<222> LOCATION: (8)..(8)
<223> OTHER INFORMATION: Xaa = D-Cys
<220> FEATURE:
<221> NAME/KEY: MOD_RES
<222> LOCATION: (9)..(9)
<223> OTHER INFORMATION: AMIDATION

<400> SEQUENCE: 25

Xaa Cys His Xaa Arg Xaa Xaa Xaa Thr
1               5

<210> SEQ ID NO 26
<211> LENGTH: 9
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = D-Phe
<220> FEATURE:
<221> NAME/KEY: DOMAIN
<222> LOCATION: (2)..(8)
<223> OTHER INFORMATION: Cyclic
<220> FEATURE:
```

```
<221> NAME/KEY: MISC_FEATURE
<222> LOCATION: (4)..(4)
<223> OTHER INFORMATION: Xaa = D-Phe or D-(Et)Tyr
<220> FEATURE:
<221> NAME/KEY: MISC_FEATURE
<222> LOCATION: (5)..(5)
<223> OTHER INFORMATION: Xaa = homo-Arg (hArg)
<220> FEATURE:
<221> NAME/KEY: MISC_FEATURE
<222> LOCATION: (6)..(6)
<223> OTHER INFORMATION: Xaa = 4,4'-biphenylAla (Bip)
<220> FEATURE:
<221> NAME/KEY: MISC_FEATURE
<222> LOCATION: (7)..(7)
<223> OTHER INFORMATION: Xaa = beta-Ala
<220> FEATURE:
<221> NAME/KEY: MISC_FEATURE
<222> LOCATION: (8)..(8)
<223> OTHER INFORMATION: Xaa = D-Cys
<220> FEATURE:
<221> NAME/KEY: MOD_RES
<222> LOCATION: (9)..(9)
<223> OTHER INFORMATION: AMIDATION

<400> SEQUENCE: 26

Xaa Cys His Xaa Xaa Xaa Xaa Xaa Thr
1               5

<210> SEQ ID NO 27
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 5-aminopentanoic acid (Apn)
<220> FEATURE:
<221> NAME/KEY: MOD_RES
<222> LOCATION: (8)..(8)
<223> OTHER INFORMATION: AMIDATION

<400> SEQUENCE: 27

Xaa Cys His Xaa Arg Trp Xaa Cys
1               5

<210> SEQ ID NO 28
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
```

```
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = Trp or 3-benzothienylAla (Bal)
<220> FEATURE:
<221> NAME/KEY: MOD_RES
<222> LOCATION: (8)..(8)
<223> OTHER INFORMATION: AMIDATION

<400> SEQUENCE: 28

Xaa Asp Xaa His Xaa Arg Xaa Lys
1               5

<210> SEQ ID NO 29
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (8)..(8)
<223> OTHER INFORMATION: Xaa = penicillamine (Pen) or Cys
<220> FEATURE:
<221> NAME/KEY: MOD_RES
<222> LOCATION: (8)..(8)
<223> OTHER INFORMATION: C-terminus is the free acid

<400> SEQUENCE: 29

Xaa Cys Xaa His Xaa Arg Trp Xaa
1               5

<210> SEQ ID NO 30
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (3)..(3)
```

```
<223> OTHER INFORMATION: Xaa = D-alpha-aminobutyric acid (D-Abu),  D-Val,
      D-Ile, D-Leu, D-tert-Leu (D-Tle) or D-beta-cyclohexylAla (D-Cha)
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MOD_RES
<222> LOCATION: (8)..(8)
<223> OTHER INFORMATION: AMIDATION

<400> SEQUENCE: 30

Xaa Cys Xaa His Xaa Arg Trp Cys
1               5

<210> SEQ ID NO 31
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (2)..(2)
<223> OTHER INFORMATION: Xaa = penicillamine (Pen)
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MOD_RES
<222> LOCATION: (8)..(8)
<223> OTHER INFORMATION: AMIDATION

<400> SEQUENCE: 31

Xaa Xaa His Xaa Arg Trp Xaa Cys
1               5

<210> SEQ ID NO 32
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (2)..(2)
<223> OTHER INFORMATION: Xaa = Cys or penicillamine (Pen)
<220> FEATURE:
<221> NAME/KEY: MISC_FEATURE
<222> LOCATION: (4)..(4)
<223> OTHER INFORMATION: Xaa = D-Phe
<220> FEATURE:
```

```
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MISC_FEATURE
<222> LOCATION: (8)..(8)
<223> OTHER INFORMATION: Xaa = penicillamine (Pen)
<220> FEATURE:
<221> NAME/KEY: MOD_RES
<222> LOCATION: (8)..(8)
<223> OTHER INFORMATION: AMIDATION

<400> SEQUENCE: 32

Xaa Xaa His Xaa Arg Trp Xaa Xaa
1               5

<210> SEQ ID NO 33
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Leu, beta-cyclohexylAla (Cha), Ile, Phe,
      Val or beta-(2-naphthyl)Ala (2-Nal), all modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MOD_RES
<222> LOCATION: (8)..(8)
<223> OTHER INFORMATION: AMIDATION

<400> SEQUENCE: 33

Xaa Cys His Xaa Arg Trp Xaa Cys
1               5

<210> SEQ ID NO 34
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle or Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MOD_RES
<222> LOCATION: (8)..(8)
```

```
<223> OTHER INFORMATION: AMIDATION

<400> SEQUENCE: 34

Xaa Cys His Xaa Arg Trp Xaa Cys
1               5

<210> SEQ ID NO 35
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (3)..(3)
<223> OTHER INFORMATION: Xaa =  beta-(3-pyridiyl)Ala (3-Pal)
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MOD_RES
<222> LOCATION: (8)..(8)
<223> OTHER INFORMATION: AMIDATION

<400> SEQUENCE: 35

Xaa Cys Xaa Xaa Arg Trp Xaa Cys
1               5

<210> SEQ ID NO 36
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MOD_RES
<222> LOCATION: (8)..(8)
<223> OTHER INFORMATION: C-terminus is the free acid

<400> SEQUENCE: 36

Xaa Cys Xaa His Xaa Arg Trp Cys
1               5
```

```
<210> SEQ ID NO 37
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (6)..(6)
<223> OTHER INFORMATION: Xaa = D-Trp
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MOD_RES
<222> LOCATION: (8)..(8)
<223> OTHER INFORMATION: AMIDATION

<400> SEQUENCE: 37

Xaa Cys His Phe Arg Xaa Xaa Cys
1               5

<210> SEQ ID NO 38
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (7)..(7)
<223> OTHER INFORMATION: Xaa = Ala or beta-Ala
<220> FEATURE:
<221> NAME/KEY: MOD_RES
<222> LOCATION: (8)..(8)
<223> OTHER INFORMATION: AMIDATION

<400> SEQUENCE: 38

Xaa Asp His Xaa Arg Trp Xaa Lys
1               5

<210> SEQ ID NO 39
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
```

```
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (7)..(7)
<223> OTHER INFORMATION: Xaa = 4-aminobutyric acid (Gaba) or 6-
      aminohexanoic acid (Ahx)
<220> FEATURE:
<221> NAME/KEY: MOD_RES
<222> LOCATION: (8)..(8)
<223> OTHER INFORMATION: AMIDATION

<400> SEQUENCE: 39

Xaa Cys His Xaa Arg Trp Xaa Cys
1               5

<210> SEQ ID NO 40
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = homo-Phe (hPhe) or beta-cyclohexylAla
      (Cha), both modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MOD_RES
<222> LOCATION: (8)..(8)
<223> OTHER INFORMATION: AMIDATION

<400> SEQUENCE: 40

Xaa Asp His Xaa Arg Trp Xaa Lys
1               5

<210> SEQ ID NO 41
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
```

```
<220> FEATURE:
<221> NAME/KEY: MISC_FEATURE
<222> LOCATION: (7)..(7)
<223> OTHER INFORMATION: Xaa = beta-Ala or 5-aminopentanoic acid (Apn)
<220> FEATURE:
<221> NAME/KEY: MOD_RES
<222> LOCATION: (8)..(8)
<223> OTHER INFORMATION: C-terminus is the free acid

<400> SEQUENCE: 41

Xaa Asp His Xaa Arg Trp Xaa Lys
1               5

<210> SEQ ID NO 42
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 6-aminohexanoic acid (Ahx) or
      5-aminopentanoic acid (Apn)
<220> FEATURE:
<221> NAME/KEY: MOD_RES
<222> LOCATION: (8)..(8)
<223> OTHER INFORMATION: C-terminus is the free acid

<400> SEQUENCE: 42

Xaa Cys His Xaa Arg Trp Xaa Cys
1               5

<210> SEQ ID NO 43
<211> LENGTH: 9
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = Ala, beta-Ala or 4-aminobutyric acid
      (Gaba)
<220> FEATURE:
<221> NAME/KEY: MISC_FEATURE
<222> LOCATION: (8)..(8)
<223> OTHER INFORMATION: Xaa = D-Cys
<220> FEATURE:
```

```
<221> NAME/KEY: MOD_RES
<222> LOCATION: (9)..(9)
<223> OTHER INFORMATION: C-terminus is the free acid

<400> SEQUENCE: 43

Xaa Cys His Xaa Arg Trp Xaa Xaa Thr
1               5

<210> SEQ ID NO 44
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = beta-cyclohexylAla (Cha), Nle,
      cyclohexylGly (Chg), D-Cha, homo-cyclohexylAla (hCha), D-Chg or
      homo-Phe (hPhe), all modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MOD_RES
<222> LOCATION: (8)..(8)
<223> OTHER INFORMATION: C-terminus is the free acid

<400> SEQUENCE: 44

Xaa Asp His Xaa Arg Trp Xaa Lys
1               5

<210> SEQ ID NO 45
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (6)..(6)
<223> OTHER INFORMATION: Xaa = D-Trp
<220> FEATURE:
<221> NAME/KEY: MISC_FEATURE
<222> LOCATION: (7)..(7)
<223> OTHER INFORMATION: Xaa = 4-aminobutyric acid (Gaba),
      6-aminohexanoic acid (Ahx), beta-Ala or D-Ala
<220> FEATURE:
<221> NAME/KEY: MOD_RES
<222> LOCATION: (8)..(8)
<223> OTHER INFORMATION: C-terminus is the free acid
```

```
<400> SEQUENCE: 45

Xaa Cys His Xaa Arg Xaa Xaa Cys
1               5

<210> SEQ ID NO 46
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-beta-(2-naphthyl)Ala (D-2-Nal)
<220> FEATURE:
<221> NAME/KEY: MISC_FEATURE
<222> LOCATION: (7)..(7)
<223> OTHER INFORMATION: Xaa = Trp, beta-(2-naphthyl)Ala (2-Nal),
      beta-(1-naphthyl)Ala (1-Nal) or 3-benzothienylalanine (Bal)
<220> FEATURE:
<221> NAME/KEY: MOD_RES
<222> LOCATION: (8)..(8)
<223> OTHER INFORMATION: C-terminus is the free acid

<400> SEQUENCE: 46

Xaa Cys Xaa His Xaa Arg Xaa Cys
1               5

<210> SEQ ID NO 47
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (2)..(2)
<223> OTHER INFORMATION: Xaa = penicillamine (Pen)
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MOD_RES
<222> LOCATION: (8)..(8)
<223> OTHER INFORMATION: C-terminus is the free acid

<400> SEQUENCE: 47
```

Xaa Xaa Xaa His Xaa Arg Trp Cys
1               5

<210> SEQ ID NO 48
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MISC_FEATURE
<222> LOCATION: (8)..(8)
<223> OTHER INFORMATION: Xaa = penicillamine (Pen)
<220> FEATURE:
<221> NAME/KEY: MOD_RES
<222> LOCATION: (8)..(8)
<223> OTHER INFORMATION: C-terminus is the free acid

<400> SEQUENCE: 48

Xaa Cys His Xaa Arg Trp Xaa Xaa
1               5

<210> SEQ ID NO 49
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-beta-(2-naphthyl)Ala (D-2-Nal)
<220> FEATURE:
<221> NAME/KEY: MOD_RES
<222> LOCATION: (8)..(8)
<223> OTHER INFORMATION: AMIDATION

<400> SEQUENCE: 49

Arg Cys Xaa His Xaa Arg Trp Cys
1               5

<210> SEQ ID NO 50
<211> LENGTH: 8
<212> TYPE: PRT

```
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Arg or D-Arg, both modified with acyl
      (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MOD_RES
<222> LOCATION: (8)..(8)
<223> OTHER INFORMATION: AMIDATION

<400> SEQUENCE: 50

Xaa Cys Xaa His Xaa Arg Trp Cys
1               5

<210> SEQ ID NO 51
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = D-Arg or Arg, both modified with acyl
      (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (8)..(8)
<223> OTHER INFORMATION: Xaa = penicillamine (Pen)
<220> FEATURE:
<221> NAME/KEY: MOD_RES
<222> LOCATION: (8)..(8)
<223> OTHER INFORMATION: AMIDATION

<400> SEQUENCE: 51

Xaa Cys Xaa His Xaa Arg Trp Xaa
1               5

<210> SEQ ID NO 52
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
```

```
<221> NAME/KEY: MISC_FEATURE
<222> LOCATION: (1)..(1)
<223> OTHER INFORMATION: Xaa = D-Arg or Arg, both modified with acyl
      (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MISC_FEATURE
<222> LOCATION: (8)..(8)
<223> OTHER INFORMATION: Xaa = penicillamine (Pen)
<220> FEATURE:
<221> NAME/KEY: MOD_RES
<222> LOCATION: (8)..(8)
<223> OTHER INFORMATION: AMIDATION

<400> SEQUENCE: 52

Xaa Cys His Xaa Arg Trp Xaa Xaa
1               5

<210> SEQ ID NO 53
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = D-Arg or Arg, both modified with acyl
      (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (8)..(8)
<223> OTHER INFORMATION: AMIDATION

<400> SEQUENCE: 53

Xaa Asp His Xaa Arg Trp Ala Lys
1               5

<210> SEQ ID NO 54
<211> LENGTH: 9
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(9)
<223> OTHER INFORMATION: Cyclic
<220> FEATURE:
<221> NAME/KEY: MISC_FEATURE
```

```
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (8)..(8)
<223> OTHER INFORMATION: Xaa = Gly, D-Ala, beta-Ala, 4-aminobutyric
      acid (Gaba) or 5-aminopentanoic acid (Apn)
<220> FEATURE:
<221> NAME/KEY: MOD_RES
<222> LOCATION: (9)..(9)
<223> OTHER INFORMATION: AMIDATION

<400> SEQUENCE: 54

Xaa Cys Xaa His Xaa Arg Trp Xaa Cys
1               5

<210> SEQ ID NO 55
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (6)..(6)
<223> OTHER INFORMATION: Xaa = Trp or beta-(2-naphthyl)alanine (2-Nal)
<220> FEATURE:
<221> NAME/KEY: MOD_RES
<222> LOCATION: (8)..(8)
<223> OTHER INFORMATION: AMIDATION

<400> SEQUENCE: 55

Cys Glu His Xaa Arg Xaa Ala Cys
1               5

<210> SEQ ID NO 56
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<223> OTHER INFORMATION: Cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
```

```
<220> FEATURE:
<221> NAME/KEY: MISC_FEATURE
<222> LOCATION: (6)..(6)
<223> OTHER INFORMATION: Xaa = Trp or beta-(2-naphthyl)Ala (2-Nal)
<220> FEATURE:
<221> NAME/KEY: MOD_RES
<222> LOCATION: (8)..(8)
<223> OTHER INFORMATION: AMIDATION

<400> SEQUENCE: 56

Cys Xaa His Xaa Arg Xaa Ala Cys
1               5

<210> SEQ ID NO 57
<211> LENGTH: 9
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(9)
<223> OTHER INFORMATION: Cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (8)..(8)
<223> OTHER INFORMATION: Xaa = Ala, beta-Ala or 4-aminobutyric acid
      (Gaba)
<220> FEATURE:
<221> NAME/KEY: MOD_RES
<222> LOCATION: (9)..(9)
<223> OTHER INFORMATION: AMIDATION

<400> SEQUENCE: 57

Xaa Cys Xaa His Xaa Arg Trp Xaa Cys
1               5

<210> SEQ ID NO 58
<211> LENGTH: 9
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(9)
<223> OTHER INFORMATION: Cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
```

```
<222> LOCATION: (7)..(7)
<223> OTHER INFORMATION: Xaa = 3-benzothienylAla (Bal)
<220> FEATURE:
<221> NAME/KEY: MOD_RES
<222> LOCATION: (9)..(9)
<223> OTHER INFORMATION: AMIDATION

<400> SEQUENCE: 58

Xaa Asp Xaa His Xaa Arg Xaa Ala Lys
1               5

<210> SEQ ID NO 59
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (3)..(3)
<223> OTHER INFORMATION: Xaa = D-Glu
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MOD_RES
<222> LOCATION: (8)..(8)
<223> OTHER INFORMATION: AMIDATION

<400> SEQUENCE: 59

Xaa Cys Xaa His Xaa Arg Trp Cys
1               5

<210> SEQ ID NO 60
<211> LENGTH: 18
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (12)..(12)
<223> OTHER INFORMATION: Xaa = Nle
<220> FEATURE:
<221> NAME/KEY: DOMAIN
<222> LOCATION: (13)..(18)
<223> OTHER INFORMATION: cyclic
<220> FEATURE:
<221> NAME/KEY: MISC_FEATURE
<222> LOCATION: (15)..(15)
<223> OTHER INFORMATION: Xaa = D-beta-(2-naphthyl)Ala (D-2-Nal)
<220> FEATURE:
<221> NAME/KEY: MOD_RES
<222> LOCATION: (18)..(18)
<223> OTHER INFORMATION: AMIDATION

<400> SEQUENCE: 60

Tyr Gly Arg Lys Lys Arg Arg Gln Arg Arg Arg Xaa Asp His Xaa Arg
1               5                   10                  15

Trp Lys
```

```
<210> SEQ ID NO 61
<211> LENGTH: 19
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (12)..(12)
<223> OTHER INFORMATION: Xaa = 8-amino-3,6-dioxaoctanoic acid (Doc)
<220> FEATURE:
<221> NAME/KEY: MISC_FEATURE
<222> LOCATION: (13)..(13)
<223> OTHER INFORMATION: Xaa = Nle
<220> FEATURE:
<221> NAME/KEY: DOMAIN
<222> LOCATION: (14)..(19)
<223> OTHER INFORMATION: cyclic
<220> FEATURE:
<221> NAME/KEY: MISC_FEATURE
<222> LOCATION: (16)..(16)
<223> OTHER INFORMATION: Xaa = D-beta-(2-naphthyl)Ala (D-2-Nal)
<220> FEATURE:
<221> NAME/KEY: MOD_RES
<222> LOCATION: (19)..(19)
<223> OTHER INFORMATION: AMIDATION

<400> SEQUENCE: 61

Tyr Gly Arg Lys Lys Arg Arg Gln Arg Arg Xaa Xaa Asp His Xaa
1               5                   10                  15

Arg Trp Lys

<210> SEQ ID NO 62
<211> LENGTH: 19
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle or Nle modified with acyl (Ac)
<220> FEATURE:
<221> NAME/KEY: DOMAIN
<222> LOCATION: (2)..(7)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (8)..(8)
<223> OTHER INFORMATION: Xaa = beta-Ala
<220> FEATURE:
<221> NAME/KEY: MOD_RES
<222> LOCATION: (19)..(19)
<223> OTHER INFORMATION: AMIDATION

<400> SEQUENCE: 62

Xaa Asp His Xaa Arg Trp Lys Xaa Tyr Gly Arg Lys Lys Arg Arg Gln
1               5                   10                  15

Arg Arg Arg

<210> SEQ ID NO 63
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
```

```
<220> FEATURE:
<221> NAME/KEY: MISC_FEATURE
<222> LOCATION: (1)..(1)
<223> OTHER INFORMATION: Xaa = Nle
<220> FEATURE:
<221> NAME/KEY: DOMAIN
<222> LOCATION: (2)..(7)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (8)..(9)
<223> OTHER INFORMATION: Xaa = 8-amino-3,6-dioxaoctanoic acid (Doc)
<220> FEATURE:
<221> NAME/KEY: MOD_RES
<222> LOCATION: (20)..(20)
<223> OTHER INFORMATION: AMIDATION

<400> SEQUENCE: 63

Xaa Asp His Xaa Arg Trp Lys Xaa Xaa Tyr Gly Arg Lys Lys Arg Arg
1               5                   10                  15

Gln Arg Arg Arg
            20

<210> SEQ ID NO 64
<211> LENGTH: 22
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(7)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MOD_RES
<222> LOCATION: (22)..(22)
<223> OTHER INFORMATION: AMIDATION

<400> SEQUENCE: 64

Xaa Asp His Xaa Arg Trp Lys Pro Pro Lys Asp Tyr Gly Arg Lys Lys
1               5                   10                  15

Arg Arg Gln Arg Arg Arg
            20

<210> SEQ ID NO 65
<211> LENGTH: 23
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: DOMAIN
<222> LOCATION: (1)..(8)
<223> OTHER INFORMATION: cyclic
<220> FEATURE:
<221> NAME/KEY: MOD_RES
<222> LOCATION: (1)..(1)
<223> OTHER INFORMATION: modified with acyl (Ac)
<220> FEATURE:
```

```
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MOD_RES
<222> LOCATION: (23)..(23)
<223> OTHER INFORMATION: AMIDATION

<400> SEQUENCE: 65

Cys Glu His Xaa Arg Trp Gly Cys Pro Pro Lys Asp Tyr Gly Arg Lys
1               5                   10                  15

Lys Arg Gln Arg Arg Arg
            20

<210> SEQ ID NO 66
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(7)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (8)..(9)
<223> OTHER INFORMATION: Xaa = beta-Ala
<220> FEATURE:
<221> NAME/KEY: MOD_RES
<222> LOCATION: (20)..(20)
<223> OTHER INFORMATION: AMIDATION

<400> SEQUENCE: 66

Xaa Asp His Xaa Arg Trp Lys Xaa Xaa Tyr Gly Arg Lys Lys Arg Arg
1               5                   10                  15

Gln Arg Arg Arg
            20

<210> SEQ ID NO 67
<211> LENGTH: 23
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(7)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (12)..(12)
<223> OTHER INFORMATION: Xaa = 8-amino-3,6-dioxaoctanoic acid (Doc)
<220> FEATURE:
<221> NAME/KEY: MOD_RES
```

```
<222> LOCATION: (23)..(23)
<223> OTHER INFORMATION: AMIDATION

<400> SEQUENCE: 67

Xaa Asp His Xaa Arg Trp Lys Pro Pro Lys Asp Xaa Tyr Gly Arg Lys
1               5                   10                  15

Lys Arg Arg Gln Arg Arg Arg
            20

<210> SEQ ID NO 68
<211> LENGTH: 24
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: DOMAIN
<222> LOCATION: (1)..(8)
<223> OTHER INFORMATION: cyclic
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (13)..(13)
<223> OTHER INFORMATION: Xaa = 8-amino-3,6-dioxaoctanoic acid (Doc)
<220> FEATURE:
<221> NAME/KEY: MOD_RES
<222> LOCATION: (24)..(24)
<223> OTHER INFORMATION: AMIDATION

<400> SEQUENCE: 68

Cys Glu His Xaa Arg Trp Gly Cys Pro Pro Lys Asp Xaa Tyr Gly Arg
1               5                   10                  15

Lys Lys Arg Arg Gln Arg Arg Arg
            20

<210> SEQ ID NO 69
<211> LENGTH: 24
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: DOMAIN
<222> LOCATION: (1)..(8)
<223> OTHER INFORMATION: cyclic
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (13)..(13)
<223> OTHER INFORMATION: Xaa = beta-Ala or 8-amino-3,6-dioxaoctanoic
      acid (Doc)
<220> FEATURE:
<221> NAME/KEY: MOD_RES
<222> LOCATION: (24)..(24)
<223> OTHER INFORMATION: AMIDATION

<400> SEQUENCE: 69
```

Cys Glu His Xaa Arg Trp Ala Cys Pro Pro Lys Asp Xaa Tyr Gly Arg
1               5                   10                  15

Lys Lys Arg Arg Gln Arg Arg
            20

<210> SEQ ID NO 70
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(7)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (8)..(9)
<223> OTHER INFORMATION: Xaa = 8-amino-3,6-dioxaoctanoic acid  (Doc)
<220> FEATURE:
<221> NAME/KEY: MOD_RES
<222> LOCATION: (20)..(20)
<223> OTHER INFORMATION: AMIDATION

<400> SEQUENCE: 70

Xaa Asp His Xaa Arg Trp Lys Xaa Xaa Tyr Gly Arg Lys Lys Arg Arg
1               5                   10                  15

Gln Arg Arg Arg
            20

<210> SEQ ID NO 71
<211> LENGTH: 24
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: DOMAIN
<222> LOCATION: (1)..(8)
<223> OTHER INFORMATION: cyclic
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = beta-(2-naphthyl)Ala (2-Nal), beta-(1-
      naphthyl)Ala (1-Nal) or 3-benzothienylAla (Bal)
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (24)..(24)
<223> OTHER INFORMATION: AMIDATION

<400> SEQUENCE: 71

```
Cys Glu His Xaa Arg Xaa Ala Cys Pro Pro Lys Asp Xaa Tyr Gly Arg
1               5                   10                  15

Lys Lys Arg Arg Gln Arg Arg Arg
            20

<210> SEQ ID NO 72
<211> LENGTH: 22
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: DOMAIN
<222> LOCATION: (1)..(8)
<223> OTHER INFORMATION: cyclic
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = 3-benzothienylAla (Bal)
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (22)..(22)
<223> OTHER INFORMATION: AMIDATION

<400> SEQUENCE: 72

Cys Glu His Xaa Arg Xaa Ala Cys Pro Pro Lys Asp Xaa Arg Arg Arg
1               5                   10                  15

Arg Arg Gln Arg Arg Arg
            20

<210> SEQ ID NO 73
<211> LENGTH: 23
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: DOMAIN
<222> LOCATION: (1)..(8)
<223> OTHER INFORMATION: cyclic
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (4)..(4)
<223> OTHER INFORMATION: Xaa = beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = 3-benzothienylAla (Bal)
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (23)..(23)
```

<223> OTHER INFORMATION: AMIDATION

<400> SEQUENCE: 73

Cys Glu His Xaa Arg Xaa Ala Cys Pro Pro Lys Asp Xaa Gly Arg Arg
1               5                   10                  15

Arg Arg Arg Gln Arg Arg Arg
            20

<210> SEQ ID NO 74
<211> LENGTH: 24
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: DOMAIN
<222> LOCATION: (1)..(8)
<223> OTHER INFORMATION: cyclic
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = 3-benzothienylAla (Bal)
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (24)..(24)
<223> OTHER INFORMATION: AMIDATION

<400> SEQUENCE: 74

Cys Glu His Xaa Arg Xaa Ala Cys Pro Pro Lys Asp Xaa Tyr Gly Arg
1               5                   10                  15

Arg Arg Arg Arg Gln Arg Arg Arg
            20

<210> SEQ ID NO 75
<211> LENGTH: 24
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: DOMAIN
<222> LOCATION: (1)..(8)
<223> OTHER INFORMATION: cyclic
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (24)..(24)
<223> OTHER INFORMATION: AMIDATION -continued

<400> SEQUENCE: 75

Cys Glu His Xaa Arg Trp Ala Cys Pro Pro Lys Asp Xaa Tyr Gly Arg
1               5                   10                  15

Lys Lys Arg Gln Arg Arg Arg Arg
            20

<210> SEQ ID NO 76
<211> LENGTH: 24
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: DOMAIN
<222> LOCATION: (1)..(8)
<223> OTHER INFORMATION: cyclic
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (24)..(24)
<223> OTHER INFORMATION: AMIDATION

<400> SEQUENCE: 76

Cys Glu His Xaa Arg Trp Ala Cys Pro Pro Lys Asp Xaa Tyr Gly Arg
1               5                   10                  15

Lys Lys Gln Arg Arg Arg Arg Arg
            20

<210> SEQ ID NO 77
<211> LENGTH: 24
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: DOMAIN
<222> LOCATION: (1)..(8)
<223> OTHER INFORMATION: cyclic
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (24)..(24)
<223> OTHER INFORMATION: AMIDATION

<400> SEQUENCE: 77

Cys Glu His Xaa Arg Trp Ala Cys Pro Pro Lys Asp Xaa Tyr Gly Arg
1               5                   10                  15

```
Lys Gln Lys Arg Arg Arg Arg Arg
            20

<210> SEQ ID NO 78
<211> LENGTH: 24
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: DOMAIN
<222> LOCATION: (1)..(8)
<223> OTHER INFORMATION: cyclic
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (24)..(24)
<223> OTHER INFORMATION: AMIDATION

<400> SEQUENCE: 78

Cys Glu His Xaa Arg Trp Ala Cys Pro Pro Lys Asp Xaa Tyr Gly Arg
1               5                   10                  15

Lys Lys Arg Arg Arg Arg Gln Arg
            20

<210> SEQ ID NO 79
<211> LENGTH: 24
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: DOMAIN
<222> LOCATION: (1)..(8)
<223> OTHER INFORMATION: cyclic
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = 3-benzothienylAla (Bal)
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MISC_FEATURE
<222> LOCATION: (15)..(15)
<223> OTHER INFORMATION: Xaa = alpha-aminoisobutyric acid (Aib)
<220> FEATURE:
<221> NAME/KEY: MOD_RES
<222> LOCATION: (24)..(24)
<223> OTHER INFORMATION: AMIDATION

<400> SEQUENCE: 79
```

Cys Glu His Xaa Arg Xaa Ala Cys Pro Pro Lys Asp Xaa Tyr Xaa Arg
1               5                   10                  15

Lys Lys Arg Arg Gln Arg Arg Arg
            20

<210> SEQ ID NO 80
<211> LENGTH: 22
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: DOMAIN
<222> LOCATION: (1)..(8)
<223> OTHER INFORMATION: cyclic
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = beta-(1-naphthyl)Ala (1-Nal)
<220> FEATURE:
<221> NAME/KEY: MISC_FEATURE
<222> LOCATION: (11)..(11)
<223> OTHER INFORMATION: Xaa = Arg or Lys
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (22)..(22)
<223> OTHER INFORMATION: AMIDATION

<400> SEQUENCE: 80

Cys Glu His Xaa Arg Xaa Ala Cys Pro Pro Xaa Asp Xaa Arg Arg Arg
1               5                   10                  15

Arg Arg Gln Arg Arg Arg
            20

<210> SEQ ID NO 81
<211> LENGTH: 23
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: DOMAIN
<222> LOCATION: (1)..(8)
<223> OTHER INFORMATION: cyclic
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = beta-(1-naphthyl)Ala (1-Nal) or beta-
      (2-naphthyl)Ala (2-Nal)
<220> FEATURE:
<221> NAME/KEY: MISC_FEATURE

```
<222> LOCATION: (13)..(13)
<223> OTHER INFORMATION: Xaa = beta-Ala
<220> FEATURE:
<221> NAME/KEY: MOD_RES
<222> LOCATION: (23)..(23)
<223> OTHER INFORMATION: AMIDATION

<400> SEQUENCE: 81

Cys Glu His Xaa Arg Xaa Ala Cys Pro Pro Lys Asp Xaa Arg Arg Arg
1               5                   10                  15

Arg Arg Arg Gln Arg Arg Arg
            20

<210> SEQ ID NO 82
<211> LENGTH: 22
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: DOMAIN
<222> LOCATION: (1)..(8)
<223> OTHER INFORMATION: cyclic
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = beta-(2-naphthyl)Ala (2-Nal)
<220> FEATURE:
<221> NAME/KEY: MISC_FEATURE
<222> LOCATION: (11)..(11)
<223> OTHER INFORMATION: Xaa = Arg or Lys
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (22)..(22)
<223> OTHER INFORMATION: AMIDATION

<400> SEQUENCE: 82

Cys Glu His Xaa Arg Xaa Ala Cys Pro Pro Xaa Asp Xaa Arg Arg Arg
1               5                   10                  15

Arg Arg Gln Arg Arg Arg
            20

<210> SEQ ID NO 83
<211> LENGTH: 23
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: DOMAIN
<222> LOCATION: (1)..(8)
<223> OTHER INFORMATION: cyclic
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (4)..(4)
```

```
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = 3-benzothienylAla (Bal)
<220> FEATURE:
<221> NAME/KEY: MISC_FEATURE
<222> LOCATION: (11)..(11)
<223> OTHER INFORMATION: Xaa = Arg or Lys
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (23)..(23)
<223> OTHER INFORMATION: AMIDATION

<400> SEQUENCE: 83

Cys Glu His Xaa Arg Xaa Ala Cys Pro Pro Xaa Asp Xaa Arg Arg
1               5                   10                  15

Arg Arg Arg Gln Arg Arg Arg
            20

<210> SEQ ID NO 84
<211> LENGTH: 22
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: DOMAIN
<222> LOCATION: (1)..(8)
<223> OTHER INFORMATION: cyclic
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = 3-benzothienylAla (Bal)
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (22)..(22)
<223> OTHER INFORMATION: AMIDATION

<400> SEQUENCE: 84

Cys Glu His Xaa Arg Xaa Ala Cys Pro Pro Arg Asp Xaa Arg Arg
1               5                   10                  15

Arg Arg Gln Arg Arg Arg
            20

<210> SEQ ID NO 85
<211> LENGTH: 24
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: DOMAIN
<222> LOCATION: (1)..(8)
<223> OTHER INFORMATION: cyclic
```

```
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (24)..(24)
<223> OTHER INFORMATION: AMIDATION

<400> SEQUENCE: 85

Cys Glu His Xaa Arg Trp Ala Cys Pro Pro Lys Asp Xaa Tyr Gly Arg
1               5                   10                  15

Lys Lys Arg Arg Arg Gln Arg Arg
            20

<210> SEQ ID NO 86
<211> LENGTH: 24
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: DOMAIN
<222> LOCATION: (1)..(8)
<223> OTHER INFORMATION: cyclic
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (24)..(24)
<223> OTHER INFORMATION: AMIDATION

<400> SEQUENCE: 86

Cys Glu His Xaa Arg Trp Ala Cys Pro Pro Lys Asp Xaa Tyr Gly Arg
1               5                   10                  15

Gln Lys Lys Arg Arg Arg Arg Arg
            20

<210> SEQ ID NO 87
<211> LENGTH: 24
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<223> OTHER INFORMATION: cyclic
<220> FEATURE:
```

```
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (24)..(24)
<223> OTHER INFORMATION: AMIDATION

<400> SEQUENCE: 87

Cys Glu His Xaa Arg Trp Ala Cys Pro Pro Lys Asp Xaa Tyr Gly Arg
1               5                   10                  15

Lys Lys Arg Arg Arg Arg Arg Gln
            20

<210> SEQ ID NO 88
<211> LENGTH: 22
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: DOMAIN
<222> LOCATION: (1)..(8)
<223> OTHER INFORMATION: cyclic
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = beta-(1-naphthyl)Ala (1-Nal) or beta-
      (2-naphthyl)Ala (2-Nal)
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (22)..(22)
<223> OTHER INFORMATION: AMIDATION

<400> SEQUENCE: 88

Cys Glu His Xaa Arg Xaa Ala Cys Pro Pro Lys Asp Xaa Arg Arg Lys
1               5                   10                  15

Arg Arg Gln Arg Arg Arg
            20

<210> SEQ ID NO 89
<211> LENGTH: 22
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: DOMAIN
<222> LOCATION: (1)..(8)
<223> OTHER INFORMATION: cyclic
<220> FEATURE:
<221> NAME/KEY: MOD_RES
<222> LOCATION: (1)..(1)
<223> OTHER INFORMATION: modified with acyl (Ac)
<220> FEATURE:
```

```
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = beta-(1-naphthyl)Ala (1-Nal)
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (22)..(22)
<223> OTHER INFORMATION: AMIDATION

<400> SEQUENCE: 89

Cys Glu His Xaa Arg Xaa Ala Cys Pro Pro Lys Asp Xaa Arg Lys Arg
1               5                   10                  15

Arg Arg Gln Arg Arg Arg
            20

<210> SEQ ID NO 90
<211> LENGTH: 24
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: DOMAIN
<222> LOCATION: (1)..(8)
<223> OTHER INFORMATION: cyclic
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = beta-(2-naphthyl)Ala (2-Nal)
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (24)..(24)
<223> OTHER INFORMATION: AMIDATION

<400> SEQUENCE: 90

Cys Glu His Xaa Arg Xaa Ala Cys Pro Pro Lys Asp Xaa Tyr Gly Arg
1               5                   10                  15

Arg Lys Arg Arg Gln Arg Arg Arg
            20

<210> SEQ ID NO 91
<211> LENGTH: 23
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: DOMAIN
<222> LOCATION: (1)..(8)
<223> OTHER INFORMATION: cyclic
<220> FEATURE:
<221> NAME/KEY: MOD_RES
```

```
<222> LOCATION: (1)..(1)
<223> OTHER INFORMATION: modified with acyl (Ac)
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = beta-(2-naphthyl)Ala (2-Nal)
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (23)..(23)
<223> OTHER INFORMATION: AMIDATION

<400> SEQUENCE: 91

Cys Glu His Xaa Arg Xaa Ala Cys Pro Pro Lys Asp Xaa Gly Arg Arg
1               5                   10                  15

Lys Arg Arg Gln Arg Arg Arg
            20

<210> SEQ ID NO 92
<211> LENGTH: 23
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: DOMAIN
<222> LOCATION: (1)..(8)
<223> OTHER INFORMATION: cyclic
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = beta-(2-naphthyl)Ala (2-Nal) or beta-
      (1-naphthyl)Ala (1-Nal)
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (23)..(23)
<223> OTHER INFORMATION: AMIDATION

<400> SEQUENCE: 92

Cys Glu His Xaa Arg Xaa Ala Cys Pro Pro Lys Asp Xaa Gly Arg Lys
1               5                   10                  15

Arg Arg Arg Gln Arg Arg Arg
            20

<210> SEQ ID NO 93
<211> LENGTH: 22
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
```

```
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = beta-(1-naphthyl)Ala (1-Nal)
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (22)..(22)
<223> OTHER INFORMATION: AMIDATION

<400> SEQUENCE: 93

Cys Glu His Xaa Arg Xaa Ala Cys Pro Pro Lys Asp Xaa Arg Arg Lys
1               5                   10                  15

Arg Arg Gln Arg Arg
            20

<210> SEQ ID NO 94
<211> LENGTH: 22
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = beta-(1-naphthyl)Ala (1-Nal)
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (22)..(22)
<223> OTHER INFORMATION: AMIDATION

<400> SEQUENCE: 94

Cys Glu His Xaa Arg Xaa Ala Cys Pro Pro Lys Asp Xaa Arg Lys Arg
1               5                   10                  15

Arg Arg Gln Arg Arg
            20

<210> SEQ ID NO 95
<211> LENGTH: 24
<212> TYPE: PRT
<213> ORGANISM: Artificial Sequence
<220> FEATURE:
<223> OTHER INFORMATION: Melanocortin receptor ligand to treat insulin
```

```
        sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = beta-(1-naphthyl)Ala (1-Nal)
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (24)..(24)
<223> OTHER INFORMATION: AMIDATION

<400> SEQUENCE: 95

Cys Glu His Xaa Arg Xaa Ala Cys Pro Pro Lys Asp Xaa Tyr Gly Arg
1               5                   10                  15

Arg Lys Arg Arg Gln Arg Arg Arg
            20

<210> SEQ ID NO 96
<211> LENGTH: 24
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = beta-(1-naphthyl)Ala (1-Nal)
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (24)..(24)
<223> OTHER INFORMATION: AMIDATION

<400> SEQUENCE: 96

Cys Glu His Xaa Arg Xaa Ala Cys Pro Pro Lys Asp Xaa Tyr Gly Arg
1               5                   10                  15

Lys Arg Arg Arg Gln Arg Arg Arg
            20

<210> SEQ ID NO 97
<211> LENGTH: 23
<212> TYPE: PRT
<213> ORGANISM: Artificial Sequence
```

```
<220> FEATURE:
<223> OTHER INFORMATION: Melanocortin receptor ligand to treat insulin
      sensitivity
<220> FEATURE:
<221> NAME/KEY: DOMAIN
<222> LOCATION: (1)..(8)
<223> OTHER INFORMATION: cyclic
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = beta-(1-naphthyl)Ala (1-Nal)
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (23)..(23)
<223> OTHER INFORMATION: AMIDATION

<400> SEQUENCE: 97

Cys Glu His Xaa Arg Xaa Ala Cys Pro Pro Lys Asp Xaa Gly Arg Arg
1               5                   10                  15

Lys Arg Arg Gln Arg Arg Arg
            20

<210> SEQ ID NO 98
<211> LENGTH: 22
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: DOMAIN
<222> LOCATION: (1)..(8)
<223> OTHER INFORMATION: cyclic
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = beta-(2-naphthyl)Ala (2-Nal)
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (22)..(22)
<223> OTHER INFORMATION: AMIDATION

<400> SEQUENCE: 98

Cys Glu His Xaa Arg Xaa Ala Cys Pro Pro Lys Asp Xaa Arg Arg Lys
1               5                   10                  15

Arg Arg Gln Arg Arg Arg
            20

<210> SEQ ID NO 99
```

```
<211> LENGTH: 22
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = beta-(2-naphthyl)Ala (2-Nal)
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (22)..(22)
<223> OTHER INFORMATION: AMIDATION

<400> SEQUENCE: 99

Cys Glu His Xaa Arg Xaa Ala Cys Pro Pro Lys Asp Xaa Arg Lys Arg
1               5                   10                  15

Arg Arg Gln Arg Arg Arg
            20

<210> SEQ ID NO 100
<211> LENGTH: 24
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = beta-(2-naphthyl)Ala (2-Nal) or 3-
      benzothienylAla (Bal)
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (24)..(24)
<223> OTHER INFORMATION: AMIDATION

<400> SEQUENCE: 100

Cys Glu His Xaa Arg Xaa Ala Cys Pro Pro Lys Asp Xaa Tyr Gly Arg
1               5                   10                  15

Arg Lys Arg Arg Gln Arg Arg Arg
```

```
<210> SEQ ID NO 101
<211> LENGTH: 24
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = beta-(2-naphthyl)Ala (2-Nal) or 3-
      benzothienylAla (Bal)
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (24)..(24)
<223> OTHER INFORMATION: AMIDATION

<400> SEQUENCE: 101

Cys Glu His Xaa Arg Xaa Ala Cys Pro Pro Lys Asp Xaa Tyr Gly Arg
1               5                   10                  15

Lys Arg Arg Gln Arg Arg Arg Arg
            20

<210> SEQ ID NO 102
<211> LENGTH: 23
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = beta-(2-naphthyl)Ala (2-Nal) or 3-
      benzothienylAla (Bal)
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (23)..(23)
<223> OTHER INFORMATION: AMIDATION

<400> SEQUENCE: 102
```

```
Cys Glu His Xaa Arg Xaa Ala Cys Pro Pro Lys Asp Xaa Gly Arg Arg
1               5                   10                  15

Lys Arg Arg Gln Arg Arg Arg
            20

<210> SEQ ID NO 103
<211> LENGTH: 23
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = beta-(2-naphthyl)Ala (2-Nal) or 3-
      benzothienylAla (Bal)
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (23)..(23)
<223> OTHER INFORMATION: AMIDATION

<400> SEQUENCE: 103

Cys Glu His Xaa Arg Xaa Ala Cys Pro Pro Lys Asp Xaa Gly Arg Lys
1               5                   10                  15

Arg Arg Arg Gln Arg Arg Arg
            20

<210> SEQ ID NO 104
<211> LENGTH: 22
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = 3-benzothienylAla (Bal)
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
```

```
<222> LOCATION: (22)..(22)
<223> OTHER INFORMATION: AMIDATION

<400> SEQUENCE: 104

Cys Glu His Xaa Arg Xaa Ala Cys Pro Pro Lys Asp Xaa Arg Arg Lys
1               5                   10                  15

Arg Arg Gln Arg Arg Arg
            20

<210> SEQ ID NO 105
<211> LENGTH: 22
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = 3-benzothienylAla (Bal)
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (22)..(22)
<223> OTHER INFORMATION: AMIDATION

<400> SEQUENCE: 105

Cys Glu His Xaa Arg Xaa Ala Cys Pro Pro Lys Asp Xaa Arg Lys Arg
1               5                   10                  15

Arg Arg Gln Arg Arg Arg
            20

<210> SEQ ID NO 106
<211> LENGTH: 24
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (24)..(24)
```

```
<223> OTHER INFORMATION: AMIDATION

<400> SEQUENCE: 106

Cys Glu His Xaa Arg Trp Ala Cys Pro Pro Lys Asp Xaa Tyr Gly Arg
1               5                   10                  15

Lys Lys Arg Gln Arg Arg Arg Arg
            20

<210> SEQ ID NO 107
<211> LENGTH: 24
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (24)..(24)
<223> OTHER INFORMATION: AMIDATION

<400> SEQUENCE: 107

Cys Glu His Xaa Arg Trp Ala Cys Pro Pro Lys Asp Xaa Tyr Gly Arg
1               5                   10                  15

Lys Lys Gln Arg Arg Arg Arg
            20

<210> SEQ ID NO 108
<211> LENGTH: 24
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (24)..(24)
<223> OTHER INFORMATION: AMIDATION

<400> SEQUENCE: 108

Cys Glu His Xaa Arg Trp Ala Cys Pro Pro Lys Asp Xaa Tyr Gly Arg
```

```
1               5                   10                  15

Lys Gln Lys Arg Arg Arg Arg Arg
            20

<210> SEQ ID NO 109
<211> LENGTH: 24
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (24)..(24)
<223> OTHER INFORMATION: AMIDATION

<400> SEQUENCE: 109

Cys Glu His Xaa Arg Trp Ala Cys Pro Pro Lys Asp Xaa Tyr Gly Arg
1               5                   10                  15

Gln Lys Lys Arg Arg Arg Arg Arg
            20

<210> SEQ ID NO 110
<211> LENGTH: 24
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (24)..(24)
<223> OTHER INFORMATION: AMIDATION

<400> SEQUENCE: 110

Cys Glu His Xaa Arg Trp Ala Cys Pro Pro Lys Asp Xaa Tyr Gly Arg
1               5                   10                  15

Lys Lys Arg Arg Arg Gln Arg Arg
            20
```

```
<210> SEQ ID NO 111
<211> LENGTH: 24
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (24)..(24)
<223> OTHER INFORMATION: AMIDATION

<400> SEQUENCE: 111

Cys Glu His Xaa Arg Trp Ala Cys Pro Pro Lys Asp Xaa Tyr Gly Arg
1               5                   10                  15

Lys Lys Arg Arg Arg Arg Gln Arg
            20

<210> SEQ ID NO 112
<211> LENGTH: 24
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (24)..(24)
<223> OTHER INFORMATION: AMIDATION

<400> SEQUENCE: 112

Cys Glu His Xaa Arg Trp Ala Cys Pro Pro Lys Asp Xaa Tyr Gly Arg
1               5                   10                  15

Lys Lys Arg Arg Arg Arg Arg Gln
            20

<210> SEQ ID NO 113
<211> LENGTH: 22
<212> TYPE: PRT
<213> ORGANISM: Artificial Sequence
```

```
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (11)..(11)
<223> OTHER INFORMATION: Xaa = Lys or Arg
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (22)..(22)
<223> OTHER INFORMATION: AMIDATION

<400> SEQUENCE: 113

Cys Glu His Xaa Arg Trp Ala Cys Pro Pro Xaa Asp Xaa Arg Arg Arg
1               5                   10                  15

Arg Arg Gln Arg Arg Arg
            20

<210> SEQ ID NO 114
<211> LENGTH: 24
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (11)..(11)
<223> OTHER INFORMATION: Xaa = Lys or Arg
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (24)..(24)
<223> OTHER INFORMATION: AMIDATION

<400> SEQUENCE: 114

Cys Glu His Xaa Arg Trp Ala Cys Pro Pro Xaa Asp Xaa Tyr Gly Arg
1               5                   10                  15

Arg Arg Arg Arg Gln Arg Arg Arg
            20

<210> SEQ ID NO 115
```

```
<211> LENGTH: 23
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (11)..(11)
<223> OTHER INFORMATION: Xaa = Lys or Arg
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (23)..(23)
<223> OTHER INFORMATION: AMIDATION

<400> SEQUENCE: 115

Cys Glu His Xaa Arg Trp Ala Cys Pro Pro Xaa Asp Xaa Arg Arg
1               5                  10                  15

Arg Arg Gln Arg Arg Arg Arg
                20

<210> SEQ ID NO 116
<211> LENGTH: 25
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (11)..(11)
<223> OTHER INFORMATION: Xaa = Lys or Arg
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (25)..(25)
<223> OTHER INFORMATION: AMIDATION

<400> SEQUENCE: 116

Cys Glu His Xaa Arg Trp Ala Cys Pro Pro Xaa Asp Xaa Tyr Gly Arg
1               5                  10                  15

Arg Arg Arg Arg Gln Arg Arg Arg
                20                  25
```

```
<210> SEQ ID NO 117
<211> LENGTH: 22
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = beta-(1-naphthyl)Ala (1-Nal)
<220> FEATURE:
<221> NAME/KEY: MISC_FEATURE
<222> LOCATION: (11)..(11)
<223> OTHER INFORMATION: Xaa = Lys or Arg
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (22)..(22)
<223> OTHER INFORMATION: AMIDATION

<400> SEQUENCE: 117

Cys Glu His Xaa Arg Xaa Ala Cys Pro Pro Xaa Asp Xaa Arg Arg
1               5                   10                  15

Arg Arg Gln Arg Arg Arg
            20

<210> SEQ ID NO 118
<211> LENGTH: 23
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = beta-(1-naphthyl)Ala (1-Nal)
<220> FEATURE:
<221> NAME/KEY: MISC_FEATURE
<222> LOCATION: (11)..(11)
<223> OTHER INFORMATION: Xaa = Lys or Arg
<220> FEATURE:
<221> NAME/KEY: MISC_FEATURE
<222> LOCATION: (13)..(13)
<223> OTHER INFORMATION: Xaa = beta-Ala
<220> FEATURE:
```

```
<221> NAME/KEY: MOD_RES
<222> LOCATION: (23)..(23)
<223> OTHER INFORMATION: AMIDATION

<400> SEQUENCE: 118

Cys Glu His Xaa Arg Xaa Ala Cys Pro Pro Xaa Asp Xaa Arg Arg Arg
1               5                   10                  15

Arg Arg Gln Arg Arg Arg Arg
            20

<210> SEQ ID NO 119
<211> LENGTH: 23
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = beta-(1-naphthyl)Ala (1-Nal)
<220> FEATURE:
<221> NAME/KEY: MISC_FEATURE
<222> LOCATION: (11)..(11)
<223> OTHER INFORMATION: Xaa = Lys or Arg
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (23)..(23)
<223> OTHER INFORMATION: AMIDATION

<400> SEQUENCE: 119

Cys Glu His Xaa Arg Xaa Ala Cys Pro Pro Xaa Asp Xaa Arg Arg Arg
1               5                   10                  15

Arg Arg Arg Gln Arg Arg Arg
            20

<210> SEQ ID NO 120
<211> LENGTH: 24
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
```

```
<222> LOCATION: (6)..(6)
<223> OTHER INFORMATION: Xaa = beta-(1-naphthyl)Ala (1-Nal)
<220> FEATURE:
<221> NAME/KEY: MISC_FEATURE
<222> LOCATION: (11)..(11)
<223> OTHER INFORMATION: Xaa = Lys or Arg
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (24)..(24)
<223> OTHER INFORMATION: AMIDATION

<400> SEQUENCE: 120

Cys Glu His Xaa Arg Xaa Ala Cys Pro Pro Xaa Asp Xaa Tyr Gly Arg
1               5                   10                  15

Arg Arg Arg Arg Gln Arg Arg Arg
            20

<210> SEQ ID NO 121
<211> LENGTH: 25
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = beta-(1-naphthyl)Ala (1-Nal)
<220> FEATURE:
<221> NAME/KEY: MISC_FEATURE
<222> LOCATION: (11)..(11)
<223> OTHER INFORMATION: Xaa = Lys or Arg
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (25)..(25)
<223> OTHER INFORMATION: AMIDATION

<400> SEQUENCE: 121

Cys Glu His Xaa Arg Xaa Ala Cys Pro Pro Xaa Asp Xaa Tyr Gly Arg
1               5                   10                  15

Arg Arg Arg Arg Gln Arg Arg Arg Arg
            20                  25

<210> SEQ ID NO 122
<211> LENGTH: 25
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
```

```
<223> OTHER INFORMATION: modified with acyl (Ac)
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = beta-(1-naphthyl)Ala (1-Nal)
<220> FEATURE:
<221> NAME/KEY: MISC_FEATURE
<222> LOCATION: (11)..(11)
<223> OTHER INFORMATION: Xaa = Lys or Arg
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (25)..(25)
<223> OTHER INFORMATION: AMIDATION

<400> SEQUENCE: 122

Cys Glu His Xaa Arg Xaa Ala Cys Pro Pro Xaa Asp Xaa Tyr Gly Arg
1               5                   10                  15

Arg Arg Arg Arg Arg Gln Arg Arg Arg
            20                  25

<210> SEQ ID NO 123
<211> LENGTH: 22
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = beta-(2-naphthyl)Ala (2-Nal)
<220> FEATURE:
<221> NAME/KEY: MISC_FEATURE
<222> LOCATION: (11)..(11)
<223> OTHER INFORMATION: Xaa = Lys or Arg
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (22)..(22)
<223> OTHER INFORMATION: AMIDATION

<400> SEQUENCE: 123

Cys Glu His Xaa Arg Xaa Ala Cys Pro Pro Xaa Asp Xaa Arg Arg Arg
1               5                   10                  15

Arg Arg Gln Arg Arg Arg
            20
```

```
<210> SEQ ID NO 124
<211> LENGTH: 23
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = beta-(2-naphthyl)Ala (2-Nal)
<220> FEATURE:
<221> NAME/KEY: MISC_FEATURE
<222> LOCATION: (11)..(11)
<223> OTHER INFORMATION: Xaa = Lys or Arg
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (23)..(23)
<223> OTHER INFORMATION: AMIDATION

<400> SEQUENCE: 124

Cys Glu His Xaa Arg Xaa Ala Cys Pro Pro Xaa Asp Xaa Arg Arg Arg
1               5                   10                  15

Arg Arg Arg Gln Arg Arg Arg
            20

<210> SEQ ID NO 125
<211> LENGTH: 23
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = beta-(2-naphthyl)Ala (2-Nal)
<220> FEATURE:
<221> NAME/KEY: MISC_FEATURE
<222> LOCATION: (11)..(11)
<223> OTHER INFORMATION: Xaa = Lys or Arg
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
```

```
<222> LOCATION: (23)..(23)
<223> OTHER INFORMATION: AMIDATION

<400> SEQUENCE: 125

Cys Glu His Xaa Arg Xaa Ala Cys Pro Pro Xaa Asp Xaa Arg Arg
1               5                   10                  15

Arg Arg Gln Arg Arg Arg Arg
            20

<210> SEQ ID NO 126
<211> LENGTH: 24
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = beta-(2-naphthyl)Ala (2-Nal)
<220> FEATURE:
<221> NAME/KEY: MISC_FEATURE
<222> LOCATION: (11)..(11)
<223> OTHER INFORMATION: Xaa = Lys or Arg
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (24)..(24)
<223> OTHER INFORMATION: AMIDATION

<400> SEQUENCE: 126

Cys Glu His Xaa Arg Xaa Ala Cys Pro Pro Xaa Asp Xaa Tyr Gly Arg
1               5                   10                  15

Arg Arg Arg Arg Gln Arg Arg Arg
            20

<210> SEQ ID NO 127
<211> LENGTH: 25
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
```

```
<223> OTHER INFORMATION: Xaa = beta-(2-naphthyl)Ala (2-Nal)
<220> FEATURE:
<221> NAME/KEY: MISC_FEATURE
<222> LOCATION: (11)..(11)
<223> OTHER INFORMATION: Xaa = Lys or Arg
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (25)..(25)
<223> OTHER INFORMATION: AMIDATION

<400> SEQUENCE: 127

Cys Glu His Xaa Arg Xaa Ala Cys Pro Pro Xaa Asp Xaa Tyr Gly Arg
1               5                   10                  15

Arg Arg Arg Arg Arg Gln Arg Arg Arg
            20                  25

<210> SEQ ID NO 128
<211> LENGTH: 25
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = beta-(2-naphthyl)Ala (2-Nal)
<220> FEATURE:
<221> NAME/KEY: MISC_FEATURE
<222> LOCATION: (11)..(11)
<223> OTHER INFORMATION: Xaa = Lys or Arg
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (25)..(25)
<223> OTHER INFORMATION: AMIDATION

<400> SEQUENCE: 128

Cys Glu His Xaa Arg Xaa Ala Cys Pro Pro Xaa Asp Xaa Tyr Gly Arg
1               5                   10                  15

Arg Arg Arg Arg Gln Arg Arg Arg Arg
            20                  25

<210> SEQ ID NO 129
<211> LENGTH: 22
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
```

```
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = 3-benzothienylAla (Bal)
<220> FEATURE:
<221> NAME/KEY: MISC_FEATURE
<222> LOCATION: (11)..(11)
<223> OTHER INFORMATION: Xaa = Lys or Arg
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (22)..(22)
<223> OTHER INFORMATION: AMIDATION

<400> SEQUENCE: 129

Cys Glu His Xaa Arg Xaa Ala Cys Pro Pro Xaa Asp Xaa Arg Arg Arg
1               5                   10                  15

Arg Arg Gln Arg Arg Arg
            20

<210> SEQ ID NO 130
<211> LENGTH: 23
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = 3-benzothienylAla (Bal)
<220> FEATURE:
<221> NAME/KEY: MISC_FEATURE
<222> LOCATION: (11)..(11)
<223> OTHER INFORMATION: Xaa = Lys or Arg
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (23)..(23)
<223> OTHER INFORMATION: AMIDATION

<400> SEQUENCE: 130

Cys Glu His Xaa Arg Xaa Ala Cys Pro Pro Xaa Asp Xaa Arg Arg Arg
1               5                   10                  15

Arg Arg Gln Arg Arg Arg Arg
            20
```

```
<210> SEQ ID NO 131
<211> LENGTH: 23
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = 3-benzothienylAla (Bal)
<220> FEATURE:
<221> NAME/KEY: MISC_FEATURE
<222> LOCATION: (11)..(11)
<223> OTHER INFORMATION: Xaa = Lys or Arg
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (23)..(23)
<223> OTHER INFORMATION: AMIDATION

<400> SEQUENCE: 131

Cys Glu His Xaa Arg Xaa Ala Cys Pro Pro Xaa Asp Xaa Arg Arg Arg
1               5                   10                  15

Arg Arg Arg Gln Arg Arg Arg
            20

<210> SEQ ID NO 132
<211> LENGTH: 23
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = 3-benzothienylAla (Bal)
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (23)..(23)
<223> OTHER INFORMATION: AMIDATION

<400> SEQUENCE: 132
```

```
Cys Glu His Xaa Arg Xaa Ala Cys Pro Pro Lys Asp Xaa Gly Arg Arg
1               5                   10                  15

Arg Arg Arg Gln Arg Arg Arg
            20
```

<210> SEQ ID NO 133
<211> LENGTH: 24
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = 3-benzothienylAla (Bal)
<220> FEATURE:
<221> NAME/KEY: MISC_FEATURE
<222> LOCATION: (11)..(11)
<223> OTHER INFORMATION: Xaa = Lys or Arg
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (24)..(24)
<223> OTHER INFORMATION: AMIDATION

<400> SEQUENCE: 133

```
Cys Glu His Xaa Arg Xaa Ala Cys Pro Pro Xaa Asp Xaa Tyr Gly Arg
1               5                   10                  15

Arg Arg Arg Arg Gln Arg Arg Arg
            20
```

<210> SEQ ID NO 134
<211> LENGTH: 25
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = 3-benzothienylAla (Bal)
<220> FEATURE:
<221> NAME/KEY: MISC_FEATURE
<222> LOCATION: (11)..(11)
<223> OTHER INFORMATION: Xaa = Lys or Arg

```
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (25)..(25)
<223> OTHER INFORMATION: AMIDATION

<400> SEQUENCE: 134

Cys Glu His Xaa Arg Xaa Ala Cys Pro Pro Xaa Asp Xaa Tyr Gly Arg
1               5                   10                  15

Arg Arg Arg Arg Gln Arg Arg Arg Arg
            20                  25

<210> SEQ ID NO 135
<211> LENGTH: 25
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = 3-benzothienylAla (Bal)
<220> FEATURE:
<221> NAME/KEY: MISC_FEATURE
<222> LOCATION: (11)..(11)
<223> OTHER INFORMATION: Xaa = Lys or Arg
<220> FEATURE:
<221> NAME/KEY: MISC_FEATURE
<222> LOCATION: (13)..(13)
<223> OTHER INFORMATION: Xaa = beta-Ala
<220> FEATURE:
<221> NAME/KEY: MOD_RES
<222> LOCATION: (25)..(25)
<223> OTHER INFORMATION: AMIDATION

<400> SEQUENCE: 135

Cys Glu His Xaa Arg Xaa Ala Cys Pro Pro Xaa Asp Xaa Tyr Gly Arg
1               5                   10                  15

Arg Arg Arg Arg Arg Gln Arg Arg Arg
            20                  25

<210> SEQ ID NO 136
<211> LENGTH: 21
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
```

```
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (9)..(9)
<223> OTHER INFORMATION: Xaa = 8-amino-3,6-dioxaoctanoic acid (Doc)
<220> FEATURE:
<221> NAME/KEY: MISC_FEATURE
<222> LOCATION: (10)..(10)
<223> OTHER INFORMATION: Xaa = 8-amino-3,6-dioxaoctanoic acid (Doc) or
      absent
<220> FEATURE:
<221> NAME/KEY: MOD_RES
<222> LOCATION: (21)..(21)
<223> OTHER INFORMATION: AMIDATION

<400> SEQUENCE: 136

Xaa Cys Xaa His Xaa Arg Trp Cys Xaa Xaa Tyr Gly Arg Lys Lys Arg
1               5                   10                  15

Arg Gln Arg Arg Arg
            20

<210> SEQ ID NO 137
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MOD_RES
<222> LOCATION: (20)..(20)
<223> OTHER INFORMATION: AMIDATION

<400> SEQUENCE: 137

Xaa Cys Xaa His Xaa Arg Trp Cys Xaa Tyr Gly Arg Lys Lys Arg Gln
1               5                   10                  15

Arg Arg Arg Arg
            20

<210> SEQ ID NO 138
<211> LENGTH: 19
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
```

```
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MISC_FEATURE
<222> LOCATION: (10)..(10)
<223> OTHER INFORMATION: Xaa = Gly or absent
<220> FEATURE:
<221> NAME/KEY: MOD_RES
<222> LOCATION: (19)..(19)
<223> OTHER INFORMATION: AMIDATION

<400> SEQUENCE: 138

Xaa Cys Xaa His Xaa Arg Trp Cys Xaa Xaa Arg Arg Arg Arg Gln
1               5                   10                  15

Arg Arg Arg

<210> SEQ ID NO 139
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MISC_FEATURE
<222> LOCATION: (10)..(10)
<223> OTHER INFORMATION: Xaa = Tyr or absent
<220> FEATURE:
<221> NAME/KEY: MOD_RES
<222> LOCATION: (20)..(20)
<223> OTHER INFORMATION: AMIDATION

<400> SEQUENCE: 139

Xaa Cys Xaa His Xaa Arg Trp Cys Xaa Xaa Gly Arg Arg Arg Arg
1               5                   10                  15

Gln Arg Arg Arg
            20
```

<210> SEQ ID NO 140
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MOD_RES
<222> LOCATION: (20)..(20)
<223> OTHER INFORMATION: AMIDATION

<400> SEQUENCE: 140

Xaa Cys Xaa His Xaa Arg Trp Cys Xaa Gly Arg Arg Arg Arg Gln
1               5                   10                  15

Arg Arg Arg Arg
            20

<210> SEQ ID NO 141
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MISC_FEATURE
<222> LOCATION: (10)..(10)
<223> OTHER INFORMATION: Xaa = Tyr or absent
<220> FEATURE:
<221> NAME/KEY: MOD_RES
<222> LOCATION: (20)..(20)
<223> OTHER INFORMATION: AMIDATION -continued

```
<400> SEQUENCE: 141

Xaa Cys Xaa His Xaa Arg Trp Cys Xaa Xaa Gly Arg Arg Lys Arg Arg
1               5                   10                  15

Gln Arg Arg Arg
            20

<210> SEQ ID NO 142
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MISC_FEATURE
<222> LOCATION: (10)..(10)
<223> OTHER INFORMATION: Xaa = Tyr or absent
<220> FEATURE:
<221> NAME/KEY: MOD_RES
<222> LOCATION: (20)..(20)
<223> OTHER INFORMATION: AMIDATION

<400> SEQUENCE: 142

Xaa Cys Xaa His Xaa Arg Trp Cys Xaa Xaa Gly Arg Lys Arg Arg Arg
1               5                   10                  15

Gln Arg Arg Arg
            20

<210> SEQ ID NO 143
<211> LENGTH: 18
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
```

```
<222> LOCATION: (9)..(9)
<223> OTHER INFORMATION: Xaa = beta-Ala
<220> FEATURE:
<221> NAME/KEY: MOD_RES
<222> LOCATION: (18)..(18)
<223> OTHER INFORMATION: AMIDATION

<400> SEQUENCE: 143

Xaa Cys Xaa His Xaa Arg Trp Cys Xaa Arg Arg Lys Arg Arg Gln Arg
1               5                   10                  15

Arg Arg

<210> SEQ ID NO 144
<211> LENGTH: 18
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MOD_RES
<222> LOCATION: (18)..(18)
<223> OTHER INFORMATION: AMIDATION

<400> SEQUENCE: 144

Xaa Cys Xaa His Xaa Arg Trp Cys Xaa Arg Lys Arg Arg Gln Arg
1               5                   10                  15

Arg Arg

<210> SEQ ID NO 145
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
```

```
<221> NAME/KEY: MISC_FEATURE
<222> LOCATION: (9)..(9)
<223> OTHER INFORMATION: Xaa = beta-Ala
<220> FEATURE:
<221> NAME/KEY: MOD_RES
<222> LOCATION: (20)..(20)
<223> OTHER INFORMATION: AMIDATION

<400> SEQUENCE: 145

Xaa Cys Xaa His Xaa Arg Trp Cys Xaa Tyr Gly Arg Lys Lys Arg Gln
1               5                   10                  15

Arg Arg Arg Arg
            20

<210> SEQ ID NO 146
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (9)..(9)
<223> OTHER INFORMATION: Xaa = 8-amino-3,6-dioxaoctanoic acid (Doc)
<220> FEATURE:
<221> NAME/KEY: MOD_RES
<222> LOCATION: (20)..(20)
<223> OTHER INFORMATION: AMIDATION

<400> SEQUENCE: 146

Xaa Cys Xaa His Xaa Arg Trp Cys Xaa Tyr Gly Arg Lys Lys Arg Arg
1               5                   10                  15

Gln Arg Arg Arg
            20

<210> SEQ ID NO 147
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
```

```
<222> LOCATION: (5)..(5)
<223> OTHER INFORMATION: Xaa = D-Phe
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MISC_FEATURE
<222> LOCATION: (10)..(10)
<223> OTHER INFORMATION: Xaa = Tyr or absent
<220> FEATURE:
<221> NAME/KEY: MOD_RES
<222> LOCATION: (20)..(20)
<223> OTHER INFORMATION: AMIDATION

<400> SEQUENCE: 147

Xaa Cys Xaa His Xaa Arg Trp Cys Xaa Xaa Gly Arg Arg Arg Arg
1               5                   10                  15

Gln Arg Arg Arg
            20

<210> SEQ ID NO 148
<211> LENGTH: 19
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MISC_FEATURE
<222> LOCATION: (10)..(10)
<223> OTHER INFORMATION: Xaa = beta-Ala or absent
<220> FEATURE:
<221> NAME/KEY: MOD_RES
<222> LOCATION: (19)..(19)
<223> OTHER INFORMATION: AMIDATION

<400> SEQUENCE: 148

Xaa Cys Xaa His Xaa Arg Trp Cys Xaa Xaa Arg Arg Arg Arg Gln
1               5                   10                  15

Arg Arg Arg

<210> SEQ ID NO 149
<211> LENGTH: 21
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
```

```
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (9)..(10)
<223> OTHER INFORMATION: Xaa = beta-Ala
<220> FEATURE:
<221> NAME/KEY: MISC_FEATURE
<222> LOCATION: (11)..(11)
<223> OTHER INFORMATION: Xaa = Tyr or absent
<220> FEATURE:
<221> NAME/KEY: MOD_RES
<222> LOCATION: (21)..(21)
<223> OTHER INFORMATION: AMIDATION

<400> SEQUENCE: 149

Xaa Cys Xaa His Xaa Arg Trp Cys Xaa Xaa Xaa Gly Arg Arg Arg
1               5                   10                  15

Arg Gln Arg Arg Arg
            20

<210> SEQ ID NO 150
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (9)..(9)
<223> OTHER INFORMATION: Xaa = 8-amino-3,6-dioxaoctanoic acid (Doc)
<220> FEATURE:
<221> NAME/KEY: MISC_FEATURE
<222> LOCATION: (10)..(10)
<223> OTHER INFORMATION: Xaa = Tyr or absent
<220> FEATURE:
<221> NAME/KEY: MOD_RES
<222> LOCATION: (20)..(20)
<223> OTHER INFORMATION: AMIDATION

<400> SEQUENCE: 150

Xaa Cys Xaa His Xaa Arg Trp Cys Xaa Xaa Gly Arg Arg Arg Arg
1               5                   10                  15

Gln Arg Arg Arg
            20
```

```
<210> SEQ ID NO 151
<211> LENGTH: 19
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (9)..(9)
<223> OTHER INFORMATION: Xaa = 8-amino-3,6-dioxaoctanoic acid (Doc)
<220> FEATURE:
<221> NAME/KEY: MISC_FEATURE
<222> LOCATION: (10)..(10)
<223> OTHER INFORMATION: Xaa = 8-amino-3,6-dioxaoctanoic acid (Doc) or
      absent
<220> FEATURE:
<221> NAME/KEY: MOD_RES
<222> LOCATION: (19)..(19)
<223> OTHER INFORMATION: AMIDATION

<400> SEQUENCE: 151

Xaa Cys Xaa His Xaa Arg Trp Cys Xaa Xaa Arg Arg Arg Arg Gln
1               5                   10                  15

Arg Arg Arg

<210> SEQ ID NO 152
<211> LENGTH: 21
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (9)..(10)
<223> OTHER INFORMATION: Xaa = 8-amino-3,6-dioxaoctanoic acid (Doc)
<220> FEATURE:
<221> NAME/KEY: MISC_FEATURE
<222> LOCATION: (11)..(11)
<223> OTHER INFORMATION: Xaa = Tyr or absent
<220> FEATURE:
<221> NAME/KEY: MOD_RES
<222> LOCATION: (21)..(21)
```

<223> OTHER INFORMATION: AMIDATION

<400> SEQUENCE: 152

Xaa Cys Xaa His Xaa Arg Trp Cys Xaa Xaa Xaa Gly Arg Arg Arg Arg
1               5                   10                  15

Arg Gln Arg Arg Arg
        20

<210> SEQ ID NO 153
<211> LENGTH: 21
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MISC_FEATURE
<222> LOCATION: (10)..(10)
<223> OTHER INFORMATION: Xaa = Tyr or absent
<220> FEATURE:
<221> NAME/KEY: MOD_RES
<222> LOCATION: (21)..(21)
<223> OTHER INFORMATION: AMIDATION

<400> SEQUENCE: 153

Xaa Cys Xaa His Xaa Arg Trp Cys Xaa Xaa Gly Arg Arg Arg Arg
1               5                   10                  15

Gln Arg Arg Arg
        20

<210> SEQ ID NO 154
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe -continued

```
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MISC_FEATURE
<222> LOCATION: (10)..(10)
<223> OTHER INFORMATION: Xaa = beta-Ala or absent
<220> FEATURE:
<221> NAME/KEY: MOD_RES
<222> LOCATION: (20)..(20)
<223> OTHER INFORMATION: AMIDATION

<400> SEQUENCE: 154

Xaa Cys Xaa His Xaa Arg Trp Cys Xaa Xaa Arg Arg Arg Arg Arg Gln
1               5                   10                  15

Arg Arg Arg Arg
            20

<210> SEQ ID NO 155
<211> LENGTH: 22
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (9)..(10)
<223> OTHER INFORMATION: Xaa = beta-Ala
<220> FEATURE:
<221> NAME/KEY: MISC_FEATURE
<222> LOCATION: (11)..(11)
<223> OTHER INFORMATION: Xaa = Tyr or absent
<220> FEATURE:
<221> NAME/KEY: MOD_RES
<222> LOCATION: (22)..(22)
<223> OTHER INFORMATION: AMIDATION

<400> SEQUENCE: 155

Xaa Cys Xaa His Xaa Arg Trp Cys Xaa Xaa Xaa Gly Arg Arg Arg
1               5                   10                  15

Arg Gln Arg Arg Arg Arg
            20

<210> SEQ ID NO 156
<211> LENGTH: 21
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
```

```
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (9)..(9)
<223> OTHER INFORMATION: Xaa = 8-amino-3,6-dioxaoctanoic acid (Doc)
<220> FEATURE:
<221> NAME/KEY: MISC_FEATURE
<222> LOCATION: (10)..(10)
<223> OTHER INFORMATION: Xaa = Tyr or absent
<220> FEATURE:
<221> NAME/KEY: MOD_RES
<222> LOCATION: (21)..(21)
<223> OTHER INFORMATION: AMIDATION

<400> SEQUENCE: 156

Xaa Cys Xaa His Xaa Arg Trp Cys Xaa Xaa Gly Arg Arg Arg Arg
1               5                   10                  15

Gln Arg Arg Arg Arg
            20

<210> SEQ ID NO 157
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (9)..(9)
<223> OTHER INFORMATION: Xaa = 8-amino-3,6-dioxaoctanoic acid (Doc)
<220> FEATURE:
<221> NAME/KEY: MISC_FEATURE
<222> LOCATION: (10)..(10)
<223> OTHER INFORMATION: Xaa = 8-amino-3,6-dioxaoctanoic acid (Doc) or
      absent
<220> FEATURE:
<221> NAME/KEY: MOD_RES
<222> LOCATION: (20)..(20)
<223> OTHER INFORMATION: AMIDATION

<400> SEQUENCE: 157

Xaa Cys Xaa His Xaa Arg Trp Cys Xaa Xaa Arg Arg Arg Arg Gln
1               5                   10                  15

Arg Arg Arg Arg
            20
```

```
<210> SEQ ID NO 158
<211> LENGTH: 22
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (9)..(10)
<223> OTHER INFORMATION: Xaa = 8-amino-3,6-dioxaoctanoic acid (Doc)
<220> FEATURE:
<221> NAME/KEY: MISC_FEATURE
<222> LOCATION: (11)..(11)
<223> OTHER INFORMATION: Xaa = Tyr or absent
<220> FEATURE:
<221> NAME/KEY: MOD_RES
<222> LOCATION: (22)..(22)
<223> OTHER INFORMATION: AMIDATION

<400> SEQUENCE: 158

Xaa Cys Xaa His Xaa Arg Trp Cys Xaa Xaa Xaa Gly Arg Arg Arg Arg
1               5                   10                  15

Arg Gln Arg Arg Arg Arg
            20

<210> SEQ ID NO 159
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MOD_RES
<222> LOCATION: (20)..(20)
<223> OTHER INFORMATION: AMIDATION

<400> SEQUENCE: 159
```

```
Xaa Cys His Xaa Arg Trp Xaa Cys Xaa Tyr Gly Arg Arg Arg Arg
1               5                   10                  15

Gln Arg Arg Arg
            20
```

<210> SEQ ID NO 160
<211> LENGTH: 18
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MOD_RES
<222> LOCATION: (18)..(18)
<223> OTHER INFORMATION: AMIDATION

<400> SEQUENCE: 160

```
Xaa Cys His Xaa Arg Trp Xaa Cys Xaa Arg Arg Arg Arg Gln Arg
1               5                   10                  15

Arg Arg
```

<210> SEQ ID NO 161
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MOD_RES
<222> LOCATION: (20)..(20)
<223> OTHER INFORMATION: AMIDATION

<400> SEQUENCE: 161

```
Xaa Asp His Xaa Arg Trp Ala Lys Xaa Tyr Gly Arg Arg Arg Arg
1               5                   10                  15
```

```
Gln Arg Arg Arg
        20

<210> SEQ ID NO 162
<211> LENGTH: 18
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MOD_RES
<222> LOCATION: (18)..(18)
<223> OTHER INFORMATION: AMIDATION

<400> SEQUENCE: 162

Xaa Asp His Xaa Arg Trp Ala Lys Xaa Arg Arg Arg Arg Gln Arg
1               5                   10                  15

Arg Arg

<210> SEQ ID NO 163
<211> LENGTH: 18
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(7)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (8)..(8)
<223> OTHER INFORMATION: Xaa = beta-Ala
<220> FEATURE:
<221> NAME/KEY: MISC_FEATURE
<222> LOCATION: (9)..(9)
<223> OTHER INFORMATION: Xaa = Gly or absent
<220> FEATURE:
<221> NAME/KEY: MOD_RES
<222> LOCATION: (18)..(18)
<223> OTHER INFORMATION: AMIDATION

<400> SEQUENCE: 163

Xaa Asp His Xaa Arg Trp Lys Xaa Xaa Arg Arg Arg Arg Gln Arg
1               5                   10                  15

Arg Arg
```

```
<210> SEQ ID NO 164
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(7)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (8)..(8)
<223> OTHER INFORMATION: Xaa = beta-Ala
<220> FEATURE:
<221> NAME/KEY: MISC_FEATURE
<222> LOCATION: (9)..(9)
<223> OTHER INFORMATION: Xaa = beta-Ala or absent
<220> FEATURE:
<221> NAME/KEY: MOD_RES
<222> LOCATION: (20)..(20)
<223> OTHER INFORMATION: AMIDATION

<400> SEQUENCE: 164

Xaa Asp His Xaa Arg Trp Lys Xaa Xaa Tyr Gly Arg Arg Arg Arg
1               5                   10                  15

Gln Arg Arg Arg
            20

<210> SEQ ID NO 165
<211> LENGTH: 19
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(7)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (8)..(10)
<223> OTHER INFORMATION: Xaa = beta-Ala
<220> FEATURE:
<221> NAME/KEY: MISC_FEATURE
<222> LOCATION: (10)..(10)
<223> OTHER INFORMATION: Xaa = Gly or absent
<220> FEATURE:
<221> NAME/KEY: MOD_RES
<222> LOCATION: (19)..(19)
<223> OTHER INFORMATION: AMIDATION

<400> SEQUENCE: 165

Xaa Asp His Xaa Arg Trp Lys Xaa Xaa Xaa Arg Arg Arg Arg Gln
1               5                   10                  15
```

Arg Arg Arg

<210> SEQ ID NO 166
<211> LENGTH: 19
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(7)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (8)..(8)
<223> OTHER INFORMATION: Xaa = 8-amino-3,6-dioxaoctanoic acid (Doc)
<220> FEATURE:
<221> NAME/KEY: MISC_FEATURE
<222> LOCATION: (9)..(9)
<223> OTHER INFORMATION: Xaa = Tyr or absent
<220> FEATURE:
<221> NAME/KEY: MOD_RES
<222> LOCATION: (19)..(19)
<223> OTHER INFORMATION: AMIDATION

<400> SEQUENCE: 166

Xaa Asp His Xaa Arg Trp Lys Xaa Xaa Gly Arg Arg Arg Arg Gln
1               5                   10                  15

Arg Arg Arg

<210> SEQ ID NO 167
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(7)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (8)..(9)
<223> OTHER INFORMATION: Xaa = 8-amino-3,6-dioxaoctanoic acid (Doc)
<220> FEATURE:
<221> NAME/KEY: MISC_FEATURE
<222> LOCATION: (10)..(10)
<223> OTHER INFORMATION: Xaa = Tyr or absent
<220> FEATURE:
<221> NAME/KEY: MOD_RES
<222> LOCATION: (20)..(20)
<223> OTHER INFORMATION: AMIDATION

<400> SEQUENCE: 167

Xaa Asp His Xaa Arg Trp Lys Xaa Xaa Xaa Gly Arg Arg Arg Arg Arg

```
                   1               5                  10                 15

Gln Arg Arg Arg
            20

<210> SEQ ID NO 168
<211> LENGTH: 18
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(7)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (8)..(8)
<223> OTHER INFORMATION: Xaa = 8-amino-3,6-dioxaoctanoic acid (Doc)
<220> FEATURE:
<221> NAME/KEY: MISC_FEATURE
<222> LOCATION: (9)..(9)
<223> OTHER INFORMATION: Xaa = 8-amino-3,6-dioxaoctanoic acid (Doc) or
      absent
<220> FEATURE:
<221> NAME/KEY: MOD_RES
<222> LOCATION: (18)..(18)
<223> OTHER INFORMATION: AMIDATION

<400> SEQUENCE: 168

Xaa Asp His Xaa Arg Trp Lys Xaa Xaa Arg Arg Arg Arg Gln Arg
1               5                   10                  15

Arg Arg

<210> SEQ ID NO 169
<211> LENGTH: 19
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(7)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (8)..(8)
<223> OTHER INFORMATION: Xaa = beta-Ala
<220> FEATURE:
<221> NAME/KEY: MISC_FEATURE
<222> LOCATION: (9)..(9)
<223> OTHER INFORMATION: Xaa = Gly or absent
<220> FEATURE:
<221> NAME/KEY: MOD_RES
<222> LOCATION: (19)..(19)
<223> OTHER INFORMATION: AMIDATION
```

```
<400> SEQUENCE: 169

Xaa Asp His Xaa Arg Trp Lys Xaa Xaa Arg Arg Arg Arg Gln Arg
1               5                   10                  15

Arg Arg Arg

<210> SEQ ID NO 170
<211> LENGTH: 21
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(7)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (8)..(8)
<223> OTHER INFORMATION: Xaa = beta-Ala
<220> FEATURE:
<221> NAME/KEY: MISC_FEATURE
<222> LOCATION: (9)..(9)
<223> OTHER INFORMATION: Xaa = beta-Ala or absent
<220> FEATURE:
<221> NAME/KEY: MOD_RES
<222> LOCATION: (21)..(21)
<223> OTHER INFORMATION: AMIDATION

<400> SEQUENCE: 170

Xaa Asp His Xaa Arg Trp Lys Xaa Xaa Tyr Gly Arg Arg Arg Arg
1               5                   10                  15

Gln Arg Arg Arg
            20

<210> SEQ ID NO 171
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(7)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (8)..(9)
<223> OTHER INFORMATION: Xaa = beta-Ala
<220> FEATURE:
<221> NAME/KEY: MISC_FEATURE
<222> LOCATION: (10)..(10)
<223> OTHER INFORMATION: Xaa = Gly or absent
<220> FEATURE:
<221> NAME/KEY: MOD_RES
<222> LOCATION: (20)..(20)
```

<223> OTHER INFORMATION: AMIDATION

<400> SEQUENCE: 171

Xaa Asp His Xaa Arg Trp Lys Xaa Xaa Xaa Arg Arg Arg Arg Gln
1               5                   10                  15

Arg Arg Arg Arg
            20

<210> SEQ ID NO 172
<211> LENGTH: 19
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(7)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (8)..(8)
<223> OTHER INFORMATION: Xaa = 8-amino-3,6-dioxaoctanoic acid (Doc)
<220> FEATURE:
<221> NAME/KEY: MISC_FEATURE
<222> LOCATION: (9)..(9)
<223> OTHER INFORMATION: Xaa = Gly or absent
<220> FEATURE:
<221> NAME/KEY: MOD_RES
<222> LOCATION: (19)..(19)
<223> OTHER INFORMATION: AMIDATION

<400> SEQUENCE: 172

Xaa Asp His Xaa Arg Trp Lys Xaa Xaa Arg Arg Arg Arg Gln Arg
1               5                   10                  15

Arg Arg Arg

<210> SEQ ID NO 173
<211> LENGTH: 21
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(7)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (8)..(8)
<223> OTHER INFORMATION: Xaa = 8-amino-3,6-dioxaoctanoic acid (Doc)
<220> FEATURE:
<221> NAME/KEY: MISC_FEATURE
<222> LOCATION: (9)..(9)
<223> OTHER INFORMATION: Xaa = 8-amino-3,6-dioxaoctanoic acid (Doc) or
      absent

```
<220> FEATURE:
<221> NAME/KEY: MOD_RES
<222> LOCATION: (21)..(21)
<223> OTHER INFORMATION: AMIDATION

<400> SEQUENCE: 173

Xaa Asp His Xaa Arg Trp Lys Xaa Xaa Tyr Gly Arg Arg Arg Arg
1               5                   10                  15

Gln Arg Arg Arg Arg
            20

<210> SEQ ID NO 174
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(7)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (8)..(9)
<223> OTHER INFORMATION: Xaa = 8-amino-3,6-dioxaoctanoic acid (Doc)
<220> FEATURE:
<221> NAME/KEY: MISC_FEATURE
<222> LOCATION: (10)..(10)
<223> OTHER INFORMATION: Xaa = Gly or absent
<220> FEATURE:
<221> NAME/KEY: MOD_RES
<222> LOCATION: (20)..(20)
<223> OTHER INFORMATION: AMIDATION

<400> SEQUENCE: 174

Xaa Asp His Xaa Arg Trp Lys Xaa Xaa Xaa Arg Arg Arg Arg Gln
1               5                   10                  15

Arg Arg Arg Arg
            20

<210> SEQ ID NO 175
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = beta-Ala
<220> FEATURE:
```

```
<221> NAME/KEY: MISC_FEATURE
<222> LOCATION: (9)..(9)
<223> OTHER INFORMATION: Xaa = beta-Ala
<220> FEATURE:
<221> NAME/KEY: MOD_RES
<222> LOCATION: (20)..(20)
<223> OTHER INFORMATION: AMIDATION

<400> SEQUENCE: 175

Xaa Asp His Xaa Arg Trp Xaa Lys Xaa Tyr Gly Arg Arg Arg Arg
1               5                   10                  15

Gln Arg Arg Arg
            20

<210> SEQ ID NO 176
<211> LENGTH: 18
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = beta-Ala
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MOD_RES
<222> LOCATION: (18)..(18)
<223> OTHER INFORMATION: AMIDATION

<400> SEQUENCE: 176

Xaa Asp His Xaa Arg Trp Xaa Lys Xaa Arg Arg Arg Arg Gln Arg
1               5                   10                  15

Arg Arg

<210> SEQ ID NO 177
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
```

```
<223> OTHER INFORMATION: Xaa = 6-aminohexanoic acid (Ahx)
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MOD_RES
<222> LOCATION: (20)..(20)
<223> OTHER INFORMATION: AMIDATION

<400> SEQUENCE: 177

Xaa Cys His Xaa Arg Trp Xaa Cys Xaa Tyr Gly Arg Arg Arg Arg
1               5                  10                  15

Gln Arg Arg Arg
            20

<210> SEQ ID NO 178
<211> LENGTH: 18
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 6-aminohexanoic acid (Ahx)
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MOD_RES
<222> LOCATION: (18)..(18)
<223> OTHER INFORMATION: AMIDATION

<400> SEQUENCE: 178

Xaa Cys His Xaa Arg Trp Xaa Cys Xaa Arg Arg Arg Arg Gln Arg
1               5                  10                  15

Arg Arg

<210> SEQ ID NO 179
<211> LENGTH: 21
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = D-Phe
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
```

```
<221> NAME/KEY: MISC_FEATURE
<222> LOCATION: (7)..(7)
<223> OTHER INFORMATION: Xaa = beta-Ala
<220> FEATURE:
<221> NAME/KEY: MISC_FEATURE
<222> LOCATION: (8)..(8)
<223> OTHER INFORMATION: Xaa = D-Cys
<220> FEATURE:
<221> NAME/KEY: MISC_FEATURE
<222> LOCATION: (10)..(10)
<223> OTHER INFORMATION: Xaa = beta-Ala
<220> FEATURE:
<221> NAME/KEY: MOD_RES
<222> LOCATION: (21)..(21)
<223> OTHER INFORMATION: AMIDATION

<400> SEQUENCE: 179

Xaa Cys His Xaa Arg Trp Xaa Xaa Thr Xaa Tyr Gly Arg Arg Arg
 1               5                  10                  15

Arg Gln Arg Arg Arg
            20

<210> SEQ ID NO 180
<211> LENGTH: 19
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = D-Phe
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = beta-Ala
<220> FEATURE:
<221> NAME/KEY: MISC_FEATURE
<222> LOCATION: (8)..(8)
<223> OTHER INFORMATION: Xaa = D-Cys
<220> FEATURE:
<221> NAME/KEY: MISC_FEATURE
<222> LOCATION: (10)..(10)
<223> OTHER INFORMATION: Xaa = beta-Ala
<220> FEATURE:
<221> NAME/KEY: MOD_RES
<222> LOCATION: (19)..(19)
<223> OTHER INFORMATION: AMIDATION

<400> SEQUENCE: 180

Xaa Cys His Xaa Arg Trp Xaa Xaa Thr Xaa Arg Arg Arg Arg Gln
 1               5                  10                  15

Arg Arg Arg

<210> SEQ ID NO 181
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
```

```
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 5-aminopentanoic acid (Apn)
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MOD_RES
<222> LOCATION: (20)..(20)
<223> OTHER INFORMATION: AMIDATION

<400> SEQUENCE: 181

Xaa Cys His Xaa Arg Trp Xaa Cys Xaa Tyr Gly Arg Arg Arg Arg
1               5                   10                  15

Gln Arg Arg Arg
            20

<210> SEQ ID NO 182
<211> LENGTH: 18
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 5-aminopentanoic acid (Apn)
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MOD_RES
<222> LOCATION: (18)..(18)
<223> OTHER INFORMATION: AMIDATION

<400> SEQUENCE: 182

Xaa Cys His Xaa Arg Trp Xaa Cys Xaa Arg Arg Arg Arg Gln Arg
1               5                   10                  15

Arg Arg

<210> SEQ ID NO 183
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
```

```
<221> NAME/KEY: MISC_FEATURE
<222> LOCATION: (1)..(1)
<223> OTHER INFORMATION: Xaa = beta-cyclohexylAla (Cha),
      homo-cyclohexylAla (hCha), or Nle, all modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MOD_RES
<222> LOCATION: (20)..(20)
<223> OTHER INFORMATION: AMIDATION

<400> SEQUENCE: 183

Xaa Asp His Xaa Arg Trp Xaa Lys Xaa Tyr Gly Arg Arg Arg Arg
1               5                   10                  15

Gln Arg Arg Arg
            20

<210> SEQ ID NO 184
<211> LENGTH: 18
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = beta-cyclohexylAla (Cha) or homo-
      cyclohexylAla (hCha), both modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MOD_RES
<222> LOCATION: (18)..(18)
<223> OTHER INFORMATION: AMIDATION

<400> SEQUENCE: 184

Xaa Asp His Xaa Arg Trp Xaa Lys Xaa Arg Arg Arg Arg Gln Arg
1               5                   10                  15

Arg Arg

<210> SEQ ID NO 185
<211> LENGTH: 18
<212> TYPE: PRT
<213> ORGANISM: Artificial Sequence
```

```
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle or cyclohexylGly (Chg), both modified
      with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MOD_RES
<222> LOCATION: (18)..(18)
<223> OTHER INFORMATION: AMIDATION

<400> SEQUENCE: 185

Xaa Asp His Xaa Arg Trp Xaa Lys Xaa Arg Arg Arg Arg Gln Arg
1               5                   10                  15

Arg Arg

<210> SEQ ID NO 186
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = cyclohexylGly (Chg) or homo-cyclohexylAla
      (hCha), both modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MOD_RES
<222> LOCATION: (20)..(20)
<223> OTHER INFORMATION: AMIDATION

<400> SEQUENCE: 186

Xaa Asp His Xaa Arg Trp Xaa Lys Xaa Tyr Gly Arg Arg Arg Arg
1               5                   10                  15

Gln Arg Arg Arg
            20
```

```
<210> SEQ ID NO 187
<211> LENGTH: 21
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = homo-cyclohexylAla (hCha) modified with
      acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MISC_FEATURE
<222> LOCATION: (9)..(10)
<223> OTHER INFORMATION: Xaa = beta-Ala
<220> FEATURE:
<221> NAME/KEY: MOD_RES
<222> LOCATION: (21)..(21)
<223> OTHER INFORMATION: AMIDATION

<400> SEQUENCE: 187

Xaa Asp His Xaa Arg Trp Xaa Lys Xaa Xaa Tyr Gly Arg Arg Arg
1               5                   10                  15

Arg Gln Arg Arg Arg
            20

<210> SEQ ID NO 188
<211> LENGTH: 19
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = homo-cyclohexylAla (hCha) modified with
      acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MISC_FEATURE
<222> LOCATION: (10)..(10)
<223> OTHER INFORMATION: Xaa = beta-Ala or absent
<220> FEATURE:
<221> NAME/KEY: MOD_RES
<222> LOCATION: (19)..(19)
<223> OTHER INFORMATION: AMIDATION
```

<400> SEQUENCE: 188

Xaa Asp His Xaa Arg Trp Xaa Lys Xaa Xaa Arg Arg Arg Arg Gln
1               5                   10                  15

Arg Arg Arg

<210> SEQ ID NO 189
<211> LENGTH: 21
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = homo-cyclohexylAla (hCha) modified with
      acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MISC_FEATURE
<222> LOCATION: (9)..(9)
<223> OTHER INFORMATION: Xaa = 8-amino-3,6-dioxaoctanoic acid (Doc)
<220> FEATURE:
<221> NAME/KEY: MISC_FEATURE
<222> LOCATION: (10)..(10)
<223> OTHER INFORMATION: Xaa = 8-amino-3,6-dioxaoctanoic acid (Doc) or
      absent
<220> FEATURE:
<221> NAME/KEY: MOD_RES
<222> LOCATION: (21)..(21)
<223> OTHER INFORMATION: AMIDATION

<400> SEQUENCE: 189

Xaa Asp His Xaa Arg Trp Xaa Lys Xaa Xaa Tyr Gly Arg Arg Arg
1               5                   10                  15

Arg Gln Arg Arg Arg
            20

<210> SEQ ID NO 190
<211> LENGTH: 19
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = homo-cyclohexylAla (hCha) modified with
      acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)

```
<220> FEATURE:
<221> NAME/KEY: MISC_FEATURE
<222> LOCATION: (9)..(9)
<223> OTHER INFORMATION: Xaa = 8-amino-3,6-dioxaoctanoic acid (Doc)
<220> FEATURE:
<221> NAME/KEY: MISC_FEATURE
<222> LOCATION: (10)..(10)
<223> OTHER INFORMATION: Xaa = 8-amino-3,6-dioxaoctanoic acid (Doc) or
      absent
<220> FEATURE:
<221> NAME/KEY: MOD_RES
<222> LOCATION: (19)..(19)
<223> OTHER INFORMATION: AMIDATION

<400> SEQUENCE: 190

Xaa Asp His Xaa Arg Trp Xaa Lys Xaa Xaa Arg Arg Arg Arg Gln
1               5                   10                  15

Arg Arg Arg

<210> SEQ ID NO 191
<211> LENGTH: 22
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = homo-cyclohexylAla (hCha) modified with
      acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MISC_FEATURE
<222> LOCATION: (10)..(10)
<223> OTHER INFORMATION: Xaa = beta-Ala or absent
<220> FEATURE:
<221> NAME/KEY: MOD_RES
<222> LOCATION: (22)..(22)
<223> OTHER INFORMATION: AMIDATION

<400> SEQUENCE: 191

Xaa Asp His Xaa Arg Trp Xaa Lys Xaa Xaa Tyr Gly Arg Arg Arg
1               5                   10                  15

Arg Gln Arg Arg Arg Arg
            20

<210> SEQ ID NO 192
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = homo-cyclohexylAla (hCha) modified with
```

```
            acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MISC_FEATURE
<222> LOCATION: (10)..(10)
<223> OTHER INFORMATION: Xaa = beta-Ala or absent
<220> FEATURE:
<221> NAME/KEY: MOD_RES
<222> LOCATION: (20)..(20)
<223> OTHER INFORMATION: AMIDATION

<400> SEQUENCE: 192

Xaa Asp His Xaa Arg Trp Xaa Lys Xaa Xaa Arg Arg Arg Arg Gln
1               5                   10                  15

Arg Arg Arg Arg
            20

<210> SEQ ID NO 193
<211> LENGTH: 22
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = homo-cyclohexylAla (hCha) modified with
      acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MISC_FEATURE
<222> LOCATION: (9)..(9)
<223> OTHER INFORMATION: Xaa = 8-amino-3,6-dioxaoctanoic acid (Doc)
<220> FEATURE:
<221> NAME/KEY: MISC_FEATURE
<222> LOCATION: (10)..(10)
<223> OTHER INFORMATION: Xaa = 8-amino-3,6-dioxaoctanoic acid (Doc) or
      absent
<220> FEATURE:
<221> NAME/KEY: MOD_RES
<222> LOCATION: (22)..(22)
<223> OTHER INFORMATION: AMIDATION

<400> SEQUENCE: 193

Xaa Asp His Xaa Arg Trp Xaa Lys Xaa Xaa Tyr Gly Arg Arg Arg
1               5                   10                  15

Arg Gln Arg Arg Arg Arg
```

```
                       20

<210> SEQ ID NO 194
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = homo-cyclohexylAla (hCha) modified with
      acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MISC_FEATURE
<222> LOCATION: (9)..(9)
<223> OTHER INFORMATION: Xaa = 8-amino-3,6-dioxaoctanoic acid (Doc)
<220> FEATURE:
<221> NAME/KEY: MISC_FEATURE
<222> LOCATION: (10)..(10)
<223> OTHER INFORMATION: Xaa = 8-amino-3,6-dioxaoctanoic acid (Doc) or
      absent
<220> FEATURE:
<221> NAME/KEY: MOD_RES
<222> LOCATION: (20)..(20)
<223> OTHER INFORMATION: AMIDATION

<400> SEQUENCE: 194

Xaa Asp His Xaa Arg Trp Xaa Lys Xaa Xaa Arg Arg Arg Arg Gln
1               5                   10                  15

Arg Arg Arg Arg
            20

<210> SEQ ID NO 195
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = D-cyclohexylGly (D-Chg) modified with
      acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MISC_FEATURE
<222> LOCATION: (9)..(9)
<223> OTHER INFORMATION: Xaa = beta-Ala
<220> FEATURE:
```

```
<221> NAME/KEY: MOD_RES
<222> LOCATION: (20)..(20)
<223> OTHER INFORMATION: AMIDATION

<400> SEQUENCE: 195

Xaa Asp His Xaa Arg Trp Xaa Lys Xaa Tyr Gly Arg Arg Arg Arg
1               5                   10                  15

Gln Arg Arg Arg
            20

<210> SEQ ID NO 196
<211> LENGTH: 18
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = D-cyclohexylGly (D-Chg) modified with
      acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MOD_RES
<222> LOCATION: (18)..(18)
<223> OTHER INFORMATION: AMIDATION

<400> SEQUENCE: 196

Xaa Asp His Xaa Arg Trp Xaa Lys Xaa Arg Arg Arg Arg Gln Arg
1               5                   10                  15

Arg Arg

<210> SEQ ID NO 197
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = homo-phenylAla (hPhe) modified with acyl
      (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
```

```
<221> NAME/KEY: MISC_FEATURE
<222> LOCATION: (9)..(9)
<223> OTHER INFORMATION: Xaa = beta-Ala
<220> FEATURE:
<221> NAME/KEY: MOD_RES
<222> LOCATION: (20)..(20)
<223> OTHER INFORMATION: AMIDATION

<400> SEQUENCE: 197

Xaa Asp His Xaa Arg Trp Xaa Lys Xaa Tyr Gly Arg Arg Arg Arg
1               5                   10                  15

Gln Arg Arg Arg
            20

<210> SEQ ID NO 198
<211> LENGTH: 18
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = homo-phenylAla (hPhe) modified with acyl
      (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MOD_RES
<222> LOCATION: (18)..(18)
<223> OTHER INFORMATION: AMIDATION

<400> SEQUENCE: 198

Xaa Asp His Xaa Arg Trp Xaa Lys Xaa Arg Arg Arg Arg Gln Arg
1               5                   10                  15

Arg Arg

<210> SEQ ID NO 199
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
```

```
<222> LOCATION: (6)..(6)
<223> OTHER INFORMATION: Xaa = D-Trp
<220> FEATURE:
<221> NAME/KEY: MISC_FEATURE
<222> LOCATION: (7)..(7)
<223> OTHER INFORMATION: Xaa = 5-aminopentanoic acid (Apn) or 6-
      aminohexanoic acid (Ahx)
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MOD_RES
<222> LOCATION: (20)..(20)
<223> OTHER INFORMATION: AMIDATION

<400> SEQUENCE: 199

Xaa Cys His Xaa Arg Xaa Xaa Cys Xaa Tyr Gly Arg Arg Arg Arg
1               5                   10                  15

Gln Arg Arg Arg
            20

<210> SEQ ID NO 200
<211> LENGTH: 18
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (6)..(6)
<223> OTHER INFORMATION: Xaa = D-Trp
<220> FEATURE:
<221> NAME/KEY: MISC_FEATURE
<222> LOCATION: (7)..(7)
<223> OTHER INFORMATION: Xaa = 5-aminopentanoic acid (Apn) or 6-
      aminohexanoic acid (Ahx)
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MOD_RES
<222> LOCATION: (18)..(18)
<223> OTHER INFORMATION: AMIDATION

<400> SEQUENCE: 200

Xaa Cys His Xaa Arg Xaa Xaa Cys Xaa Arg Arg Arg Arg Gln Arg
1               5                   10                  15

Arg Arg

<210> SEQ ID NO 201
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
```

```
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (6)..(6)
<223> OTHER INFORMATION: Xaa = D-Trp
<220> FEATURE:
<221> NAME/KEY: MISC_FEATURE
<222> LOCATION: (7)..(7)
<223> OTHER INFORMATION: Xaa = beta-Ala
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MOD_RES
<222> LOCATION: (20)..(20)
<223> OTHER INFORMATION: AMIDATION

<400> SEQUENCE: 201

Xaa Cys His Xaa Arg Xaa Xaa Cys Xaa Tyr Gly Arg Arg Arg Arg
1               5                   10                  15

Gln Arg Arg Arg
            20

<210> SEQ ID NO 202
<211> LENGTH: 18
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (6)..(6)
<223> OTHER INFORMATION: Xaa = D-Trp
<220> FEATURE:
<221> NAME/KEY: MISC_FEATURE
<222> LOCATION: (7)..(7)
<223> OTHER INFORMATION: Xaa = beta-Ala
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MOD_RES
<222> LOCATION: (18)..(18)
<223> OTHER INFORMATION: AMIDATION

<400> SEQUENCE: 202

Xaa Cys His Xaa Arg Xaa Xaa Cys Xaa Arg Arg Arg Arg Gln Arg
1               5                   10                  15

Arg Arg
```

```
<210> SEQ ID NO 203
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (8)..(8)
<223> OTHER INFORMATION: Xaa = penicillamine (Pen)
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MISC_FEATURE
<222> LOCATION: (10)..(10)
<223> OTHER INFORMATION: Xaa = Tyr or absent
<220> FEATURE:
<221> NAME/KEY: MOD_RES
<222> LOCATION: (20)..(20)
<223> OTHER INFORMATION: AMIDATION

<400> SEQUENCE: 203

Xaa Cys Xaa His Xaa Arg Trp Xaa Xaa Xaa Gly Arg Arg Arg Arg
1               5                   10                  15

Gln Arg Arg Arg
            20

<210> SEQ ID NO 204
<211> LENGTH: 21
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (8)..(8)
<223> OTHER INFORMATION: Xaa = penicillamine (Pen)
<220> FEATURE:
<221> NAME/KEY: MISC_FEATURE
```

```
<222> LOCATION: (9)..(10)
<223> OTHER INFORMATION: Xaa = beta-Ala
<220> FEATURE:
<221> NAME/KEY: MISC_FEATURE
<222> LOCATION: (11)..(11)
<223> OTHER INFORMATION: Xaa = Tyr or absent
<220> FEATURE:
<221> NAME/KEY: MOD_RES
<222> LOCATION: (21)..(21)
<223> OTHER INFORMATION: AMIDATION

<400> SEQUENCE: 204

Xaa Cys Xaa His Xaa Arg Trp Xaa Xaa Xaa Xaa Gly Arg Arg Arg
1               5                   10                  15

Arg Gln Arg Arg Arg
            20

<210> SEQ ID NO 205
<211> LENGTH: 19
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (8)..(8)
<223> OTHER INFORMATION: Xaa = penicillamine (Pen)
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MISC_FEATURE
<222> LOCATION: (10)..(10)
<223> OTHER INFORMATION: Xaa = beta-Ala or absent
<220> FEATURE:
<221> NAME/KEY: MOD_RES
<222> LOCATION: (19)..(19)
<223> OTHER INFORMATION: AMIDATION

<400> SEQUENCE: 205

Xaa Cys Xaa His Xaa Arg Trp Xaa Xaa Xaa Arg Arg Arg Arg Gln
1               5                   10                  15

Arg Arg Arg

<210> SEQ ID NO 206
<211> LENGTH: 19
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
```

```
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (8)..(8)
<223> OTHER INFORMATION: Xaa = penicillamine (Pen)
<220> FEATURE:
<221> NAME/KEY: MISC_FEATURE
<222> LOCATION: (9)..(9)
<223> OTHER INFORMATION: Xaa = 8-amino-3,6-dioxaoctanoic acid (Doc)
<220> FEATURE:
<221> NAME/KEY: MISC_FEATURE
<222> LOCATION: (10)..(10)
<223> OTHER INFORMATION: Xaa = Gly or absent
<220> FEATURE:
<221> NAME/KEY: MOD_RES
<222> LOCATION: (19)..(19)
<223> OTHER INFORMATION: AMIDATION

<400> SEQUENCE: 206

Xaa Cys Xaa His Xaa Arg Trp Xaa Xaa Xaa Arg Arg Arg Arg Gln
1               5                   10                  15

Arg Arg Arg

<210> SEQ ID NO 207
<211> LENGTH: 21
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (8)..(8)
<223> OTHER INFORMATION: Xaa = penicillamine (Pen)
<220> FEATURE:
<221> NAME/KEY: MISC_FEATURE
<222> LOCATION: (9)..(9)
<223> OTHER INFORMATION: Xaa = 8-amino-3,6-dioxaoctanoic acid (Doc)
<220> FEATURE:
<221> NAME/KEY: MISC_FEATURE
<222> LOCATION: (10)..(10)
<223> OTHER INFORMATION: Xaa = 8-amino-3,6-dioxaoctanoic acid (Doc) or
      absent
<220> FEATURE:
<221> NAME/KEY: MOD_RES
<222> LOCATION: (21)..(21)
<223> OTHER INFORMATION: AMIDATION

<400> SEQUENCE: 207
```

```
Xaa Cys Xaa His Xaa Arg Trp Xaa Xaa Xaa Tyr Gly Arg Arg Arg
1               5                   10                  15

Arg Gln Arg Arg Arg
            20
```

<210> SEQ ID NO 208
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (8)..(8)
<223> OTHER INFORMATION: Xaa = penicillamine (Pen)
<220> FEATURE:
<221> NAME/KEY: MISC_FEATURE
<222> LOCATION: (9)..(10)
<223> OTHER INFORMATION: Xaa = 8-amino-3,6-dioxaoctanoic acid (Doc)
<220> FEATURE:
<221> NAME/KEY: MISC_FEATURE
<222> LOCATION: (11)..(11)
<223> OTHER INFORMATION: Xaa = Gly or absent
<220> FEATURE:
<221> NAME/KEY: MOD_RES
<222> LOCATION: (20)..(20)
<223> OTHER INFORMATION: AMIDATION

<400> SEQUENCE: 208

```
Xaa Cys Xaa His Xaa Arg Trp Xaa Xaa Xaa Xaa Arg Arg Arg Arg
1               5                   10                  15

Gln Arg Arg Arg
            20
```

<210> SEQ ID NO 209
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = D-Phe
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-(Et)Tyr
<220> FEATURE:
<221> NAME/KEY: MISC_FEATURE
<222> LOCATION: (7)..(7)

```
<223> OTHER INFORMATION: Xaa = beta-Ala
<220> FEATURE:
<221> NAME/KEY: MISC_FEATURE
<222> LOCATION: (8)..(8)
<223> OTHER INFORMATION: Xaa = D-Cys
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MISC_FEATURE
<222> LOCATION: (10)..(10)
<223> OTHER INFORMATION: Xaa = Tyr or absent
<220> FEATURE:
<221> NAME/KEY: MOD_RES
<222> LOCATION: (20)..(20)
<223> OTHER INFORMATION: AMIDATION

<400> SEQUENCE: 209

Xaa Cys His Xaa Arg Trp Xaa Xaa Xaa Xaa Gly Arg Arg Arg Arg
1               5                   10                  15

Gln Arg Arg Arg
            20

<210> SEQ ID NO 210
<211> LENGTH: 18
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = D-Phe
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-(Et)Tyr
<220> FEATURE:
<221> NAME/KEY: MISC_FEATURE
<222> LOCATION: (7)..(7)
<223> OTHER INFORMATION: Xaa = beta-Ala
<220> FEATURE:
<221> NAME/KEY: MISC_FEATURE
<222> LOCATION: (8)..(8)
<223> OTHER INFORMATION: Xaa = D-Cys
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MOD_RES
<222> LOCATION: (18)..(18)
<223> OTHER INFORMATION: AMIDATION

<400> SEQUENCE: 210

Xaa Cys His Xaa Arg Trp Xaa Xaa Xaa Arg Arg Arg Arg Gln Arg
1               5                   10                  15

Arg Arg

<210> SEQ ID NO 211
<211> LENGTH: 19
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
```

```
<221> NAME/KEY: MISC_FEATURE
<222> LOCATION: (1)..(1)
<223> OTHER INFORMATION: Xaa = D-Phe
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-(Et)Tyr
<220> FEATURE:
<221> NAME/KEY: MISC_FEATURE
<222> LOCATION: (7)..(7)
<223> OTHER INFORMATION: Xaa = beta-Ala
<220> FEATURE:
<221> NAME/KEY: MISC_FEATURE
<222> LOCATION: (8)..(8)
<223> OTHER INFORMATION: Xaa = D-Cys
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MOD_RES
<222> LOCATION: (19)..(19)
<223> OTHER INFORMATION: AMIDATION

<400> SEQUENCE: 211

Xaa Cys His Xaa Arg Trp Xaa Xaa Xaa Arg Arg Arg Arg Gln Arg
1               5                   10                  15

Arg Arg Arg

<210> SEQ ID NO 212
<211> LENGTH: 21
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = D-Phe
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-(Et)Tyr
<220> FEATURE:
<221> NAME/KEY: MISC_FEATURE
<222> LOCATION: (7)..(7)
<223> OTHER INFORMATION: Xaa = beta-Ala
<220> FEATURE:
<221> NAME/KEY: MISC_FEATURE
<222> LOCATION: (8)..(8)
<223> OTHER INFORMATION: Xaa = D-Cys
<220> FEATURE:
<221> NAME/KEY: MISC_FEATURE
<222> LOCATION: (9)..(10)
<223> OTHER INFORMATION: Xaa = beta-Ala
<220> FEATURE:
<221> NAME/KEY: MOD_RES
<222> LOCATION: (21)..(21)
<223> OTHER INFORMATION: AMIDATION

<400> SEQUENCE: 212

Xaa Cys His Xaa Arg Trp Xaa Xaa Xaa Tyr Gly Arg Arg Arg
1               5                   10                  15

Arg Gln Arg Arg Arg
            20
```

<210> SEQ ID NO 213
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = D-Phe
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-(Et)Tyr
<220> FEATURE:
<221> NAME/KEY: MISC_FEATURE
<222> LOCATION: (7)..(7)
<223> OTHER INFORMATION: Xaa = beta-Ala
<220> FEATURE:
<221> NAME/KEY: MISC_FEATURE
<222> LOCATION: (8)..(8)
<223> OTHER INFORMATION: Xaa = D-Cys
<220> FEATURE:
<221> NAME/KEY: MISC_FEATURE
<222> LOCATION: (9)..(10)
<223> OTHER INFORMATION: Xaa = beta-Ala
<220> FEATURE:
<221> NAME/KEY: MISC_FEATURE
<222> LOCATION: (11)..(11)
<223> OTHER INFORMATION: Xaa = Gly or absent
<220> FEATURE:
<221> NAME/KEY: MOD_RES
<222> LOCATION: (20)..(20)
<223> OTHER INFORMATION: AMIDATION

<400> SEQUENCE: 213

Xaa Cys His Xaa Arg Trp Xaa Xaa Xaa Xaa Xaa Arg Arg Arg Arg Arg
1               5                   10                  15

Gln Arg Arg Arg
            20

<210> SEQ ID NO 214
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = D-Phe
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-(Et)Tyr
<220> FEATURE:
<221> NAME/KEY: MISC_FEATURE
<222> LOCATION: (7)..(7)
<223> OTHER INFORMATION: Xaa = beta-Ala
<220> FEATURE:
<221> NAME/KEY: MISC_FEATURE
<222> LOCATION: (8)..(8)
<223> OTHER INFORMATION: Xaa = D-Cys
<220> FEATURE:

```
<221> NAME/KEY: MISC_FEATURE
<222> LOCATION: (9)..(9)
<223> OTHER INFORMATION: Xaa = 8-amino-3,6-dioxaoctanoic acid (Doc)
<220> FEATURE:
<221> NAME/KEY: MISC_FEATURE
<222> LOCATION: (10)..(10)
<223> OTHER INFORMATION: Xaa = Tyr or absent
<220> FEATURE:
<221> NAME/KEY: MOD_RES
<222> LOCATION: (20)..(20)
<223> OTHER INFORMATION: AMIDATION

<400> SEQUENCE: 214

Xaa Cys His Xaa Arg Trp Xaa Xaa Xaa Xaa Gly Arg Arg Arg Arg
1               5                   10                  15

Gln Arg Arg Arg
            20

<210> SEQ ID NO 215
<211> LENGTH: 21
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = D-Phe
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-(Et)Tyr
<220> FEATURE:
<221> NAME/KEY: MISC_FEATURE
<222> LOCATION: (7)..(7)
<223> OTHER INFORMATION: Xaa = beta-Ala
<220> FEATURE:
<221> NAME/KEY: MISC_FEATURE
<222> LOCATION: (8)..(8)
<223> OTHER INFORMATION: Xaa = D-Cys
<220> FEATURE:
<221> NAME/KEY: MISC_FEATURE
<222> LOCATION: (9)..(10)
<223> OTHER INFORMATION: Xaa = 8-amino-3,6-dioxaoctanoic acid (Doc)
<220> FEATURE:
<221> NAME/KEY: MISC_FEATURE
<222> LOCATION: (11)..(11)
<223> OTHER INFORMATION: Xaa = Tyr or absent
<220> FEATURE:
<221> NAME/KEY: MOD_RES
<222> LOCATION: (21)..(21)
<223> OTHER INFORMATION: AMIDATION

<400> SEQUENCE: 215

Xaa Cys His Xaa Arg Trp Xaa Xaa Xaa Xaa Xaa Gly Arg Arg Arg
1               5                   10                  15

Arg Gln Arg Arg Arg
                20

<210> SEQ ID NO 216
<211> LENGTH: 19
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
```

```
<222> LOCATION: (1)..(1)
<223> OTHER INFORMATION: Xaa = D-Phe
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-(Et)Tyr
<220> FEATURE:
<221> NAME/KEY: MISC_FEATURE
<222> LOCATION: (7)..(7)
<223> OTHER INFORMATION: Xaa = beta-Ala
<220> FEATURE:
<221> NAME/KEY: MISC_FEATURE
<222> LOCATION: (8)..(8)
<223> OTHER INFORMATION: Xaa = D-Cys
<220> FEATURE:
<221> NAME/KEY: MISC_FEATURE
<222> LOCATION: (9)..(9)
<223> OTHER INFORMATION: Xaa = 8-amino-3,6-dioxaoctanoic acid (Doc)
<220> FEATURE:
<221> NAME/KEY: MISC_FEATURE
<222> LOCATION: (10)..(10)
<223> OTHER INFORMATION: Xaa = 8-amino-3,6-dioxaoctanoic acid (Doc) or
      absent
<220> FEATURE:
<221> NAME/KEY: MOD_RES
<222> LOCATION: (19)..(19)
<223> OTHER INFORMATION: AMIDATION

<400> SEQUENCE: 216

Xaa Cys His Xaa Arg Trp Xaa Xaa Xaa Xaa Arg Arg Arg Arg Gln
1               5                   10                  15

Arg Arg Arg

<210> SEQ ID NO 217
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = D-Phe
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-(Et)Tyr
<220> FEATURE:
<221> NAME/KEY: MISC_FEATURE
<222> LOCATION: (7)..(7)
<223> OTHER INFORMATION: Xaa = beta-Ala
<220> FEATURE:
<221> NAME/KEY: MISC_FEATURE
<222> LOCATION: (8)..(8)
<223> OTHER INFORMATION: Xaa = D-Cys
<220> FEATURE:
<221> NAME/KEY: MISC_FEATURE
<222> LOCATION: (9)..(9)
<223> OTHER INFORMATION: Xaa = 8-amino-3,6-dioxaoctanoic acid (Doc)
<220> FEATURE:
<221> NAME/KEY: MISC_FEATURE
<222> LOCATION: (10)..(10)
<223> OTHER INFORMATION: Xaa = 8-amino-3,6-dioxaoctanoic acid (Doc) or
      absent
<220> FEATURE:
<221> NAME/KEY: MOD_RES
<222> LOCATION: (20)..(20)
```

<223> OTHER INFORMATION: AMIDATION

<400> SEQUENCE: 217

Xaa Cys His Xaa Arg Trp Xaa Xaa Xaa Xaa Arg Arg Arg Arg Gln
1               5                   10                  15

Arg Arg Arg Arg
            20

<210> SEQ ID NO 218
<211> LENGTH: 22
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = D-Phe
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-(Et)Tyr
<220> FEATURE:
<221> NAME/KEY: MISC_FEATURE
<222> LOCATION: (5)..(5)
<223> OTHER INFORMATION: Xaa = homo-Arg (hArg)
<220> FEATURE:
<221> NAME/KEY: MISC_FEATURE
<222> LOCATION: (7)..(7)
<223> OTHER INFORMATION: Xaa = beta-Ala
<220> FEATURE:
<221> NAME/KEY: MISC_FEATURE
<222> LOCATION: (8)..(8)
<223> OTHER INFORMATION: Xaa = D-Cys
<220> FEATURE:
<221> NAME/KEY: MISC_FEATURE
<222> LOCATION: (10)..(10)
<223> OTHER INFORMATION: Xaa = beta-Ala
<220> FEATURE:
<221> NAME/KEY: MISC_FEATURE
<222> LOCATION: (11)..(11)
<223> OTHER INFORMATION: Xaa = beta-Ala or absent
<220> FEATURE:
<221> NAME/KEY: MOD_RES
<222> LOCATION: (22)..(22)
<223> OTHER INFORMATION: AMIDATION

<400> SEQUENCE: 218

Xaa Cys His Xaa Xaa Trp Xaa Xaa Thr Xaa Xaa Tyr Gly Arg Arg
1               5                   10                  15

Arg Arg Gln Arg Arg Arg
            20

<210> SEQ ID NO 219
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = D-Phe
<220> FEATURE:
<221> NAME/KEY: DOMAIN
<222> LOCATION: (2)..(8)
<223> OTHER INFORMATION: cyclic

```
<220> FEATURE:
<221> NAME/KEY: MISC_FEATURE
<222> LOCATION: (4)..(4)
<223> OTHER INFORMATION: Xaa = D-(Et)Tyr
<220> FEATURE:
<221> NAME/KEY: MISC_FEATURE
<222> LOCATION: (5)..(5)
<223> OTHER INFORMATION: Xaa = homo-Arg (hArg)
<220> FEATURE:
<221> NAME/KEY: MISC_FEATURE
<222> LOCATION: (7)..(7)
<223> OTHER INFORMATION: Xaa = beta-Ala
<220> FEATURE:
<221> NAME/KEY: MISC_FEATURE
<222> LOCATION: (8)..(8)
<223> OTHER INFORMATION: Xaa = D-Cys
<220> FEATURE:
<221> NAME/KEY: MISC_FEATURE
<222> LOCATION: (10)..(10)
<223> OTHER INFORMATION: Xaa = beta-Ala
<220> FEATURE:
<221> NAME/KEY: MISC_FEATURE
<222> LOCATION: (11)..(11)
<223> OTHER INFORMATION: Xaa = beta-Ala or absent
<220> FEATURE:
<221> NAME/KEY: MOD_RES
<222> LOCATION: (20)..(20)
<223> OTHER INFORMATION: AMIDATION

<400> SEQUENCE: 219

Xaa Cys His Xaa Xaa Trp Xaa Xaa Thr Xaa Xaa Arg Arg Arg Arg
1               5                   10                  15

Gln Arg Arg Arg
            20

<210> SEQ ID NO 220
<211> LENGTH: 19
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = D-Phe
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-(Et)Tyr
<220> FEATURE:
<221> NAME/KEY: MISC_FEATURE
<222> LOCATION: (5)..(5)
<223> OTHER INFORMATION: Xaa = homo-Arg (hArg)
<220> FEATURE:
<221> NAME/KEY: MISC_FEATURE
<222> LOCATION: (7)..(7)
<223> OTHER INFORMATION: Xaa = beta-Ala
<220> FEATURE:
<221> NAME/KEY: MISC_FEATURE
<222> LOCATION: (8)..(8)
<223> OTHER INFORMATION: Xaa = D-Cys
<220> FEATURE:
<221> NAME/KEY: MISC_FEATURE
<222> LOCATION: (10)..(10)
<223> OTHER INFORMATION: Xaa = 8-amino-3,6-dioxaoctanoic acid (Doc)
<220> FEATURE:
<221> NAME/KEY: MOD_RES
<222> LOCATION: (19)..(19)
<223> OTHER INFORMATION: AMIDATION

<400> SEQUENCE: 220
```

Xaa Cys His Xaa Xaa Trp Xaa Xaa Thr Xaa Arg Arg Arg Arg Gln
1               5                   10                  15

Arg Arg Arg

<210> SEQ ID NO 221
<211> LENGTH: 22
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = D-Phe
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-(Et)Tyr
<220> FEATURE:
<221> NAME/KEY: MISC_FEATURE
<222> LOCATION: (5)..(5)
<223> OTHER INFORMATION: Xaa = homo-Arg (hArg)
<220> FEATURE:
<221> NAME/KEY: MISC_FEATURE
<222> LOCATION: (7)..(7)
<223> OTHER INFORMATION: Xaa = beta-Ala
<220> FEATURE:
<221> NAME/KEY: MISC_FEATURE
<222> LOCATION: (8)..(8)
<223> OTHER INFORMATION: Xaa = D-Cys
<220> FEATURE:
<221> NAME/KEY: MISC_FEATURE
<222> LOCATION: (10)..(10)
<223> OTHER INFORMATION: Xaa = 8-amino-3,6-dioxaoctanoic acid (Doc)
<220> FEATURE:
<221> NAME/KEY: MISC_FEATURE
<222> LOCATION: (11)..(11)
<223> OTHER INFORMATION: Xaa = 8-amino-3,6-dioxaoctanoic acid (Doc) or
      absent
<220> FEATURE:
<221> NAME/KEY: MOD_RES
<222> LOCATION: (22)..(22)
<223> OTHER INFORMATION: AMIDATION

<400> SEQUENCE: 221

Xaa Cys His Xaa Xaa Trp Xaa Xaa Thr Xaa Xaa Tyr Gly Arg Arg
1               5                   10                  15

Arg Arg Gln Arg Arg Arg
            20

<210> SEQ ID NO 222
<211> LENGTH: 23
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = D-Phe
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)

```
<223> OTHER INFORMATION: Xaa = D-(Et)Tyr
<220> FEATURE:
<221> NAME/KEY: MISC_FEATURE
<222> LOCATION: (5)..(5)
<223> OTHER INFORMATION: Xaa = homo-Arg (hArg)
<220> FEATURE:
<221> NAME/KEY: MISC_FEATURE
<222> LOCATION: (7)..(7)
<223> OTHER INFORMATION: Xaa = beta-Ala
<220> FEATURE:
<221> NAME/KEY: MISC_FEATURE
<222> LOCATION: (8)..(8)
<223> OTHER INFORMATION: Xaa = D-Cys
<220> FEATURE:
<221> NAME/KEY: MISC_FEATURE
<222> LOCATION: (10)..(10)
<223> OTHER INFORMATION: Xaa = beta-Ala
<220> FEATURE:
<221> NAME/KEY: MISC_FEATURE
<222> LOCATION: (11)..(11)
<223> OTHER INFORMATION: Xaa = beta-Ala or absent
<220> FEATURE:
<221> NAME/KEY: MOD_RES
<222> LOCATION: (23)..(23)
<223> OTHER INFORMATION: AMIDATION

<400> SEQUENCE: 222

Xaa Cys His Xaa Xaa Trp Xaa Xaa Thr Xaa Xaa Tyr Gly Arg Arg Arg
1               5                   10                  15

Arg Arg Gln Arg Arg Arg Arg
            20

<210> SEQ ID NO 223
<211> LENGTH: 21
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = D-Phe
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-(Et)Tyr
<220> FEATURE:
<221> NAME/KEY: MISC_FEATURE
<222> LOCATION: (5)..(5)
<223> OTHER INFORMATION: Xaa = homo-Arg (hArg)
<220> FEATURE:
<221> NAME/KEY: MISC_FEATURE
<222> LOCATION: (7)..(7)
<223> OTHER INFORMATION: Xaa = beta-Ala
<220> FEATURE:
<221> NAME/KEY: MISC_FEATURE
<222> LOCATION: (8)..(8)
<223> OTHER INFORMATION: Xaa = D-Cys
<220> FEATURE:
<221> NAME/KEY: MISC_FEATURE
<222> LOCATION: (10)..(10)
<223> OTHER INFORMATION: Xaa = beta-Ala
<220> FEATURE:
<221> NAME/KEY: MISC_FEATURE
<222> LOCATION: (11)..(11)
<223> OTHER INFORMATION: Xaa = beta-Ala or absent
<220> FEATURE:
<221> NAME/KEY: MOD_RES
<222> LOCATION: (21)..(21)
<223> OTHER INFORMATION: AMIDATION
```

<400> SEQUENCE: 223

Xaa Cys His Xaa Xaa Trp Xaa Xaa Thr Xaa Xaa Arg Arg Arg Arg
1               5                   10                  15

Gln Arg Arg Arg Arg
            20

<210> SEQ ID NO 224
<211> LENGTH: 23
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = D-Phe
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-(Et)Tyr
<220> FEATURE:
<221> NAME/KEY: MISC_FEATURE
<222> LOCATION: (5)..(5)
<223> OTHER INFORMATION: Xaa = homo-Arg (hArg)
<220> FEATURE:
<221> NAME/KEY: MISC_FEATURE
<222> LOCATION: (7)..(7)
<223> OTHER INFORMATION: Xaa = beta-Ala
<220> FEATURE:
<221> NAME/KEY: MISC_FEATURE
<222> LOCATION: (8)..(8)
<223> OTHER INFORMATION: Xaa = D-Cys
<220> FEATURE:
<221> NAME/KEY: MISC_FEATURE
<222> LOCATION: (10)..(10)
<223> OTHER INFORMATION: Xaa = 8-amino-3,6-dioxaoctanoic acid (Doc)
<220> FEATURE:
<221> NAME/KEY: MISC_FEATURE
<222> LOCATION: (11)..(11)
<223> OTHER INFORMATION: Xaa = 8-amino-3,6-dioxaoctanoic acid (Doc) or
      absent
<220> FEATURE:
<221> NAME/KEY: MOD_RES
<222> LOCATION: (23)..(23)
<223> OTHER INFORMATION: AMIDATION

<400> SEQUENCE: 224

Xaa Cys His Xaa Xaa Trp Xaa Xaa Thr Xaa Xaa Tyr Gly Arg Arg
1               5                   10                  15

Arg Arg Gln Arg Arg Arg Arg
            20

<210> SEQ ID NO 225
<211> LENGTH: 21
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = D-Phe
<220> FEATURE:
<221> NAME/KEY: DOMAIN
<222> LOCATION: (2)..(8)
<223> OTHER INFORMATION: cyclic
<220> FEATURE:

```
<221> NAME/KEY: MISC_FEATURE
<222> LOCATION: (4)..(4)
<223> OTHER INFORMATION: Xaa = D-(Et)Tyr
<220> FEATURE:
<221> NAME/KEY: MISC_FEATURE
<222> LOCATION: (5)..(5)
<223> OTHER INFORMATION: Xaa = homo-Arg (hArg)
<220> FEATURE:
<221> NAME/KEY: MISC_FEATURE
<222> LOCATION: (7)..(7)
<223> OTHER INFORMATION: Xaa = beta-Ala
<220> FEATURE:
<221> NAME/KEY: MISC_FEATURE
<222> LOCATION: (8)..(8)
<223> OTHER INFORMATION: Xaa = D-Cys
<220> FEATURE:
<221> NAME/KEY: MISC_FEATURE
<222> LOCATION: (10)..(10)
<223> OTHER INFORMATION: Xaa = 8-amino-3,6-dioxaoctanoic acid (Doc)
<220> FEATURE:
<221> NAME/KEY: MISC_FEATURE
<222> LOCATION: (11)..(11)
<223> OTHER INFORMATION: Xaa = 8-amino-3,6-dioxaoctanoic acid (Doc) or
      absent
<220> FEATURE:
<221> NAME/KEY: MOD_RES
<222> LOCATION: (21)..(21)
<223> OTHER INFORMATION: AMIDATION

<400> SEQUENCE: 225

Xaa Cys His Xaa Xaa Trp Xaa Xaa Thr Xaa Xaa Arg Arg Arg Arg
1               5                   10                  15

Gln Arg Arg Arg Arg
            20

<210> SEQ ID NO 226
<211> LENGTH: 22
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = D-Phe
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-(Et)Tyr
<220> FEATURE:
<221> NAME/KEY: MISC_FEATURE
<222> LOCATION: (5)..(5)
<223> OTHER INFORMATION: Xaa = homo-Arg (hArg)
<220> FEATURE:
<221> NAME/KEY: MISC_FEATURE
<222> LOCATION: (6)..(6)
<223> OTHER INFORMATION: Xaa = 4,4'-biphenylAla (Bip)
<220> FEATURE:
<221> NAME/KEY: MISC_FEATURE
<222> LOCATION: (7)..(7)
<223> OTHER INFORMATION: Xaa = beta-Ala
<220> FEATURE:
<221> NAME/KEY: MISC_FEATURE
<222> LOCATION: (8)..(8)
<223> OTHER INFORMATION: Xaa = D-Cys
<220> FEATURE:
<221> NAME/KEY: MISC_FEATURE
<222> LOCATION: (10)..(10)
<223> OTHER INFORMATION: Xaa = beta-Ala
<220> FEATURE:
<221> NAME/KEY: MOD_RES
```

```
<222> LOCATION: (22)..(22)
<223> OTHER INFORMATION: AMIDATION

<400> SEQUENCE: 226

Xaa Cys His Xaa Xaa Xaa Xaa Xaa Thr Xaa Tyr Gly Arg Arg Arg
1               5                   10                  15

Arg Gln Arg Arg Arg Arg
            20

<210> SEQ ID NO 227
<211> LENGTH: 22
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = D-Phe
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-(Et)Tyr
<220> FEATURE:
<221> NAME/KEY: MISC_FEATURE
<222> LOCATION: (5)..(5)
<223> OTHER INFORMATION: Xaa = homo-Arg (hArg)
<220> FEATURE:
<221> NAME/KEY: MISC_FEATURE
<222> LOCATION: (6)..(6)
<223> OTHER INFORMATION: Xaa = 4,4'-biphenylAla (Bip)
<220> FEATURE:
<221> NAME/KEY: MISC_FEATURE
<222> LOCATION: (7)..(7)
<223> OTHER INFORMATION: Xaa = beta-Ala
<220> FEATURE:
<221> NAME/KEY: MISC_FEATURE
<222> LOCATION: (8)..(8)
<223> OTHER INFORMATION: Xaa = D-Cys
<220> FEATURE:
<221> NAME/KEY: MISC_FEATURE
<222> LOCATION: (10)..(10)
<223> OTHER INFORMATION: Xaa = beta-Ala
<220> FEATURE:
<221> NAME/KEY: MISC_FEATURE
<222> LOCATION: (11)..(11)
<223> OTHER INFORMATION: Xaa = beta-Ala or absent
<220> FEATURE:
<221> NAME/KEY: MOD_RES
<222> LOCATION: (22)..(22)
<223> OTHER INFORMATION: AMIDATION

<400> SEQUENCE: 227

Xaa Cys His Xaa Xaa Xaa Xaa Thr Xaa Xaa Tyr Gly Arg Arg Arg
1               5                   10                  15

Arg Arg Gln Arg Arg Arg
            20

<210> SEQ ID NO 228
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
```

```
<223> OTHER INFORMATION: Xaa = D-Phe
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-(Et)Tyr
<220> FEATURE:
<221> NAME/KEY: MISC_FEATURE
<222> LOCATION: (5)..(5)
<223> OTHER INFORMATION: Xaa = homo-Arg (hArg)
<220> FEATURE:
<221> NAME/KEY: MISC_FEATURE
<222> LOCATION: (6)..(6)
<223> OTHER INFORMATION: Xaa = 4,4'-biphenylAla (Bip)
<220> FEATURE:
<221> NAME/KEY: MISC_FEATURE
<222> LOCATION: (7)..(7)
<223> OTHER INFORMATION: Xaa = beta-Ala
<220> FEATURE:
<221> NAME/KEY: MISC_FEATURE
<222> LOCATION: (8)..(8)
<223> OTHER INFORMATION: Xaa = D-Cys
<220> FEATURE:
<221> NAME/KEY: MISC_FEATURE
<222> LOCATION: (10)..(10)
<223> OTHER INFORMATION: Xaa = beta-Ala
<220> FEATURE:
<221> NAME/KEY: MISC_FEATURE
<222> LOCATION: (11)..(11)
<223> OTHER INFORMATION: Xaa = beta-Ala or absent
<220> FEATURE:
<221> NAME/KEY: MOD_RES
<222> LOCATION: (20)..(20)
<223> OTHER INFORMATION: AMIDATION

<400> SEQUENCE: 228

Xaa Cys His Xaa Xaa Xaa Xaa Xaa Thr Xaa Xaa Arg Arg Arg Arg Arg
1               5                   10                  15

Gln Arg Arg Arg
            20

<210> SEQ ID NO 229
<211> LENGTH: 21
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = D-Phe
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-(Et)Tyr
<220> FEATURE:
<221> NAME/KEY: MISC_FEATURE
<222> LOCATION: (5)..(5)
<223> OTHER INFORMATION: Xaa = homo-Arg (hArg)
<220> FEATURE:
<221> NAME/KEY: MISC_FEATURE
<222> LOCATION: (5)..(5)
<223> OTHER INFORMATION: Xaa = 4,4'-biphenylAla (Bip)
<220> FEATURE:
<221> NAME/KEY: MISC_FEATURE
<222> LOCATION: (7)..(7)
<223> OTHER INFORMATION: Xaa = beta-Ala
<220> FEATURE:
```

<221> NAME/KEY: MISC_FEATURE
<222> LOCATION: (8)..(8)
<223> OTHER INFORMATION: Xaa = D-Cys
<220> FEATURE:
<221> NAME/KEY: MISC_FEATURE
<222> LOCATION: (10)..(10)
<223> OTHER INFORMATION: Xaa = 8-amino-3,6-dioxaoctanoic acid (Doc)
<220> FEATURE:
<221> NAME/KEY: MOD_RES
<222> LOCATION: (21)..(21)
<223> OTHER INFORMATION: AMIDATION

<400> SEQUENCE: 229

Xaa Cys His Xaa Xaa Xaa Xaa Xaa Thr Xaa Tyr Gly Arg Arg Arg
1               5                   10                  15

Arg Gln Arg Arg Arg
            20

<210> SEQ ID NO 230
<211> LENGTH: 22
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = D-Phe
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-(Et)Tyr
<220> FEATURE:
<221> NAME/KEY: MISC_FEATURE
<222> LOCATION: (5)..(5)
<223> OTHER INFORMATION: Xaa = homo-Arg (hArg)
<220> FEATURE:
<221> NAME/KEY: MISC_FEATURE
<222> LOCATION: (6)..(6)
<223> OTHER INFORMATION: Xaa = 4,4'-biphenylAla (Bip)
<220> FEATURE:
<221> NAME/KEY: MISC_FEATURE
<222> LOCATION: (7)..(7)
<223> OTHER INFORMATION: Xaa = beta-Ala
<220> FEATURE:
<221> NAME/KEY: MISC_FEATURE
<222> LOCATION: (8)..(8)
<223> OTHER INFORMATION: Xaa = D-Cys
<220> FEATURE:
<221> NAME/KEY: MISC_FEATURE
<222> LOCATION: (10)..(10)
<223> OTHER INFORMATION: Xaa = 8-amino-3,6-dioxaoctanoic acid (Doc)
<220> FEATURE:
<221> NAME/KEY: MOD_RES
<222> LOCATION: (22)..(22)
<223> OTHER INFORMATION: AMIDATION

<400> SEQUENCE: 230

Xaa Cys His Xaa Xaa Xaa Xaa Xaa Thr Xaa Tyr Gly Arg Arg Arg
1               5                   10                  15

Arg Gln Arg Arg Arg Arg
            20

<210> SEQ ID NO 231
<211> LENGTH: 22
<212> TYPE: PRT
<213> ORGANISM: Artificial Sequence
<220> FEATURE:

```
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = D-Phe
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-(Et)Tyr
<220> FEATURE:
<221> NAME/KEY: MISC_FEATURE
<222> LOCATION: (5)..(5)
<223> OTHER INFORMATION: Xaa = homo-Arg (hArg)
<220> FEATURE:
<221> NAME/KEY: MISC_FEATURE
<222> LOCATION: (6)..(6)
<223> OTHER INFORMATION: Xaa = 4,4'-biphenylAla (Bip)
<220> FEATURE:
<221> NAME/KEY: MISC_FEATURE
<222> LOCATION: (7)..(7)
<223> OTHER INFORMATION: Xaa = beta-Ala
<220> FEATURE:
<221> NAME/KEY: MISC_FEATURE
<222> LOCATION: (8)..(8)
<223> OTHER INFORMATION: Xaa = D-Cys
<220> FEATURE:
<221> NAME/KEY: MISC_FEATURE
<222> LOCATION: (10)..(11)
<223> OTHER INFORMATION: Xaa = 8-amino-3,6-dioxaoctanoic acid (Doc)
<220> FEATURE:
<221> NAME/KEY: MOD_RES
<222> LOCATION: (22)..(22)
<223> OTHER INFORMATION: AMIDATION

<400> SEQUENCE: 231

Xaa Cys His Xaa Xaa Xaa Xaa Xaa Thr Xaa Xaa Tyr Gly Arg Arg Arg
1               5                   10                  15

Arg Arg Gln Arg Arg Arg
            20

<210> SEQ ID NO 232
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = D-Phe
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-(Et)Tyr
<220> FEATURE:
<221> NAME/KEY: MISC_FEATURE
<222> LOCATION: (5)..(5)
<223> OTHER INFORMATION: Xaa = homo-Arg (hArg)
<220> FEATURE:
<221> NAME/KEY: MISC_FEATURE
<222> LOCATION: (6)..(6)
<223> OTHER INFORMATION: Xaa = 4,4'-biphenylAla (Bip)
<220> FEATURE:
<221> NAME/KEY: MISC_FEATURE
<222> LOCATION: (7)..(7)
<223> OTHER INFORMATION: Xaa = beta-Ala
```

```
<220> FEATURE:
<221> NAME/KEY: MISC_FEATURE
<222> LOCATION: (8)..(8)
<223> OTHER INFORMATION: Xaa = D-Cys
<220> FEATURE:
<221> NAME/KEY: MISC_FEATURE
<222> LOCATION: (10)..(10)
<223> OTHER INFORMATION: Xaa = 8-amino-3,6-dioxaoctanoic acid (Doc)
<220> FEATURE:
<221> NAME/KEY: MISC_FEATURE
<222> LOCATION: (11)..(11)
<223> OTHER INFORMATION: Xaa = 8-amino-3,6-dioxaoctanoic acid (Doc) or
      absent
<220> FEATURE:
<221> NAME/KEY: MOD_RES
<222> LOCATION: (20)..(20)
<223> OTHER INFORMATION: AMIDATION

<400> SEQUENCE: 232

Xaa Cys His Xaa Xaa Xaa Xaa Xaa Thr Xaa Xaa Arg Arg Arg Arg Arg
1               5                   10                  15

Gln Arg Arg Arg
            20

<210> SEQ ID NO 233
<211> LENGTH: 21
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(9)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (10)..(10)
<223> OTHER INFORMATION: Xaa = beta-Ala
<220> FEATURE:
<221> NAME/KEY: MOD_RES
<222> LOCATION: (21)..(21)
<223> OTHER INFORMATION: AMIDATION

<400> SEQUENCE: 233

Xaa Cys Xaa His Xaa Arg Trp Gly Cys Xaa Tyr Gly Arg Arg Arg Arg
1               5                   10                  15

Arg Gln Arg Arg Arg
            20

<210> SEQ ID NO 234
<211> LENGTH: 19
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
```

```
<220> FEATURE:
<221> NAME/KEY: DOMAIN
<222> LOCATION: (2)..(9)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (10)..(10)
<223> OTHER INFORMATION: Xaa = beta-Ala
<220> FEATURE:
<221> NAME/KEY: MOD_RES
<222> LOCATION: (19)..(19)
<223> OTHER INFORMATION: AMIDATION

<400> SEQUENCE: 234

Xaa Cys Xaa His Xaa Arg Trp Gly Cys Xaa Arg Arg Arg Arg Gln
1               5                   10                  15

Arg Arg Arg

<210> SEQ ID NO 235
<211> LENGTH: 21
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 5-aminopentanoic acid (Apn)
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MISC_FEATURE
<222> LOCATION: (10)..(10)
<223> OTHER INFORMATION: Xaa = beta-Ala or absent
<220> FEATURE:
<221> NAME/KEY: MOD_RES
<222> LOCATION: (21)..(21)
<223> OTHER INFORMATION: AMIDATION

<400> SEQUENCE: 235

Xaa Cys His Xaa Arg Trp Xaa Cys Xaa Xaa Tyr Gly Arg Arg Arg
1               5                   10                  15

Arg Gln Arg Arg Arg
            20

<210> SEQ ID NO 236
<211> LENGTH: 19
<212> TYPE: PRT
<213> ORGANISM: Artificial Sequence
<220> FEATURE:
```

<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 5-aminopentanoic acid (Apn)
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MISC_FEATURE
<222> LOCATION: (10)..(10)
<223> OTHER INFORMATION: Xaa = beta-Ala or absent
<220> FEATURE:
<221> NAME/KEY: MOD_RES
<222> LOCATION: (19)..(19)
<223> OTHER INFORMATION: AMIDATION

<400> SEQUENCE: 236

Xaa Cys His Xaa Arg Trp Xaa Cys Xaa Xaa Arg Arg Arg Arg Gln
1               5                   10                  15

Arg Arg Arg

<210> SEQ ID NO 237
<211> LENGTH: 22
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 5-aminopentanoic acid (Apn)
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MISC_FEATURE
<222> LOCATION: (10)..(10)
<223> OTHER INFORMATION: Xaa = beta-Ala or absent
<220> FEATURE:
<221> NAME/KEY: MOD_RES
<222> LOCATION: (22)..(22)
<223> OTHER INFORMATION: AMIDATION

<400> SEQUENCE: 237

Xaa Cys His Xaa Arg Trp Xaa Cys Xaa Xaa Tyr Gly Arg Arg Arg Arg
1               5                   10                  15

Arg Gln Arg Arg Arg Arg
            20

<210> SEQ ID NO 238
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 5-aminopentanoic acid (Apn)
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MISC_FEATURE
<222> LOCATION: (10)..(10)
<223> OTHER INFORMATION: Xaa = beta-Ala or absent
<220> FEATURE:
<221> NAME/KEY: MOD_RES
<222> LOCATION: (20)..(20)
<223> OTHER INFORMATION: AMIDATION

<400> SEQUENCE: 238

Xaa Cys His Xaa Arg Trp Xaa Cys Xaa Xaa Arg Arg Arg Arg Gln
1               5                   10                  15

Arg Arg Arg Arg
            20

<210> SEQ ID NO 239
<211> LENGTH: 21
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 5-aminopentanoic acid (Apn)
<220> FEATURE:
<221> NAME/KEY: MISC_FEATURE
<222> LOCATION: (9)..(9)
<223> OTHER INFORMATION: Xaa = 8-amino-3,6-dioxaoctanoic acid (Doc)
<220> FEATURE:
<221> NAME/KEY: MISC_FEATURE

```
<222> LOCATION: (10)..(10)
<223> OTHER INFORMATION: Xaa = 8-amino-3,6-dioxaoctanoic acid (Doc) or
      absent
<220> FEATURE:
<221> NAME/KEY: MOD_RES
<222> LOCATION: (21)..(21)
<223> OTHER INFORMATION: AMIDATION

<400> SEQUENCE: 239

Xaa Cys His Xaa Arg Trp Xaa Cys Xaa Xaa Tyr Gly Arg Arg Arg
1               5                   10                  15

Arg Gln Arg Arg Arg
            20

<210> SEQ ID NO 240
<211> LENGTH: 19
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 5-aminopentanoic acid (Apn)
<220> FEATURE:
<221> NAME/KEY: MISC_FEATURE
<222> LOCATION: (9)..(9)
<223> OTHER INFORMATION: Xaa = 8-amino-3,6-dioxaoctanoic acid (Doc)
<220> FEATURE:
<221> NAME/KEY: MISC_FEATURE
<222> LOCATION: (10)..(10)
<223> OTHER INFORMATION: Xaa = 8-amino-3,6-dioxaoctanoic acid (Doc) or
      absent
<220> FEATURE:
<221> NAME/KEY: MOD_RES
<222> LOCATION: (19)..(19)
<223> OTHER INFORMATION: AMIDATION

<400> SEQUENCE: 240

Xaa Cys His Xaa Arg Trp Xaa Cys Xaa Xaa Arg Arg Arg Arg Gln
1               5                   10                  15

Arg Arg Arg

<210> SEQ ID NO 241
<211> LENGTH: 22
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
```

```
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 5-aminopentanoic acid (Apn)
<220> FEATURE:
<221> NAME/KEY: MISC_FEATURE
<222> LOCATION: (9)..(9)
<223> OTHER INFORMATION: Xaa = 8-amino-3,6-dioxaoctanoic acid (Doc)
<220> FEATURE:
<221> NAME/KEY: MISC_FEATURE
<222> LOCATION: (10)..(10)
<223> OTHER INFORMATION: Xaa = 8-amino-3,6-dioxaoctanoic acid (Doc) or
      absent
<220> FEATURE:
<221> NAME/KEY: MOD_RES
<222> LOCATION: (22)..(22)
<223> OTHER INFORMATION: AMIDATION

<400> SEQUENCE: 241

Xaa Cys His Xaa Arg Trp Xaa Cys Xaa Xaa Tyr Gly Arg Arg Arg Arg
1               5                   10                  15

Arg Gln Arg Arg Arg Arg
            20

<210> SEQ ID NO 242
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 5-aminopentanoic acid (Apn)
<220> FEATURE:
<221> NAME/KEY: MISC_FEATURE
<222> LOCATION: (9)..(9)
<223> OTHER INFORMATION: Xaa = 8-amino-3,6-dioxaoctanoic acid (Doc)
<220> FEATURE:
<221> NAME/KEY: MISC_FEATURE
<222> LOCATION: (10)..(10)
<223> OTHER INFORMATION: Xaa = 8-amino-3,6-dioxaoctanoic acid (Doc) or
      absent
<220> FEATURE:
<221> NAME/KEY: MOD_RES
<222> LOCATION: (20)..(20)
<223> OTHER INFORMATION: AMIDATION

<400> SEQUENCE: 242

Xaa Cys His Xaa Arg Trp Xaa Cys Xaa Xaa Arg Arg Arg Arg Gln
1               5                   10                  15

Arg Arg Arg Arg
            20

<210> SEQ ID NO 243
<211> LENGTH: 21
<212> TYPE: PRT
<213> ORGANISM: Artificial Sequence
```

```
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-Leu
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MISC_FEATURE
<222> LOCATION: (10)..(10)
<223> OTHER INFORMATION: Xaa = beta-Ala or absent
<220> FEATURE:
<221> NAME/KEY: MOD_RES
<222> LOCATION: (21)..(21)
<223> OTHER INFORMATION: AMIDATION

<400> SEQUENCE: 243

Xaa Cys Xaa His Xaa Arg Trp Cys Xaa Xaa Tyr Gly Arg Arg Arg
1               5                   10                  15

Arg Gln Arg Arg Arg
            20

<210> SEQ ID NO 244
<211> LENGTH: 19
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-Leu
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MISC_FEATURE
<222> LOCATION: (10)..(10)
<223> OTHER INFORMATION: Xaa = beta-Ala or absent
<220> FEATURE:
<221> NAME/KEY: MOD_RES
<222> LOCATION: (19)..(19)
<223> OTHER INFORMATION: AMIDATION

<400> SEQUENCE: 244
```

```
Xaa Cys Xaa His Xaa Arg Trp Cys Xaa Xaa Arg Arg Arg Arg Gln
1               5                   10                  15

Arg Arg Arg

<210> SEQ ID NO 245
<211> LENGTH: 21
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-Leu
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (9)..(9)
<223> OTHER INFORMATION: Xaa = 8-amino-3,6-dioxaoctanoic acid (Doc)
<220> FEATURE:
<221> NAME/KEY: MISC_FEATURE
<222> LOCATION: (10)..(10)
<223> OTHER INFORMATION: Xaa = 8-amino-3,6-dioxaoctanoic acid (Doc) or
      absent
<220> FEATURE:
<221> NAME/KEY: MOD_RES
<222> LOCATION: (21)..(21)
<223> OTHER INFORMATION: AMIDATION

<400> SEQUENCE: 245

Xaa Cys Xaa His Xaa Arg Trp Cys Xaa Xaa Tyr Gly Arg Arg Arg
1               5                   10                  15

Arg Gln Arg Arg Arg
                20

<210> SEQ ID NO 246
<211> LENGTH: 19
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-Leu
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (9)..(9)
<223> OTHER INFORMATION: Xaa = 8-amino-3,6-dioxaoctanoic acid (Doc)
```

```
<220> FEATURE:
<221> NAME/KEY: MISC_FEATURE
<222> LOCATION: (10)..(10)
<223> OTHER INFORMATION: Xaa = 8-amino-3,6-dioxaoctanoic acid (Doc) or
      absent
<220> FEATURE:
<221> NAME/KEY: MOD_RES
<222> LOCATION: (19)..(19)
<223> OTHER INFORMATION: AMIDATION

<400> SEQUENCE: 246

Xaa Cys Xaa His Xaa Arg Trp Cys Xaa Xaa Arg Arg Arg Arg Arg Gln
1               5                   10                  15

Arg Arg Arg

<210> SEQ ID NO 247
<211> LENGTH: 22
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-Leu
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MISC_FEATURE
<222> LOCATION: (10)..(10)
<223> OTHER INFORMATION: Xaa = beta-Ala or absent
<220> FEATURE:
<221> NAME/KEY: MOD_RES
<222> LOCATION: (22)..(22)
<223> OTHER INFORMATION: AMIDATION

<400> SEQUENCE: 247

Xaa Cys Xaa His Xaa Arg Trp Cys Xaa Xaa Tyr Gly Arg Arg Arg
1               5                   10                  15

Arg Gln Arg Arg Arg Arg
            20

<210> SEQ ID NO 248
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
```

```
<221> NAME/KEY: MISC_FEATURE
<222> LOCATION: (3)..(3)
<223> OTHER INFORMATION: Xaa = D-Leu
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MISC_FEATURE
<222> LOCATION: (10)..(10)
<223> OTHER INFORMATION: Xaa = beta-Ala or absent
<220> FEATURE:
<221> NAME/KEY: MOD_RES
<222> LOCATION: (20)..(20)
<223> OTHER INFORMATION: AMIDATION

<400> SEQUENCE: 248

Xaa Cys Xaa His Xaa Arg Trp Cys Xaa Xaa Arg Arg Arg Arg Gln
1               5                   10                  15

Arg Arg Arg Arg
            20

<210> SEQ ID NO 249
<211> LENGTH: 22
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-Leu
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (9)..(9)
<223> OTHER INFORMATION: Xaa = 8-amino-3,6-dioxaoctanoic acid (Doc)
<220> FEATURE:
<221> NAME/KEY: MISC_FEATURE
<222> LOCATION: (10)..(10)
<223> OTHER INFORMATION: Xaa = 8-amino-3,6-dioxaoctanoic acid (Doc) or
      absent
<220> FEATURE:
<221> NAME/KEY: MOD_RES
<222> LOCATION: (22)..(22)
<223> OTHER INFORMATION: AMIDATION

<400> SEQUENCE: 249

Xaa Cys Xaa His Xaa Arg Trp Cys Xaa Xaa Tyr Gly Arg Arg Arg
1               5                   10                  15

Arg Gln Arg Arg Arg Arg
            20

<210> SEQ ID NO 250
<211> LENGTH: 20
<212> TYPE: PRT
<213> ORGANISM: Artificial Sequence
```

```
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-Leu
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (9)..(9)
<223> OTHER INFORMATION: Xaa = 8-amino-3,6-dioxaoctanoic acid (Doc)
<220> FEATURE:
<221> NAME/KEY: MISC_FEATURE
<222> LOCATION: (10)..(10)
<223> OTHER INFORMATION: Xaa = 8-amino-3,6-dioxaoctanoic acid (Doc) or
      absent
<220> FEATURE:
<221> NAME/KEY: MOD_RES
<222> LOCATION: (20)..(20)
<223> OTHER INFORMATION: AMIDATION

<400> SEQUENCE: 250

Xaa Cys Xaa His Xaa Arg Trp Cys Xaa Xaa Arg Arg Arg Arg Arg Gln
1               5                   10                  15

Arg Arg Arg Arg
            20

<210> SEQ ID NO 251
<211> LENGTH: 21
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-beta-cyclohexylAla (D-Cha)
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MISC_FEATURE
<222> LOCATION: (10)..(10)
<223> OTHER INFORMATION: Xaa = beta-Ala or absent
<220> FEATURE:
<221> NAME/KEY: MOD_RES
<222> LOCATION: (21)..(21)
<223> OTHER INFORMATION: AMIDATION

<400> SEQUENCE: 251
```

```
Xaa Cys Xaa His Xaa Arg Trp Cys Xaa Xaa Tyr Gly Arg Arg Arg
1               5                   10                  15

Arg Gln Arg Arg Arg
            20

<210> SEQ ID NO 252
<211> LENGTH: 19
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-beta-cyclohexylAla (D-Cha)
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MISC_FEATURE
<222> LOCATION: (10)..(10)
<223> OTHER INFORMATION: Xaa = beta-Ala or absent
<220> FEATURE:
<221> NAME/KEY: MOD_RES
<222> LOCATION: (19)..(19)
<223> OTHER INFORMATION: AMIDATION

<400> SEQUENCE: 252

Xaa Cys Xaa His Xaa Arg Trp Cys Xaa Xaa Arg Arg Arg Arg Gln
1               5                   10                  15

Arg Arg Arg

<210> SEQ ID NO 253
<211> LENGTH: 21
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-beta-cyclohexylAla (D-Cha)
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (9)..(9)
<223> OTHER INFORMATION: Xaa = 8-amino-3,6-dioxaoctanoic acid (Doc)
```

```
<220> FEATURE:
<221> NAME/KEY: MISC_FEATURE
<222> LOCATION: (10)..(10)
<223> OTHER INFORMATION: Xaa = 8-amino-3,6-dioxaoctanoic acid (Doc) or
      absent
<220> FEATURE:
<221> NAME/KEY: MOD_RES
<222> LOCATION: (21)..(21)
<223> OTHER INFORMATION: AMIDATION

<400> SEQUENCE: 253

Xaa Cys Xaa His Xaa Arg Trp Cys Xaa Xaa Tyr Gly Arg Arg Arg Arg
1               5                   10                  15

Arg Gln Arg Arg Arg
            20

<210> SEQ ID NO 254
<211> LENGTH: 19
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = beta-cyclohexylAla (D-Cha)
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (9)..(9)
<223> OTHER INFORMATION: Xaa = 8-amino-3,6-dioxaoctanoic acid (Doc)
<220> FEATURE:
<221> NAME/KEY: MISC_FEATURE
<222> LOCATION: (10)..(10)
<223> OTHER INFORMATION: Xaa = 8-amino-3,6-dioxaoctanoic acid (Doc) or
      absent
<220> FEATURE:
<221> NAME/KEY: MOD_RES
<222> LOCATION: (19)..(19)
<223> OTHER INFORMATION: AMIDATION

<400> SEQUENCE: 254

Xaa Cys Xaa His Xaa Arg Trp Cys Xaa Xaa Arg Arg Arg Arg Arg Gln
1               5                   10                  15

Arg Arg Arg

<210> SEQ ID NO 255
<211> LENGTH: 22
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
```

```
<220> FEATURE:
<221> NAME/KEY: MISC_FEATURE
<222> LOCATION: (3)..(3)
<223> OTHER INFORMATION: Xaa = D-beta-cyclohexylAla (D-Cha)
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MISC_FEATURE
<222> LOCATION: (10)..(10)
<223> OTHER INFORMATION: Xaa = beta-Ala or absent
<220> FEATURE:
<221> NAME/KEY: MOD_RES
<222> LOCATION: (22)..(22)
<223> OTHER INFORMATION: AMIDATION

<400> SEQUENCE: 255

Xaa Cys Xaa His Xaa Arg Trp Cys Xaa Xaa Tyr Gly Arg Arg Arg
 1               5                  10                  15

Arg Gln Arg Arg Arg Arg
                20

<210> SEQ ID NO 256
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-beta-cyclohexylAla (D-Cha)
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MISC_FEATURE
<222> LOCATION: (10)..(10)
<223> OTHER INFORMATION: Xaa = beta-Ala or absent
<220> FEATURE:
<221> NAME/KEY: MOD_RES
<222> LOCATION: (20)..(20)
<223> OTHER INFORMATION: AMIDATION

<400> SEQUENCE: 256

Xaa Cys Xaa His Xaa Arg Trp Cys Xaa Xaa Arg Arg Arg Arg Gln
 1               5                  10                  15

Arg Arg Arg Arg
                20

<210> SEQ ID NO 257
<211> LENGTH: 22
<212> TYPE: PRT
<213> ORGANISM: Artificial Sequence
```

```
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-beta-cyclohexylAla (D-Cha)
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (9)..(9)
<223> OTHER INFORMATION: Xaa = 8-amino-3,6-dioxaoctanoic acid (Doc)
<220> FEATURE:
<221> NAME/KEY: MISC_FEATURE
<222> LOCATION: (10)..(10)
<223> OTHER INFORMATION: Xaa = 8-amino-3,6-dioxaoctanoic acid (Doc) or
      absent
<220> FEATURE:
<221> NAME/KEY: MOD_RES
<222> LOCATION: (22)..(22)
<223> OTHER INFORMATION: AMIDATION

<400> SEQUENCE: 257

Xaa Cys Xaa His Xaa Arg Trp Cys Xaa Xaa Tyr Gly Arg Arg Arg
1               5                   10                  15

Arg Gln Arg Arg Arg Arg
            20

<210> SEQ ID NO 258
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-beta-cyclohexylAla (D-Cha)
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (9)..(9)
<223> OTHER INFORMATION: Xaa = 8-amino-3,6-dioxaoctanoic acid (Doc)
<220> FEATURE:
<221> NAME/KEY: MISC_FEATURE
<222> LOCATION: (10)..(10)
<223> OTHER INFORMATION: Xaa = 8-amino-3,6-dioxaoctanoic acid (Doc) or
      absent
<220> FEATURE:
<221> NAME/KEY: MOD_RES
<222> LOCATION: (20)..(20)
<223> OTHER INFORMATION: AMIDATION
```

-continued

```
<400> SEQUENCE: 258

Xaa Cys Xaa His Xaa Arg Trp Cys Xaa Xaa Arg Arg Arg Arg Gln
1               5                   10                  15

Arg Arg Arg Arg
            20

<210> SEQ ID NO 259
<211> LENGTH: 21
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MISC_FEATURE
<222> LOCATION: (10)..(10)
<223> OTHER INFORMATION: Xaa = beta-Ala or absent
<220> FEATURE:
<221> NAME/KEY: MOD_RES
<222> LOCATION: (21)..(21)
<223> OTHER INFORMATION: AMIDATION

<400> SEQUENCE: 259

Xaa Cys His Xaa Arg Trp Xaa Cys Xaa Xaa Tyr Gly Arg Arg Arg
1               5                   10                  15

Arg Gln Arg Arg Arg
            20

<210> SEQ ID NO 260
<211> LENGTH: 19
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MISC_FEATURE
```

```
<222> LOCATION: (9)..(9)
<223> OTHER INFORMATION: Xaa = beta-Ala
<220> FEATURE:
<221> NAME/KEY: MISC_FEATURE
<222> LOCATION: (10)..(10)
<223> OTHER INFORMATION: Xaa = beta-Ala or absent
<220> FEATURE:
<221> NAME/KEY: MOD_RES
<222> LOCATION: (19)..(19)
<223> OTHER INFORMATION: AMIDATION

<400> SEQUENCE: 260

Xaa Cys His Xaa Arg Trp Xaa Cys Xaa Xaa Arg Arg Arg Arg Gln
1               5                   10                  15

Arg Arg Arg

<210> SEQ ID NO 261
<211> LENGTH: 22
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MISC_FEATURE
<222> LOCATION: (10)..(10)
<223> OTHER INFORMATION: Xaa = beta-Ala or absent
<220> FEATURE:
<221> NAME/KEY: MOD_RES
<222> LOCATION: (22)..(22)
<223> OTHER INFORMATION: AMIDATION

<400> SEQUENCE: 261

Xaa Cys His Xaa Arg Trp Xaa Cys Xaa Xaa Tyr Gly Arg Arg Arg
1               5                   10                  15

Arg Gln Arg Arg Arg Arg
            20

<210> SEQ ID NO 262
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle
<220> FEATURE:
<221> NAME/KEY: DOMAIN
<222> LOCATION: (2)..(8)
<223> OTHER INFORMATION: cyclic
```

```
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MISC_FEATURE
<222> LOCATION: (9)..(9)
<223> OTHER INFORMATION: Xaa = beta-Ala
<220> FEATURE:
<221> NAME/KEY: MISC_FEATURE
<222> LOCATION: (10)..(10)
<223> OTHER INFORMATION: Xaa = beta-Ala or absent
<220> FEATURE:
<221> NAME/KEY: MOD_RES
<222> LOCATION: (20)..(20)
<223> OTHER INFORMATION: AMIDATION

<400> SEQUENCE: 262

Xaa Cys His Xaa Arg Trp Xaa Cys Xaa Xaa Arg Arg Arg Arg Gln
1               5                   10                  15

Arg Arg Arg Arg
            20

<210> SEQ ID NO 263
<211> LENGTH: 21
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MISC_FEATURE
<222> LOCATION: (9)..(9)
<223> OTHER INFORMATION: Xaa = 8-amino-3,6-dioxaoctanoic acid (Doc)
<220> FEATURE:
<221> NAME/KEY: MISC_FEATURE
<222> LOCATION: (10)..(10)
<223> OTHER INFORMATION: Xaa = 8-amino-3,6-dioxaoctanoic acid (Doc) or
      absent
<220> FEATURE:
<221> NAME/KEY: MOD_RES
<222> LOCATION: (21)..(21)
<223> OTHER INFORMATION: AMIDATION

<400> SEQUENCE: 263

Xaa Cys His Xaa Arg Trp Xaa Cys Xaa Xaa Tyr Gly Arg Arg Arg
1               5                   10                  15

Arg Gln Arg Arg Arg
            20

<210> SEQ ID NO 264
<211> LENGTH: 19
<212> TYPE: PRT
```

```
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MISC_FEATURE
<222> LOCATION: (9)..(9)
<223> OTHER INFORMATION: Xaa = 8-amino-3,6-dioxaoctanoic acid (Doc)
<220> FEATURE:
<221> NAME/KEY: MISC_FEATURE
<222> LOCATION: (10)..(10)
<223> OTHER INFORMATION: Xaa = 8-amino-3,6-dioxaoctanoic acid (Doc) or
      absent
<220> FEATURE:
<221> NAME/KEY: MOD_RES
<222> LOCATION: (19)..(19)
<223> OTHER INFORMATION: AMIDATION

<400> SEQUENCE: 264

Xaa Cys His Xaa Arg Trp Xaa Cys Xaa Xaa Arg Arg Arg Arg Arg Gln
1               5                   10                  15

Arg Arg Arg

<210> SEQ ID NO 265
<211> LENGTH: 22
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MISC_FEATURE
<222> LOCATION: (9)..(9)
<223> OTHER INFORMATION: Xaa = 8-amino-3,6-dioxaoctanoic acid (Doc)
<220> FEATURE:
<221> NAME/KEY: MISC_FEATURE
<222> LOCATION: (10)..(10)
<223> OTHER INFORMATION: Xaa = 8-amino-3,6-dioxaoctanoic acid (Doc) or
      absent
<220> FEATURE:
<221> NAME/KEY: MOD_RES
<222> LOCATION: (22)..(22)
<223> OTHER INFORMATION: AMIDATION
```

<400> SEQUENCE: 265

Xaa Cys His Xaa Arg Trp Xaa Cys Xaa Xaa Tyr Gly Arg Arg Arg
1               5                   10                  15

Arg Gln Arg Arg Arg Arg
            20

<210> SEQ ID NO 266
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Nle
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MISC_FEATURE
<222> LOCATION: (9)..(9)
<223> OTHER INFORMATION: Xaa = 8-amino-3,6-dioxaoctanoic acid (Doc)
<220> FEATURE:
<221> NAME/KEY: MISC_FEATURE
<222> LOCATION: (10)..(10)
<223> OTHER INFORMATION: Xaa = 8-amino-3,6-dioxaoctanoic acid (Doc) or
      absent
<220> FEATURE:
<221> NAME/KEY: MOD_RES
<222> LOCATION: (20)..(20)
<223> OTHER INFORMATION: AMIDATION

<400> SEQUENCE: 266

Xaa Cys His Xaa Arg Trp Xaa Cys Xaa Xaa Arg Arg Arg Arg Gln
1               5                   10                  15

Arg Arg Arg Arg
            20

<210> SEQ ID NO 267
<211> LENGTH: 20
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = D-Phe
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-(Et)Tyr
<220> FEATURE:
<221> NAME/KEY: MISC_FEATURE
<222> LOCATION: (7)..(7)
<223> OTHER INFORMATION: Xaa = beta-Ala
<220> FEATURE:

```
<221> NAME/KEY: MISC_FEATURE
<222> LOCATION: (8)..(8)
<223> OTHER INFORMATION: Xaa = D-Cys
<220> FEATURE:
<221> NAME/KEY: MISC_FEATURE
<222> LOCATION: (9)..(10)
<223> OTHER INFORMATION: Xaa = beta-Ala
<220> FEATURE:
<221> NAME/KEY: MOD_RES
<222> LOCATION: (20)..(20)
<223> OTHER INFORMATION: AMIDATION

<400> SEQUENCE: 267

Xaa Cys His Xaa Arg Trp Xaa Xaa Xaa Xaa Arg Arg Arg Arg Gln
1               5                   10                  15

Arg Arg Arg Arg
            20

<210> SEQ ID NO 268
<211> LENGTH: 12
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: DOMAIN
<222> LOCATION: (1)..(8)
<223> OTHER INFORMATION: cyclic
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (4)..(4)
<223> OTHER INFORMATION: Xaa = D-4-bromo-phenylAla (D-4-Br-Phe)
<220> FEATURE:
<221> NAME/KEY: MOD_RES
<222> LOCATION: (12)..(12)
<223> OTHER INFORMATION: AMIDATION

<400> SEQUENCE: 268

Cys Glu His Xaa Arg Trp Gly Cys Pro Pro Lys Asp
1               5                   10

<210> SEQ ID NO 269
<211> LENGTH: 12
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: DOMAIN
<222> LOCATION: (1)..(8)
<223> OTHER INFORMATION: cyclic
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = Trp, beta-(2-naphthyl)Ala (2-Nal), beta-
      (1-naphthyl)Ala (1-Nal) or 3-benzothienylAla (Bal)
<220> FEATURE:
<221> NAME/KEY: MOD_RES
<222> LOCATION: (12)..(12)
<223> OTHER INFORMATION: AMIDATION
```

<400> SEQUENCE: 269

Cys Glu His Xaa Arg Xaa Ala Cys Pro Pro Lys Asp
1               5                   10

<210> SEQ ID NO 270
<211> LENGTH: 12
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: DOMAIN
<222> LOCATION: (1)..(8)
<223> OTHER INFORMATION: cyclic
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (6)..(6)
<223> OTHER INFORMATION: Xaa = beta-(2-naphthyl)Ala (2-Nal)
<220> FEATURE:
<221> NAME/KEY: MISC_FEATURE
<222> LOCATION: (7)..(7)
<223> OTHER INFORMATION: Xaa = beta-Ala or alpha-aminoisobutyric acid
      (Aib)
<220> FEATURE:
<221> NAME/KEY: MOD_RES
<222> LOCATION: (12)..(12)
<223> OTHER INFORMATION: AMIDATION

<400> SEQUENCE: 270

Cys Glu His Xaa Arg Xaa Xaa Cys Pro Pro Lys Asp
1               5                   10

<210> SEQ ID NO 271
<211> LENGTH: 7
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: DOMAIN
<222> LOCATION: (1)..(7)
<223> OTHER INFORMATION: cyclic
<220> FEATURE:
<221> NAME/KEY: MOD_RES
<222> LOCATION: (1)..(1)
<223> OTHER INFORMATION: modified with hydantoin(CO)
<220> FEATURE:
<221> NAME/KEY: MISC_FEATURE
<222> LOCATION: (1)..(1)
<223> OTHER INFORMATION: Xaa = Cys or homocyteine (hCys)
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 271

```
Xaa Xaa His Xaa Arg Trp Cys
1               5

<210> SEQ ID NO 272
<211> LENGTH: 7
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: DOMAIN
<222> LOCATION: (1)..(7)
<223> OTHER INFORMATION: Cyclic
<220> FEATURE:
<221> NAME/KEY: MOD_RES
<222> LOCATION: (1)..(1)
<223> OTHER INFORMATION: modified with hydantoin(CO)
<220> FEATURE:
<221> NAME/KEY: MISC_FEATURE
<222> LOCATION: (1)..(1)
<223> OTHER INFORMATION: Xaa = Cys or homocysteine (hCys)
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-beta-(2-naphythyl)alanine (D-2-Nal)
<220> FEATURE:
<221> NAME/KEY: MOD_RES
<222> LOCATION: (7)..(7)
<223> OTHER INFORMATION: AMIDATION

<400> SEQUENCE: 272

Xaa Xaa His Xaa Arg Trp Cys
1               5

<210> SEQ ID NO 273
<211> LENGTH: 7
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: DOMAIN
<222> LOCATION: (1)..(7)
<223> OTHER INFORMATION: cyclic
<220> FEATURE:
<221> NAME/KEY: MOD_RES
<222> LOCATION: (1)..(1)
<223> OTHER INFORMATION: modified with hydantoin(CO)
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = Lys, ornithine (Orn), 2,4-diaminobutyric
      acid (Dab), or 2,3-diaminopropionic acid (Dap)
<220> FEATURE:
<221> NAME/KEY: MOD_RES
<222> LOCATION: (7)..(7)
<223> OTHER INFORMATION: AMIDATION

<400> SEQUENCE: 273

Asp Xaa His Xaa Arg Trp Xaa
```

```
<210> SEQ ID NO 274
<211> LENGTH: 6
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with hydantoin(CO)
<220> FEATURE:
<221> NAME/KEY: DOMAIN
<222> LOCATION: (1)..(6)
<223> OTHER INFORMATION: cyclic
<220> FEATURE:
<221> NAME/KEY: MISC_FEATURE
<222> LOCATION: (2)..(2)
<223> OTHER INFORMATION: Xaa = His, 1-amino-1-cyclopropanecarboxylic
      acid (A3c),
      1-amino-1cyclopentanecarboxylic acid (A5c),
      1-amino-1-cyclohexanecarboxylic acid (A6c),
      2-aminoindan-2-carboxylic acid (Aic), or Apc
<220> FEATURE:
<221> NAME/KEY: MISC_FEATURE
<222> LOCATION: (3)..(3)
<223> OTHER INFORMATION: Xaa = D-Phe
<220> FEATURE:
<221> NAME/KEY: MOD_RES
<222> LOCATION: (6)..(6)
<223> OTHER INFORMATION: AMIDATION

<400> SEQUENCE: 274

Asp Xaa Xaa Arg Trp Lys
1               5

<210> SEQ ID NO 275
<211> LENGTH: 6
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: DOMAIN
<222> LOCATION: (1)..(6)
<223> OTHER INFORMATION: cyclic
<220> FEATURE:
<221> NAME/KEY: MOD_RES
<222> LOCATION: (1)..(1)
<223> OTHER INFORMATION: modified with hydantoin(CO)
<220> FEATURE:
<221> NAME/KEY: MISC_FEATURE
<222> LOCATION: (2)..(2)
<223> OTHER INFORMATION: Xaa = His, 1-amino-1-cyclopropanecarboxylic
      acid (A3c),
      1-amino-1cyclopentanecarboxylic acid (A5c),
      1-amino-1-cyclohexanecarboxylic acid (A6c),
      2-aminoindan-2-carboxylic acid (Aic), or Apc
<220> FEATURE:
<221> NAME/KEY: MISC_FEATURE
<222> LOCATION: (3)..(3)
<223> OTHER INFORMATION: Xaa = D-beta-(2-naphythyl)alanine (D-2-Nal)
<220> FEATURE:
<221> NAME/KEY: MOD_RES
<222> LOCATION: (6)..(6)
<223> OTHER INFORMATION: AMIDATION

<400> SEQUENCE: 275

Asp Xaa Xaa Arg Trp Lys
1               5
```

```
<210> SEQ ID NO 276
<211> LENGTH: 7
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with hydantoin(CO)
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = Lys, ornithine (Orn), 2,4-diaminobutyric
      acid (Dab), or 2,3-diaminopropionic acid (Dap)
<220> FEATURE:
<221> NAME/KEY: MOD_RES
<222> LOCATION: (7)..(7)
<223> OTHER INFORMATION: AMIDATION

<400> SEQUENCE: 276

Glu Xaa His Xaa Arg Trp Xaa
1               5

<210> SEQ ID NO 277
<211> LENGTH: 6
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: DOMAIN
<222> LOCATION: (1)..(6)
<223> OTHER INFORMATION: cyclic
<220> FEATURE:
<221> NAME/KEY: MOD_RES
<222> LOCATION: (1)..(1)
<223> OTHER INFORMATION: modified with hydantoin(CO)
<220> FEATURE:
<221> NAME/KEY: MISC_FEATURE
<222> LOCATION: (3)..(3)
<223> OTHER INFORMATION: Xaa = D-Phe
<220> FEATURE:
<221> NAME/KEY: MOD_RES
<222> LOCATION: (6)..(6)
<223> OTHER INFORMATION: AMIDATION
<220> FEATURE:
<221> NAME/KEY: MISC_FEATURE
<222> LOCATION: (6)..(6)
<223> OTHER INFORMATION: Xaa = Lys or 2,3-diaminopropionic acid (Dap)

<400> SEQUENCE: 277

Glu His Xaa Arg Trp Xaa
1               5

<210> SEQ ID NO 278
<211> LENGTH: 9
<212> TYPE: PRT
<213> ORGANISM: Artificial Sequence
<220> FEATURE:
<223> OTHER INFORMATION: Melanocortin receptor ligand to treat insulin
```

```
      sensitivity
<220> FEATURE:
<221> NAME/KEY: MISC_FEATURE
<222> LOCATION: (1)..(1)
<223> OTHER INFORMATION: Xaa = Arg, norleucine (Nle), Gly, or D-Arg
<220> FEATURE:
<221> NAME/KEY: MOD_RES
<222> LOCATION: (1)..(1)
<223> OTHER INFORMATION: modified with hydantoin(CO)
<220> FEATURE:
<221> NAME/KEY: DOMAIN
<222> LOCATION: (3)..(9)
<223> OTHER INFORMATION: cyclic
<220> FEATURE:
<221> NAME/KEY: MISC_FEATURE
<222> LOCATION: (6)..(6)
<223> OTHER INFORMATION: Xaa = D-Phe
<220> FEATURE:
<221> NAME/KEY: MOD_RES
<222> LOCATION: (9)..(9)
<223> OTHER INFORMATION: AMIDATION

<400> SEQUENCE: 278

Xaa Gly Cys Glu His Xaa Arg Trp Cys
1               5

<210> SEQ ID NO 279
<211> LENGTH: 9
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = norleucine (Nle), Gly, Ala, D-Ala, alpha-
      aminoisobutyric acid (Aib), Val, Ile, Leu, D-Arg, or Arg
<220> FEATURE:
<221> NAME/KEY: MOD_RES
<222> LOCATION: (1)..(1)
<223> OTHER INFORMATION: modified with hydantoin(CO)
<220> FEATURE:
<221> NAME/KEY: DOMAIN
<222> LOCATION: (3)..(9)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Ala
<220> FEATURE:
<221> NAME/KEY: MISC_FEATURE
<222> LOCATION: (6)..(6)
<223> OTHER INFORMATION: Xaa = D-Phe
<220> FEATURE:
<221> NAME/KEY: MOD_RES
<222> LOCATION: (9)..(9)
<223> OTHER INFORMATION: AMIDATION

<400> SEQUENCE: 279

Xaa Gly Cys Xaa His Xaa Arg Trp Cys
1               5

<210> SEQ ID NO 280
<211> LENGTH: 9
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = norleucine (Nle) or Gly
<220> FEATURE:
```

```
<221> NAME/KEY: MOD_RES
<222> LOCATION: (1)..(1)
<223> OTHER INFORMATION: modified with hydantoin(CO)
<220> FEATURE:
<221> NAME/KEY: DOMAIN
<222> LOCATION: (3)..(9)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Ala
<220> FEATURE:
<221> NAME/KEY: MISC_FEATURE
<222> LOCATION: (6)..(6)
<223> OTHER INFORMATION: Xaa = D-Phe
<220> FEATURE:
<221> NAME/KEY: MISC_FEATURE
<222> LOCATION: (9)..(9)
<223> OTHER INFORMATION: Xaa = penicillamine (Pen)
<220> FEATURE:
<221> NAME/KEY: MOD_RES
<222> LOCATION: (9)..(9)
<223> OTHER INFORMATION: AMIDATION

<400> SEQUENCE: 280

Xaa Gly Cys Xaa His Xaa Arg Trp Xaa
1               5

<210> SEQ ID NO 281
<211> LENGTH: 9
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = norleucine (Nle) or Gly
<220> FEATURE:
<221> NAME/KEY: MOD_RES
<222> LOCATION: (1)..(1)
<223> OTHER INFORMATION: modified with hydantoin(CO)
<220> FEATURE:
<221> NAME/KEY: DOMAIN
<222> LOCATION: (3)..(9)
<223> OTHER INFORMATION: cyclic
<220> FEATURE:
<221> NAME/KEY: MISC_FEATURE
<222> LOCATION: (6)..(6)
<223> OTHER INFORMATION: Xaa = D-beta-(2-naphythyl)alanine (D-2-Nal)
<220> FEATURE:
<221> NAME/KEY: MOD_RES
<222> LOCATION: (9)..(9)
<223> OTHER INFORMATION: AMIDATION

<400> SEQUENCE: 281

Xaa Gly Cys Glu His Xaa Arg Trp Cys
1               5

<210> SEQ ID NO 282
<211> LENGTH: 9
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = D-Arg or Arg
<220> FEATURE:
<221> NAME/KEY: MOD_RES
<222> LOCATION: (1)..(1)
<223> OTHER INFORMATION: modified with hydantoin(CO)
```

```
<220> FEATURE:
<221> NAME/KEY: DOMAIN
<222> LOCATION: (3)..(9)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Ala
<220> FEATURE:
<221> NAME/KEY: MISC_FEATURE
<222> LOCATION: (6)..(6)
<223> OTHER INFORMATION: Xaa = D-beta-(2-naphythyl)alanine (D-2-Nal)
<220> FEATURE:
<221> NAME/KEY: MOD_RES
<222> LOCATION: (9)..(9)
<223> OTHER INFORMATION: AMIDATION

<400> SEQUENCE: 282

Xaa Gly Cys Xaa His Xaa Arg Trp Cys
1               5

<210> SEQ ID NO 283
<211> LENGTH: 9
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Ala, Val, or Gly
<220> FEATURE:
<221> NAME/KEY: MOD_RES
<222> LOCATION: (1)..(1)
<223> OTHER INFORMATION: modified with hydantoin(CO)
<220> FEATURE:
<221> NAME/KEY: MISC_FEATURE
<222> LOCATION: (2)..(2)
<223> OTHER INFORMATION: Xaa = norleucine (Nle)
<220> FEATURE:
<221> NAME/KEY: DOMAIN
<222> LOCATION: (3)..(9)
<223> OTHER INFORMATION: cyclic
<220> FEATURE:
<221> NAME/KEY: MISC_FEATURE
<222> LOCATION: (6)..(6)
<223> OTHER INFORMATION: Xaa = D-Phe
<220> FEATURE:
<221> NAME/KEY: MOD_RES
<222> LOCATION: (9)..(9)
<223> OTHER INFORMATION: AMIDATION

<400> SEQUENCE: 283

Xaa Xaa Cys Glu His Xaa Arg Trp Cys
1               5

<210> SEQ ID NO 284
<211> LENGTH: 9
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with hydantoin(CO)
<220> FEATURE:
<221> NAME/KEY: MISC_FEATURE
<222> LOCATION: (1)..(1)
<223> OTHER INFORMATION: Xaa = 1-amino-1-cyclohexanecarboxylic acid
      (A6c), Gly, Ala, D-Ala, Val, Leu, beta-cyclohexylalanine (Cha), or
      alpha-aminoisobutyric acid (Aib)
<220> FEATURE:
```

```
<221> NAME/KEY: MISC_FEATURE
<222> LOCATION: (2)..(2)
<223> OTHER INFORMATION: Xaa = norleucine (Nle)
<220> FEATURE:
<221> NAME/KEY: DOMAIN
<222> LOCATION: (3)..(9)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Ala
<220> FEATURE:
<221> NAME/KEY: MISC_FEATURE
<222> LOCATION: (6)..(6)
<223> OTHER INFORMATION: Xaa = D-Phe
<220> FEATURE:
<221> NAME/KEY: MOD_RES
<222> LOCATION: (9)..(9)
<223> OTHER INFORMATION: AMIDATION

<400> SEQUENCE: 284

Xaa Xaa Cys Xaa His Xaa Arg Trp Cys
1               5

<210> SEQ ID NO 285
<211> LENGTH: 9
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with hydantoin(CO)
<220> FEATURE:
<221> NAME/KEY: DOMAIN
<222> LOCATION: (3)..(9)
<223> OTHER INFORMATION: cyclic
<220> FEATURE:
<221> NAME/KEY: MISC_FEATURE
<222> LOCATION: (6)..(6)
<223> OTHER INFORMATION: Xaa = D-Phe or D-beta-(2-naphythyl)alanine
      (D-2-Nal)
<220> FEATURE:
<221> NAME/KEY: MOD_RES
<222> LOCATION: (9)..(9)
<223> OTHER INFORMATION: AMIDATION

<400> SEQUENCE: 285

Gly Arg Cys Glu His Xaa Arg Trp Cys
1               5

<210> SEQ ID NO 286
<211> LENGTH: 9
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with hydantoin(CO)
<220> FEATURE:
<221> NAME/KEY: DOMAIN
<222> LOCATION: (3)..(9)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Ala
<220> FEATURE:
<221> NAME/KEY: MISC_FEATURE
<222> LOCATION: (6)..(6)
```

```
<223> OTHER INFORMATION: Xaa = D-Phe or D-beta-(2-naphythyl)alanine
      (D-2-Nal)
<220> FEATURE:
<221> NAME/KEY: MOD_RES
<222> LOCATION: (9)..(9)
<223> OTHER INFORMATION: AMIDATION

<400> SEQUENCE: 286

Gly Arg Cys Xaa His Xaa Arg Trp Cys
1               5

<210> SEQ ID NO 287
<211> LENGTH: 9
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with hydantoin(CO)
<220> FEATURE:
<221> NAME/KEY: MISC_FEATURE
<222> LOCATION: (2)..(2)
<223> OTHER INFORMATION: Xaa = D-Arg
<220> FEATURE:
<221> NAME/KEY: DOMAIN
<222> LOCATION: (3)..(9)
<223> OTHER INFORMATION: cyclic
<220> FEATURE:
<221> NAME/KEY: MISC_FEATURE
<222> LOCATION: (6)..(6)
<223> OTHER INFORMATION: Xaa = D-Phe
<220> FEATURE:
<221> NAME/KEY: MOD_RES
<222> LOCATION: (9)..(9)
<223> OTHER INFORMATION: AMIDATION

<400> SEQUENCE: 287

Gly Xaa Cys Glu His Xaa Arg Trp Cys
1               5

<210> SEQ ID NO 288
<211> LENGTH: 9
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with hydantoin(CO)
<220> FEATURE:
<221> NAME/KEY: MISC_FEATURE
<222> LOCATION: (2)..(2)
<223> OTHER INFORMATION: Xaa = D-Arg
<220> FEATURE:
<221> NAME/KEY: DOMAIN
<222> LOCATION: (3)..(9)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Ala
<220> FEATURE:
<221> NAME/KEY: MISC_FEATURE
<222> LOCATION: (6)..(6)
<223> OTHER INFORMATION: Xaa = D-Phe or D-beta-(2-naphythyl)alanine
      (D-2-Nal)
<220> FEATURE:
<221> NAME/KEY: MOD_RES
<222> LOCATION: (9)..(9)
<223> OTHER INFORMATION: AMIDATION
```

```
<400> SEQUENCE: 288

Gly Xaa Cys Xaa His Xaa Arg Trp Cys
1               5

<210> SEQ ID NO 289
<211> LENGTH: 9
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with hydantoin(CO)
<220> FEATURE:
<221> NAME/KEY: MISC_FEATURE
<222> LOCATION: (1)..(1)
<223> OTHER INFORMATION: Xaa = norleucine (Nle)
<220> FEATURE:
<221> NAME/KEY: DOMAIN
<222> LOCATION: (3)..(9)
<223> OTHER INFORMATION: cyclic
<220> FEATURE:
<221> NAME/KEY: MISC_FEATURE
<222> LOCATION: (6)..(6)
<223> OTHER INFORMATION: Xaa = D-Phe
<220> FEATURE:
<221> NAME/KEY: MOD_RES
<222> LOCATION: (9)..(9)
<223> OTHER INFORMATION: AMIDATION

<400> SEQUENCE: 289

Xaa Ala Cys Glu His Xaa Arg Trp Cys
1               5

<210> SEQ ID NO 290
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MOD_RES
<222> LOCATION: (1)..(1)
<223> OTHER INFORMATION: modified with hydantoin(CO)
<220> FEATURE:
<221> NAME/KEY: MISC_FEATURE
<222> LOCATION: (1)..(1)
<223> OTHER INFORMATION: Xaa = norleucine (Nle), Ala, D-Ala, alpha-
      aminoisobutyric acid (Aib), Val, alpha-aminobutyric acid (Abu),
      Leu, Ile, beta-cyclohexylalanine (Cha), 1-amino-1-
      cyclohexanecarboxylic acid (A6c), Phe, or Gly
<220> FEATURE:
<221> NAME/KEY: DOMAIN
<222> LOCATION: (1)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MOD_RES
<222> LOCATION: (8)..(8)
<223> OTHER INFORMATION: AMIDATION

<400> SEQUENCE: 290

Xaa Cys Xaa His Xaa Arg Trp Cys
```

```
<210> SEQ ID NO 291
<211> LENGTH: 8
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: DOMAIN
<222> LOCATION: (1)..(8)
<223> OTHER INFORMATION: cyclic
<220> FEATURE:
<221> NAME/KEY: MOD_RES
<222> LOCATION: (1)..(1)
<223> OTHER INFORMATION: modified with hydantoin(CO)
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MOD_RES
<222> LOCATION: (8)..(8)
<223> OTHER INFORMATION: AMIDATION

<400> SEQUENCE: 291

Gly Cys Glu His Xaa Arg Trp Cys
1               5

<210> SEQ ID NO 292
<211> LENGTH: 9
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: MISC_FEATURE
<222> LOCATION: (1)..(1)
<223> OTHER INFORMATION: Xaa = Tyr, beta-(2-naphthyl)alanine (2-Nal),
      beta-(1-naphthyl)alanine (1-Nal), Phe, Trp,
      (S)-pentafluorophenylalanine (Pff), or His, all modified with
      acyl group (Ac)
<220> FEATURE:
<221> NAME/KEY: DOMAIN
<222> LOCATION: (3)..(9)
<223> OTHER INFORMATION: cylic
<220> FEATURE:
<221> NAME/KEY: MISC_FEATURE
<222> LOCATION: (4)..(4)
<223> OTHER INFORMATION: Xaa = D-Ala
<220> FEATURE:
<221> NAME/KEY: MISC_FEATURE
<222> LOCATION: (6)..(6)
<223> OTHER INFORMATION: Xaa = D-Phe
<220> FEATURE:
<221> NAME/KEY: MOD_RES
<222> LOCATION: (9)..(9)
<223> OTHER INFORMATION: AMIDATION

<400> SEQUENCE: 292

Xaa Arg Cys Xaa His Xaa Arg Trp Cys
1               5

<210> SEQ ID NO 293
<211> LENGTH: 9
<212> TYPE: PRT
<213> ORGANISM: Artificial Sequence
<220> FEATURE:
<223> OTHER INFORMATION: Melanocortin receptor ligand to treat insulin
      sensitivity
<220> FEATURE:
<221> NAME/KEY: DOMAIN
```

```
<222> LOCATION: (3)..(9)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Ala
<220> FEATURE:
<221> NAME/KEY: MISC_FEATURE
<222> LOCATION: (6)..(6)
<223> OTHER INFORMATION: Xaa = D-Phe
<220> FEATURE:
<221> NAME/KEY: MOD_RES
<222> LOCATION: (9)..(9)
<223> OTHER INFORMATION: AMIDATION

<400> SEQUENCE: 293

His Arg Cys Xaa His Xaa Arg Trp Cys
1               5

<210> SEQ ID NO 294
<211> LENGTH: 9
<212> TYPE: PRT
<213> ORGANISM: Artificial Sequence
<220> FEATURE:
<223> OTHER INFORMATION: amino acid moiety of synthetic melanocortin
      peptide ligand

<400> SEQUENCE: 294

Arg Lys Lys Arg Arg Gln Arg Arg Arg
1               5

<210> SEQ ID NO 295
<211> LENGTH: 11
<212> TYPE: PRT
<213> ORGANISM: Artificial Sequence
<220> FEATURE:
<223> OTHER INFORMATION: amino acid moiety of synthetic melanocortin
      peptide ligand

<400> SEQUENCE: 295

Tyr Ala Arg Lys Ala Arg Arg Gln Ala Arg Arg
1               5                   10

<210> SEQ ID NO 296
<211> LENGTH: 11
<212> TYPE: PRT
<213> ORGANISM: Artificial Sequence
<220> FEATURE:
<223> OTHER INFORMATION: amino acid moiety of synthetic melanocortin
      peptide ligand

<400> SEQUENCE: 296

Tyr Ala Arg Ala Ala Arg Arg Ala Ala Arg Arg
1               5                   10

<210> SEQ ID NO 297
<211> LENGTH: 11
<212> TYPE: PRT
<213> ORGANISM: Artificial Sequence
<220> FEATURE:
<223> OTHER INFORMATION: amino acid moiety of synthetic melanocortin
      peptide ligand

<400> SEQUENCE: 297

Tyr Ala Arg Arg Arg Arg Arg Arg Arg Arg Arg
1               5                   10

<210> SEQ ID NO 298
<211> LENGTH: 11
```

```
<212> TYPE: PRT
<213> ORGANISM: Artificial Sequence
<220> FEATURE:
<223> OTHER INFORMATION: amino acid moiety of synthetic melanocortin
      peptide ligand

<400> SEQUENCE: 298

Tyr Ala Ala Ala Arg Arg Arg Arg Arg Arg
1               5                   10

<210> SEQ ID NO 299
<211> LENGTH: 11
<212> TYPE: PRT
<213> ORGANISM: Artificial Sequence
<220> FEATURE:
<223> OTHER INFORMATION: amino acid moiety of synthetic melanocortin
      peptide ligand

<400> SEQUENCE: 299

Tyr Ala Arg Ala Pro Arg Arg Ala Arg Arg
1               5                   10

<210> SEQ ID NO 300
<211> LENGTH: 10
<212> TYPE: PRT
<213> ORGANISM: Artificial Sequence
<220> FEATURE:
<223> OTHER INFORMATION: amino acid moiety of synthetic melanocortin
      peptide ligand

<400> SEQUENCE: 300

Tyr Ala Arg Ala Pro Arg Arg Pro Arg Arg
1               5                   10

<210> SEQ ID NO 301
<211> LENGTH: 9
<212> TYPE: PRT
<213> ORGANISM: Artificial Sequence
<220> FEATURE:
<223> OTHER INFORMATION: amino acid moiety of synthetic melanocortin
      peptide ligand

<400> SEQUENCE: 301

Arg Lys Gln Lys Arg Arg Arg Arg Arg
1               5

<210> SEQ ID NO 302
<211> LENGTH: 9
<212> TYPE: PRT
<213> ORGANISM: Artificial Sequence
<220> FEATURE:
<223> OTHER INFORMATION: amino acid moiety of synthetic melanocortin
      peptide ligand

<400> SEQUENCE: 302

Arg Lys Lys Arg Gln Arg Arg Arg Arg
1               5

<210> SEQ ID NO 303
<211> LENGTH: 9
<212> TYPE: PRT
<213> ORGANISM: Artificial Sequence
<220> FEATURE:
<223> OTHER INFORMATION: amino acid moiety of synthetic melanocortin
      peptide ligand

<400> SEQUENCE: 303

Arg Lys Lys Arg Arg Arg Gln Arg Arg
```

```
1               5
```

<210> SEQ ID NO 304
<211> LENGTH: 9
<212> TYPE: PRT
<213> ORGANISM: Artificial Sequence
<220> FEATURE:
<223> OTHER INFORMATION: amino acid moiety of synthetic melanocortin
      peptide ligand

<400> SEQUENCE: 304

```
Arg Lys Lys Arg Arg Arg Arg Gln Arg
1               5
```

<210> SEQ ID NO 305
<211> LENGTH: 9
<212> TYPE: PRT
<213> ORGANISM: Artificial Sequence
<220> FEATURE:
<223> OTHER INFORMATION: amino acid moiety of synthetic melanocortin
      peptide ligand

<400> SEQUENCE: 305

```
Arg Lys Lys Arg Arg Arg Arg Arg Gln
1               5
```

<210> SEQ ID NO 306
<211> LENGTH: 9
<212> TYPE: PRT
<213> ORGANISM: Artificial Sequence
<220> FEATURE:
<223> OTHER INFORMATION: amino acid moiety of synthetic melanocortin
      peptide ligand

<400> SEQUENCE: 306

```
Arg Lys Lys Gln Arg Arg Arg Arg Arg
1               5
```

<210> SEQ ID NO 307
<211> LENGTH: 9
<212> TYPE: PRT
<213> ORGANISM: Artificial Sequence
<220> FEATURE:
<223> OTHER INFORMATION: amino acid moiety of synthetic melanocortin
      peptide ligand

<400> SEQUENCE: 307

```
Arg Gln Lys Lys Arg Arg Arg Arg Arg
1               5
```

<210> SEQ ID NO 308
<211> LENGTH: 9
<212> TYPE: PRT
<213> ORGANISM: Artificial Sequence
<220> FEATURE:
<223> OTHER INFORMATION: amino acid moiety of synthetic melanocortin
      peptide ligand

<400> SEQUENCE: 308

```
Arg Gln Arg Arg Arg Arg Arg Arg Arg
1               5
```

<210> SEQ ID NO 309
<211> LENGTH: 10
<212> TYPE: PRT
<213> ORGANISM: Artificial Sequence
<220> FEATURE:
<223> OTHER INFORMATION: amino acid moiety of synthetic melanocortin peptide ligand

<400> SEQUENCE: 309

Arg Gln Arg Arg Arg Arg Arg Arg Arg
1               5                   10

<210> SEQ ID NO 310
<211> LENGTH: 9
<212> TYPE: PRT
<213> ORGANISM: Artificial Sequence
<220> FEATURE:
<223> OTHER INFORMATION: amino acid moiety of synthetic melanocortin
      peptide ligand

<400> SEQUENCE: 310

Arg Arg Gln Arg Arg Arg Arg Arg Arg
1               5

<210> SEQ ID NO 311
<211> LENGTH: 10
<212> TYPE: PRT
<213> ORGANISM: Artificial Sequence
<220> FEATURE:
<223> OTHER INFORMATION: amino acid moiety of synthetic melanocortin
      peptide ligand

<400> SEQUENCE: 311

Arg Arg Gln Arg Arg Arg Arg Arg Arg Arg
1               5                   10

<210> SEQ ID NO 312
<211> LENGTH: 9
<212> TYPE: PRT
<213> ORGANISM: Artificial Sequence
<220> FEATURE:
<223> OTHER INFORMATION: amino acid moiety of synthetic melanocortin
      peptide ligand

<400> SEQUENCE: 312

Arg Arg Arg Gln Arg Arg Arg Arg Arg
1               5

<210> SEQ ID NO 313
<211> LENGTH: 10
<212> TYPE: PRT
<213> ORGANISM: Artificial Sequence
<220> FEATURE:
<223> OTHER INFORMATION: amino acid moiety of synthetic melanocortin
      peptide ligand

<400> SEQUENCE: 313

Arg Arg Arg Gln Arg Arg Arg Arg Arg Arg
1               5                   10

<210> SEQ ID NO 314
<211> LENGTH: 9
<212> TYPE: PRT
<213> ORGANISM: Artificial Sequence
<220> FEATURE:
<223> OTHER INFORMATION: amino acid moiety of synthetic melanocortin
      peptide ligand

<400> SEQUENCE: 314

Arg Arg Arg Arg Gln Arg Arg Arg Arg
1               5

<210> SEQ ID NO 315

```
<211> LENGTH: 10
<212> TYPE: PRT
<213> ORGANISM: Artificial Sequence
<220> FEATURE:
<223> OTHER INFORMATION: amino acid moiety of synthetic melanocortin
      peptide ligand

<400> SEQUENCE: 315

Arg Arg Arg Arg Gln Arg Arg Arg Arg Arg
1               5                   10

<210> SEQ ID NO 316
<211> LENGTH: 5
<212> TYPE: PRT
<213> ORGANISM: Artificial Sequence
<220> FEATURE:
<223> OTHER INFORMATION: amino acid moiety of synthetic melanocortin
      peptide ligand

<400> SEQUENCE: 316

Arg Arg Arg Arg Arg
1               5

<210> SEQ ID NO 317
<211> LENGTH: 9
<212> TYPE: PRT
<213> ORGANISM: Artificial Sequence
<220> FEATURE:
<223> OTHER INFORMATION: amino acid moiety of synthetic melanocortin
      peptide ligand

<400> SEQUENCE: 317

Arg Arg Arg Arg Arg Gln Arg Arg Arg
1               5

<210> SEQ ID NO 318
<211> LENGTH: 10
<212> TYPE: PRT
<213> ORGANISM: Artificial Sequence
<220> FEATURE:
<223> OTHER INFORMATION: amino acid moiety of synthetic melanocortin
      peptide ligand

<400> SEQUENCE: 318

Arg Arg Arg Arg Arg Gln Arg Arg Arg Arg
1               5                   10

<210> SEQ ID NO 319
<211> LENGTH: 6
<212> TYPE: PRT
<213> ORGANISM: Artificial Sequence
<220> FEATURE:
<223> OTHER INFORMATION: amino acid moiety of synthetic melanocortin
      peptide ligand

<400> SEQUENCE: 319

Arg Arg Arg Arg Arg Arg
1               5

<210> SEQ ID NO 320
<211> LENGTH: 10
<212> TYPE: PRT
<213> ORGANISM: Artificial Sequence
<220> FEATURE:
<223> OTHER INFORMATION: amino acid moiety of synthetic melanocortin
      peptide ligand

<400> SEQUENCE: 320
```

Arg Arg Arg Arg Arg Arg Gln Arg Arg
1               5               10

<210> SEQ ID NO 321
<211> LENGTH: 7
<212> TYPE: PRT
<213> ORGANISM: Artificial Sequence
<220> FEATURE:
<223> OTHER INFORMATION: amino acid moiety of synthetic melanocortin
      peptide ligand

<400> SEQUENCE: 321

Arg Arg Arg Arg Arg Arg Arg
1               5

<210> SEQ ID NO 322
<211> LENGTH: 10
<212> TYPE: PRT
<213> ORGANISM: Artificial Sequence
<220> FEATURE:
<223> OTHER INFORMATION: amino acid moiety of synthetic melanocortin
      peptide ligand

<400> SEQUENCE: 322

Arg Arg Arg Arg Arg Arg Arg Gln Arg Arg
1               5               10

<210> SEQ ID NO 323
<211> LENGTH: 8
<212> TYPE: PRT
<213> ORGANISM: Artificial Sequence
<220> FEATURE:
<223> OTHER INFORMATION: amino acid moiety of synthetic melanocortin
      peptide ligand

<400> SEQUENCE: 323

Arg Arg Arg Arg Arg Arg Arg Arg
1               5

<210> SEQ ID NO 324
<211> LENGTH: 10
<212> TYPE: PRT
<213> ORGANISM: Artificial Sequence
<220> FEATURE:
<223> OTHER INFORMATION: amino acid moiety of synthetic melanocortin
      peptide ligand

<400> SEQUENCE: 324

Arg Arg Arg Arg Arg Arg Arg Arg Gln Arg
1               5               10

<210> SEQ ID NO 325
<211> LENGTH: 9
<212> TYPE: PRT
<213> ORGANISM: Artificial Sequence
<220> FEATURE:
<223> OTHER INFORMATION: amino acid moiety of synthetic melanocortin
      peptide ligand

<400> SEQUENCE: 325

Arg Arg Arg Arg Arg Arg Arg Arg Arg
1               5

<210> SEQ ID NO 326
<211> LENGTH: 10
<212> TYPE: PRT
<213> ORGANISM: Artificial Sequence
<220> FEATURE:

<223> OTHER INFORMATION: amino acid moiety of synthetic melanocortin
    peptide ligand

<400> SEQUENCE: 326

Arg Arg Arg Arg Arg Arg Arg Arg Arg Gln
1               5                   10

<210> SEQ ID NO 327
<211> LENGTH: 9
<212> TYPE: PRT
<213> ORGANISM: Artificial Sequence
<220> FEATURE:
<223> OTHER INFORMATION: amino acid moiety of synthetic melanocortin
    peptide ligand

<400> SEQUENCE: 327

Gln Arg Lys Lys Arg Arg Arg Arg Arg
1               5

<210> SEQ ID NO 328
<211> LENGTH: 9
<212> TYPE: PRT
<213> ORGANISM: Artificial Sequence
<220> FEATURE:
<223> OTHER INFORMATION: amino acid moiety of synthetic melanocortin
    peptide ligand

<400> SEQUENCE: 328

Gln Arg Arg Arg Arg Arg Arg Arg Arg
1               5

<210> SEQ ID NO 329
<211> LENGTH: 10
<212> TYPE: PRT
<213> ORGANISM: Artificial Sequence
<220> FEATURE:
<223> OTHER INFORMATION: amino acid moiety of synthetic melanocortin
    peptide ligand

<400> SEQUENCE: 329

Gln Arg Arg Arg Arg Arg Arg Arg Arg Arg
1               5                   10

<210> SEQ ID NO 330
<211> LENGTH: 11
<212> TYPE: PRT
<213> ORGANISM: Artificial Sequence
<220> FEATURE:
<223> OTHER INFORMATION: amino acid moiety of synthetic melanocortin
    peptide ligand

<400> SEQUENCE: 330

Tyr Gly Arg Lys Lys Arg Arg Gln Arg Arg Arg
1               5                   10

<210> SEQ ID NO 331
<211> LENGTH: 12
<212> TYPE: PRT
<213> ORGANISM: Artificial Sequence
<220> FEATURE:
<223> OTHER INFORMATION: amino acid moiety of synthetic melanocortin
    peptide ligand
<220> FEATURE:
<221> NAME/KEY: MISC_FEATURE
<222> LOCATION: (12)..(12)
<223> OTHER INFORMATION: Xaa = 8-amino-3,6-dioxaoctanoic acid (Doc)

<400> SEQUENCE: 331

-continued

```
Tyr Gly Arg Lys Lys Arg Arg Gln Arg Arg Xaa
1               5                   10

<210> SEQ ID NO 332
<211> LENGTH: 4
<212> TYPE: PRT
<213> ORGANISM: Artificial Sequence
<220> FEATURE:
<223> OTHER INFORMATION: amino acid moiety of synthetic melanocortin
      peptide ligand
<220> FEATURE:
<221> NAME/KEY: MISC_FEATURE
<222> LOCATION: (1)..(1)
<223> OTHER INFORMATION: Xaa = beta-alanine (B-Ala)
<220> FEATURE:
<221> NAME/KEY: MISC_FEATURE
<222> LOCATION: (2)..(2)
<223> OTHER INFORMATION: Xaa = beta-alanine (B-Ala)

<400> SEQUENCE: 332

Xaa Xaa Tyr Gly
1

<210> SEQ ID NO 333
<211> LENGTH: 4
<212> TYPE: PRT
<213> ORGANISM: Artificial Sequence
<220> FEATURE:
<223> OTHER INFORMATION: amino acid moiety of synthetic melanocortin
      peptide ligand
<220> FEATURE:
<221> NAME/KEY: MISC_FEATURE
<222> LOCATION: (1)..(1)
<223> OTHER INFORMATION: Xaa = 8-amino-3,6-dioxaoctanoic acid (Doc)
<220> FEATURE:
<221> NAME/KEY: MISC_FEATURE
<222> LOCATION: (2)..(2)
<223> OTHER INFORMATION: Xaa = 8-amino-3,6-dioxaoctanoic acid (Doc)

<400> SEQUENCE: 333

Xaa Xaa Tyr Gly
1

<210> SEQ ID NO 334
<211> LENGTH: 9
<212> TYPE: PRT
<213> ORGANISM: Artificial Sequence
<220> FEATURE:
<223> OTHER INFORMATION: amino acid moiety of synthetic melanocortin
      peptide ligand

<400> SEQUENCE: 334

Arg Lys Arg Arg Arg Gln Arg Arg Arg
1               5

<210> SEQ ID NO 335
<211> LENGTH: 9
<212> TYPE: PRT
<213> ORGANISM: Artificial Sequence
<220> FEATURE:
<223> OTHER INFORMATION: amino acid moiety of synthetic melanocortin
      peptide ligand

<400> SEQUENCE: 335

Arg Arg Lys Arg Arg Gln Arg Arg Arg
1               5
```